US009345739B2

(12) United States Patent
Reiser

(10) Patent No.: US 9,345,739 B2
(45) Date of Patent: May 24, 2016

(54) METHODS AND COMPOSITIONS FOR THE TREATMENT OF PROTEINURIC DISEASES

(75) Inventor: Jochen Reiser, Miami, FL (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/740,090

(22) PCT Filed: Nov. 7, 2008

(86) PCT No.: PCT/US2008/012541
§ 371 (c)(1),
(2), (4) Date: Aug. 10, 2010

(87) PCT Pub. No.: WO2009/061448
PCT Pub. Date: May 14, 2009

(65) Prior Publication Data
US 2010/0297139 A1    Nov. 25, 2010

Related U.S. Application Data

(60) Provisional application No. 61/002,445, filed on Nov. 8, 2007.

(51) Int. Cl.
| *A61K 39/395* | (2006.01) |
| *G01N 33/53* | (2006.01) |
| *A61K 38/06* | (2006.01) |
| *A61K 31/506* | (2006.01) |
| *A61K 38/07* | (2006.01) |
| *A61K 38/12* | (2006.01) |
| *C07K 16/28* | (2006.01) |
| *A61K 39/00* | (2006.01) |

(52) U.S. Cl.
CPC ............... *A61K 38/06* (2013.01); *A61K 31/506* (2013.01); *A61K 38/07* (2013.01); *A61K 38/12* (2013.01); *C07K 16/2848* (2013.01); *A61K 2039/505* (2013.01); *C07K 2317/55* (2013.01)

(58) Field of Classification Search
None
See application file for complete search history.

(56) References Cited

U.S. PATENT DOCUMENTS

| 6,410,526 | B1 | 6/2002 | Duggan et al. |
| 6,794,186 | B2 | 9/2004 | Buhler et al. |
| 6,825,167 | B1 | 11/2004 | Yokoyama et al. |
| 6,852,318 | B1 | 2/2005 | Varner |
| 6,955,808 | B2 | 10/2005 | Curiel |
| 7,045,280 | B2 | 5/2006 | Elvin et al. |
| 7,094,752 | B2 | 8/2006 | Rosenberg et al. |
| 7,132,405 | B2 | 11/2006 | Welsh |
| 7,157,238 | B2 | 1/2007 | Schmitt et al. |
| 7,163,681 | B2 * | 1/2007 | Giles-Komar et al. .... 424/144.1 |
| 7,670,817 | B2 | 3/2010 | Reiser |
| 7,723,483 | B2 | 5/2010 | Clemmons et al. |
| 8,101,726 | B2 | 1/2012 | Parry et al. |
| 8,187,595 | B2 | 5/2012 | Clemmons et al. |
| 2002/0094956 | A1 | 7/2002 | Cosgrove |
| 2004/0063934 | A1 | 4/2004 | Geneste et al. |
| 2004/0265797 | A1 | 12/2004 | Rosenberg et al. |
| 2005/0084491 | A1 | 4/2005 | Shealy et al. |
| 2005/0153337 | A1 | 7/2005 | Manoharan |
| 2006/0148716 | A1 | 7/2006 | Jonczyk et al. |
| 2006/0240437 | A1 * | 10/2006 | Krolewski et al. ................ 435/6 |
| 2007/0244046 | A1 | 10/2007 | Gutova et al. |
| 2007/0249002 | A1 | 10/2007 | Hu et al. |
| 2008/0020979 | A1 * | 1/2008 | Rapraeger et al. .............. 514/12 |
| 2008/0152587 | A1 | 6/2008 | Zhou et al. |
| 2009/0274713 | A1 | 11/2009 | Chari et al. |
| 2011/0212083 | A1 | 9/2011 | Reiser |
| 2012/0213775 | A1 | 8/2012 | Reiser |

FOREIGN PATENT DOCUMENTS

| EP | 404 097 | 6/1990 |
| EP | 0982036 A1 | 3/2000 |
| EP | 1700606 A1 | 9/2000 |
| EP | 1049718 A1 | 11/2000 |
| EP | 1409668 A2 | 4/2004 |
| WO | 98/21230 | 5/1998 |
| WO | WO004803 A1 | 2/2000 |
| WO | WO0072801 A2 | 12/2000 |
| WO | WO0117544 A1 | 3/2001 |
| WO | WO02074730 A1 | 9/2002 |
| WO | WO2004087193 A1 | 10/2004 |
| WO | WO/2004/020435 | * 11/2004 |
| WO | WO2005007654 A1 | 1/2005 |
| WO | WO2005116077 A2 | 5/2005 |
| WO | 2005/117936 | 12/2005 |
| WO | WO2005117936 A2 | 12/2005 |
| WO | 2007/056435 | 5/2007 |
| WO | 2008/077958 | 7/2008 |
| WO | 2009/055613 | 4/2009 |
| WO | 2009/061448 | 5/2009 |

OTHER PUBLICATIONS

Maile et al, aVb3 Integrin and Diabetic Nephropathy. Diabetes, vol. 60, Suppl. IA. 71st Sceintific sessions. Jun. 24-28, 2011. Abstract 8-LB.*
Breyer et al., Mouse models of diabetic nephropathy. J Am Soc Nephrol. Jan. 2005;16(1):27-45.*
Breyer MD., Translating experimental diabetic nephropathy studies from mice to men. Contrib Nephrol. 2011;170:156-64.*
Doublier et al. HIV-1 Tat reduces nephrin in human podocytes: a potential mechanism for enhanced glomerular permeability in HIV-associated nephropathy. AIDS. Feb. 19, 2007;21(4):423-32.*
Xu et al. Fibrinogen mediates platelet-polymorphonuclear leukocyte cooperation during immune-complex glomerulonephritis in rats. J Clin Invest. Sep. 1994; 94(3): 928-936.*
Wu, X., et al., "Fibrinogen mediates platelet-polymorphonuclear leukocyte cooperation during immune-complex glomerilonephritis in rats," Journal of Clinical Investigation, American Society for Clinical Investigation, US, vol. 94, No. 2, Sep. 24, pp. 928-936, 1994.
D.L. Brassard, et al., Integrin αvβ3 -Mediated Activation of Apoptosis, Experimental Cell Research vol. 251, pp. 33-45 (1999).

(Continued)

*Primary Examiner* — Maher Haddad
(74) *Attorney, Agent, or Firm* — Fish & Richardson P.C.

(57) ABSTRACT

The present invention is directed to methods of treating proteinuric diseases by the administration of αvβ3 integrin inhibitors.

10 Claims, 18 Drawing Sheets

(56) References Cited

OTHER PUBLICATIONS

Vadim K. Pedchenko, et al., Mechanism of Perturbation of Integrin-Mediated Cell-Matrix Interactions by Reactive Carbonyl Compounds and Its Implication for Pathogenesis of Diabetic Nephropathy, Diabetes, vol. 54, pp. 2952-2960, Oct. 2005.
Raveendra Dayam, et al., Discovery of Small Molecule Integrin αvβ3 Antagonists as Novel Anticancer Agents, Journal of Medicinal Chemistry, vol. 49, No. 15, pp, 4526-4534, 2006.
Rakesh Verma, et al., Nephrin Ectodomain Engagement Results in Src Kinase Activation, Nephrin Phosphorylation, Nck Recruitment, and Actin Polymerization, The Journal of Clinical Investigation, vol. 116, No. 5, pp. 1346-1359, May 2006.
Roy-Chaudhury P, et al., Importance of the Tubulointerstitium in Human Glornerulonephritis, II., Distribution of Integrin Chains Beta 1, Alpha 1 to 6 and Alpha V., Kidney Int., vol. 52, pp. 103-10, Jul. 1997.
Wei Xue, et al., Urokinase-Type Plasminogen Activator Receptors Associate with β1 and β2 Integrins of Fibrosarcoma Celles: Dependence on Extracellular Matrix Components, Cancer Research vol. 57, pp. 1682-1689, May 1, 1997.
Mayra Yebra, et al., Requirement of Receptor-bound Urokinase-type Plasminogen Activator for Integrin αvβ5-directed Cell Migration, The Journal of Biological Chemistry, vol. 271, No, 46. pp. 29393-29399, Nov. 15, 1996.
Elzbieta Pluskota, et al., Convergence of the Adhesive and Fibrinolytic Systems: Recognition of Urokinase by Integrin αMβ2 as well as by the Urokinase Receptor Regulates Cell Adhension and Migration, Blood, vol. 101, No. 4, pp. 1582-1590, Feb. 13, 2003.
Paola Franco, et al., Activation of Urokinase Receptor by a Novel Interaction Between the Connecting Peptide Region of Urokinase and αvβ5 Integrin, Journal of Cell Science, vol. 119, No. 16, pp. 3424-3434, 2006.
Mohammad Hasanuzzaman, et al., A Doxycycline-Inducible Urokinase Receptor (uPAR) Uoregulates uPAR Activities Including Resistance to Anoikis in Human Prostate Cancer Cell Lines, Molecular Cancer, vol. 6, No. 34, pp. 1-8, 2007.
Baraldi et al., "β1 and β3 Integrin Upregulation in Rapidly Progressive Glomerulonephritis" European Dialysis and Transplant Association-European Renal Association; Nephrology Dialysis Transplantation (1995) 10: 1155-1161.
Bedke et al., "Anti-Inflammatory Effects of av Integrin Antagonism in Acute Kidney Allograft Rejection" The American Journal of Pathology (Oct. 2007) 17(4):1127-1139.
Reinmuth et al., "a,B, Integrin Antagonist S248 Decreases Colon Cancer Metastasis and Angiogenesis and Improve Survival in Mice" Cancer Research (2003) 63:2079-2087.
Dechiara et al., "Mice Lacking the CNTF Receptor, Unlike Mice Lacking CNTF, Exhibit Profound Motor Neuron Deficits at Birth" Cell (1995) 83:313-322.
European Patent Office, "Extended Search Report" for European Application No. 09825472.5 prepared by Examiner Tlmur Albayrak, Munich, dated Feb. 9, 2012, pp. 1-8.
Helene "The Anti-Gene Strategy: Control of Gene Expression by Triplex-Forming-Oligonucleotides," Anticancer Drug Design (1991) 6:569-584.
Helene et al., "Control of Gene Expression by Triple Helix-forming Oligonucleotides: The Antigene Strategy" Ann. NY Acad. Sci. (1992) 660-27-36.
Holliger et al., "Diabodies: Small Bivalent and Bispecific Antibody Fragments" Proc. Nat. Acad. Sci. USA (1993) 90:6444-6448.
International Search Report for Application No. PCT/US11/49563 dated Jan. 27, 2012.
Kirschke et al., "Antisense RNA Inhibition of Cathepsin L Expression Reduces Tumorigenicity of Malignant Cells" European Journal of Cancer (2000) 36:787-795.
Larrick et al., "PCT Amplification of Antibody Genes, Methods" A Companion to Methods in Enzymology (1991) 2(2)106-110.
Letsinger et al., "Cholesteryl-Conjugated Oligonucleotides: Synthesis, Properties and Activity as Inhibitors of Replication of Human Immunodeficiency Virus in Cell Culture," Proc. Natl. Acad. Sci. USA (1989) 86:6553-6556.
Maher, "DNA Triple-Helix Formation: An Approach to Artificial Gene Repressors?" Bioassays (1992) 14(12):807-815.
Pluckthun, "Chapter II: Antibodies from *Escherichia coli*," The Pharmacology of Monoclonal Antibodies (1994) 113:269-315, Rosenburg and Moore Eds, Springer-Verlag, NY.
Sarver et al., "Ribozymes as Potential Anti-HIV-1 Therapeutic Agents" Science (1990) 247:1222-1225.
Smithies et al., "Insertion of DNA Sequences into the Human Chromosomal Beta-Globin Locus by Homologous Recombination" Nature (1985) 317:230-234.
Thomas and Capecchi, "Site-Directed Mutagenesis by Gene Targeting in Mouse Embryo-Derived Stem Cells," Cell (1987) 51:503-512.
Trikha et al., "CNTO95, A Fully Human Monoclonal Antibody that Inhibits av Integrins, Has Antiturmor and Antiangiogenic Activity in Vivo," Int J. Cancer (2004) 100:326-335.
Van De Krol et al., "Modulation of Eukaryotic Gene Expression by Complementary RNA or DNA Sequences," Bio Techniques (1988) 6(10):958-976.
Wagner, "Gene Inhibition Using Antisense Oligodeoxynucleotides," Nature (1994) 372:333-335.
Wei et al., "Modification of Kidney Barrier Function by the Urokinase Receptor" Nature Medicine (2008) 14(1):55-63.
Whitlow et al., "Single-Chain Fv Proteins and their Fusion Proteins," Methods: A Companion to Methods in Enzymology (1991) 2(2):97-105.
Wittenhagen et al., "The plasma level of soluble urokinase receptor is elevated in patients with *Streptococcus pneumoniae* bacteraemia and predicts mortality," Clin. Microbiol. Infect. (May 2004) 10(5):409-415.
Written Opinion of the International Searching Authority (US) for International Application No. PCT/US09/63542, opinion completed Feb. 8, 2010.
Zon, "Oligonucleotide Analogues as Potential Chemotherapeutic Agents," Pharmaceutical Research (1988) 5 (9):539-549.
Wu et al., "Fibrinogen mediates platelet-polymorphonuclear leukocyte cooperation during immune-complex glomerulonephritis in rats" Journal of Clinical Investigation, American Society for Clinical Investigation (Sep. 1, 1994) 94(3):928-936.
Maile et al., "aVb3 Integrin and Diabetic Nephropathy," Diabetes, 60 Suppl. 1A, (Jul. 2011).
Maile et al., "Disruption of IAP/SHPS-1 association inhibits pathophysiologic changes in retinal endothelial function in diabetic rats," Diabetologia, 55(3): 835-844 (Mar. 2012).
Maile et al., "Glucose Regulation of Thrombospondin and Its Role in the Modulation of Smooth Muscle Cell Proliferation," Experimental Diabetes Research, vol. 2010, Article ID 617052 (2010).
Maile et al., "IAP association with Src homology 2 domain containing tyrosine phosphatase substrate 1 regulates IGF-I signaling in vivo," Diabetes, 57(10): 2637-2643 (Oct. 2008).
Miller et al., "Regulation of IGF-I signaling in retinal endothelial cells by hyperglycemia," Invest. Opthamol. Vis Sci., 48(8): 3878-3887 (Aug. 2007).
Wei et al., "uPAR Mediates beta3 Integrin Activation at the Slit Diaphragm," Podocyte Biology I, J. Am. Soc. Nephrol., 17:290A TH-P0863 (Nov. 2006).

* cited by examiner

METHODS AND COMPOSITIONS FOR THE TREATMENT OF PROTEINURIC DISEASES

FEDERALLY SPONSORED RESEARCH

This invention was made with Government support under NIH grants DK 073495, DK 057683, DK 062472 and George M. O'Brien kidney Center DK 064236. The Government has certain rights to this invention.

SEQUENCE LISTING

The instant application contains a Sequence Listing which has been submitted in ASCII format via EFS-Web and is hereby incorporated by reference in its entirety. Said ASCII copy, created on Feb. 22, 2012, is named F6456125.txt and is 6,729 bytes in size.

FIELD OF INVENTION

This invention relates generally to the treatment of proteinuric diseases by αvβ3 integrin inhibitors.

BACKGROUND OF INVENTION

Urinary protein loss (proteinuria) affects some 100 million people worldwide and is a feature of kidney dysfunction of glomerular origin and itself a risk factor for both renal and extra-renal diseases[1]. Kidney podocytes and their foot processes (FP) are a key component of the ultrafiltration system in the glomerulus where they comprise the filtration barrier together with endothelial cells and the glomerular basement membrane (GBM). Podocytes are located within the glomerulus of the kidney where they are attached to the GBM via α3β1 integrin[2,3], and α/β dystroglycan[4]. Podocyte FPs are interconnected by the slit diaphragm (SD), a modified adherens junction[5]. Proteinuric kidney diseases are typically associated with various degrees of podocyte membrane remodeling (FP effacement and/or SD disruption) driven by a rearrangement of the podocyte microfilament system[6]. Recent work has advanced our understanding of the molecular framework underlying podocyte structure largely through the analysis of hereditary proteinuria syndromes and genetic models[7]. A few studies suggest also mechanisms for the far more common acquired proteinuric diseases[8,9]. Despite this progress, there are currently no cell-specific therapeutics for podocytes available. An emerging concept for the regulation of podocyte structure and function is the regulation of the podocyte cytoskeleton by proteases such as cathepsin L[8,10]. Cathepsin L induction in podocytes is accompanied by an increase in cell motility of cultured podocytes[10]. The increased motility of in vitro podocytes[10,11] is best translated into FP dynamics in vivo where podocytes remain locally attached to the GBM but may have altered FP dynamics resulting in FP fusion. In some forms of inflammatory glomerular diseases such as crescentic glomerulonephritis, podocytes have been reported to move out of their microenvironment into areas of crescentic glomerular damage[12]. The concept of dynamic podocyte FPs dates far back into the 1970's where elegant studies of Seiler and colleagues have shown that infusion of polycations such as protamine sulfate can induce rapid changes in FP dynamics and FP effacement[13]. Moreover, this event could be largely reversed by the infusion of polyanions such as heparin[13]. Even so it is impossible to image FP dynamics continuously in live animals, results from above studies suggest a highly dynamic podocyte FP system. Moreover the electron-microscopical analysis of normal kidney commonly reveals small areas of FP effacement which probably represents FPs during transition. Cancer cell motility is another example where cells can be hyperdynamic or participate in tissue invasion[14].

SUMMARY OF INVENTION

According to the invention methods for treating a proteinuric disorder are provided comprising administering to a patient in need thereof an avβ3 integrin inhibitor in an amount effective to reduce or eliminate the proteinuric disorder. In one aspect of the invention the proteinuric disorder is a kidney proteinuric disorder. In one aspect of the invention the kidney proteinuric disorder is selected from a list comprising of:
Diabetic nephropathy,
Nephrotic syndromes (i.e. intrinsic renal failure),
Nephritic syndromes,
Toxic lesions of kidneys,
Glomerular diseases, such as membranous glomerulonephritis,
Focal segmental glomerulosclerosis (FSGS),
IgA nephropathy (i.e., Berger's disease),
IgM nephropathy,
Membranoproliferative glomerulonephritis,
Membranous nephropathy,
Minimal change disease,
Hypertensive nephrosclerosis and
Interstitial nephritis.

In a certain embodiment of the invention the kidney proteinuric disorder is diabetic nephropathy.

In a certain other embodiment of the invention the kidney proteinuric disorder is selected from a list comprising of:
Pre-eclampsia,
Eclampsia,
Collagen vascular diseases (e.g., systemic lupus erythematosus),
Dehydration,
Strenuous exercise,
Stress,
Benign Orthostatic (postural) proteinuria,
Sarcoidosis,
Alport's syndrome,
Diabetes mellitus,
Fabry's disease,
Infections (e.g., HIV, syphilis, hepatitis, post-streptococcal infection),
Aminoaciduria,
Fanconi syndrome,
Heavy metal ingestion,
Sickle cell disease,
Hemoglobinuria,
Multiple myeloma,
Myoglobinuria,
Organ rejection,
Ebola hemorrhagic fever and
Nail Patella Syndrome.

In one aspect of the invention the avβ3 integrin inhibitor is a avβ3 monoclonal antibody or a peptide which contains a RGD binding sequence. In one aspect of the invention the avβ3 integrin inhibitor is a avβ3 monoclonal antibody. In one embodiment of the invention the αvβ3 monoclonal antibody is anti-CD61.

In one embodiment of the invention the αvβ3 integrin inhibitor is a peptide which contains a RGD binding sequence. In a certain embodiment of the invention the peptide which contains a RGD binding sequence is cyclo-[Arg-Gly-Asp-D-Phe-Val] (SEQ ID NO: 1).

In one aspect of the invention the avβ3 integrin inhibitors is a compound of the formula:

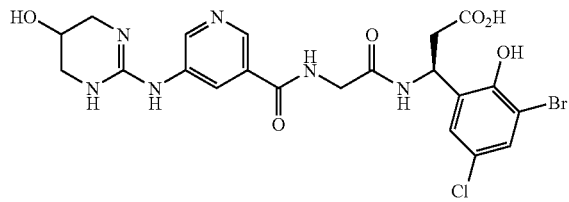 [SMILES: O=C(O)C[C@H](NC(=O)CNC(=O)c1cncc(NC2=NCC(O)CN2)c1)c1cc(Cl)cc(Br)c1O]

or a pharmaceutically acceptable salt thereof.

In one aspect of the invention the avβ3 integrin inhibitors is selected from the compounds described herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

Figure 1A:
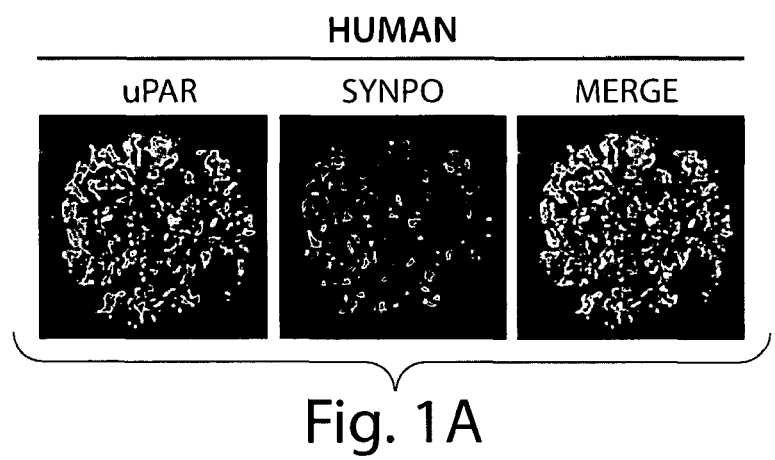
FIG. 1. is a panel of immunostaining images and a bar graph showing uPAR is induced in podocytes in proteinuric patients and experimental proteinuric models.

(a) uPAR protein (green) is expressed in glomeruli of human kidney. Some uPAR is found in podocytes as displayed by double immunofluorescence with the podocyte marker synaptopodin (synpo, red) resulting in a partial yellow overlap. (b) Induction of glomerular uPAR mRNA in proteinuric patients. Quantitative Real-time RT-PCR was performed on the isolated glomeruli from human biopsies. Glomerular uPAR mRNA is upregulated in focal segmental glomerulosclerosis (FSGS, n=14) and diabetic nephropathy (DN, n=20). Values are presented as Mean±SEM. *$p<0.05$ for FSGS or DN vs con (control patients). (c) Induction of uPAR protein in podocytes in rodent models of proteinuria revealed by immunocytochemistry. As shown by confocal microscopy, uPAR expression (green) is low in control glomeruli (con) from rat or mouse and colocalized partially with the podocyte marker synaptopodin (synpo, red). In podocytes during proteinuria (PAN, LPS, NZB/W F1), uPAR expression is significantly induced in podocytes, resulting in a yellow overlap with synaptopodin (merge). Original magnification, 600×. Note that uPAR expression in New Zealand black/white (NZB/W) F1 mice (Lupus) appears more segmental within the glomerulus. (d) Immunogold analysis of uPAR in glomerular walls of normal (control) and 12 months old diabetic rats. uPAR expression is found in all cells of the glomerulus including podocytes. uPAR expression is significantly induced in foot processes of diabetic rats. Original magnification, 35.000× Black arrows mark uPAR expression in podocyte foot processes. MC=mesangial cell, P=podocyte, End=endothelial cell, GBM=glomerular basement membrane, US=urinary space, CL=capillary lumen.

FIG. 2. is a panel of immunostaining images and bar graphs showing uPAR is required in podocytes for the development of foot process effacement and proteinuria.

(a) The morphology of podocyte foot processes is normal in PBS injected wild type and uPAR$^{-/-}$ mice. LPS treatment leads to foot process effacement in wild type but not in uPAR$^{-/-}$ mice. Original magnification, 31700×. (b) Restoration of uPAR expression in uPAR$^{-/-}$ mice using transient gene transfer of uPAR-cDNA leads to podocyte uPAR expression as shown by partial overlap of uPAR with synaptopodin (merge). Original magnification, 600×. (c) Immunoblot showing the amounts of exogenous uPAR expressed in liver and glomeruli from uPAR$^{-/-}$ mice 14 h after gene delivery. (d) Gene delivery of uPAR-cDNA or empty vector does not change the ultrastructure of podocyte foot processes in uPAR$^{-/-}$ mice. However, concomitant LPS treatment leads to foot process effacement in uPAR-restored uPAR$^{-/-}$ mice, but not in uPAR$^{-/-}$ mice given vector control. Original magnification, 31700×. (e) Urine Bradford assay. Whereas PBS treated control mice and uPAR$^{-/-}$ mice do not have any significant proteinuria, the injection of LPS induces significant proteinuria in wild type mice (0.29±0.21 (wt con); (0.82±0.32 (wt LPS), *$p<0.003$) but not in uPAR$^{-/-}$ mice (0.25±0.15 (uPAR$^{-/-}$ con); (0.32±0.14 (uPAR$^{-/-}$ LPS) or uPAR$^{-/-}$ mice which received control plasmids (0.14±0.06 (uPAR$^{-/-}$ con); (0.26±0.15 (uPAR$^{-/-}$ LPS). These data indicate that uPAR$^{-/-}$ mice were protected from urinary protein loss. uPAR$^{-/-}$ mice reconstituted with uPAR-cDNA develop heavy proteinuria but like wild type mice only after LPS injection (0.11±0.11 (uPAR$^{-/-}$ uPAR-cDNA); (0.92±0.46 (uPAR$^{-/-}$ uPAR-cDNA LPS), *$p<0.002$). The degree of proteinuria was comparable in LPS treated wild type and uPAR-cDNA reconstituted uPAR$^{-/-}$ mice. n=15 for each group.

(f) Podocyte-uPAR expression in uPAR$^{-/-}$ mice is achieved by gene transfer of podocin-driven uPAR cDNA (Pod-uPAR) and monitored by synaptopodin staining. Note the merge of uPAR$^{-/-}$ and synaptopodin labeling (merge).

(g) Endothelial-uPAR expression in uPAR$^{-/-}$ mice achieved by gene transfer of ICAM-2-driven uPAR cDNA (ICAM-2-uPAR) is monitored by staining with the endothelial marker CD31. Note the merge of uPAR$^{-/-}$ and CD31 labeling (merge).

(h) Fold-change in urinary protein loss in uPAR$^{-/-}$ mice following gene-transfer of Podocin-uPAR$^{-/-}$ or ICAM-2-uPAR with and without LPS treatment.

FIG. 3. is a panel of immunostaining images and bar graphs showing uPAR mediates podocyte migration.

(a) Multiwell Boyden chamber assay on vitronectin-coated surface under normal conditions and in the presence of LPS or PAN. Podocytes, which migrated randomly through the membrane, were stained with DAN (blue). (b) When compared to control, LPS and PAN treatment for 24 h promoted podocyte migration (wild type 41±3.7; LPS 72±5.5; PAN 67±4.9). Wild type: *$P<0.001$ for LPS vs control; *$p<0.002$ for PAN vs control. Knockdown of uPAR by siRNA strongly reduced podocyte migration in comparison with wild type podocytes under normal conditions and after treatment with LPS or PAN (uPAR-siRNA 16±2.4); (uPAR-siRNA LPS12±3.6; uPAR-siRNA PAN 15±2.9). Wild type vs uPAR-siRNA *$p<0.001$. (b) Scrape wound assay on vitronectin-coated surface to assess directed podocyte motility. 24 h after scraping, wild type podocytes started to move into the wound track (61.37±8.05). The treatment with LPS (85.34±4.1) or with PAN (79.31±3.72) for 24 h significantly enhanced directed podocyte motility (*$p<0.015$ for LPS vs control); (*$p<0.025$ for PAN vs control). uPAR-siRNA expressing podocytes displayed defects in directed motility (uPAR-siRNA17.24±10.48); (uPAR-siRNA LPS 28.00±7.17); (uPAR-siRNA PAN 22.26±6.92). Compared to wild type podocytes, uPAR-siRNA showed decreased capability to migrate into the wound track within 24 hours (*$p<0.0024$ for wild type vs uPAR-siRNA). Solid red lines indicate the initial margins of scrape wound. Data were based on six independent experiments. Original magnification, 40×.

FIG. 4. is a panel of a scheme, immunostaining image and a bar graph showing uPAR, β3 integrin and vitronectin are important for LPS induced proteinuria.

(a) Schematic depiction of uPAR in complex with αvβ3 integrin and vitronectin. Domain 2 of uPAR has been shown to interact with αvβ3 integrin but other domains of uPAR may also contribute. The association of uPAR with αvβ3 integrin can lead to conformational changes of the integrin consistent with activation that facilitates binding to ligands such as vitronectin. (b) Immunogold analysis of uPAR$^{-/-}$ and β3 integrin in podocyte foot processes shows similarities in their distribution pattern. Both uPAR$^{-/-}$ and β3 integrin are often located in vicinity to the slit diaphragm (black arrows). (c) The absence of uPAR (see FIG. 2e), β3 integrin (β3) and vitronection (Vn) is associated with normal renal permselective function and lack of proteinuria after LPS stimulation. In contrast, mice deficient in urokinase (uPA) have no proteinuria under normal conditions, but readily develop urinary protein loss after LPS administration. The same is observed for LPS treated uPAR$^{-/-}$ mice after gene delivery of uPAR-cDNA (uPAR-WT) or of an uPAR-cDNA encoding for a uPAR which is deficient in binding α3β1 integrin (uPAR-D262A).

FIG. 5. is a panel of immunostaining images and a bar graph showing uPAR activates β3 integrin.

(a) Double-immunofluoresence staining for 133 integrin (green) and the podocyte marker synaptopodin (synpo, red) in glomeruli from wild type and uPAR$^{-/-}$ mice before and after treatment with LPS using confocal microscopy (original magnification, 600×). LPS treatment does not change podocyte β3 integrin in wild type and uPAR$^{-/-}$ mice. (b) Flow cytometry of AP5 in LPS treated podocytes in the presence of various amounts of Ca$^{2+}$. Fluorescent intensity units: EDTA: 3020.64±302.06; 0.1 mM Ca$^{++}$: 3055.76±400; 0.4 mM Ca$^{++}$: 1644.7±200; 1.0 mM Ca$^{++}$: 534.52±121; 2.0 mM Ca$^{++}$: 312.5±53.45. (c) same as (a) but now with the antibody AP5 which recognizes active β3 integrin. LPS treatment induces staining for AP5 in wild type but not in uPAR$^{-/-}$ mice. (d) Immunofluorescent analysis and confocal microscopy of AP5 labeling (red) and uPAR (green) in uPAR downregulated podocytes using siRNA, in control podocytes and in podocytes overexpressing GFP-uPAR. (f) Activity assay of the small GTPases cdc42 and Rac1 in isolated glomeruli form wild type and uPAR$^{-/-}$ mice before and after treatment with LPS. In some experiments, wild type mice were treated with LPS and Cyclo-RGDfV (SEQ ID NO: 1) which blocks αvβ3 integrin. (FIG. 5E discloses "CYCLO-RGDfV" as SEQ ID NO: 1)

FIG. 6. is a panel of immunostaining images and bar graphs showing the active uPAR-αvβ3 integrin complex is lipid dependent and can be targeted pharmacologically to modify proteinuria.

(a) Sucrose gradient differential centrifugation was performed on podocyte whole cell extracts of normal and LPS treated cells. Each fraction was separated and blotted with raft (anti-caveolin), and non-rafts marker (anti-transferrin receptor), as well as anti-uPAR and anti-β3 integrin. Under normal conditions, uPAR and β3 integrin are preferentially associated with non-rafts fractions. Both, uPAR and β3 integrin are enriched within the lipid raft fraction after LPS treatment. (b) Localization of uPAR and active β3 integrin (AP5-labeling) in podocytes before and after LPS treatment and in the presence of the cholesterol depleting agent Methyl-P-cyclodextrine (MBCD). (c) Immunofluorescent staining of active β3 integrin in glomeruli of uPAR$^{-/-}$ mice (con) and of uPAR$^{-/-}$ mice which received β3 integrin cDNA (β3 integrin) and a cDNA encoding for the β3 integrin with a deletion of aminoacids 616-690 (β3Δ$_{616-690}$)—The latter confers constitutive activity to β3 integrin which is heavily stained by WOW-1 Fab antibody. (d) Gene transfer of cDNA encoding for the constitutively active β3 integrin but not the gene transfer of a cDNA coding for normal β3 integrin is sufficient to cause proteinuria in uPAR$^{-/-}$ mice even in the absence of LPS (con 0.25±0.06); (β3 integrin 0.19±0.05); (β3Δ$_{616-690}$ integrin 0.43±0.09). * P<0.01 for β3 vs β3Δ$_{616-690}$ integrin, injected mice, n=6 for each group. (e) Co-injection of LPS and a β3 integrin blocking antibody (anti-CD61) in wild type mice prevents the development of proteinuria (PBS con 0.12±0.03);
(LPS+IgG con 0.84±0.14); (LPS+anti-(β3 integrin 0.13±0.01). *p<0.001 for LPS+anti-β3 integrin vs IgG con. n=6. (f) Co-administration of LPS and anti-CD61 (anti-β3 integrin) antibody to cultured podocytes reduces podocyte motility (LPS+IgG con 88.56±7.26); (LPS+anti-β3 integrin 54.53±10.15). *p<0.03 for LPS+anti-(β3 integrin vs IgG con. (g) The injection of cyclo-[Arg-Gly-Asp-D-Phe-Val] RGDfV (SEQ ID NO: 1) blocks αvβ3 integrin and significantly reduces the degree of proteinuria in LPS treated mice. The injection of RGDfV (SEQ ID NO: 1) reduces proteinuria in a dose dependent manner (Con, 0.2064±0.038; cyclo-RGDfV (SEQ ID NO: 1), 0.28±0.0535; LPS, 0.924±0.1055; LPS+cyclo-RGDfV (SEQ ID NO: 1) (1 mg), 0.712±0.0817; LPS+cyclo-RGDfV (SEQ ID NO: 1) (5 mg), 0.5683±0.0729; LPS+cyclo-RGDfV (SEQ ID NO: 1) (20 mg), 0.4172±0.0423. *p<0.013 for LPS vs LPS+cyclo-RGD).

Figure 7A:
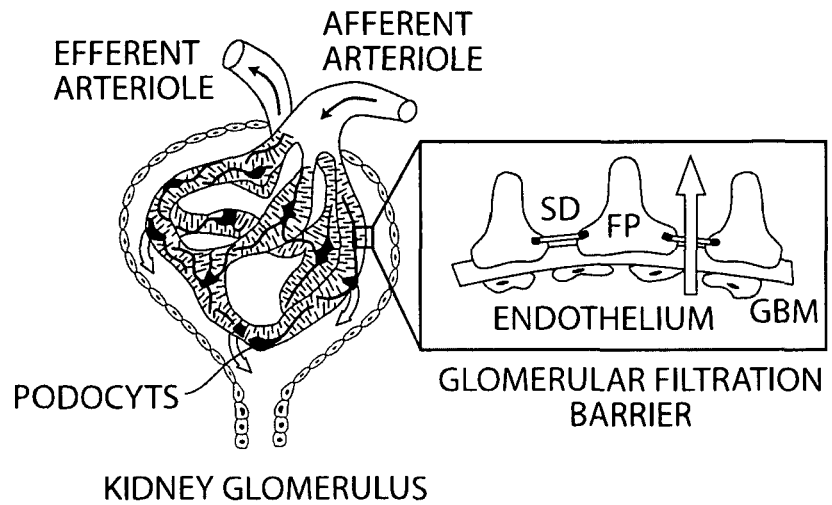
Figure 7B:
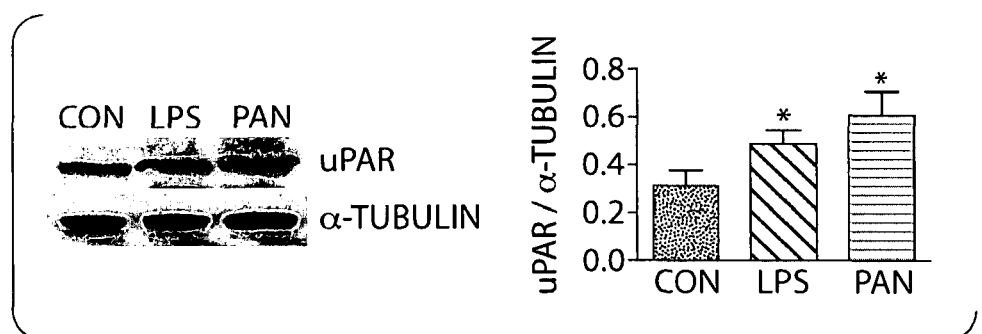

FIG. 7. is a panel of a scheme, immunostaining images and a bar graph showing induction of uPAR in cultured podocyte in response to LPS and PAN.

(a) Schematic representing of a kidney glomerulus and the glomerular filtration barrier. (b) Induction of uPAR in cultured podocyte in response to LPS and PAN. Relative quantification of uPAR induction: Con: 0.31±0.06; LPS: 0.49±0.06; PAN: 0.61±0.10. *P<0.025 for Con vs LPS and *P<0.015 for Con vs PAN. (c) Induced uPAR in podocytes localizes preferentially to the leading edge of migrating podocytes, arrows indicate plasma membrane localization.

FIG. 8. is a panel of immunostaining images showing Vitronectin is expressed in the human glomerulus and mainly in podocytes.

(a) Vitronectin (green) is expressed in the human glomerulus and mainly in podocytes, as displayed by double immunofluorescence with the podocyte marker synaptopodin (synpo, red) resulting in a partial yellow overlap. Podocytes are able to produce vitronectin as tested by RT-PCR. The vitronectin primers are as follows:
Forward: 5' AGT GGA GCA ACA GGA GGA GA 3' (SEQ ID NO: 2)
Reverse: 5' CAA GGC AAA GTG CTC AAA CA 3' (SEQ ID NO: 3) (data not shown). (b) Induction of vitronectin in podocytes in rodent models of proteinuria revealed by immunocytochemistry. As shown by confocal microscopy, vitronectin expression (green) is low in control glomeruli (con) from rat or mouse and colocalized partially with the podocyte marker synaptopodin (synpo, red). In nephrotic conditions however (PAN, LPS, NZB/W F1), vitronectin expression is significantly induced in podocytes, resulting in a yellow overlap with synaptopodin (merge). Original magnification, 600×. Note that vitronectin expression in New Zealand black/white (NZB/W) F1 mice (model for Lupus glomerulonephritis) appears more segmental within the glomerulus.

FIG. 9. is a panel of immunostaining images and graphs showing stable knockdown of uPAR mRNA using siRNA.

(a) Stable knockdown of uPAR mRNA using siRNA. (b) Decreased uPAR protein levels in uPAR siRNA expressing podocytes. (c) Time-course of wound closure in cultured podocytes. The distance migrated by cells from the wound margin was related to the width of the scar at different time points. (d) The addition of urokinase (uPA) to cultured podocytes did not modify podocyte motility.

FIG. 10. is a panel of immunostaining images showing uPAR interacts with β3 integrin.

(a) Heterogeneous Co-IP was performed on the lysates of HEK cells co-transfected with uPAR$^{-/-}$ and β3 integrin, and blotted with HA or Flag antibodies. The results show that uPAR interacts with β3 integrin. (b) Heterogeneous Co-IP was performed on the lysates of HEK cells co-transfected with mouse β1 integrin and full length human uPAR$^{-/-}$ or an uPAR cDNA (uPAR D262A) deficient in the binding of (31 integrin. After blotting with HA or Flag antibodies the results show that full length human uPAR but not uPAR D262A interacts with mouse β1 integrin.

Figure 11:
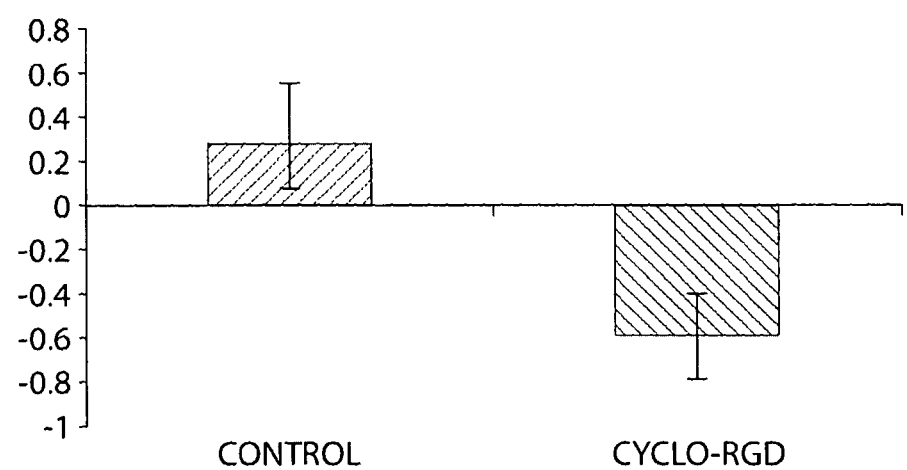

FIG. 11. is a bar graph showing the effect of cyclo-RGDfV (SEQ ID NO: 1) on recovery of proteinuria.

DETAILED DESCRIPTION

The present invention is directed to methods of treating proteinuric diseases by the administration of avβ3 integrin inhibitors. The invention is based at least in part on the discovery that induction of urokinase receptor signaling in podocytes leads to foot process effacement and urinary protein loss via a mechanism including lipid dependent activation of avβ3 integrin.

The invention involves, at least in part, the study of molecules which are associated with cellular motility such as the urokinase plasminogen activator receptor (uPAR)[15,16]. uPAR is a glycosylphosphatidylinositol (GPI)-anchored protein that has been recognized as a proteinase receptor but has also be involved in non-proteolytic pathways, mainly through its ability to form complexes with other membrane proteins such as integrins for signal transduction[15]. uPAR plays important roles during wound healing, inflammation, and stem cell mobilization, as well as in severe pathological conditions such as HIV-1 infection, tumor invasion and metastasis[17]. Besides uPAR's well-established role in the regulation of pericellular proteolysis, it is also involved in cell adhesion, migration, and proliferation through interactions with proteins present in the extracellular matrix, including vitronectin (Vn)[18]. Most recently, the importance of uPAR-Vn interactions was demonstrated by the direct requirement of uPAR to bind Vn for the sufficient induction of downstream signaling aimed at cell motility and morphology[19].

Although not wishing to be bound by theory the invention is based on the experimental observations discussed herein that present a mechanism that involves activation of avβ3 integrin within lipid rafts[24]. The inhibition of uPAR/avβ3 integrin function in podocytes ameliorated the course of proteinuria and opens novel avenues for pharmacological interventions. Blockade of avβ3 integrin reduces podocyte motility in vitro and proteinuria in mice. Mice deficient of uPAR are protected from proteinuria unless a constitutively active in integrin is expressed. Gene transfer of uPAR into podocytes but not into endothelial cells conferred the ability to develop urinary protein loss. Mechanistically, uPAR may be required to activate αvβ3 integrin in podocytes which promotes cell motility and activation of small GTPases cdc42 and Rac1. There is induction of uPAR expression in podocytes during human and rodent proteinuric kidney diseases. uPAR is required for podocyte migration and LPS-induced FP effacement and proteinuria in mice via a mechanism that includes lipid-dependent activation of αvβ3 integrin. These findings define a novel signaling pathway in podocytes which involves uPAR, αvβ3 integrin and Vn. The examples also describe a mechanism whereby widely expressed proteins such as uPAR are utilized in cell-specific manner to regulate basic mechanisms such as kidney filtration. uPAR expression is present in all glomerular cells, yet uPAR expression is not required for normal renal function in any of the cells as the uPAR$^{-/-}$ mice behave normal. Surprising is the requirement of uPAR during the development of podocyte FP effacement and proteinuria which suggests that inducible pathways are required for the remodeling of the filtration barrier. uPAR action for the development of proteinuria stems from its action in the podocyte, which was demonstrated using cell-specific promoter elements. In one aspect of the invention methods for treating proteinuria are provided by inhibiting avβ3 integrin function by inhibiting uPAR function. uPAR is induced during proteinuria and that uPAR–/– mice are protected from the development of proteinurea. In one aspect of the invention the uPAR inhibitors, including small molecules, peptides and antibodies can be used to inhibit avβ3 integrin function.

Accordingly, the methods of the present invention are used to treat disorders characterized by proteinuria. As used herein "proteinuria" refers to any amount of protein passing through a podocyte, such as a podocyte that has suffered podocyte damage. For example, the processing of protein by cultured podocytes that have undergone actin-cytoskeleton rearrangement and FP effacement would result in proteinuria. As used herein "podocyte damage" refers to FP effacement and/or cortical actin rearrangement or any other reversible structural or functional change in podocytes that results in proteinuria. In an in vivo system the term "proteinuria" refers to the presence of excessive amounts of serum protein in the urine. In a certain embodiment the excessive amount of serum protein in the urine is greater than 50, 100, 150, or 200 mg of serum protein/day. In a preferred embodiment the amount of serum protein in the urine is greater than 150 mg/day. Proteinuria is a characteristic symptom of either renal (kidney), urinary, pancreatic distress, nephrotic syndromes (for example, proteinuria larger than 3.5 grams per clay), eclampsia, toxic lesions of kidneys, and it is frequently a symptom of diabetes mellitus. With severe proteinuria general hypoproteinemia can develop and it results in diminished oncotic pressure (ascites, edema, hydrothorax).

As used herein a proteinuric disorder refers to, but it is not limited to: Diabetic nephropathy, Nephrotic syndromes (i.e. intrinsic renal failure), Nephritic syndromes, Toxic lesions of kidneys, Glomerular diseases, such as membranous glomerulonephritis, Focal segmental glomerulosclerosis (FSGS), IgA nephropathy (i.e., Berger's disease), IgM nephropathy, Membranoproliferative glomerulonephritis, Membranous nephropathy, Minimal change disease, Hypertensive nephrosclerosis and Interstitial nephritis.

In certain embodiments as used herein, a proteinuric disorder refers to: Pre-eclampsia, Eclampsia, Collagen vascular diseases (e.g., systemic lupus erythematosus), Dehydration, Strenuous exercise, Stress, Benign Orthostatic (postural) proteinuria, Sarcoidosis, Alport's syndrome, Diabetes mellitus, Fabry's disease, Infections (e.g., HIV, syphilis, hepatitis, post-streptococcal infection), Aminoaciduria, Fanconi syndrome, Heavy metal ingestion, Sickle cell disease, Hemoglobinuria, Multiple myeloma, Myoglobinuria, Organ rejection, Ebola hemorrhagic fever and Nail Patella Syndrome.

In certain embodiments as used herein a proteinuric disorder refers to diabetes, hypertension, kidney disease, minimal change disease, membranous glomerulonephritis, focal segmental glomerulosclerosis, diabetic neuropathy, post-infectious glomerulonephritis, mesangioproliferative glomerulonephritis, HIV-associated nephropathy, IgA-nephropathy, and cardiovascular disease.

At the cellular level protein loss in the urine is accompanied by a structural rearrangement of podocyte cells. Renal ultrafiltration is located within the renal glomerulus, a combination of blood vessels and cells. Highly specialized podocyte cells perform the filtering work and are main target cells in kidney disease. Podocytes can reorganize their actin-based cytoskeleton in a highly dynamic fashion. Such a reorganization determines the integrity of the ultrafiltration barrier in the kidney. Reorganization of the actin cytoskeleton in podocyte foot processes from stress fibers into cortical actin leads to podocyte foot processes (FP) effacement and the development of urinary protein loss. Podocyte damage can be caused by many conditions and factors including LPS and purine aminonucleoside (PAN). These alterations lead to ongoing damage of the kidney and over time to a deterioration of the kidney function. The instant invention is based in part on the surprising discovery of the functional significance of αvβ3 integrin activation as a downstream effector for increased podocyte motility and FP effacement.

Integrins belong to the family of heterodimeric class I transmembrane receptors, which play an important role in numerous cell-matrix and cell-cell adhesion processes (Tuckwell et al., 1996, Symp. Soc. Exp. Biol. 47). They can be divided roughly into three classes: the β1 integrins, which are receptors for the extracellular matrix, the β2 integrins, which can be activated on leucocytes and are triggered during inflammatory processes, and the αv integrins, which influence the cell response in wound-healing and other pathological processes (Marshall and Hart, 1996, Semin. Cancer Biol. 7, 191).

The αvβ3 integrin, also called that the vitronectin receptor, mediates adhesion to a multiplicity of ligand's-plasma proteins, extracellular matrix proteins, cell surface proteins, of which the majority contain the amino acid sequence Arg-Gly-Asp (RGD), such as, for example, fibronectin or vitronectin. Soluble RGD-containing peptides are capable of inhibiting the interaction of each of these integrins with the corresponding natural ligands. Integrin αvβ3 antagonistic action has been shown for a multiplicity of compounds, such as anti-αvβ3 monoclonal antibodies, peptides which contain the RGD binding sequence, natural, RGD-containing proteins (e.g. disintegrins) and low-molecular weight compounds, (FEBS Letts 1991, 291, 50-54; J. Biol. Chem. 1990, 265, 12267-12271; J. Biol. Chem. 1994, 269, 20233-20238; J. Cell Biol 1993, 51, 206-218; J. Biol. Chem. 1987, 262, 17703-17711; Bioorg. Med. Chem. 1998, 6, 1185-1208).

Advantageous αvβ3 integrin receptor ligands bind to the integrin αvβ3 receptor with an increased affinity by at least a factor of 10, preferably at least a factor of 100.

In one aspect of the invention a method for treating a proteinuric disorder comprising administering to a patient in need thereof an αvβ3 integrin inhibitors is provided. According to one embodiment of the invention the αvβ3 integrin inhibitors are the compounds described in WO 97/08145 A1, WO 00/48996 A2, WO 06043930 A1, US2002072500, US 2005043344, US 2002045645, US 2002099209, US 2005020505, US 2002072518, US 2002077321, US 2004043994, US 2003069236, US 2003144311.

In one embodiment of the invention the avβ3 integrin inhibitors are peptidic sulfonamides having the formula (I): $R^1$-Arg-X-Asp-Leu-Asp-Ser-Leu-Arg-$R^2$ (SEQ ID NO: 4), in which $R^1$ denotes H, acetyl or acyl and $R^2$ denotes -Oh, $OR^3$ $NH_2$, $NHR^3$, $N(R^3)_2$ $R^3$ denotes alkyl, aralkyl, aryl, Het and X denotes an amino acid, in which A denotes $(CH_2)_n$ $R^4$ denotes H, alkyl, aralkyl or aryl, and n denotes 1, 2, 3, 4, 5 or 6, and the amino acid is bonded to the adjacent Arg via a peptide bond of the a-amino group and to the α-amino group of the adjacent Asp via a peptide bond of the α-carboxyl group as described in US Pat. App. No. 2006/0148716 A1.

In one embodiment of the invention the αvβ3 integrin inhibitors are fluoro-alkyl-cyclopeptide derivatives as described in WO 2004/011487 A2.

In one embodiment of the invention the αvβ3 integrin inhibitors are peptido-mimetic compounds containing an RGD sequence as described in WO 2005/007654 A1 and U.S. Pat. No. 6,451,972.

In one embodiment of the invention the αvβ3 integrin inhibitors are antagonists of the αvβ3 integrin receptor based on a bicyclic structural element are described in WO 9906049, WO 9905107, WO 9814192, WO 9724124, WO 9724122 and WO 9626190.

In one embodiment of the invention the αvβ3 integrin inhibitors are compounds described in US Publication No. 2004/0063934.

The αvβ3 integrin inhibitors of the invention include isolated peptides and proteins. As used herein with respect to polypeptides, proteins or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

The αvβ3 integrin inhibitors of the invention may be produced using any of the methods and techniques known to those skilled in the art. For example, αvβ3 integrin inhibitors can be purified from a source which naturally expresses the protein, can be isolated from a recombinant host which has been altered to express the desired mutant or fragment thereof, or can be synthesized using protein synthesis techniques known in the art. The skilled artisan can readily adapt a variety of techniques in order to obtain αvβ3 integrin inhibitors that are peptides, proteins or fragments thereof.

Other agents that are αvβ3 integrin inhibitors include but are not limited to small molecules, and other drugs, including known drugs, that prevent (i.e. reduce or inhibit further increase) integrin activation. Such agents can be identified using routine screening methods. For instance, αvβ3 integrin inhibitors of the present invention can be identified using the methods and assays described herein. The screening may be a random screen or it may be rationally designed. For random screening, putative inhibitors are selected at random and assayed for their ability to produce the desired physiological effect. For instance, the putative modulators may be assayed for the ability to reduce selectively or specifically the amount or rate of αvβ3 integrin activation. Any suitable method or technique known to those skilled in the art may be employed to assay putative inhibitors.

Methods for screening using rational design employ the same types of screening methods but begin with a set of compounds that has been designed to specifically maximize function. For rational selection or design, the αvβ3 integrin inhibitors may be selected based, for example on the RGD binding domain. Any of the suitable methods and techniques known to those skilled in the art may be employed for rational selection or design. For example, one skilled in the art can readily adapt currently available procedures to generate pharmaceutical agents capable of binding to a specific peptide sequence of αvβ3 integrin or uPAR, precluding their interaction and signal transduction and thereby inhibiting αvβ3 integrin activity. Illustrative examples of such available procedures are described, for example, in Hurby et al., "Application of Synthetic Peptides: Antisense Peptides," in Synthetic Peptides, A User's Guide, W.H. Freeman, N.Y., pp. 289-307 (1992); Kaspczak et al., Biochemistry 28:9230 (1989); and Harlow, Antibodies, Cold Spring Harbor Press, N.Y. (1990).

In one aspect of the invention αvβ3 integrin inhibitors include antibodies and antibody fragments which are capable of binding to αvβ3 integrin and consequently acting as a αvβ3 integrin inhibitors. The antibodies of the present invention include polyclonal and monoclonal antibodies, as well as antibody fragments and derivatives that contain the relevant antigen binding domain of the antibodies. Such antibodies or antibody fragments are preferably used in the diagnostic and therapeutic embodiments of the present invention. In a preferred embodiment the antibody is anti-CD61 antibody.

As used herein, "treating a proteinuric disorder" includes preventing the development of proteinurea, reducing or inhibiting proteinurea, slowing the progression, and/or any other desired effect on proteinurea. According to the invention the αvβ3 integrin inhibitors can be administered prior to the onset of proteinurea, following the onset of proteinurea, or as part of any therapeutic regimen, for example, including cancer medicaments.

The methods of the invention are intended to embrace the use of more than one other medicament along with the αvβ3 integrin inhibitor. As an example, where appropriate, the αvβ3 integrin inhibitor may be administered with both a chemotherapeutic agent, anti-diabetic agent or an immunotherapeutic agent.

The invention also encompasses diagnostic assays for determining the presence of a disorder characterized by proteinuria in a subject. This aspect of the invention is based, at least in part, on the discovery that αvβ3 integrin activation is reduced in damaged or proteinuric podocytes. In the method an amount of αvβ3 integrin activity in a podocyte cell is determined. That amount is compared to a pre-determined threshold or to a control level. A disorder characterized by proteinuria is determined when the amount of αvβ3 integrin activity is below the pre-determined threshold. As used here in "pre-determined threshold or a control level" refers to αvβ3 integrin activity levels in normal, healthy podocytes, i.e. podocytes not affected by podocyte damage or proteinuria. The podocyte cells may be within a biological sample. The biological sample may be, for instance, a biopsy sample of proteinuric tissue. As used herein, activity refers to expression and well as biochemical activity as described herein.

The detection of αvβ3 integrin in podocyte cells can be readily carried out by standard immunostaining or immunocytometric methods, readily known by persons of ordinary skill in the art. As used herein "immunostaining" refers to a technique of applying coloured or fluorescent dyes to tissues in preparation for microscopic examination. The assay may be performed using immunogold electron microscopy.

In one embodiment the diagnostic assays are performed on cells and/or tissue samples wherein morphological changes of the actin-cytoskeleton can not be readily detected by any other immunocytometric methods. For example one such disorder would be minimal change disease. The term minimal change disease comes from the notion that morphological podocyte changes are only visible by electron microscopy. Detection of proteinuria in patients with minimal change disease by immunocytometric methods would be advantageous because it provide ease and speed of detection.

The immunocytometric methods may be performed using labeled antibodies. An antibody is said to be "detectably labeled" if the antibody, or fragment thereof, is attached to a molecule which is capable of identification, visualization, or localization using known methods. Suitable detectable labels include radioisotopic labels, enzyme labels, non-radioactive isotopic labels, fluorescent labels, affinity labels, chemiluminescent labels and nuclear magnetic resonance contrast agents.

Illustrative examples of suitable enzyme labels include, but are not limited to, luciferase, malate dehydrogenase, staphylococcal nuclease, delta-5-steroid isomerase, yeast-alcohol dehydrogenase, alpha-glycerol phosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include, but are not limited to, $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled monoclonal antibody by the liver. In addition, this radionucleotide has a more favorable gamma emission energy for imaging (Perkins et al., Eur. J. Nucl. Med. 10:296-301 (1985); Carasquillo et al., J. Nucl. Med. 28:281-287 (1987)). For example, $^{111}In$ coupled to monoclonal antibodies with 1-(p-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Illustrative examples of suitable non-radioactive isotopic labels include, but are not limited to, $^{157}Gd$, $^{55}Mn$, $^{162}Dy$, $^{52}Tr$, and $^{56}Fe$.

Illustrative examples of suitable fluorescent labels include, but are not limited to, an $^{152}Eu$ label, a fluorescent protein (including green fluorescent protein (GFP), enhanced green fluorescent protein (EGFP), enhanced yellow fluorescent protein (YFP) and enhanced cyan fluorescent protein (ECFP),), a fluorescein label, an isothiocyanate label, a rhodamine label, a phycoerythrin label, a phycocyanin label, an allophycocyanin label, an o-phthaldehyde label, and a fluorescamine label Illustrative examples of chemiluminescent labels include a luminal label, an isoluminol label, an aromatic acridinium ester label, an imidazole label, an acridinium salt label, an oxalate ester label, a luciferin label, a luciferase label, and an aequorin label.

Illustrative examples of nuclear magnetic resonance contrasting agents include paramagnetic heavy metal nuclei such as Gd, Mn, and Fe.

The coupling of one or more molecules to antibodies is envisioned to include many chemical mechanisms, for instance covalent binding, affinity binding, intercalation, coordinate binding, and complexation.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

According to the methods of the invention the αvβ3 integrin inhibitors are administered in pharmaceutically acceptable preparations. When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention.

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, per os, spinal or epidermal administration (e.g., by injection or infusion). Depending on the route of administration, the active compound, i.e., αvβ3 integrin inhibitor may be coated in a material to protect the compound from the action of acids and other natural conditions that may inactivate the compound. Preferably the carrier is sterile.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of the compounds, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The present invention therefore provides pharmaceutical compositions comprising one or more αvβ3 integrin inhibitors. These pharmaceutical compositions may be administered orally, rectally, parenterally, intrathecally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intrathecal, intraperitoneal, intrasternal, subcutaneous and intraarticular injection and infusion. One of ordinary skill will recognize that the choice of a particular mode of administration can be made empirically based upon considerations such as the particular disease state being treated; the type and degree of the response to be achieved; the specific agent or composition employed; the age, body weight, general health, sex and diet of the patient; the time of administration and rate of excretion of the agent or composition; the duration of the treatment; drugs used in combination or coincidental with the specific composition; and like factors well known in the medical arts.

Pharmaceutical compositions of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Illustrative examples of suitable aqueous and nonaqueous carriers, diluents, solvents or vehicles include, but are not limited to, water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain preservatives, wetting agents, emulsifying agents, and dispersing agents. Prevention of the action of microorganisms may be ensured by the inclusion of various antibacterial and antifungal agents, for example, parabens, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the therapeutic agent, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Solid dosage forms for oral administration include, but are not limited to, capsules, tablets, pills, powders, and granules. In such solid dosage forms, the active compounds are preferably mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents as appropriate.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Illustrative examples of embedding compositions which can be used include polymeric substances and waxes.

The active αvβ3 integrin inhibitors can also be in microencapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also contain adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments of the invention the αvβ3 integrin inhibitor is administered in the form of liposomes. As is known to those skilled in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the αvβ3 integrin inhibitor, stabilizers, preservatives, excipients, and the like. Preferred lipids are phospholipids and phosphatidyl cholines (lecithins), both natural and synthetic. Methods to form liposomes are known in the art. See, e.g., Prescott, ed., METHODS IN CELL BIOLOGY, Volume XIV, Academic Press, New York, N.Y. (1976), p. 33 et seq.

One of ordinary skill will appreciate that effective amounts of the therapeutic agents used in the methods of the invention can be determined empirically and may be employed in pure form or, where such forms exist, in pharmaceutically acceptable salt, ester or prodrug form. The therapeutic agents may be administered in compositions in combination with one or more pharmaceutically acceptable excipients. It will be understood that, when administered to a human patient, the total daily usage of the agents and compositions of the present invention will be decided by the attending physician within the scope of sound medical judgment. The specific therapeutically effective dose level for any particular patient will depend upon a variety of factors including the type and degree of the response to be achieved; the specific agent or composition employed; the age, body weight, general health, sex and diet of the patient; the time of administration, route of administration, and rate of excretion of the agent or composition; the duration of the treatment; drugs (such as a chemotherapeutic agent) used in combination or coincidental with the specific composition; and like factors well known in the medical arts.

Techniques of dosage determination are well known in the art. For example, satisfactory results are obtained by oral administration of therapeutic dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg per oral (p.o.), more preferably 5 to 100 mg p.o., or on the order of from 0.5 to 250 mg i.v., preferably 2.5 to 125 mg i.v. and more preferably 2.5 to 50 mg i.v.

The administration of the agents of the present invention may be for either prophylactic or therapeutic purpose. When provided prophylactically, the agent is provided in advance of any damage i.e., proteinuria or podocyte damage. The prophylactic administration of the agent serves to prevent or reduce the rate of onset of symptoms. When provided therapeutically, the agent is provided at (or after) the onset of the appearance of symptoms of actual disease. The therapeutic administration of the agent serves to reduce the severity and duration of proteinuria.

The compositions of the invention are administered in effective amounts. An "effective amount" is that amount of any of the compositions provided herein that alone, or together with further doses, produces the desired response, e.g. reduces or eliminates proteinuria. This may involve only slowing the progression of the disease temporarily, although more preferably, it involves halting the progression of the disease permanently. This can be monitored by routine methods. The desired response to treatment of the disease or condition also can be delaying the onset or even preventing the onset of the disease or condition. An amount that is effective can be the amount of a $\alpha v\beta 3$ integrin inhibitor alone which produces the desired therapeutic endpoint. An amount that is effective is also the amount of a $\alpha v\beta 3$ integrin inhibitor in combination with another agent that produces the desired result.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of $\alpha v\beta 3$ integrin inhibitors administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Based upon the composition, the dose can be delivered continuously, such as by continuous pump, or at periodic intervals. Desired time intervals of multiple doses of a particular composition can be determined without undue experimentation by one skilled in the art. Other protocols for the administration of the compositions provided will be known to one of ordinary skill in the art, in which the dose amount, schedule of administration, sites of administration, mode of administration and the like vary from the foregoing.

Administration of $\alpha v\beta 3$ integrin inhibitor compositions to mammals other than humans, e.g. for testing purposes or veterinary therapeutic purposes, is carried out under substantially the same conditions as described above.

The compositions of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is used interchangeably with the term "patient" and is intended to include humans and non-human animals including but not limited to a dog, cat, horse, cow, pig, sheep, goat, or primate, e.g., monkey. Preferred patients include a human patient having a proteinuric disorder, including disorders characterized by proteinuria as described herein.

As used herein "a patient in need thereof" refers to any patient that is affected with a disorder characterized by proteinuria. In one aspect of the invention "a patient in need thereof" refers to any patient that may have, or is at risk of having a disorder characterized by proteinuria. In one embodiment of the invention "a patient in need thereof" is a patient that has, may have or is at risk at having cancer, precancer, refractory cancer or metastatic cancer. In yet another embodiment of the invention "a patient in need thereof" is a patient that has, may have, or is at risk of having a cognitive disorder, such as Alzheimer's disease or dementia.

The compositions provided of the present invention can be used in conjunction with other therapeutic treatment modalities. Such other treatments include surgery, radiation, cryosurgery, thermotherapy, hormone treatment, chemotherapy, vaccines, and immunotherapies.

The invention also relates in some aspects to the identification and testing of candidate agents and molecules that may be $\alpha v\beta 3$ integrin inhibitors. These molecules are referred to as putative $\alpha v\beta 3$ integrin inhibitors. The putative $\alpha v\beta 3$ integrin inhibitors can be screened for activity using the same type of assays as described herein (e.g., the assays described in the Examples section). Using such assays, additional $\alpha v\beta 3$ integrin inhibitors can be can be identified.

The invention further provides efficient methods of identifying pharmacological agents or lead compounds as $\alpha v\beta 3$ integrin inhibitors. Generally, the screening methods involve assaying for compounds which inhibit the level of $\alpha v\beta 3$ integrin activity. As will be understood by one of ordinary skill in the art, the screening methods may measure the level of binding between the molecules directly, such as by using the methods employed in the Examples. In addition, screening methods may be utilized that measure a secondary effect of the $\alpha v\beta 3$ integrin inhibitors, for example the level of proteinuria in a cell or tissue sample.

A wide variety of assays for pharmacological agents can be used in accordance with this aspect of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Putative inhibitors useful in accordance with the invention encompass numerous chemical classes, although typically they are organic compounds. Preferably, the putative modulators are small organic compounds, i.e., those having a molecular weight of more than 50 yet less than about 2500, preferably less than about 1000 and, more preferably, less than about 500. Putative $\alpha v\beta 3$ integrin inhibitors comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The putative modulators can comprise cyclic carbon or heterocyclic structure and/or aromatic or polyaromatic structures substituted with one or more of the above-identified functional groups. Putative modulators also can be biomolecules such as peptides, saccharides, fatty acids, sterols, isoprenoids, purines, pyrimidines, derivatives or structural analogs of the above, or combinations thereof and the like. Where the putative modulator is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Biopsy cells and tissues as well as cell lines grown in culture are useful in the methods of the invention.

Putative $\alpha v \beta 3$ integrin inhibitors are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as antimicrobial agents, and the like may also be used.

The prerequisite for producing intact native polypeptides using $E$. $coli$ is the use of a strong, regulatable promoter and an effective ribosome binding site. Promoters which may be used for this purpose include the temperature sensitive bacteriophage $\lambda p_L$-promoter, the tac-promoter inducible with IPTG or the T7-promoter. Numerous plasmids with suitable promoter structures and efficient ribosome binding sites have been described, such as for example pKC30 ($\lambda p_L$; Shimatake and Rosenberg, Nature 292:128 (1981), pKK173-3 (tac, Amann and Brosius, Gene 40:183 (1985)) or pET-3 (T7-promoter (Studier and Moffat, J. Mol. Biol. 189:113 (1986)).

A number of other suitable vector systems for expressing the DNA according to the invention in $E$. $coli$ are known from the prior art and are described, for example, in Sambrook et al., Molecular Cloning: A Laboratory Manual, Cold Spring Harbor Laboratory Press (1989)).

Suitable $E$. $coli$ strains which are specifically tailored to a particular expression vector are known to those skilled in the art (Sambrook et al., Molecular Cloning: A Laboratory Manual, Cold Spring Harbor Laboratory Press (1989)). The experimental performance of the cloning experiments, the expression of the polypeptides in $E$. $coli$ and the working up and purification of the polypeptides are known and are described, for example, in Sambrook et al., Molecular Cloning: A Laboratory Manual, Cold Spring Harbor Laboratory Press (1989). In addition to prokaryotes, eukaryotic microorganisms such as yeast may also be used.

For expression in yeast, the plasmid YRp7 (Stinchcomb et al. Nature 282:39 (1979); Kingsman et al., Gene 7:141 (1979); Tschumper et al., Gene 10:157 (1980)) and the plasmid YEp13 (Bwach et al., Gene 8:121-133 (1979)) are used, for example. The plasmid YRp7 contains the TRP1-gene which provides a selection marker for a yeast mutant (e.g., ATCC No. 44076) which is incapable of growing in tryptophan-free medium. The presence of the TRP1 defect as a characteristic of the yeast strain used then constitutes an effective aid to detecting transformation when cultivation is carried out without tryptophan. The same is true with the plasmid YEp13, which contains the yeast gene LEU-2, which can be used to complete a LEU-2-minus mutant.

Other suitable marker genes for yeast include, for example, the URA3- and HIS3-gene. Preferably, yeast hybrid vectors also contain a replication start and a marker gene for a bacterial host, particularly $E$. $coli$, so that the construction and cloning of the hybrid vectors and their precursors can be carried out in a bacterial host. Other expression control sequences suitable for expression in yeast include, for example, those of PHO3- or PHO5-gene.

Other suitable promoter sequences for yeast vectors contain the 5'-flanking region of the genes of ADH I (Ammerer, Methods of Enzymology 101:192-210 (1983)), 3-phosphoglycerate kinase (Hitzeman et al., J. Biol. Chem. 255:2073 (1980)) or other glycolytic enzymes (Kawaski and Fraenkel, BBRC 108:1107-1112 (1982)) such as enolase, glycerinaldehyde-3-phosphate-dehydrogenase, hexokinase, pyruvate-decarboxylase, phosphofructokinase, glucose-6-phosphate isomerase, phosphoglucose-isomerase and glucokinase. When constructing suitable expression plasmids, the termination sequences associated with these genes may also be inserted in the expression vector at the 3'-end of the sequence to be expressed, in order to enable polyadenylation and termination of the mRNA.

Generally, any vector which contains a yeast-compatible promoter and origin replication and termination sequences is suitable. Thus, hybrid vectors which contain sequences homologous to the yeast $2\mu$ plasmid DNA may also be used. Such hybrid vectors are incorporated by recombination within the cells of existing $2\mu$-plasmids or replicate autonomously.

In addition to yeasts, other eukaryotic systems may, of course, be used to express the polypeptides according to the invention. Since post-translational modifications such as disulphide bridge formation, glycosylation, phosphorylation and/or oligomerization are frequently necessary for the expression of biologically active eukaryotic proteins by means of recombinant DNA, it may be desirable to express the DNA according to the invention not only in mammalian cell lines but also insect cell lines.

Functional prerequisites of the corresponding vector systems comprise, in particular, suitable promoter, termination and polyadenylation signals as well as elements which make it possible to carry out replication and selection in mammalian cell lines.

In a preferred embodiment of the invention particularly suitable promoters are podocyte specific promoters. A podocyte specific promoter is one that is expressed exclusively in podocytes, such as the podocin promoter.

For expression of the DNA molecules according to the invention it is particularly to desirable to use vectors which are replicable both in mammalian cells and also in prokaryotes such as $E$. $coli$. Vectors derived from viral systems such as SV40, Epstein-Barr-virus, etc., include, for example, pTK2, pSV2-dhfv, pRSV-neo, pKO-neo, pHyg, p205, pHEBo, etc. (Sambrook et al., Molecular Cloning: A Laboratory Manual, Cold Spring Harbor Press, N.Y. (1989)).

After transformation in suitable host cells, e.g. CHO cells, corresponding transformed cells may be obtained with the aid of selectable markers (thymidine-kinase, dihydrofolate-reductase, green fluorescent protein, etc.) and the corresponding polypeptides are isolated after expression. The host cells suitable for the vectors are known, as are the techniques for transformation (micro-injection, electroporation, calcium phosphate method, etc.) as described, for example, in Sambrook et al., Molecular Cloning: A Laboratory Manual, Cold Spring Harbor Press, N.Y. (1989).

For cloning corresponding DNA fragments in prokaryotic or eukaryotic systems, the selected vector may be cut, for example, with a restriction endonuclease and, optionally after modification of the linearized vector thus formed, an expression control sequence equipped with corresponding restriction ends is inserted. At the 3'-end (in the direction of translation) the expression control sequence contains the recognition sequence of a restriction endonuclease, so that the vector already containing the expression control sequence is digested with the said restriction enzyme and the DNA molecule according to the invention, provided with ends which fit, can be inserted. It is advantageous to cleave the vector which already contains the expression control sequence with a second restriction endonuclease inside the vector DNA and to insert the DNA molecule provided with the correct ends into the vector fragment produced. The techniques required are described, for example, by Sambrook et al. Molecular Cloning: A Laboratory Manual Cold Spring Harbor Press. N.Y. (1989).

Apart from the DNA molecules specified, the invention also relates to processes for preparing the vectors described herein, particularly expression vectors. These vectors are characterized in that a DNA provided with corresponding ends and coding for a functional derivative or a fragment of the protein is inserted into a vector DNA cut with restriction endonucleases and containing the expression control sequences described by way of example, in such a way that the expression control sequences regulate the expression of the DNA inserted. The peptides and antibody agents of the present invention which are obtained by the expression of recombinant DNA or from the native receptor molecule may, of course, also be derivatized by chemical or enzymatic processes.

Also within the scope of the invention are kits comprising the compositions of the invention and instructions for use. The kits can further contain at least one additional reagent, such as a chemotherapeutic agent.

A kit may comprise a carrier being compartmentalized to receive in close confinement therein one or more container means or series of container means such as test tubes, vials, flasks, bottles, syringes, or the like. A first of said container means or series of container means may contain one or more αvβ3 integrin inhibitors or recombinant vectors for the expression thereof. A second container means or series of container means may contain a second therapeutic, such as, cytotoxic drug or αvβ3 integrin antibodies (or fragment thereof).

Kits for use in the therapeutic methods of the invention containing the αvβ3 integrin inhibitors conjugated to other compounds or substances can be prepared. The components of the kits can be packaged either in aqueous medium or in lyophilized form. When the αvβ3 integrin inhibitors or fragments thereof are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, to and co-pending patent applications) cited throughout this application are hereby expressly incorporated by reference.

EXAMPLES

Example 1

Modification of Kidney Barrier Function by the Urokinase Receptor

In this example, the role of uPAR was analyzed in the regulation of structure and function of podocytes during normal and disease conditions. Mice deficient for uPAR[20], uPA[21], Vn[22] and β3 integrin[23] were challenged with lipopolysaccharide (LPS), a treatment known to cause FP effacement and proteinuria[9]. It is shown that uPAR is dispensable for normal renal filtration but required in podocytes but not in endothelial cells for loss of renal permselectivity seen in human and rodent kidney diseases. The proteinuric signal originating from uPAR in podocytes is independent of urokinase and is required for podocyte FP effacement and LPS-induced proteinuria.

Results uPAR Induction in Human and Rodent Proteinuric Diseases

Figure 1B:
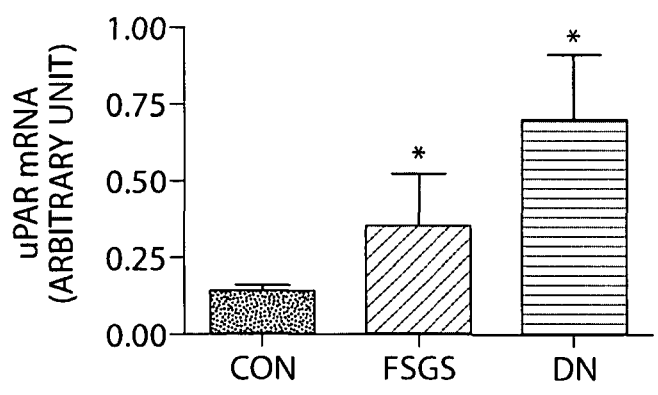

We first tested if uPAR protein is expressed in human glomeruli (FIG. 1a) and found expression in many glomerular cells including podocytes which are identified by synaptopodin labeling[25]. Next, we investigated the expression of uPAR mRNA in human proteinuric renal diseases (FIG. 1b). We performed quantitative real-time PCR using isolated glomeruli from human kidney biopsies[26]. We analyzed uPAR expression in RNA samples from patients without glomerular disease (con, n=8) and in patients with focal segmental glomerulosclerosis (FSGS, n=14) and diabetic nephropathy (DN, n=20), both conditions with podocyte FP effacement and proteinuria[6]. We found a low level of glomerular uPAR mRNA expression in patients without glomerular disease (FIG. 1b). In contrast, patients with biopsy-proven FSGS had a significant increase in glomerular uPAR expression (FSGS 0.35±0.17 vs con 0.14±0.02, **p<0.05), (FIG. 1b). An even stronger induction of glomerular uPAR mRNA expression (0.69±0.21 vs con 0.14±0.02, *p<0.012) was found in patients with diabetic nephropathy (FIG. 1b).

Figure 1C:
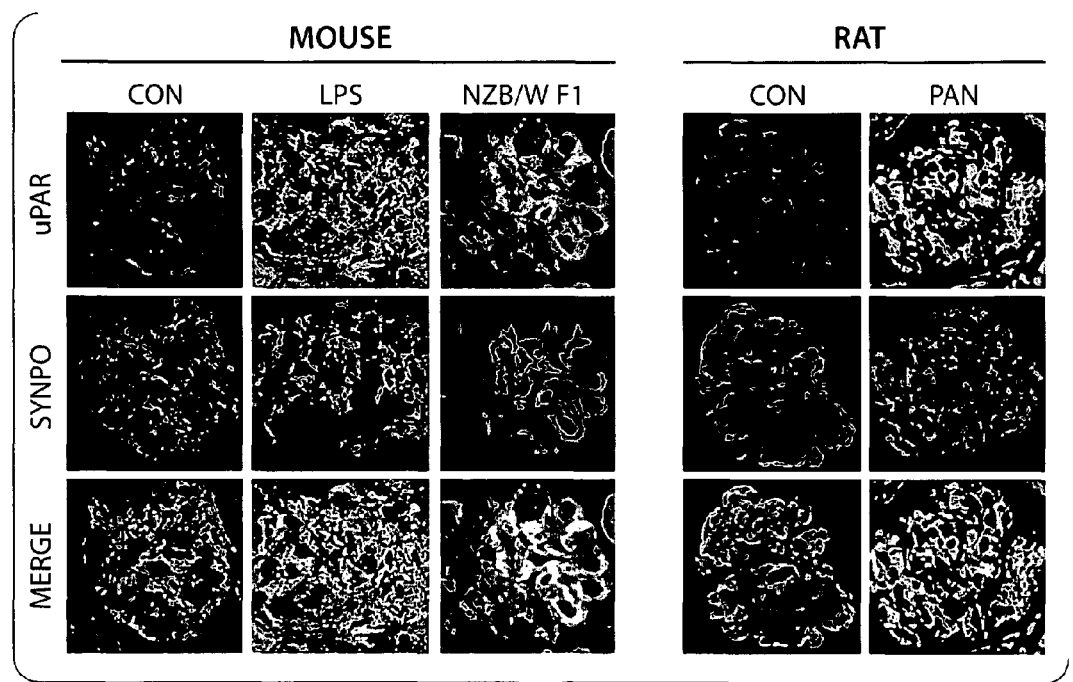
Figure 7C:
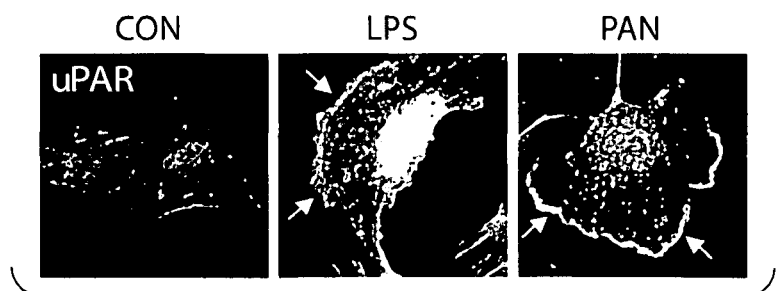
Figure 8A:
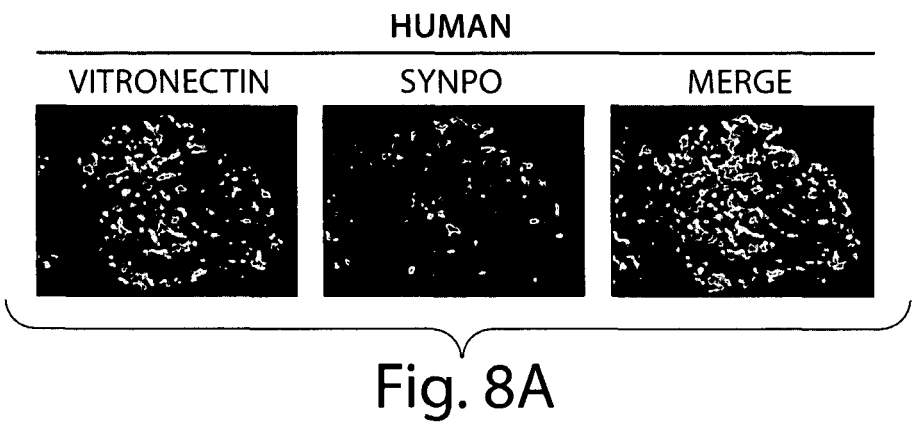
Figure 8B:
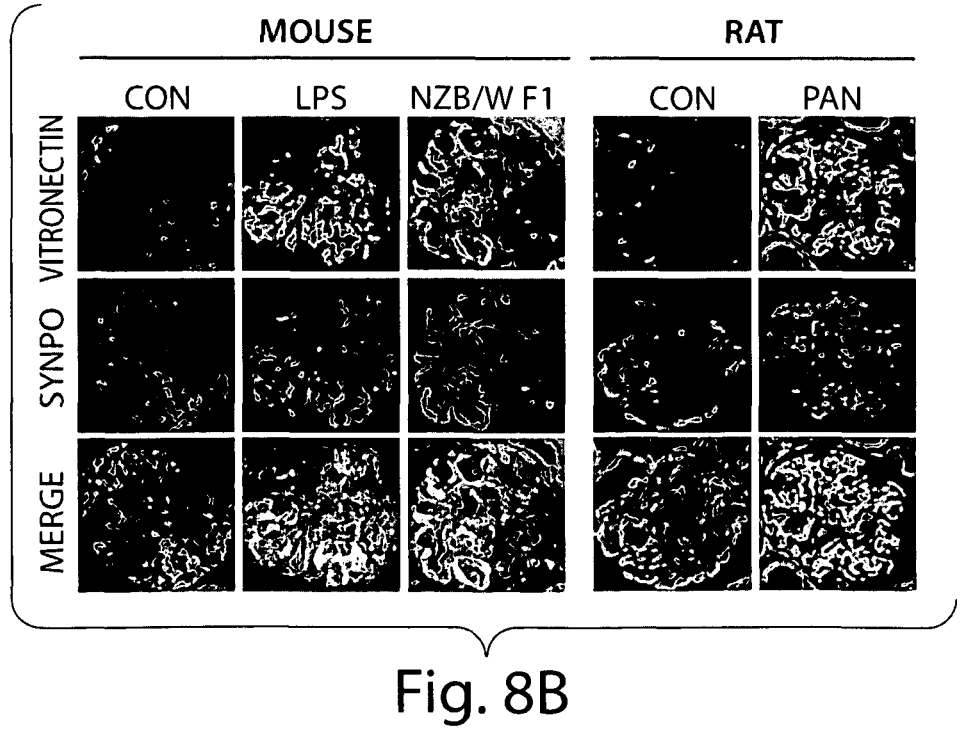

To test which cells in the glomerulus display increased uPAR expression, we examined the localization of uPAR within the kidney in three different animal models of inducible proteinuria and podocyte FP effacement, including the puromycin aminonucleoside nephrosis model in the rat (PAN)[27], the mouse model of LPS-induced transient nephrotic syndrome[9] and the NZB/W F1 murine model of systemic lupus erythematosus (SLE)[28]. Using immunofluorescence and confocal microscopy, we found low expression of uPAR in glomeruli from control rats or mice (FIG. 1c). uPAR was partially localized in podocytes as indicated by double immunofluorescent staining with synaptopodin[25]. In contrast, expression of uPAR protein in all three proteinuria models was significantly increased in glomerular cells including podocytes as demonstrated by the increased yellow staining pattern resulting from overlap with synaptopodin (FIG. 1c). Of note, in the NZB/W F1 Lupus mouse model, uPAR was preferentially found in nephritic areas of the glomerulus in a more segmental distribution. Such a distribution has been recently reported in murine glomerulonephritis where podocytes can populate cellular crescents[12]. In addition to glomerular uPAR labeling, we also found expression of uPAR in proximal tubular cells which appeared unchanged under normal and disease conditions (data not shown). Increased uPAR protein expression was also observed in LPS and PAN treated cultured podocytes (FIG. 7b) where uPAR was preferentially located at the cell membrane (FIG. 7c). Analysis of the uPAR ligand Vn revealed a prominent staining of Vn in podocytes of human kidney (FIG. 8a). We detected an induction of Vn labeling in podocytes of PAN rats as well as of LPS and Lupus mice when compared to controls (FIG. 8b). Overall, the expression profiles for Vn in podocytes were similar to the pattern we have observed for uPAR.

Figure 1D:
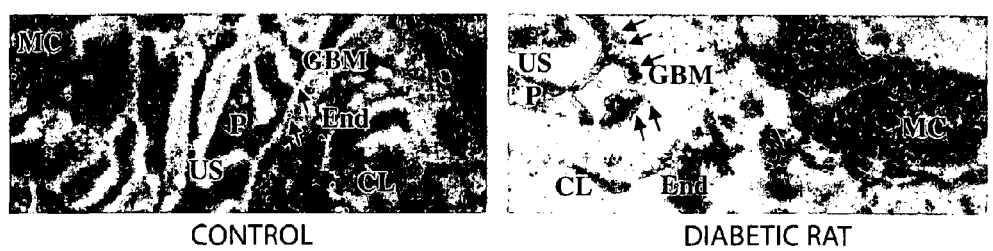

To define the subcellular localization of uPAR within the glomerular cells including podocytes, we have analyzed uPAR localization in normal and diabetic animals (FIG. 1d), since uPAR mRNA induction is strongest during diabetic nephropathy in humans (FIG. 1b). We carried out semiquantitative immunogold analysis of uPAR and transmission electron microscopy in glomerular walls of normal and 3 months as well as 12 months old diabetic rats in which hyperglycemia was induced by streptozotocin injection[29]. Under normal conditions, uPAR expression was found in all cell types of the glomerulus (Table 1) including podocytes (FIG. 1d). Morphometrical analysis revealed a homogeneous distribution of uPAR in podocytes, mesangial and endothelial cells (Table 1). 12 months old diabetic rats displayed increased uPAR labeling in all cells of the glomerular wall (FIG. 1e). Endothelial uPAR expression was stronger in luminal and basal membrane aspects when compared to controls. Interestingly, podocyte uPAR was increased in 3 and 12 months diabetic rats but only in basal membrane aspects of the FPs. Mesangial cells expressed high levels of uPAR with no difference under normal and diseased conditions.

uPAR in Podocytes is Required for Foot Process Effacement and Proteinuria

Figure 2A:
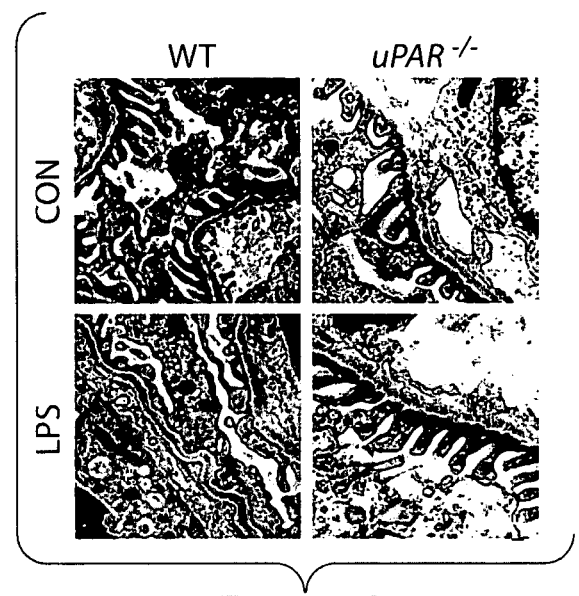
Figure 2B:
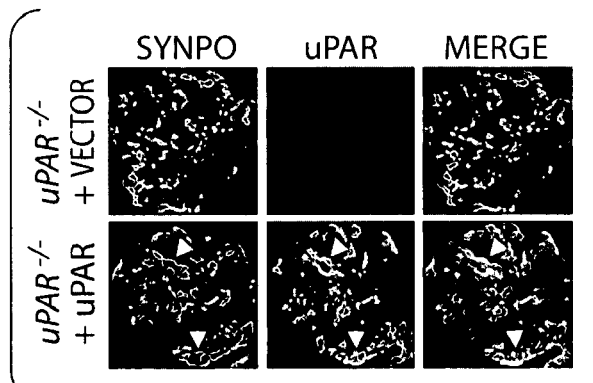
Figure 2C:
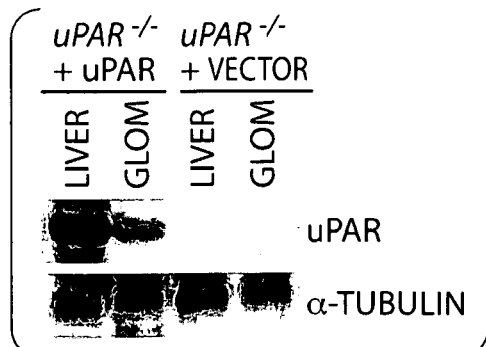
Figure 2D:
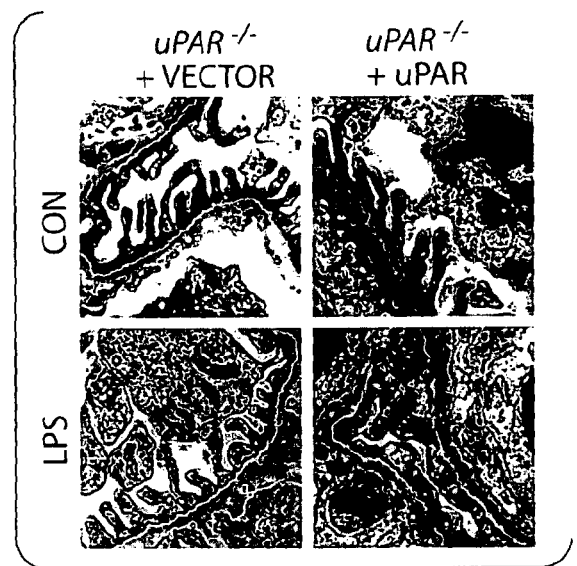

To explore whether uPAR has a direct role in the regulation of podocyte FP structure and function, we next compared FP morphology of wild type and uPAR$^{-/-}$ mice[30] before and after the administration of LPS. Morphologically, there was no difference between the structure of podocyte FP in wild type or uPAR$^{-/-}$ mice (FIG. 2a, con). However, 24 h after LPS injection, we found podocyte FP effacement in wild type but not in uPAR$^{-/-}$ mice (FIG. 2a, LPS), suggesting a functional link between the development of podocyte FP effacement and uPAR expression. To test whether the protection from LPS-induced FP effacement could be overcome by restoring glomerular uPAR in uPAR$^{-/-}$ mice, we utilized our previously reported gene delivery protocol to deliver uPAR-cDNA[31,32,8]. 24 h after gene delivery of a plasmid encoding uPAR but not of an empty vector control, we found uPAR expression in glomerular cells including podocytes of uPAR$^{-/-}$ mice, as confirmed by double-immunofluorescent labeling of uPAR$^{-/-}$ and synaptopodin (FIG. 2b). To monitor the expression levels of uPAR after gene delivery, we performed immunoblots. 14 h after uPAR gene delivery, uPAR protein was found in the liver, and at lower expression levels in glomerular extracts (FIG. 2c). The restoration of uPAR did change the morphology of podocyte FPs (FIG. 2d, con). However, concomitant administration of LPS and uPAR-cDNA into uPAR$^{-/-}$ mice resulted in FP effacement (FIG. 2d, LPS), similar to LPS-treated wild type animals (FIG. 2a, LPS). In contrast, we did not find any FP changes in uPAR$^{-/-}$ mice which had received vector control, even after co-administration of LPS (FIG. 2d, LPS).

Figure 2E:
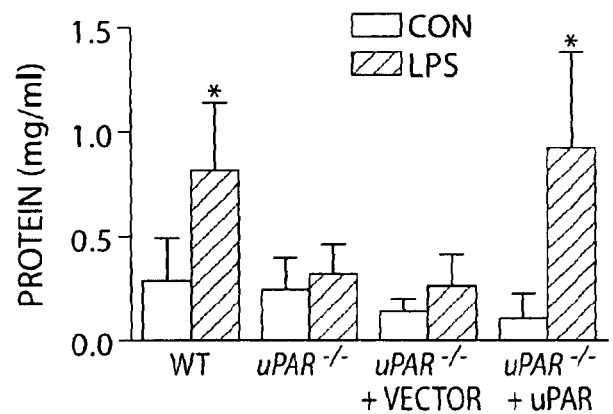

To study the functional consequences of uPAR reconstitution on the development of proteinuria, we analyzed the urine protein excretion of wild type, uPAR$^{-/-}$, and uPAR-reconstituted uPAR$^{-/-}$ mice before and after LPS injection (FIG. 2e). Whereas PBS treated control mice and uPAR$^{-/-}$ mice did not display any significant proteinuria, the injection of LPS induced significant proteinuria in wild type but not in uPAR$^{-/-}$ mice and uPAR$^{-/-}$ mice which received control plasmids. These data indicate that uPAR$^{-/-}$ mice were protected from urinary protein loss. Most importantly, uPAR$^{-/-}$ mice reconstituted with uPAR-cDNA develop heavy proteinuria but like wild type mice only after LPS injection (FIG. 2e). The degree of proteinuria was comparable in LPS treated wild type and uPAR-cDNA reconstituted uPAR$^{-/-}$ mice. In summary, these data strongly suggest that uPAR is required for the development of LPS-induced proteinuria in mice.

Figure 2F:
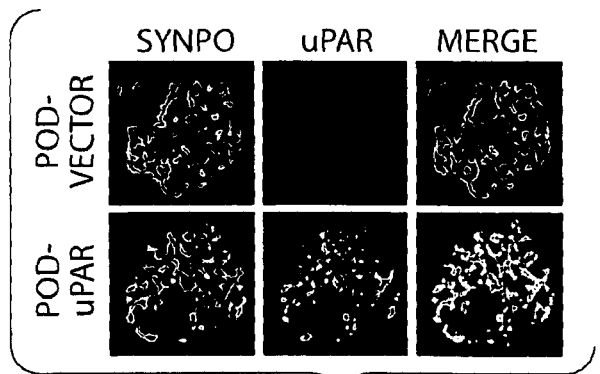
Figure 2G:
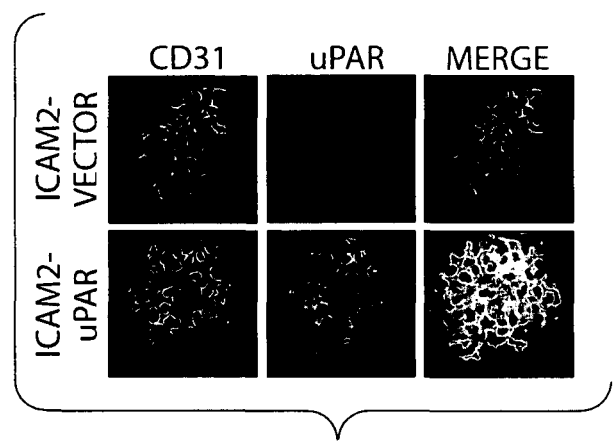
Figure 2H:
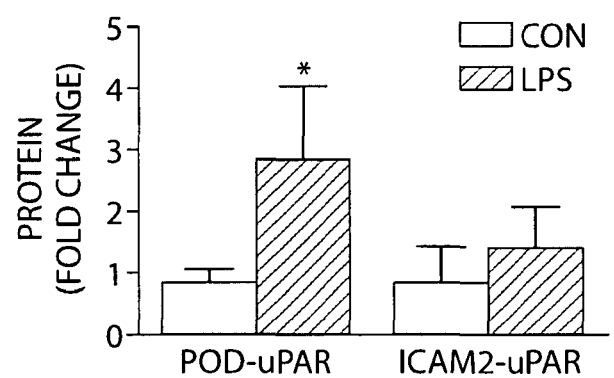

Even so it appears most logical that uPAR exerts its effects on proteinuria development by orchestrating podocyte FP effacement, it seemed still possible that uPAR in glomerular endothelial cells is contributing as well. Thus, we carried out gene-transfer of uPAR cDNA under the control of two different cell-specific promoter allowing cell-specific expression in podocytes (Podocin-uPAR),[33] or endothelial cells (ICAM2-uPAR)[34] (FIG. 2f). Cell-type specific expression of uPAR was monitored by double-immunofluorescence labeling with synaptopodin or the endothelial marker CD31[35] (FIG. 2g). While the expression of uPAR in podocytes was required for LPS-induced proteinuria, the expression of uPAR in endothelial cells was associated with LPS resistance. These results demonstrate that podocyte-uPAR is required and sufficient for LPS induced proteinuria.

uPAR Orchestrates Podocyte Motility

Figure 3A:
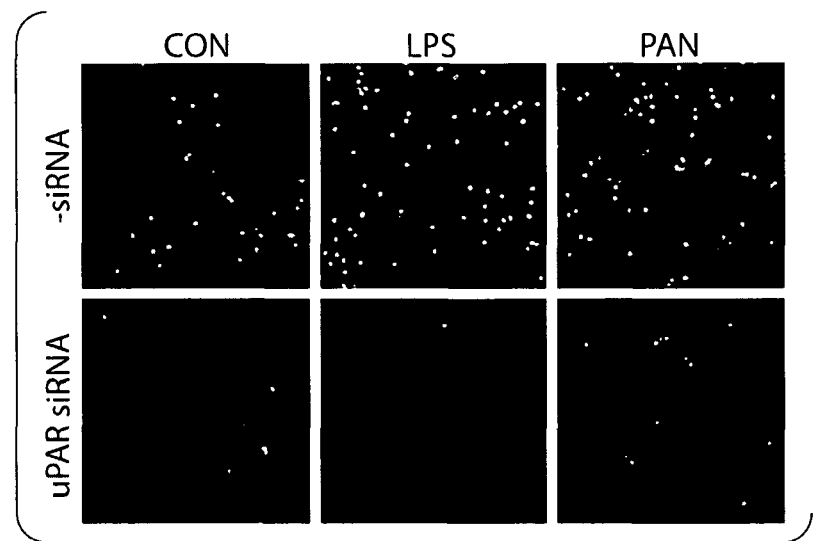
Figure 3B:
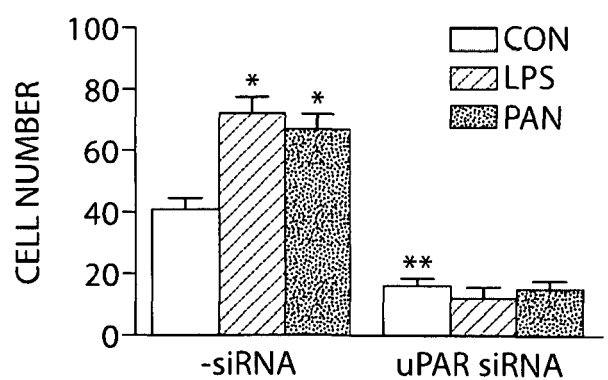
Figure 3C:
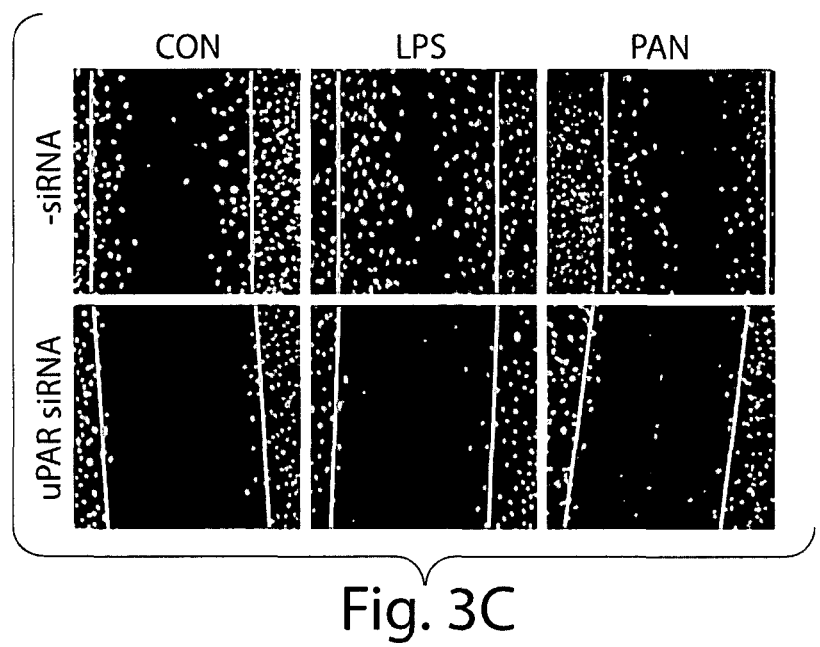
Figure 3D:
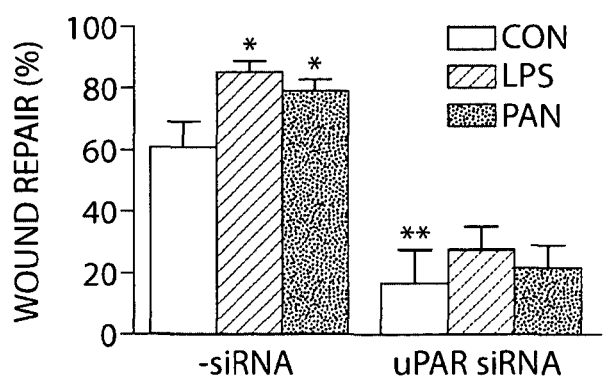
Figure 9A:
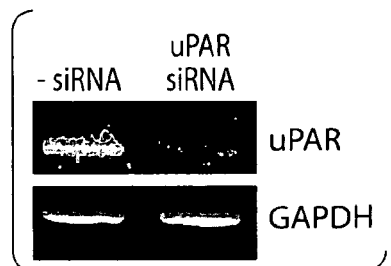
Figure 9B:
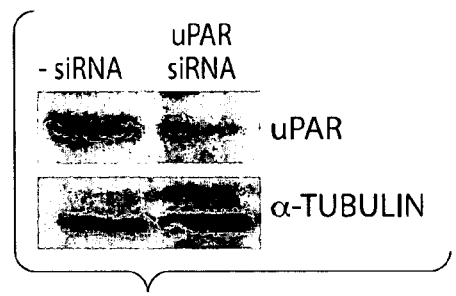

To begin to understand uPAR function in podocytes, we were considering uPAR's role in cell motility[16]. Podocyte FP effacement may represent a motile event resulting in spreading of podocyte FPs on the GBM. Thus, we studied podocyte motility in cultured podocytes before and after stable knockdown of uPAR using stable siRNA. The efficiency of uPAR-siRNA was confirmed by both semi-quantitative RT-PCR (FIG. 9a) and Western blotting (FIG. 9b). We then used a modified multi-well Boyden chamber assay to assess the random migration of differentiated podocytes on type I collagen (data not shown) and Vn, a known binding partner of uPAR[10] which is induced in proteinuric glomeruli (FIG. 8b). LPS- or PAN-treatment for 24 h significantly promoted migration of wild type podocytes (FIGS. 3a, b). In contrast, the knockdown of uPAR significantly decreased the number of migrating podocytes under normal condition and after treatment with LPS or PAN (FIGS. 3a, b). These results demonstrate that podocytes migrate in larger number in response to LPS or PAN and that uPAR is necessary for podocyte cell migration.

Figure 9C:
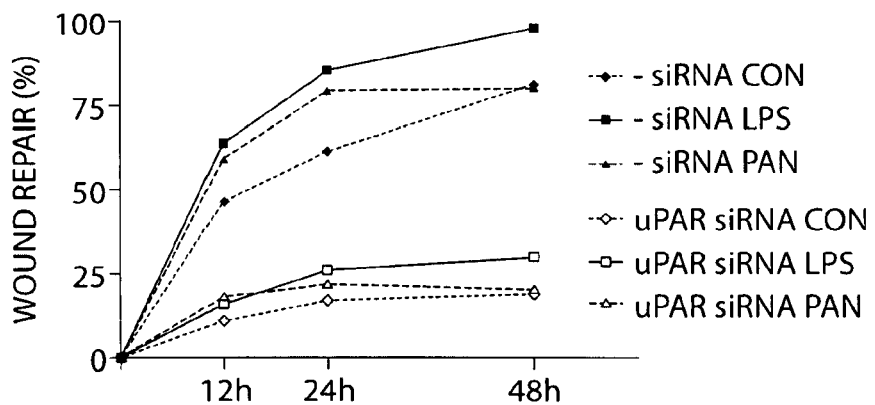
Figure 9D:
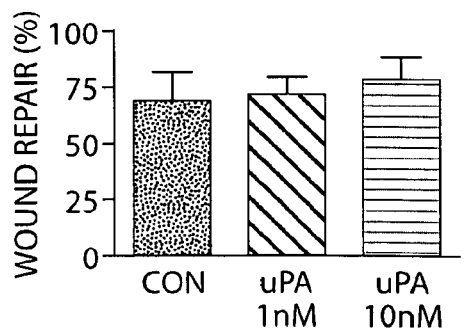

We then analyzed the role of uPAR in the spatial motility of podocytes using a modified scrape wound assay[11]. Migrated podocytes were counted at different time points and the distance migrated by cells from the wound margin was related to the total width of the scar. Compared to control cells, LPS or PAN treatment significantly promoted podocyte wound closure after 24 h (FIGS. 3c, d), a finding which was also obtained in a similar pattern at timepoints 12, 24 and 48 h (FIG. 9c). The addition of external urokinase did not alter podocyte directional migration (FIG. 9d) but the knockdown of uPAR strongly reduced podocyte directed motility before and after administration of LPS or PAN, leaving the wound largely unpopulated (FIGS. 3c, d), (FIG. 9c). Together, these data suggest that uPAR is important for random as well as directed podocyte migration.

uPAR Activates αvβ3 Integrin in Podocytes

Figure 4A:
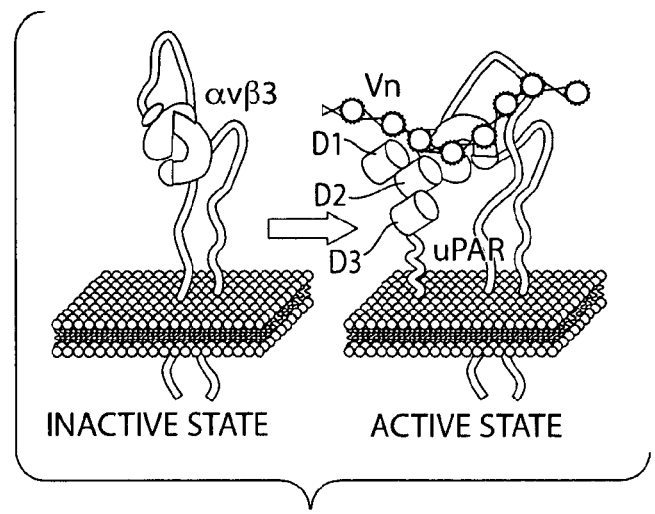
Figure 4B:
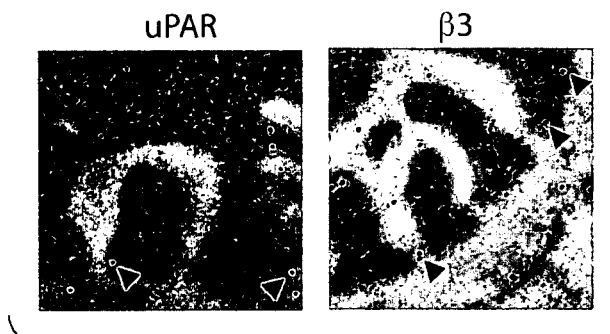
Figure 4C:
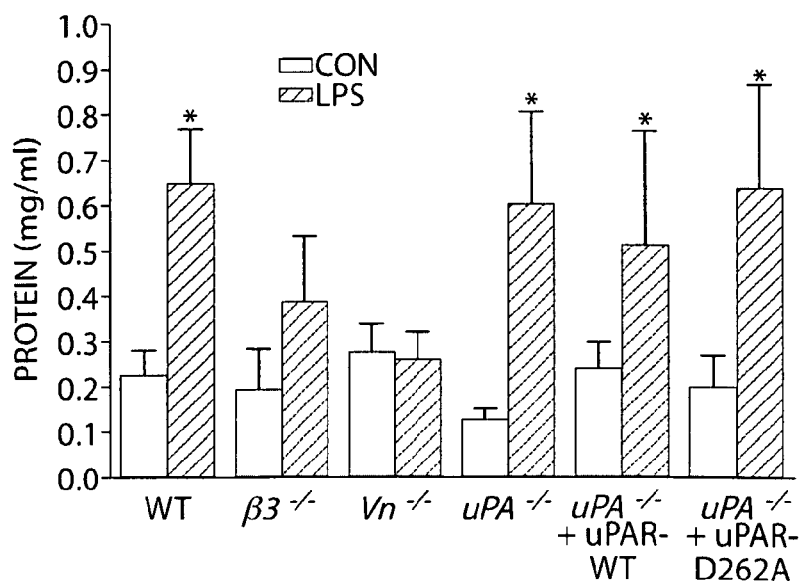
Figure 5A:
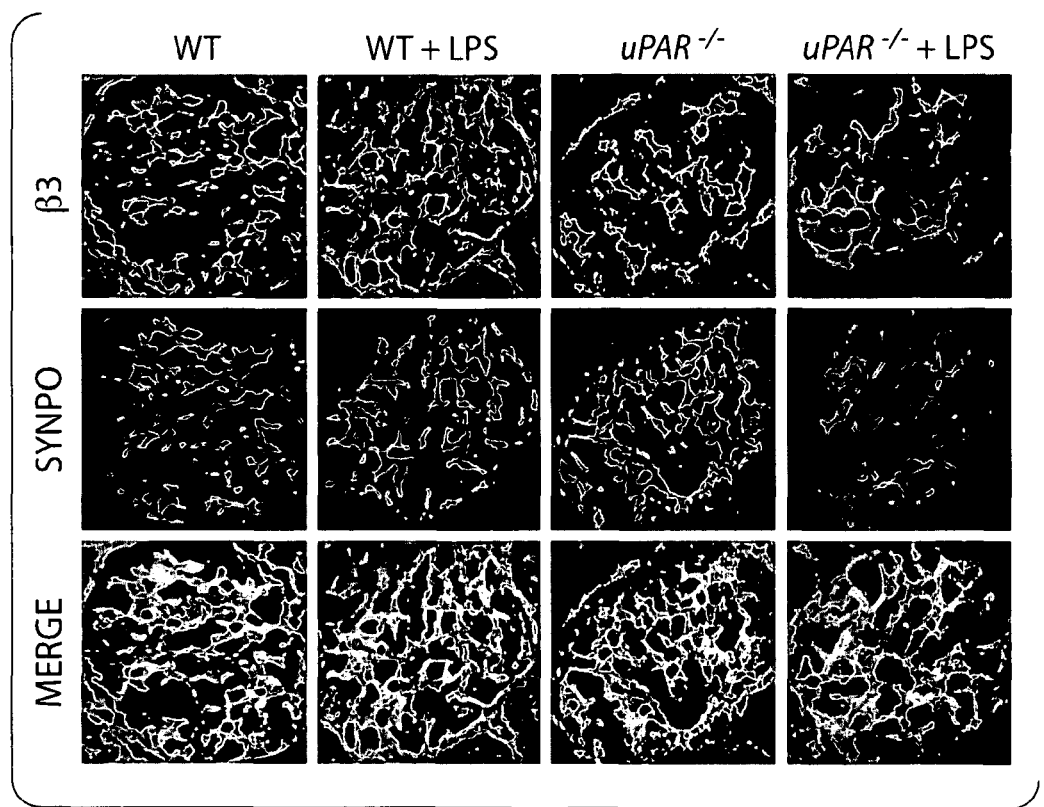
Figure 5B:
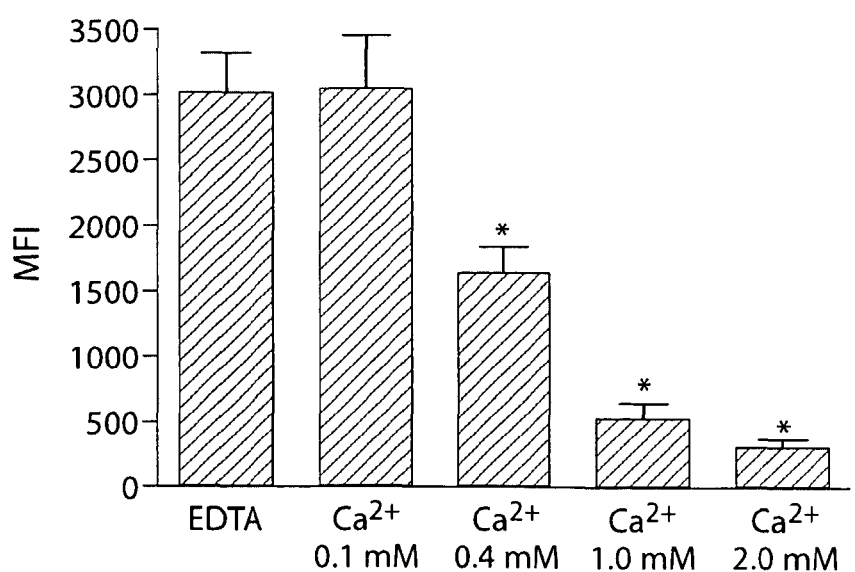
Figure 5C:
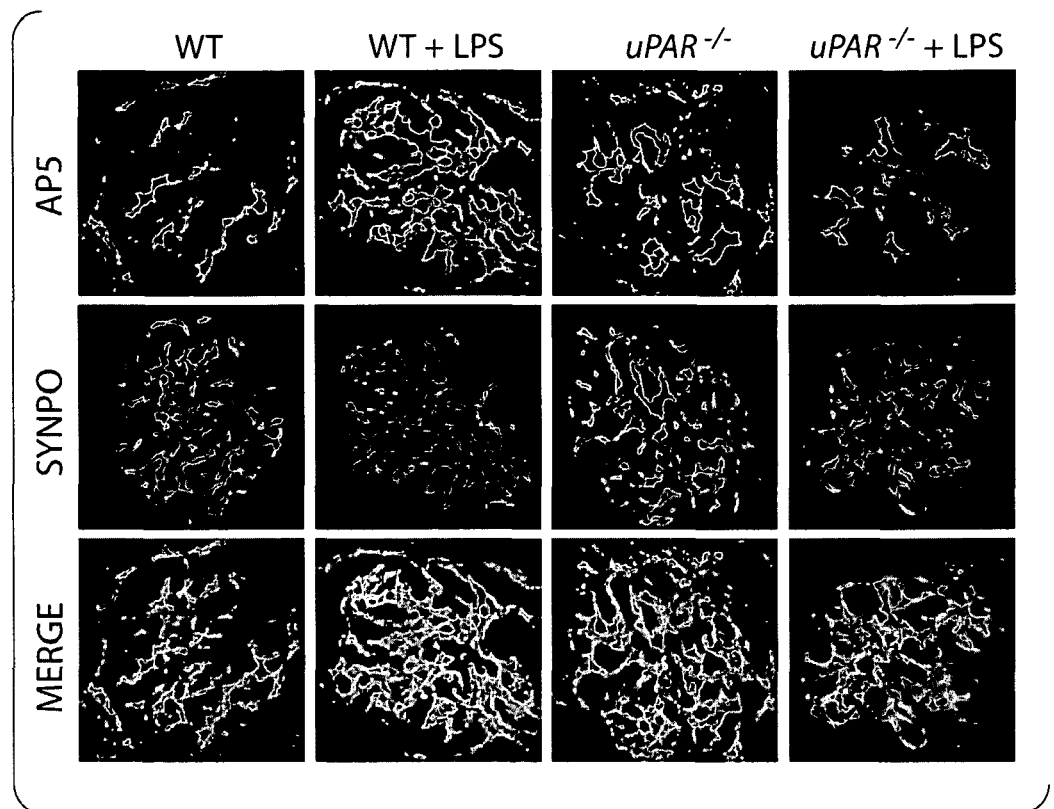
Figure 5D:
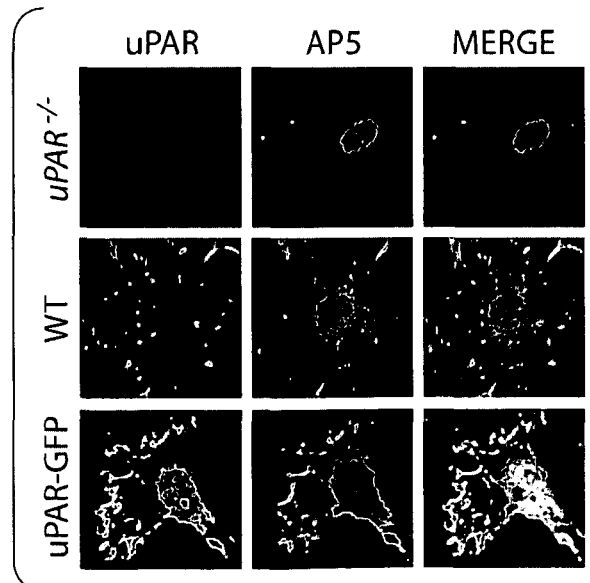
Figure 5E:
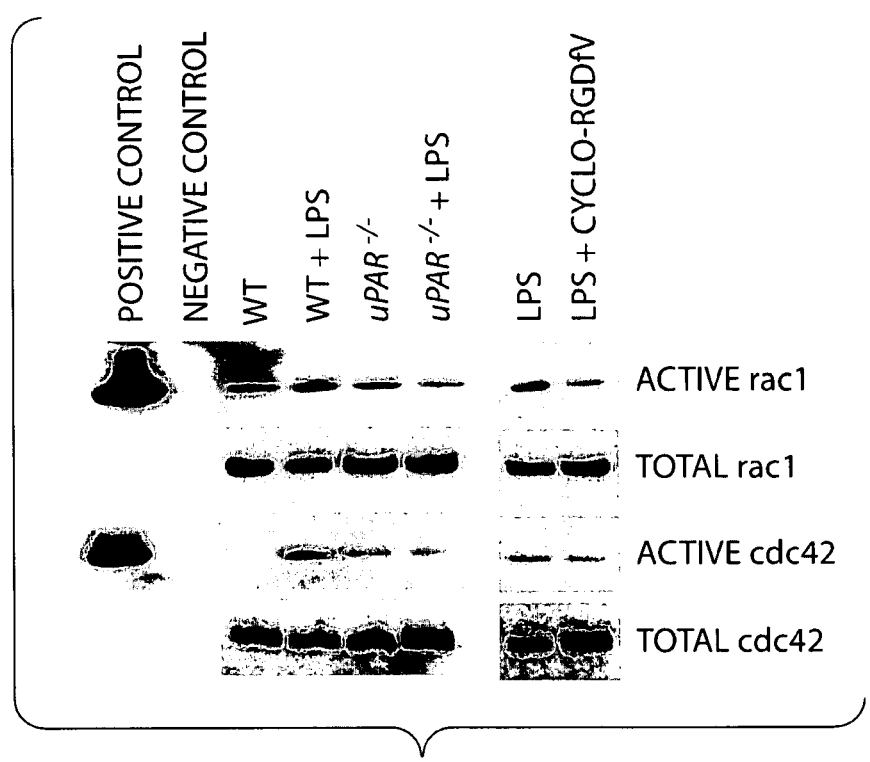
Figure 10A:
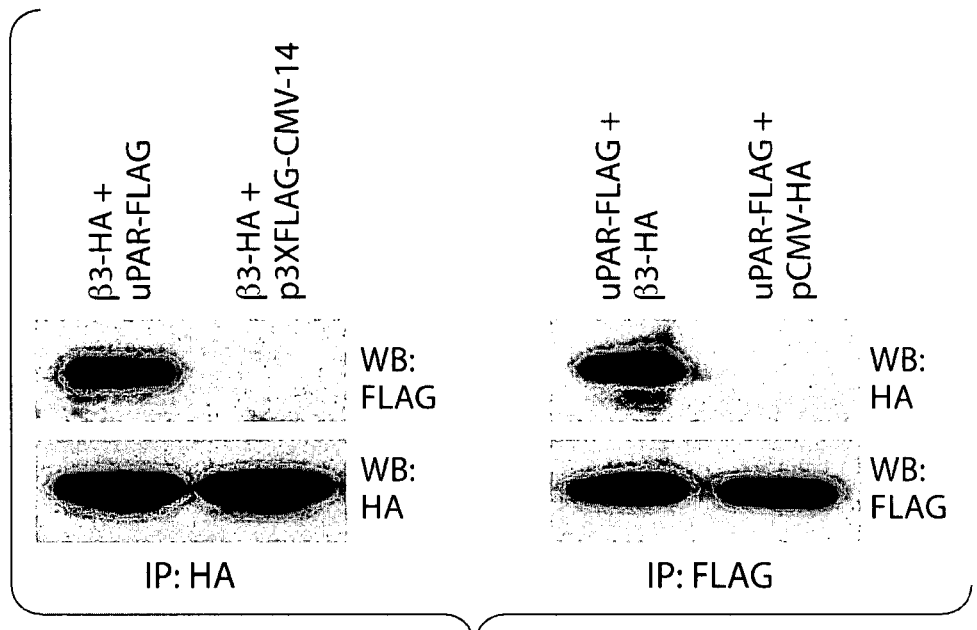
Figure 10B:
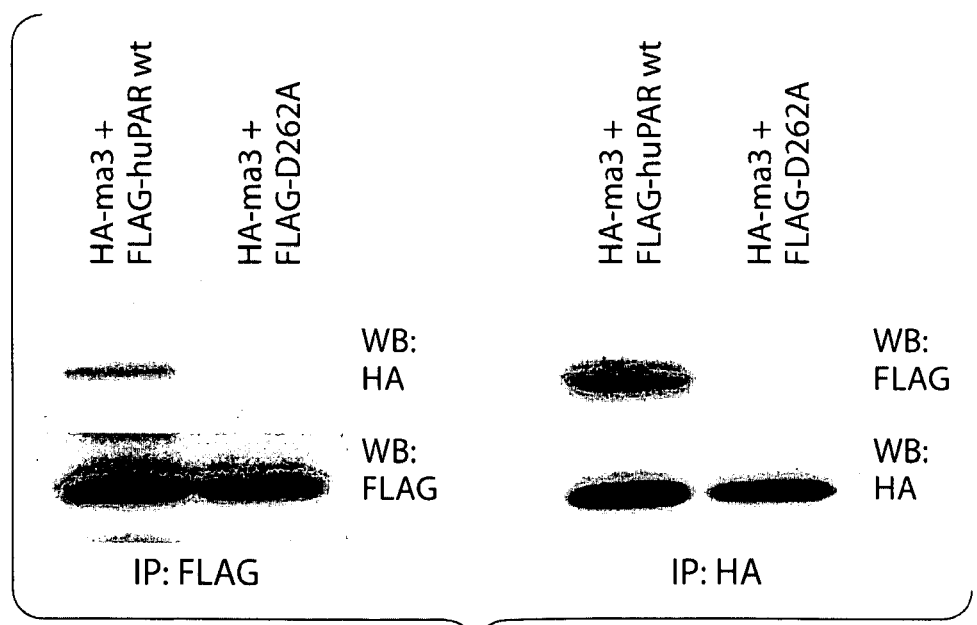

Since uPAR is a GPI-anchored protein without a cytoplasmic tail, it is generally believed that signal transduction from uPAR involves lateral interactions with membrane proteins such as integrins[16]. Most recently, a paper by Madsen et al. described that uPAR induced cell adhesion and migration required Vn binding which can occur independently of uPAR interactions with integrins[19]. Podocyte motility on Vn is enhanced in a uPAR-dependent fashion (FIG. 3) and Vn is induced in glomeruli during proteinuria (FIG. 8b). Thus, it appeared possible that an uPAR-Vn complex or an uPAR-Vn-integrin complex facilitates podocyte motility and promotes FP effacement in response to LPS. Integrins can be in an inactive or active conformation[36] (FIG. 4a). The latter is stimulated by the association with interacting agonists such as domain 3 of uPAR which is important for a5b1 integrin interaction[37,38]. Degryse and colleagues recently identified an integrin-interacting sequence in domain 2 of uPAR, that acts as a new chemotactic epitope activating αvβ3-dependent signaling pathways[39]. Given our findings of uPAR$^{-/-}$ and Vn in the glomerulus, we were particularly interested in the Vn receptor αvβ3 integrin[36]. Indeed, the localization of αvβ3 integrin in podocyte FPs (FIG. 4b)[31] and the distribution of uPAR (FIG. 4b) was similar. In addition, uPAR interacts with β3 integrin (FIG. 10a). Thus, we hypothesized that βvβ3 integrin may provide a functional link between uPAR, podocyte migration and proteinuria development. The genetic deletion of β3 integrin or of the αvβ3 integrin ligand Vn resulted in protection from proteinuria when challenged with LPS (FIG. 4c). This means that both, Vn and β3 integrin are required for LPS-induced proteinuria but either one is dispensable for normal renal development and function (FIG. 4c). Given the extent of the published uPAR interactome and the importance of α3β1 integrin in podocyte development[40], we also analyzed the potential contribution of α3β1 integrin in the uPAR signaling cascade in podocytes and utilized a cDNA for uPAR which encodes the uPAR mutant D262A that is unable to bind α3β1 integrin in humans[38] and mouse (FIG. 10b). The expression of this type of uPAR in podocytes led to the development of LPS-induced proteinuria supporting the idea that uPAR in podocytes preferentially signals through αvβ3 integrin. Since uPAR is involved in pathways dependent and independent of urokinase[16], we also explored the contribution of urokinase on uPAR-dependent proteinuria pathways. We utilized uPA$^{-/-}$ mice and treated them with LPS. Interestingly, these mice developed proteinuria suggesting that uPA is not required for the LPS-mediated effects of uPAR on the kidney filtration barrier (FIG. 4c).

uPAR$^{-/-}$, β3 integrin$^{-/-}$ and Vn$^{-/-}$ mice have no overt renal phenotypes under normal conditions suggesting that uPAR signaling in podocytes is not required for normal glomerular filtration. On the other hand, all these molecules are required for the development of urinary protein loss. Based on this, we reasoned that changes in activation of avβ3 integrin under disease conditions may be a cause for the increased podocyte motility and FP effacement after the administration of LPS. To explore this idea, we next studied the expression of total and active β3 integrin in kidney sections from wild type and uPAR$^{-/-}$ mice. Total podocyte β3 integrin expression was visualized by double labeling of β3 integrin with the podocyte marker synaptopodin in wild type and uPAR$^{-/-}$ mice before and after injection of LPS (FIG. 5a). The expression of β3 integrin in podocytes was unchanged in wild type and uPAR$^{-/-}$ mice before and after LPS administration (FIG. 5a). We next studied the presence of the active form of β3 integrin which can be detected by the use of the well-defined antibody AP5. This antibody recognizes an N-terminal epitope of β3 integrin that is only accessible when the integrin is in its active conformation[41]. To test if AP5 was capable to detect active β3 integrin in podocytes, we first evaluated the effect of divalent cations on the binding pattern of AP5 to β3 integrin by flow cytometry in normal (data not shown) and LPS treated cultured podocytes (FIG. 5b). We found a similar calcium-dependent binding pattern of AP5 as previously reported for the binding of AP5 to β3 integrin in other cells[42]. Immunofluorescence of active β3 integrin with AP5 antibody in glomeruli suggest a low baseline activity of $β_3$ integrin in wild type and uPAR$^{-/-}$ mice under normal conditions. This finding suggests that αvβ3 integrin has a low basal activity even in the absence of uPAR. LPS treatment of wild type mice was associated with a strong induction of podocyte AP5 labeling (FIG. 5c, WT+LPS). This induction was absent in LPS treated uPAR$^{-/-}$ mice (FIG. 5c, uPAR$^{-/-}$+LPS). We also observed colocalization of AP5 labeling at sites of uPAR overexpression in podocytes but not in podocytes in which uPAR was down-regulated using siRNA (FIG. 5d). As an additional readout for active β3 integrin, we analyzed the activity of the small GTPases cdc42 and Rac1 in glomerular lysates from wild type and uPAR mice before and after administration of LPS (FIG. 5e)[43]. The activity of Rac1 was increased in LPS treated wild type but not uPAR$^{-/-}$ mice (FIG. 5e, upper panel). We observed a similar induction pattern for cdc42 activity (FIG. 5e, lower panel). Of note, we could not detect activity for RhoA under normal and disease conditions in wild type or uPAR$^{-/-}$ mice (data not shown). In some experiments we co-injected wild type mice with LPS and cyclo-[Arg-Gly-Asp-D-Phe-Val] RGDfV (SEQ ID NO: 1) known from clinical cancer trials as Cilengitide which is used as a specific inhibitor of αvβ3 integrin[44]. This treatment inhibited the induction of active Rac1 and cdc42 in glomeruli of LPS treated mice (FIG. 5e). Together, these findings support the concept that uPAR is required for the activation of podocyte αvβ3 integrin after LPS treatment.

Figure 6A:
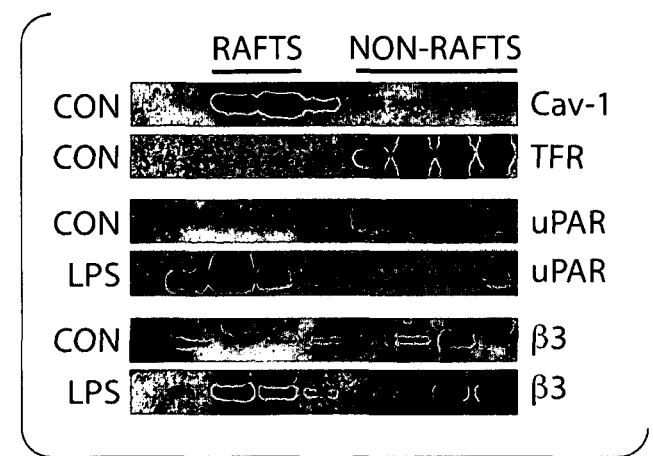
Figure 6B:
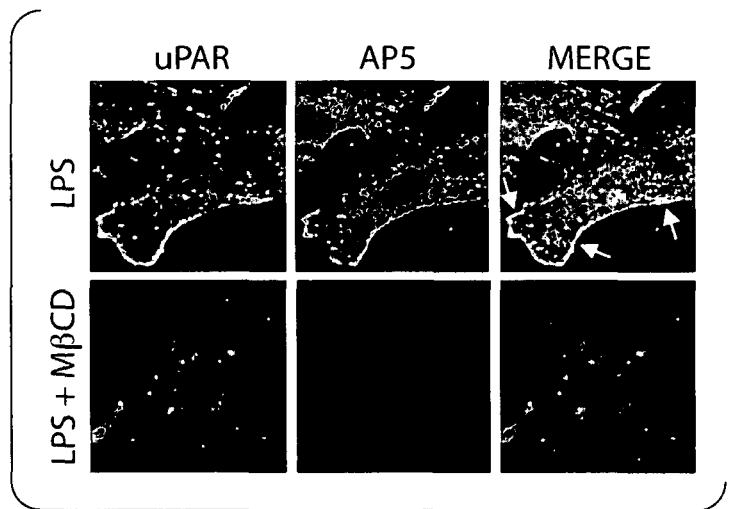
Figure 6C:
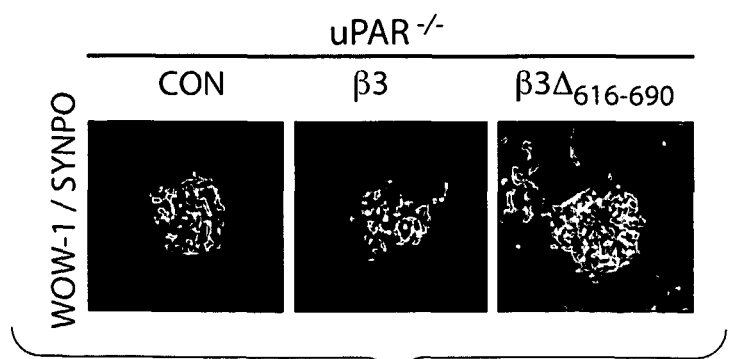

We next explored possible subcellular compartments where uPAR and β3 integrin can associate with each other. Studies suggest that many aspects of the podocyte FP membrane as well as the SD are rich in cholesterol[45] and several SD proteins like podocin and nephrin are associated with lipid rafts[46]. Plasma membrane lipid rafts help to compartmentalize signal transduction events within different regions[24] and uPAR as a GPI-anchored protein is known to be found in lipid rich membrane compartments[16]. We wondered whether uPAR$^{-/-}$ and β3 integrin associate together within lipid rafts in podocytes. We therefore performed sucrose density gradient assays of whole cellular extracts of cultured podocytes before and after LPS administration (FIG. 6a). We found that uPAR$^{-/-}$ and β3 integrin are mainly associated with the non-raft fractions in control podocytes. However, 24 h after LPS administration, both uPAR$^{-/-}$ and β3 integrin were more enriched within the lipid raft fraction (FIG. 6a). The functional association of uPAR$^{-/-}$ and β3 integrin within lipid rafts was further confirmed by the observation that disruption of lipid rafts using Methyl-β-cyclodextrin (MBCD)[47] abrogated the activation of β3 integrin in response to LPS in cultured podocytes as revealed by reduced AP5 staining (FIG.

6b). These data suggest that β3 integrin can be activated by uPAR within lipid rich domains of the podocyte plasma membrane.

Pharmacological Interference with αvβ3 Integrin Modifies Proteinuria in Mice

Figure 6D:
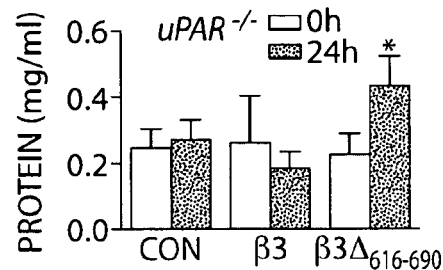

If the activation of αvβ3 integrin is an important downstream signal that mediates the uPAR-induced cellular events in podocytes leading to proteinuria, expression of a constitutively active β3 integrin should be sufficient to induce proteinuria even in the absence of uPAR. Therefore, we utilized a β3 integrin cDNA which encodes a protein lacking aminoacids 616 to 690 of the carboxy-terminal regions of the β3 ectodomain. This mutation confers constitutive activity to the β3 protein and is expressed at the cell surface[48]. We performed gene transfer of this active β3 integrin construct into uPAR$^{-/-}$ mice. 24 h after gene delivery of active β3 integrin, we monitored activity of β3 integrin in podocytes by immunofluorescent double labeling of synaptopodin and WOW-1 antibody. WOW-1 antibody is known to recognize constitutive active β3 protein[49]. uPAR$^{-/-}$ mice positive for WOW-1 labeling in the podocyte (FIG. 6d) developed proteinuria (FIG. 6d), while littermates which received normal β3 integrin or vector control had low podocyte labeling with WOW-1 antibody and no proteinuric response (FIG. 6d).

Figure 6E:
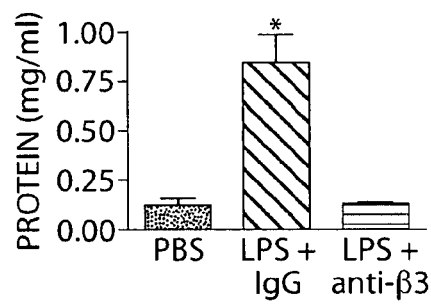
Figure 6F:
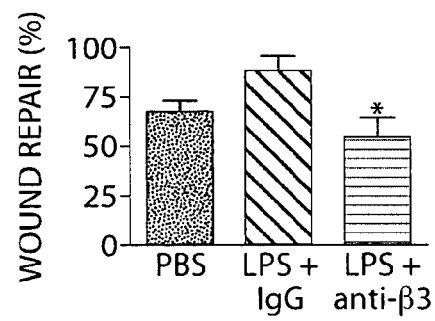

We also performed blocking experiments with an antibody inhibiting β3 integrin function. Wild type mice which were co-injected with LPS and a monoclonal anti-β3 integrin antibody failed to develop proteinuria in response to LPS (FIG. 6e). This blocking antibody was also able to reduce podocyte motility significantly during the course of LPS treatment in vitro (FIG. 6f) connecting increased podocyte motility in vitro with the development of proteinuria in vivo.

Figure 6G:
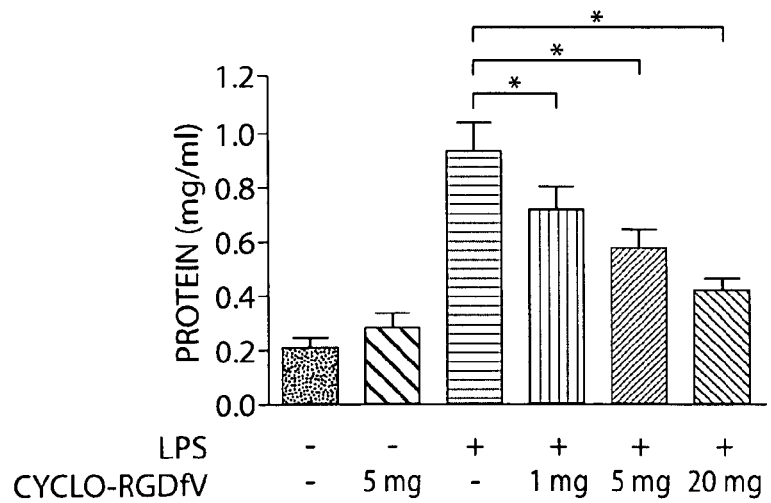

Finally, we used different concentrations of cyclo-[Arg-Gly-Asp-D-Phe-Val] RGDfV (SEQ ID NO: 1) (Cilengitide) to specifically block αvβ3 integrin. Cyclo-RGDfV (SEQ ID NO: 11 was injected in LPS treated wild type mice (FIG. 6g). While the administration of cyclo-RGDfV (SEQ ID NO: 1) in normal mice had no effect, mice which received LPS and cyclo-RGDfV (SEQ ID NO: 1) displayed an attenuated course of proteinuria in a dose dependent manner when compared to control mice that had received only LPS. These data show that activity of αvβ3 integrin is important for proteinuria development and opens novel avenues for the modulation of proteinuria by αvβ3 integrin interference in podocytes.

Methods

Antibodies:

The following antibodies were used in this study: anti-active β3 integrin (AP5), (GTI); anti-WOW-1 fragment antigen binding (Fab)[49] (kind gift from Sanford Shattil, La Jolla Calif.); anti-CD61 blocking antibody (BD Pharmagen); anti-CD31 (ER-MP12) and anti-Vn (H-270), anti-uPAR (FL-290) (Santa Cruz Biotechnology, Inc); anti-uPAR-1 (R&D Systems); anti-α-tubulin (Calbiochem); anti-β3 integrin (Chemicon International); anti-CD61 (Sigma); anti-caveolin (Sigma); anti-GAPDH (Sigma); anti-Flag (Sigma); anti-HA (Sigma); anti-transferrin receptor and anti caveolin1 (Sigma); anti-synaptopodin mouse monoclonal antibody (G1), anti-synaptopodin rabbit polyclonal (NT), (Peter Mundel, New York).

Animals and Treatments:

All animal studies were approved by the Subcommittee on Research Animal Care of the Massachusetts General Hospital. uPAR$^{-/-}$ mice and uPA$^{-/-}$ mice on a mixed background of 75% C57BL/6 and 25% 129 Swiss were obtained from University of Leuven, Belgium; Vn$^{-/-}$ mice (C57BL/6) were obtained from Dr. David Ginsburg, University of Michigan; β3 integrin$^{-/-}$ mice (C57BL/6) were obtained from Dr. Raghuram Kalluri, Boston. C57BL/6 and 129 Swiss mice were purchased from Jackson Laboratory (Bar Harbor). The LPS mouse model was utilized as previously described[9]. The induction of B7-1 was used as a control for the effectiveness of LPS. Rat PAN nephrosis model was set up by a single intraperitoneal injection of puromycin (15 mg/100 g of body weight, Sigma-Aldrich) into Sprague-Dawley rats as described before[27]. NZB/W F1 mice were purchased from the Jackson Laboratory and analyzed after 20 weeks when proteinuria and Lupus glomerulonephritis were present. As diabetic nephropathy rat model, we used Sprague Dawley rats treated with Streptozotocin. Hyperglycaemic state was induced by an intraperitoneal Streptozotocin injection (50-70 mg/kg body weight, in citrate buffer 10 mmol/L, pH 4.5). The hyperglycaemic state developed within 48 h and was maintained during the lifetime of the animals. No insulin administration was required. Glycosuria was evaluated with test strips of the Uriscan TM (YD Diagnostics, VWR, Montréal, QC, Canada) and glycaemia with the AccuSoft Monitoring System (Roche Diagnostics, Laval, QC, Canada). At the end of the study, glycaemia values were 4.3±0.53 and 8.5±0.7 mmol/L for 3 months-old and 12 months-old normoglycaemic animals, respectively, and 21.2±0.9 and 33.9±4.0 mmol/L for 3 months-old and 12 months-old diabetic animals, respectively.

Patients:

Microdissected glomeruli from 34 patients with proteinuric diseases and 8 control subjects were analyzed. Patients were stratified according to their histological diagnosis into focal and segmental glomerulosclerosis (FSGS; n=14), and diabetic nephropathy (DN, n=20). For control biopsies, renal tissue was derived from pretransplantation kidney biopsies during cold ischemia time from 7 living and 1 cadaveric donors (n=8).

Quantitative Real-Time PCR:

TaqMan real-time RT-PCR was done as previously reported[26]. In brief, commercially available predeveloped TaqMan assay reagents (Applied Biosystems) were used for uPAR mRNA analysis. The mRNA expression of uPAR was related to that of synaptopodin, which was used as a podocyte reference gene. Using this approach, the confounding factor of alterations in the proportion of podocyte cell number per total glomerular cells was counterbalanced, and only RNA from the podocyte compartment of the glomerulus was integrated in the analysis, as demonstrated recently[26].

Immunohistochemistry:

Human glomerular biopsies were fixed in cold acetone and stained with anti-uPAR antibodies, anti-Vn antibody and monoclonal anti-synaptopodin antibody following standard protocols[8]. Mouse or rat kidneys were harvested and snap-frozen. Fixation and sectioning were performed following standard protocols[8]. For double-immunofluorescent staining, sections were blocked for 30 min at room temperature, and incubated with antibodies directed against: synaptopodin (G1, NT), β3 integrin (AP5, WOW-1), uPAR, Vn, CD31. After washing with PBS, sections were incubated with appropriate fluorophore conjugated secondary antibodies (Molecular Probes) for 50 min. Thereafter, sections were washed with PBS, and H$_2$O and mounted for analysis with a confocal microscope (Bio-Rad Laboratories). For WOW-1 labeling, uPAR$^{-/-}$ mice were injected with β3$_{A616-690}$ or wild type in integrin constructs. 14 h after injection, mice were sacrificed and kidney was snap-frozen. Cyro-sections were cut at 4 μm and fixed with cold acetone for 10 min before incubated with WOW-1 Fab for 1 h. After washing with PBS, the sections were then incubated with the secondary antibody, anti-mouse Fab conjugated with 488 (Invitrogen) for 50 min and analyzed by confocal microscopy.

Cultured podocytes were immunolabeled as described previously[8].

Transmission Electron Microscopy (TEM), Immunoelectron Microscopy (IEM) and Morphometry:

TEM and IEM were performed according to the standard protocols[8]. For morphometry of uPAR labeling across the glomerular wall, we used renal tissues from 3 and 12 months-old hyperglycaemic animals with the corresponding age-matched normoglycaemic animals (3-4 animals per group). Small pieces of renal cortex were sampled from the anaesthetized animal (urethane, 1 g per kg body weight). The tissue samples were immediately fixed by immersion in periodate-lysine-paraformaldehyde solution, dehydrated in graded methanol and embedded in Lowicryl, following protocols described previously[52].

For immunogold labeling, the grids carrying the ultra thin tissue sections were incubated on a drop of a saturated solution of sodium metaperiodate for 10 min, washed with distilled water, transferred on a drop of 0.15 M glycine for 10 min and washed with PBS. Grids were then incubated on a drop of ovalbumin 1% for 5 min and transferred to the diluted anti-uPAR antibody (1:10) overnight at 4° C. The grids were washed with PBS and incubated on a drop of protein A-gold complex for 30 min at room temperature. The grids were then washed with PBS (3×5 min) and distilled water (1×5 min), dried and contrasted with uranyl acetate. Specificity of the immunolabelings was evaluated by control experiments, omitting the specific antibody step, replacing it with PBS.

Micrographs of immunolabeled renal glomeruli were recorded (>20 micrographs per animal and timepoint), printed and evaluated through morphometrical techniques[52]. We measured the length of the endothelial luminal and abluminal membranes, that of podocyte basal and apical membranes and that of the mesangial cells, the number of gold particles associated to each of those membrane domains was then counted to calculate the density of labeling. Results are expressed as number of gold particles per μm of membrane (mean values±SEM). The measurements were performed by direct planimetry and particle counting using an image processing system (Videoplan 2, Carl Zeiss Inc., Toronto, Canada).

GTPase Activity Assay:

Rho family small GTPase activity in glomerular lysates was measured by Rho/Rac/Cdc42 activation assay kit (Cell Biolabs, INC.) following the manufacturer's protocol. Isolated glomeruli from wild type and uPAR$^{-/-}$ mice, some of them treated with LPS (t=0) and with RGDfV (SEQ ID NO: 1) every 8 hours for 24 hours were obtained by standard sieve technique[25]. 2 mg of glomerular lysate were used to prepare for positive or negative control by incubating with 10 μl of GTPγS or GDP respectively. For small GTPase pull-down assay, the same amount (2 mg) of glomerulus lysates from different treatments were incubated with 40 μl of Rhotekin RBD or PAK PBD agarose bead slurry for 1 h at 4° C. After washing 3 times with 1× assay buffer, beads were harvested and resuspended in LDS sample buffer. Samples were heated for 10 min at 70° C. before SDS-PAGE. After electrophoresis and protein transfer, the membranes were blocked with 5% milk, and incubated with anti-Rho, anti-Rac, and anti-Cdc42 antibodies for 1 h, followed by second antibody incubation and detection with ECL (Pierce). For loading control, 100 μg of glomerular lysates from different treatments were applied and immunoblotted with the same anti-Rho, anti-Cdc42 and anti-Rac antibodies as used above.

In Vivo Gene Delivery:

uPAR-cDNA plasmids were introduced into uPAR$^{-/-}$ mouse using the TransIT in vivo gene delivery system (Mims) as described previously[32,8]. The following cDNAs and vector constructs were used for gene delivery: uPAR; mutated uPAR D262A[38] (kind gift from Y Wei and H A Chapman, University of California, San Francisco); β3 integrin and the constitutively active form of β3 integrin, D616-690 (β3Δ$_{616-690}$)[48]; Podocin promoter vector p2.5[33] (a kind gift from Dr. L B Holzman, University of Michigan) for Pod-uPAR; ICAM-2 promoter vector[34] for ICAM-2-uPAR. Tissues were analyzed for expression as described previously[8].

siRNA:

Mouse uPAR siRNA (sense: CTTCCTGAAGTGTTG-CAACTA (SEQ ID NO: 5)) was constructed and inserted into a pRNA-H1.2/Neo vector (Genescript). Stable transfection was done with podocytes maintaining at 33° C. by Lipofectamine 2000 (Invitrogen). Positive clones were selected by G418 (Sigma-Aldrich) at 500 μg/ml. For further experiments with uPAR siRNA, cells were grown under non-permissive conditions for 10-14 days before proceeded with migration experiments.

Flow Cytometry:

To determine the activity of AP5 in mouse podocytes, cells were cultured under non-permissive conditions for 10 days. Then medium was discarded and the cells were washed gently with PBS without $Ca^{2+}$ and $Mg^{2+}$. The cells were then exposed to LPS right before they were incubated with various amounts of calcium in the presence of 5 μg/ml AP5 for 1 h: 1 mM EDTA, PBS without $Ca^{2+}$ or $Mg^{2+}$; 0.1 mM $CaCl_2$; 0.4 mM $CaCl_2$; 1 mM $CaCl_2$; 2 mM $CaCl_2$. The cells were then harvested by cell scraper, washed and subjected to flow cytometry analysis.

Cell Culture and Transient Transfection:

HEK 293 cells were seeded on a 100 mm culture dish and maintained at 37° C. in DMEM with 10% FBS. Upon 90% confluent, cells were transfected with constructs encoding uPAR$^{-/-}$ or β3 integrin by Lipofectamine 2000 (Invitrogen). 24 h after transfection, cells were harvested for further experiments. Wild type podocytes were differentiated by culturing at 37° C. for at least 10 days (10 days for transfection and migration assay, 14 days for other experiments).

Western Blot and Co-Immunoprecipitation:

For Western blotting, podocytes or extracted glomeruli were lysed in RIPA buffer containing a cocktail of protease inhibitors. The lysate was centrifuged for 20 min at 12,000 rpm and the yielded supernatant was further used. Bradford assay was performed to ensure equal amount of loading. Proteins were separated and then transferred to a PVDF membrane. After blocking for 30 min with 5% milk, the membrane was incubated with primary antibody for 1 h, followed by secondary antibody for overnight 4° C. After washing, the membrane was visualized by chemiluminescence immunoblot detection kit (Pierce).

For Co-IP, HEK cells were co-transfected with constructs encoding uPAR, and β3 integrin for 24 h. Then cells were lysed in RIPA buffer with a cocktail of protease inhibitors. The lysate was incubated with 25 μl of Flag or HA agarose beads (Sigma) at 4° C. overnight after a pre-cleaning. The beads were then washed 5 times with RIPA buffer and were eluted by heating at 70° C. for 10 min. After a brief centrifugation, the supernatants were ready for Western blotting.

Migration Assay:

Podocyte migration was analyzed using a 12-well chemotaxis chamber (Neuro Probe) according to the manufacturer's protocol. In brief, differentiated podocytes were treated with 50 μg/ml of LPS or PAN for 24 h and then harvested for the migration assay. Bottom plates were coated with vitronectin or type I collagen, while upper plates were loaded with equal number of cells (5×10$^4$) suspended in medium. The chamber was incubated at 37° C. for 4 h before the membrane was taken out and stained with diamidino phenylindole (DAPI). The average number of migrated cells was counted in four fields in six independent experiments.

To study the directional movement of podocytes, a wound healing assay was performed. Briefly, podocytes were seeded on Vn or type I collagen coated cover-slips and cultured for 10 days at 37° C. before treated with LPS or PAN for 12-48 h. To create a scrape wound approximately 0.1 cm wide, the narrow end of a P1000 pipette tip was perpendicularly pushed through the monolayer. Then, cover-slips were washed twice with PBS and incubated in medium. After incubation, cells were fixed with 2% PFA and stained with DAPI for analysis. The cell migratory distance was calculated by averaging the distance from the wound edge to the maximally migrated cell in five distinct border zones.

Sucrose Gradient Ultracentrifugation:

Podocyte lysate was overlaid with a sucrose step gradient and centrifuged for 20 h at 120,000 g at 4° C. in a swing-out rotor. 10 fractions (1 ml each) were collected starting from the top and analyzed by Western blotting with rafts, non-rafts markers, as well as uPAR$^{-/-}$ and β3 antibodies.

Blockade of β3 Integrin in Animals:

Cyclo-RGDfV (SEQ ID NO: 1) (Biomol) was injected in mice at 1, 5 and 20 mg per kg body weight i.v. in mice every 8 h for three times. Control mice received the same amount of PBS instead or the control peptide cyclo-RAD (Biomol), (data not shown). Immediately after the first injection, 200 µg of LPS was injected intraperitoneally into each mouse to induce proteinuria. 24 h after LPS injection, urine was collected for Braford assay.

For blockade of β3 integrin with the antibody CD61, wild type mice were randomly divided into three groups (n=3 for each group) and injected with PBS alone (control), LPS+anti-CD61 or LPS+IgG isotype. The antibody was administered 4 h after LPS injection through tail vein, with a final concentration of 10 □g/ml. Urine was collected at time points 0, 4 and 24 h and analyzed by Bradford assay. Data represented in the figure was based on sample obtained after 24 h.

Statistical Analysis:

Statistical analyses were performed by using a Student paired or non-paired t-test when appropriate, and the null hypothesis was rejected at the 0.05 level. Values were presented as Mean±SD, unless stated otherwise. Statistical comparisons for the morphometrical experiments were performed using the Student t test and the Mann-Whitney U tests.

Example 2

Effect of Cyclo-RGDfV (SEQ ID NO: 1) on Recovery of Proteinuria

The following example showed that CycloRGDfV (SEQ ID NO: 1) also reduces already existing proteinuria (FIG. 11). B6 mice were injected LPS twice (0, 24 h) with LPS to induce and maintain proteinuria. 48 h after first injection, cyclo-RGD (n=6) was administered (25 mg/kg body weight) through tail vein. Control (n=5) received the same amount of PBS. 0, 48 h, 66 h urine was collected for Braford assay. The diagram shows the fold change of urinary protein at timepoint 66 h, *p<0.014.

Example 3

Effect of S247 on Recovery of Proteinuria

The following example shows that 5247 also reduces already existing proteinuria. B6 mice are injected twice (0, 24 h) with LPS to induce and maintain proteinuria. 48 h after first injection, S247 (n=6) is administered (25 mg/kg body weight) through tail vein. Control (n=5) received the same amount of PBS. 0, 48 h, 66 h urine was collected for Braford assay. Reduction of urinary protein at timepoint 66 h by 5247 is observed.

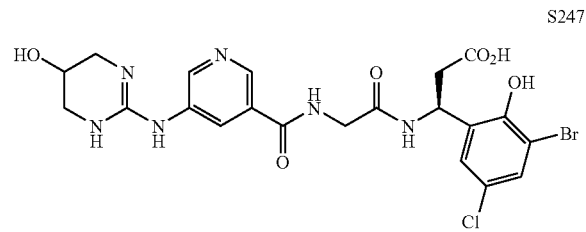 [SMILES: O=C(O)C[C@H](NC(=O)CNC(=O)c1cncc(NC2=NCC(O)CN2)c1)c1cc(Cl)cc(Br)c1O]

S247

TABLE 1

Quantitative analysis of uPAR expression and localization in normal and diabetic glomeruli. uPAR is induced in podocyte foot processes of 3 and 12 months old diabetic rats.

Table 1

| | uPAR morphometrical analysis | | | | |
|---|---|---|---|---|---|
| | Endothelial Luminal Membrane | Endothelial Basal Membrane | Podocyte Luminal Membrane | Podocyte Basal Membrane | Mesangial Membrane |
| NORMAL 3 months | 0.26 ± 0.06* (216.01 µm)** | 0.20 ± 0.05 (213.89 µm) | 0.24 ± 0.03 (576.86 µm) | 0.19 ± 0.03 (258.95 µm) | 0.38 ± 0.05 (196.62 µm) |
| NORMAL 12 months | 0.23 ± 0.06 (144.63 µm) | 0.18 ± 0.04 (141.51 µm) | 0.27 ± 0.05 (288.68 µm) | 0.19 ± 0.05 (138.03 µm) | 0.30 ± 0.06 (240.94 µm) |
| DIABETIC 3 months | 0.38 ± 0.05§ (212.17 µm) | 0.27 ± 0.06 (210.15 µm) | 0.33 ± 0.03 (519.05 µm) | 0.29 ± 0.04§ (267.88 µm) | 0.42 ± 0.06 (213.83 µm) |
| DIABETIC 12 months | 0.36 ± 0.09§ (219.79 µm) | 0.37 ± 0.08§ (234.75 µm) | 0.24 ± 0.06 (586.03 µm) | 0.27 ± 0.03§ (256.68 µm) | 0.41 ± 0.08 (253.73 µm) |

TABLE 1-continued

Quantitative analysis of uPAR expression and localization in normal and diabetic glomeruli. uPAR is induced in podocyte foot processes of 3 and 12 months old diabetic rats.

Table 1

| | uPAR morphometrical analysis | | | | |
|---|---|---|---|---|---|
| | Endothelial Luminal Membrane | Endothelial Basal Membrane | Podocyte Luminal Membrane | Podocyte Basal Membrane | Mesangial Membrane |
| CONTROL of SPECIFICITY | 0.02 ± 0.01 (95.06 μm) | 0.05 ± 0.03 (89.29 μm) | 0.05 ± 0.04 (133.65 μm) | 0.04 ± 0.03 (75.57 μm) | 0.07 ± 0.03 (172.70 μm) |

*particles per μm of membrane
**total length of membrane measured
§Significantly different from corresponding value of normal animals
*p < 0.005,
n = 3 animals for each time point

REFERENCES

1. Zandi-Nejad, K., Eddy, A. A., Glassock, R. J. & Brenner, B. M. Why is proteinuria an ominous biomarker of progressive kidney disease? *Kidney Int Suppl*, S76-89 (2004).
2. Kerjaschki, D. et al. A beta 1-integrin receptor for fibronectin in human kidney glomeruli. *Am J Pathol* 134, 481-9 (1989).
3. Kreidberg, J. A. Functions of alpha3beta1 integrin. *Curr Opin Cell Biol* 12, 548-53. (2000).
4. Regele, H. M. et al. Glomerular expression of dystroglycans is reduced in minimal change nephrosis but not in focal segmental glomerulosclerosis. *J Am Soc Nephrol* 11, 403-12 (2000).
5. Reiser, J., Kriz, W., Kretzler, M. & Mundel, P. The glomerular slit diaphragm is a modified adherens junction. *J Am Soc Nephrol* 11, 1-8 (2000).
6. Durvasula, R. V. & Shankland, S. J. Podocyte injury and targeting therapy: an update. *Curr Opin Nephrol Hypertens* 15, 1-7 (2006).
7. Tryggvason, K., Patrakka, J. & Wartiovaara, J. Hereditary proteinuria syndromes and mechanisms of proteinuria. *N Engl J Med* 354, 1387-401 (2006).
8. Sever, S. et al. Proteolytic processing of dynamin by cytoplasmic cathepsin L is a mechanism for proteinuric kidney disease. *J Clin Invest* 117, 2095-2104 (2007).
9. Reiser, J. et al. Induction of B7-1 in podocytes is associated with nephrotic syndrome. *J Clin Invest* 113, 1390-7 (2004).
10. Reiser, J. et al. Podocyte Migration during Nephrotic Syndrome Requires a Coordinated Interplay between Cathepsin L and {alpha}3 Integrin. *J Biol Chem* 279, 34827-34832 (2004).
11. Asanuma, K. et al. Synaptopodin orchestrates actin organization and cell motility via regulation of RhoA signalling. *Nat Cell Biol* (2006).
12. Moeller, M. J. et al. Podocytes populate cellular crescents in a murine model of inflammatory glomerulonephritis. *J Am Soc Nephrol* 15, 61-7 (2004).
13. Seiler, M. W., Venkatachalam, M. A. & Cotran, R. S. Glomerular epithelium: structural alterations induced by polycations. *Science* 189, 390-3 (1975).
14. Gadea, G., de Toledo, M., Anguille, C. & Roux, P. Loss of p53 promotes RhoA-ROCK-dependent cell migration and invasion in 3D matrices. *J Cell Biol* 178, 23-30 (2007).
15. Wei, Y. et al. Regulation of integrin function by the urokinase receptor. *Science* 273, 1551-5 (1996).
16. Blasi, F. & Carmeliet, P. uPAR: a versatile signalling orchestrator. *Nat Rev Mol Cell Biol* 3, 932-43 (2002).
17. Alfano, M., Sidenius, N., Panzeri, B., Blasi, F. & Poli, G. Urokinase-urokinase receptor interaction mediates an inhibitory signal for HIV-1 replication. *Proc Natl Acad Sci USA* 99, 8862-7 (2002).
18. Wei, Y. et al. Identification of the urokinase receptor as an adhesion receptor for vitronectin. *J Biol Chem* 269, 32380-8 (1994).
19. Madsen, C. D., Ferraris, G. M., Andolfo, A., Cunningham, O. & Sidenius, N. uPAR-induced cell adhesion and migration: vitronectin provides the key. *J Cell Biol* 177, 927-39 (2007).
20. Dewerchin, M. et al. Generation and characterization of urokinase receptor-deficient mice. *J Clin Invest* 97, 870-8 (1996).
21. Carmeliet, P. et al. Biological effects of disruption of the tissue-type plasminogen activator, urokinase-type plasminogen activator, and plasminogen activator inhibitor-1 genes in mice. *Ann NY Acad Sci* 748, 367-81; discussion 381-2 (1995).
22. Zheng, X., Saunders, T. L., Camper, S. A., Samuelson, L. C. & Ginsburg, D. Vitronectin is not essential for normal mammalian development and fertility. *Proc Natl Acad Sci USA* 92, 12426-30 (1995).
23. Sund, M. et al. Function of endogenous inhibitors of angiogenesis as endothelium-specific tumor suppressors. *Proc Natl Acad Sci USA* 102, 2934-9 (2005).
24. Simons, K. & Toomre, D. Lipid Rafts and Signal Transduction. *Nat. Rev Mol Cell Biol* 1, 31-39. (2000).
25. Mundel, P. et al. Synaptopodin: an actin-associated protein in telencephalic dendrites and renal podocytes. *J Cell Biol* 139, 193-204 (1997).
26. Schmid, H. et al. Validation of endogenous controls for gene expression analysis in microdissected human renal biopsies. *Kidney Int* 64, 356-60 (2003).
27. Nakamura, T., Ebihara, I., Shirato, I., Tomino, Y. & Koide, H. Modulation of basement membrane component gene expression in glomeruli of aminonucleoside nephrosis. *Lab Invest* 64, 640-7 (1991).
28. Kelley, V. E. & Cavallo, T. An ultrastructural study of the glomerular slit diaphragm in New Zealand black/white mice. *Lab Invest* 35, 213-20 (1976).
29. Mauer, S. M. et al. Effects of kidney and pancreas transplantation on streptozotocin-induced malignant kidney tumors in rats. *Cancer Res* 34, 1643-5 (1974).

30. Rijneveld, A. W. et al. Urokinase receptor is necessary for adequate host defense against pneumococcal pneumonia. *J Immunol* 168, 3507-11 (2002).
31. Mayer, G., Boileau, G. & Bendayan, M. Furin interacts with proMT1-MMP and integrin alphaV at specialized domains of renal cell plasma membrane. *J Cell Sci* 116, 1763-73 (2003).
32. Moller, C. C. et al. Induction of TRPC6 Channel in Acquired Forms of Proteinuric Kidney Disease. *J Am Soc Nephrol* (2006):
33. Moeller, M. J., Sanden, S. K., Soofi, A., Wiggins, R. C. & Holzman, L. B. Podocyte-specific expression of cre recombinase in transgenic mice. *Genesis* 35, 39-42 (2003).
34. Velasco, B. et al. Vascular gene transfer driven by endoglin and ICAM-2 endothelial-specific promoters. *Gene Ther* 8, 897-904 (2001).
35. Zeisberg, E. M. et al. Endothelial-to-mesenchymal transition contributes to cardiac fibrosis. *Nat Med* 13, 952-61 (2007).
36. Arnaout, M. A., Mahalingam, B. & Xiong, J. P. Integrin structure, allostery, and bidirectional signaling. *Annu Rev Cell Dev Biol* 21, 381-410 (2005).
37. Chaurasia, P. et al. A region in urokinase plasminogen receptor domain III controlling a functional association with alpha5beta1 integrin and tumor growth. *J Biol Chem* 281, 14852-63 (2006).
38. Wei, Y. et al. Urokinase receptors are required for alpha 5 beta 1 integrin-mediated signaling in tumor cells. *J Biol Chem* 282, 3929-39 (2007).
39. Degryse, B., Resnati, M., Czekay, R. P., Loskutoff, D. J. & Blasi, F. Domain 2 of the urokinase receptor contains an integrin-interacting epitope with intrinsic signaling activity: generation of a new avβ3 integrin inhibitors. *J Biol Chem* 280, 24792-803 (2005).
40. Kreidberg, J. A. et al. Alpha 3 beta 1 integrin has a crucial role in kidney and lung organogenesis. *Development* 122, 3537-47 (1996).
41. Pelletier, A. J., Kunicki, T. & Quaranta, V. Activation of the integrin alpha v beta 3 involves a discrete cation-binding site that regulates conformation. *J Biol Chem* 271, 1364-70 (1996).
42. Honda, S. et al. Topography of ligand-induced binding sites, including a novel cation-sensitive epitope (AP5) at the amino terminus, of the human integrin beta 3 subunit. *J Biol Chem* 270, 11947-54 (1995).
43. Dormond, O., Foletti, A., Paroz, C. & Ruegg, C. NSAIDs inhibit alpha V beta 3 integrin-mediated and Cdc42/Rac-dependent endothelial-cell spreading, migration and angiogenesis. *Nat Med* 7, 1041-7 (2001).
44. Cai, W. & Chen, X. Anti-angiogenic cancer therapy based on integrin alphavbeta3 antagonism. *Anticancer Agents Med Chem* 6, 407-28 (2006).
45. Orci, L., Singh, A., Amherdt, M., Brown, D. & Perrelet, A. Microheterogeneity of protein and sterol content in kidney podocyte membrane. *Nature* 293, 646-7 (1981).
46. Schwarz, K. et al. Podocin, a raft-associated component of the glomerular slit diaphragm, interacts with CD2AP and nephrin. *J Clin Invest* 108, 1621-9 (2001).
47. Keller, P. & Simons, K. Cholesterol is required for surface transport of influenza virus hemagglutinin. *J Cell Biol* 140, 1357-67 (1998).
48. Butta, N. et al. Disruption of the beta3 663-687 disulfide bridge confers constitutive activity to beta3 integrins. *Blood* 102, 2491-7 (2003).
49. Pampori, N. et al. Mechanisms and consequences of affinity modulation of integrin alpha(V)beta(3) detected with a novel patch-engineered monovalent ligand. *J Biol Chem* 274, 21609-16 (1999).
50. de Jong, P. E. & Brenner, B. M. From secondary to primary prevention of progressive renal disease: the case for screening for albuminuria. *Kidney Int* 66, 2109-18 (2004).
51. Silberman, S., Janulis, M. & Schultz, R. M. Characterization of downstream Ras signals that induce alternative protease-dependent invasive phenotypes. *J Biol Chem* 272, 5927-35 (1997).
52. Gugliucci, A. & Bendayan, M. Reaction of advanced glycation endproducts with renal tissue from normal and streptozotocin-induced diabetic rats: an ultrastructural study using colloidal gold cytochemistry. *J Histochem Cytochem* 43, 591-600 (1995).

It has now been found that compounds of formula (I)

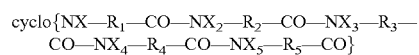

where:

$R_1$ is selected from:

$CH(CH_2)_3NHC(NH)NH_2$; $C[CH_nF_m](CH_2)_3NHC(NH)NH_2$ $R_2$ is the group $CH_2$; $CH_2-CH_2$;

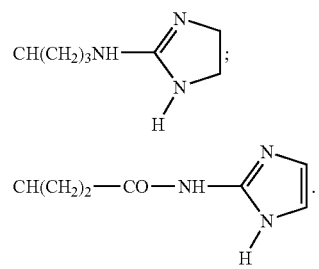

$R_3$ is selected from $CHCH_2COOH$; $C[CH_nF_m]CH_2-COOH$;

$R_4$ is selected from $CH-CH_2-Ph$; $C[CH_nF_m]CH_2-Ph$; $CH-CH_2-(4-OH)Ph$;

$CH-CH_2-(4-OMe)Ph$; $CH-CH_2-(4-F)Ph$; $CH-CH(OH)-Ph$; $C(CH_3)_2$; $CH-C(CH_3)_3$; $CH-CH_2-COOH$;

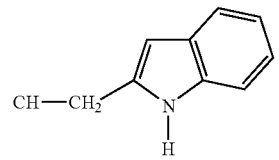

$R_5$ is selected from $CH-CH_2-Ph$; $C[CH_nF_m]CH_2-Ph$; $CH-CH(CH_3)_2$; $C[CH_nF_m]CH(CH_3)_2$; $CH-C(CH_3)_3$;

or, the $NX_4-R_4-Co-NX_5-R_5-CO$ group is 3-aminomethyl-benzoyl n+m=3

$X_1$-$X_5$, which may be the same or different, are H, ($CH_2$), $-CH_3$;

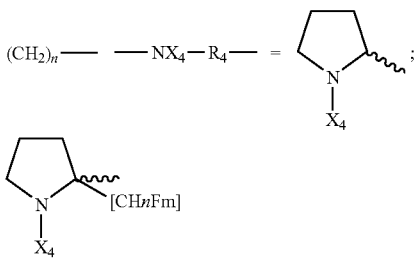

$CHF_2$; $(CH_2)_n$—$CH_2F$, $(CH_2)_n$—$CF_3$ where n=0-3;

with the proviso that at least one α-fluoroalkylated amino acid is present in the formula (I) compound.

where each NX—R—CO amino acid can have an absolute type R or type S configuration; their individual enantiomers, diastereoisomers, the related mixtures, the pharmaceutically acceptable salts are selective inhibitors of the $a_v\beta_3$ and/or $a_v\beta_5$ integrin receptors.

Therefore, objects of the present invention are compounds of formula (I), as described above, a process for their preparation, their use as medicaments and pharmaceutical compositions containing them.

Accordingly, we have found that this object is achieved by compounds of the formula I $$B\text{-}G\text{-}L \qquad\qquad I$$

where B, G and L have the following meanings:

L is a structural element of the formula $I_L$ $$—U\text{-}T \qquad\qquad I_L$$

where

T is a group COOH, a radical hydrolyzable to COOH or a radical bioisosteric to COOH and —U— is $—(X_L)_a—(CR_L^1R_L^2)_b\text{-}$, $—CR_L^1{=}CR_L^2\text{-}$, ethynylene or $={CR_L^1}\text{-}$, where a is 0 or 1, b is 0, 1 or 2, $X_L$ is $CR_L^3R_L^4$, $NR_L^5$, oxygen or sulfur, $R_L^1$, $R_L^2$, $R_L^3$, $R_L^4$ independently of one another are hydrogen, -T, —OH, —$NR_L^6R_L^7$, a halogen radical, a branched or unbranched, optionally substituted $C_1$-$C_6$-alkyl, $C_2$-$C_6$-alkenyl, $C_2$-$C_6$-alkynyl, $C_3$-$C_7$-cycloalkyl, —CO—NH($C_1$-$C_6$-alkyl), —CO—N($C_1$-$C_6$-alkyl)$_2$ or $C_1$-$C_4$-alkoxy radical, an optionally substituted radical $C_1$-$C_2$-alkylene-T, alkenylene-T or $C_2$-alkynylene-T, an optionally substituted aryl or arylalkyl radical or in each case independently of one another are two radicals $R_L^1$ and $R_L^2$ or $R_L^3$ and 110 or optionally $R_L^1$ and $R_L^3$ together are an optionally substituted 3- to 7-membered saturated or unsaturated carbocycle or heterocycle, which can contain up to three identical or different heteroatoms O, N, S, $R_L^5$, $R_L^6$, $R_L^7$ independently of one another are hydrogen, a branched or unbranched, optionally substituted $C_1$-$C_6$-alkyl, $C_3$-$C_7$-cycloalkyl, CO—O—$C_1$-$C_6$-alkyl, $SO_2$—$C_1$-$C_6$-alkyl or CO—$C_1$-$C_6$-alkyl radical or an optionally substituted CO—O-alkylenearyl, $SO_2$-aryl, CO-aryl, $SO_2$-alkylenearyl or CO-alkylenearyl radical, G is a structural element of the formula $I_G$

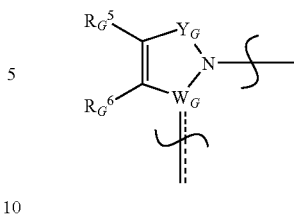

where the structural element B is bonded via the ring nitrogen and the structural element L is bonded to the structural element G via $W_G$, $Y_G$ is CO, CS, C=$NR_G^2$ or $CR_G^3R_G\text{.sup.4}$, $R_G^2$ is hydrogen, a hydroxyl group, a branched or unbranched, optionally substituted $C_1$-$C_6$-alkyl, $C_1$-$C_4$-alkoxy, $C_3$-$C_7$-cycloalkyl or —O—$C_3$-$C_7$-cycloalkyl radical or an optionally substituted aryl, —O-aryl, arylalkyl or —O-alkylenearyl radical, $R_G^3$, $R_G^4$ independently of one another are hydrogen or a branched or unbranched, optionally substituted $C_1$-$C_6$-alkyl, $C_2$-$C_6$-alkenyl, $C_2$-$C_6$-alkynyl or $C_1$-$C_4$-alkoxy radical or both radicals $R_G^3$ and $R_G^4$ together are a cyclic acetal —O—$CH_2$—$CH_2$—O— or —O—$CH_2$—O— or both radicals $R_G^3$ and $R_G^4$ together are an optionally substituted $C_3$-$C_7$-cycloalkyl radical, $R_G^5$ and $R_G^6$ independently of one another are hydrogen, a branched or unbranched, optionally substituted $C_1$-$C_6$-alkyl or $C_1$-$C_4$-alkoxy radical, an optionally substituted aryl or arylalkyl radical or both radicals $R_G^5$ and $R_G^6$ together are an optionally substituted, fused, unsaturated or aromatic 3- to 10-membered carbocycle or heterocycle, which can contain up to three different or identical heteroatoms O, N, S, where in this fused, unsaturated or aromatic 3- to 10-membered carbocycle or heterocycle, as substituents, independently of one another up to four substituents from the group consisting of hydroxyl, halogen or a branched or unbranched, optionally halogen-substituted $C_1$-$C_4$-alkoxy, $C_1$-$C_4$-thioalkyl or $C_1$-$C_4$-alkyl radical or an optionally halogen-substituted aryl, hetaryl or $C_3$-$C_7$-cycloalkyl radical or an optionally halogen-substituted radical —$SO_2$—$C_1$-$C_4$-alkyl, —SO—$C_1$-$C_4$-alkyl, —$SO_2$—$C_1$-$C_4$-alkylenearyl, —SO—$C_1$-$C_4$-alkylenearyl, —$SO_2$-aryl or —SO-aryl are selected, $W_G$ is a structural element selected from the group of structural elements of the formulae $I_WG^1$ to $I_WG^4$, 2

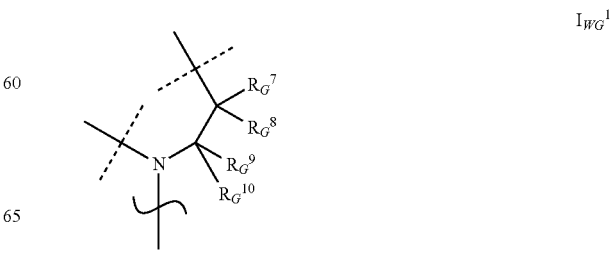

$I_{WG}^2$
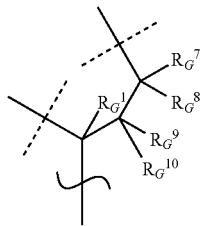

$I_{WG}^3$
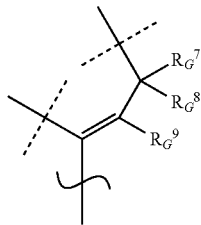

$I_{WG}^4$
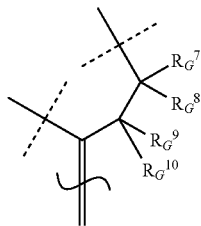

$R_G^1$ is hydrogen, halogen, a hydroxyl group or a branched or unbranched, optionally substituted $C_1$-$C_{16}$-alkyl or $C_1$-$C_4$-alkoxy radical, $R_G^7$, $R_G^8$, $R_G^9 R_G^{10}$ independently of one another are hydrogen, a hydroxyl group, —CN, halogen, a branched or unbranched, optionally substituted $C_1$-$C_6$-alkyl, $C_2$-$C_6$-alkenyl, $C_2$-$C_6$-alkynyl, $C_1$-$C_4$-alkylene-$C_3$-$C_7$-cycloalkyl, $C_1$-$C_4$-alkylene-$C_3$-$C_7$-heterocycloalkyl or $C_1$-$C_4$-alkylene-$C_3$-$C_7$-heterocycloalkenyl radical, a branched or unbranched, optionally substituted radical $C_1$-$C_4$-alkylene-$OR_G^{11}$, $C_1$-$C_4$-alkylene-CO—OR-$_G^{11}$, $C_1$-$C_4$-alkylene-O—CO—$R_G^{11}$, $C_1$-$C_4$-alkylene-CO—$R_G^{11}$, $C_1$-$C_4$-alkylene-$SO_2$—$NR_G^{12}R_G^{13}$, $C_1$-$C_4$-alkylene-CO—$NR_G^{-12}R_G^{13}$, $C_1$-$C_4$-alkylene-O—CO—$NR_G^{12}R.sub.G^{13}$, $C_1$-$C_4$-alkylene-$NR_G^{12}R_G^{13}$, or $C_1$-$C_4$-alkylene-$SR_G^{11}$, $C_1$-$C_4$-alkylene-SO—R.-sub.$G^{11}$, a radical —S—$R_G^{11}$, —O—$R_G^{11}$, —SO—$R_G^{11}$, —$SO_2$—$R_G^{11}$, —CO—$R_G^{11}$, —O—CO—$R_G^{11}$, —O—CO—$NR_G^{12}R_G^{13}$, —$SO_2$—$NR_G^{12}G^{13}$, —CO—$NR_G^{12}R_G^{13}$, —$NR_G^{12}R_G^{13}$ or CO—$R_G^{11}$, an optionally substituted $C_3$-$C_7$-cycloalkyl, aryl, hetaryl, arylalkyl or hetarylalkyl radical or in each case independently of one another two radicals $R_G^7$ and $R_G^9$ or $R_G^9$ and $R_G^{10}$ or $R_G^7$ and $R_G^8$ or $R_G^9$ and $R_G^{10}$ together are an optionally substituted, saturated or unsaturated, nonaromatic, 3- to 7-membered carbocycle or heterocycle which can contain up to 3 heteroatoms selected from the group O, N, S and up to two double bonds, $R_G^{11}$ is hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bis-alkylaminoalkylene or acylaminoalkylen radical or an optionally substituted aryl, heterocycloalkyl, heterocycloalkenyl, hetaryl, $C_3$-$C_7$-cycloalkyl, $C_1$-$C_4$-alkylene-$C_3$—$C.sub.7$-cycloalkyl, arylalkyl, $C_1$-$C_4$-alkyleneheterocycloalkyl, $C_1$-$C_4$-alkyleneheterocycloalkenyl or hetarylalkyl radical, $R_G^{12}$, $R_G^{13}$ independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bis-alkylaminoalkylene or acylaminoalkylene radical or an optionally substituted aryl, heterocycloalkyl, heterocycloalkenyl, hetaryl, $C_3$-$C_7$-cycloalkyl-, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$OR_G^{11}$, —CO—$NR_G^{11}R_G^{11}*$ or —CO—$R_G^{11}$ or both radicals $R_G^{12}$ and $R_G^{13}$ together form a 5- to 7-membered nitrogen-containing carbocycle and $R_G^{11}$ is a radical $R_G^{11}$ which is independent of $R_G^{11}$ B is a structural element containing at least one atom which, under physiological conditions, as a hydrogen acceptor can form hydrogen bridges, where at least one hydrogen acceptor atom has a distance of 4 to 15 atom bonds to structural element G along the shortest possible route along the structural element skeleton, and the physiologically tolerable salts, prodrugs and the enantiomerically pure or diastereomerically pure and tautomeric forms.

In the structural element L, T is understood as meaning a group COOH, a radical hydrolyzable to COOH or a radical bioisosteric to COOH.

A radical hydrolyzable to COOH is understood as meaning a radical which to changes into a group COOH after hydrolysis.

A group which may be mentioned by way of example as a radical hydrolyzable to COOH is

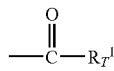

in which $R_T^1$ has the following meanings:

a) OM, where M can be a metal cation, such as an alkali metal cation, such as lithium, sodium, potassium, the equivalent of an alkaline earth metal cation, such as calcium, magnesium and barium, or an environmentally tolerable organic ammonium ion such as primary, secondary, tertiary or quaternary $C_1$-$C_4$-alkylammonium or ammonium ion, such as ONa, OK or OLi, b) a branched or unbranched, optionally halogen-substituted $C_1$-$C_8$-alkoxy radical, such as methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy, pentoxy, hexoxy, heptoxy, octoxy, difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, c) a branched or unbranched, optionally halogen-substituted $C_1$-$C_4$-alkylthio radical such as methylthio, ethylthio, propylthio, 1-methylethylthio, butylthio, 1-methylpropylthio, 2-methylpropylthio or 1,1-dimethylethylthio radical, d) an optionally substituted —O-alkylenearyl radical, such as —O-benzyl, e) $R_T^1$ is further a radical —(O)$_m$—N($R^{18}$)($R^{19}$), in which m is 0 or 1 and $R^{18}$ and $R^{19}$, which can be identical or different, have the following meanings:

hydrogen, a branched or unbranched, optionally substituted $C_1$-$C_6$-alkyl radical, such as methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl or the corresponding substituted radicals, preferably methyl, ethyl, propyl, butyl or i-butyl, $C_2$-$C_6$-alkenyl radical, such as vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl or the corresponding substituted radicals, $C_2$-$C_6$-alkynyl radical, such as ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl or 1-methyl-2-butynyl or the corresponding substituted radicals, $C_3$-$C_8$-cycloalkyl, such as cyclopropyl, cyclobutyl, cyclopentyl, cyclohexyl and cycloheptyl, cyclooctyl or the corresponding substituted radicals, or a phenyl radical, optionally mono- or polysubstituted, for example mono- to trisubstituted, by halogen, nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl, or $R^{18}$ and $R^{19}$ together form an optionally substituted, e.g. $C_1$-$C_4$-alkyl-substituted, $C_4$-$C_7$-alkylene chain closed to give a cycle, which can contain a heteroatom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_3$—, —NH—$(C_{1-12})_3$—, —$CH_2$—NH—$(CH_2)_2$—, —$CH_2$—CH.=CH—$CH_2$—, —CH=CH—$(CH_2)_3$—, —CO—$(CH_2)_2$—CO— or —CO$(CH_2)_3$—CO—.

A radical bioisosteric to COOH is understood as meaning radicals which can replace the function of a group COOH in active compounds by equivalent bond donor/acceptor capabilities or by equivalent charge distribution. Radicals which may be mentioned by way of example as radicals bioisosteric to —COOH are those such as described in "The Practice of Medicinal Chemistry, Editor: C. G. Wermuth, Academic Press 1996, pages 125 and 216, in particular the radicals —P=O(OH)$_2$, —SO$_3$H, tetrazole or acylsulfonamides.

Preferred radicals T are —COOH, —CO—O—$C_1$-$C_8$-alkyl or —CO—O—benzyl.

The radical in the structural element L is a spacer selected from the group —$(X_L)_a$—$(CR_L^1R_L^2)_b$-, —$CR_L^1$=$CR_L^2$-, ethynylene or 40=$CR_L^1$-. In the case of the radical =$CR_L^1$-, the structural element L is linked to the structural element G via a double bond.

$X_L$ is a radical $CR_L^3R_L^4$, $NR_L^5$, oxygen or sulfur.

Preferred radicals —U— are the radicals —$CR_L^1$=CR.sub.$L^2$-, ethynylene or $(X_L)_a$—$(CR_L^1R_L^2)_{-b-}$, where $X_L$ is preferably $CR_L^3R_L^4$ (a=0 or 1) or oxygen (a=1).

Particularly preferred radicals —U— are the radicals —$(X_L)_a$—$(CR_L^1R_L^2)_b$-, where $X_L$ is preferably $CR_L^3R_L^4$ (a=0 or 1) or oxygen (a=1).

Under $R_L^1$, $R_L^2$, $R_L^3$ or $R_L^4$ in structural element L, a halogen radical is understood as meaning, for example, F, Cl, Br or I, preferably F.

Under $R_L^1$, $R_L^2$, $R_L^3$ or $R_L^4$ in structural element L, a branched or unbranched $C_1$-$C_6$-alkyl radical is understood as meaning, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably branched or unbranched $C_1$-$C_4$-alkyl radicals such as methyl, ethyl, propyl, 1-methylethyl, butyl, 1-methylpropyl, 2-methylpropyl or 1,1-dimethylethyl, particularly preferably methyl.

Under $R_L^1$, $R_L^2$, $R_L^3$ or $R_L^4$ in structural element L, a branched or unbranched $C_2$-$C_6$-alkenyl radical is understood as meaning, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

Under $R_L^1$, $R_L^2$, $R_L^3$ or $R_L^4$ in structural element L, a branched or unbranched $C_2$-$C_6$-alkynyl radical is understood as meaning, for example, ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl- 2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl.

Under $R_L^1$, $R_L^2$, $R_L^3$ or $R_L^4$ in structural element L, a branched or unbranched $C_3$-$C_7$cycloalkyl radical is understood as meaning, for example, cyclopropyl, cyclobutyl, cyclopentyl, cyclohexyl or cycloheptyl.

Under $R_L^1$, $R_L^2$, $R_L^3$ or $R_L^4$ in structural element L, a branched or unbranched $C_1$-$C_4$-alkoxy radical is understood as meaning, for example, methoxy, ethoxy, propoxy, 1-methylethoxy, butoxy, 1-methylpropoxy, 2-methylpropoxy or 1,1-dimethylethoxy.

The radicals —CO—NH($C_1$-$C_6$-alkyl), —CO—N($C_1$-$C_6$-alkyl)$_2$ are secondary or tertiary amides and are composed of the amide bond and the corresponding $C_1$-$C_6$-alkyl radicals such as described above for $R_L^1$, $R_L^2$, $R_L^3$ or $R_L^4$.

The radicals $R_L^1$, $R_L^2$, $R_L^3$ or $R_L^4$ can furthermore be a radical
$C_1$-$C_2$-alkylene-T, such as methylene-T or ethylene-T, C2-alkenylene-T, such as ethenylene-T or $C_2$-alkynylene-T, such as ethynylene-T,
an aryl radical, such as phenyl, 1-naphthyl or 2-naphthyl or an arylalkyl radical, such as benzyl or ethylenephenyl (homobenzyl),
where the radicals can optionally be substituted.

Furthermore, two radicals $R_L^1$ and $R_L^2$ or $R_L^3$ and $R_L^4$ or optionally $R_L^1$ and $R_L^3$ can in each case independently of one another together be an optionally substituted 3- to 7-membered saturated or unsaturated carbocycle or heterocycle, which can contain up to three different or identical heteroatoms O, N, S.

All radicals for $R_L^1$, $R_L^2$, $R_L^3$ or $R_L^4$ can be optionally substituted. For the radicals $R_L^1$, $R_L^2$, $R_L^3$ or $R_L^4$ and all further substituted radicals of the description below, suitable substituents, if the substituents are not specified in greater detail, are independently of one another up to 5 substituents, for example selected from the following group:

—NO$_2$, —NH$_2$, —OH, —CN, —COOH, —O—CH$_2$—COOH, halogen, a branched or unbranched, optionally substituted $C_1$-$C_1$-alkyl radical, such as methyl, CF$_3$, C$_2$F$_5$ or CH$_2$F, —CO—O—$C_1$-$C_4$-alkyl, $C_3$-$C_6$-cycloalkyl, $C_1$-$C_4$-alkoxy, $C_1$-$C_4$-thioalkyl, —NH—CO—O—$C_1$-$C_4$-alkyl, —O—CH$_2$—COO—$C_1$-$C_4$-alkyl, —NH—CO—NH—$C_1$-$C_4$-alkyl, —NH—SO$_2$—$C_1$-$C_4$-alkyl, —SO$_2$—NH—$C_1$-$C_4$-alkyl, —N($C_1$-$C_4$-alkyl)$_2$, 20-NH—$C_1$-$C_4$-alkyl, or —SO$_2$—$C_1$-$C_4$-alkyl radical, such as —SO$_2$—CF$_3$, an optionally substituted —NH—CO-aryl, —CO—NH-aryl, —NH—CO—O-aryl, —NH—CO—O-alkylenearyl, —NH—SO$_2$-aryl, —SO$_2$—NH-aryl, —CO—NH-benzyl, —NH—SO$_2$-benzyl or —SO$_2$—NH-benzyl radical, an optionally substituted radical —SO$_2$—NR$^{5\,2}$R$^{5\,3}$ or —CO—NR$^{5\,2}$R$^{5\,3}$ where the radicals R$^2$ and R$^3$ independently of one another can have the meaning $R_L^5$ as below or both radicals R$^2$ and R$^3$ together can be a 3- to 6-membered, optionally substituted, saturated, unsaturated or aromatic heterocycle which, in addition to the ring nitrogen, can contain up to three further different or identical heteroatoms O, N, S, and optionally two radicals substituted on this heterocycle can together be a fused, saturated, unsaturated or aromatic carbocycle or heterocycle which can contain up to three different or identical heteroatoms O, N, S and the cycle can be optionally substituted or a further, optionally substituted cycle can be fused to this cycle.

If not specified in greater detail, in all terminally bonded, substituted hetaryl radicals of the description, two substituents can form a fused 5- to 7-membered, unsaturated or aromatic carbocycle.

Preferred radicals $R_L^1$, $R_L^2$, $R_L^3$ or $R_L^4$ are independently of one another hydrogen, halogen, a branched or unbranched, optionally substituted $C_1$-$C_4$-alkyl, $C_1$-$C_4$-alkoxy or $C_3$-$C_7$-cycloalkyl radical or the radical —NR$_L^6$R$_L^7$.

Particularly preferred radicals $R_L^1$, $R_L^2$, $R_L^3$ or $R_L^4$ are independently of one another hydrogen, fluorine or a branched or unbranched, optionally substituted $C_1$-$C_4$-alkyl radical, preferably methyl.

The radicals $R_L^5$, $R_L^6$, $R_L^7$ in structural element L are independently of one another hydrogen, a branched or unbranched, optionally substituted
$C_1$-$C_6$-alkyl radical, for example as described above for $R_L^1$,
$C_3$-$C_7$-cycloalkyl radical, for example as described above for $R_L^1$,
CO—O—$C_1$-$C_6$-alkyl, SO$_2$—$C_1$-$C_6$-alkyl or CO—$C_1$-$C_6$-alkyl radical, which is composed of the group CO—O, SO$_2$ or CO and, for example, of the $C_1$-$C_6$-alkyl radicals described above for $R_L^1$,
or an optionally substituted CO—O-alkylenearyl, SO$_2$-aryl, SO$_2$-alkylenearyl or CO-alkylenearyl radical, which is composed of the group CO—O, SO$_2$ or CO and, for example, of the aryl or arylalkyl radicals described above for $R_L^1$.

Preferred radicals for $R_L^6$ in structural element L are hydrogen, a branched or unbranched, optionally substituted $C_1$-$C_4$-alkyl, CO—O—$C_1$-$C_4$-alkyl, or SO$_2$—$C_1$-$C_4$-alkyl radical or an optionally substituted Co—O-benzyl, SO$_2$-aryl, SO$_2$-alkylenearyl or CO-aryl radical.

Preferred radicals for $R_L^7$ in structural element L are hydrogen or a branched or unbranched, optionally substituted $C_1$-$C_4$-alkyl radical.

Preferred structural elements L are composed of the preferred radicals of the structural element.

Particularly preferred structural elements L are composed of the particularly preferred radicals of the structural element.

G is a structural element of the formula $I_G$

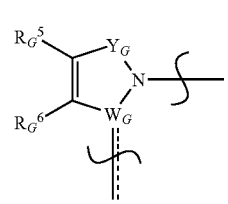

where the incorporation of the structural element G can take place in both orientations. Preferably, the incorporation of the structural element G into the compounds of the formula I can take place such that the structural element B is bonded via the ring nitrogen and the structural element L is bonded via $W_G$ to the structural element G, optionally via a double bond.

$Y_G$ in structural element G is CO, CS, C=NR$_G^2$ or CR$_G^3$R$_G^4$, preferably CO, C=NR$_G^2$ or CR$_G^3$R$_G^4$, particularly preferably CO or CR$_G^3$R$_G^4$.

$R_G^2$ in structural element G is hydrogen, a hydroxyl group, a branched or unbranched, optionally substituted $C_1$-$C_6$- alkyl, $C_1$-$C_4$-alkoxy or $C_3$-$C_7$-cycloalkyl radical, for example as described above for $R_L^1$ in each case, an optionally substituted —O—$C_3$-$C_7$-cycloalkyl radical, which is composed of an ether group and, for example, of the $C_3$-$C_7$-cycloalkyl radical described above for $R_L^1$, an optionally substituted aryl or arylalkyl radical, for example as described above for $R_L^1$ in each case or an optionally substituted —O-aryl or —O-alkylenearyl radical, which is composed of a group —O— and, for example, of the aryl or arylalkyl radicals described above for $R_L^1$.

Preferred radicals $R_G^2$ in structural element G are hydrogen, hydroxyl or a branched or unbranched, optionally substituted $C_1$-$C_6$-alkyl radical, in particular methyl or $C_1$-$C_4$-alkoxy radical, in particular methoxy.

Branched or unbranched, optionally substituted $C_1$-$C_6$-alkyl, $C_2$-$C_6$-alkenyl, $C_2$-$C_6$-alkynyl or $C_1$-$C_4$-alkoxy radicals for $R_G^3$ or $R_G^4$ in structural element G independently of one another are understood as meaning, for example, the corresponding radicals in each case described above for $R_L^1$.

Further, both radicals $R_G^3$ and $R_G^4$ can together form a cyclic acetal, such as —O—$CH_2$—$CH_2$—O— or —O—$CH_2$—O—.

Furthermore, both radicals $R_G^3$ and $R_G^4$ can together form an optionally substituted $C_3$-$C_7$-cycloalkyl radical.

Preferred radicals for $R_G^3$ or $R_G^4$ are independently of one another hydrogen, $C_1$-$C_6$-alkyl or $C_1$-$C_4$-alkoxy, and both radicals $R_G^3$ and $R_G^4$ together form a cyclic acetal, such as —O—$CH_2$—$CH_2$—O— or —O—$CH_2$—O—. Particularly preferred radicals $R_G^3$ or $R_G^4$ are independently of one another hydrogen and both radicals $R_G^3$ and $R_G^4$ together form a cyclic acetal, in particular —O—$CH_2$—$CH_2$—O— or —O—$CH_2$—O—.

Branched or unbranched, optionally substituted $C_1$-$C_6$-alkyl or $C_1$-$C_4$-alkoxy radicals and optionally substituted aryl or arylalkyl radicals for $R_G^5$ and $R_G^6$ in structural element G independently of one another are, for example, the corresponding radicals in each case described above for $R_L^1$.

Further, both radicals $R_G^5$ and $R_G^6$ can together form an optionally substituted, fused, unsaturated or aromatic 3- to 10-membered carbocycle or heterocycle, which can contain up to three different or identical heteroatoms O, N, S, where in this fused, unsaturated or aromatic 3- to 10-membered carbocycle or heterocycle, as substituents, independently of one another up to four substituents from the group hydroxyl, halogen, such as F or Cl or a branched or unbranched, optionally halogen-substituted $C_1$-$C_4$-alkoxy radical, such as methoxy, $C_1$-$C_4$-thioalkyl or $C_1$-$C_4$-alkyl radical, such as methyl, ethyl, propyl or butyl, or an optionally halogen-substituted aryl radical, such as phenyl, hetaryl, such as described below for $RG^7$, or $C_3$-$C_7$-cycloalkyl radical, such as described below for $R_G^7$, or an optionally halogen-substituted radical —$SO_2$—$C_1$-$C_4$-alkyl, —SO—$C_1$-$C_4$-alkyl, —$SO_2$—$C_1$-$C_4$-alkylenearyl, —SO—$C_1$-$C_4$-alkylenearyl, —$SO_2$-aryl or —SO-aryl are selected.

Preferred substituents are halogen, a $C_1$-$C_4$-alkyl radical, $C_1$-$C_4$-alkoxy radical or aryl radical.

Particularly preferred substituents are a $C_1$-$C_4$-alkyl radical, in particular methyl or ethyl, a $C_1$-$C_4$-alkoxy radical, in particular methoxy, or F or Cl.

Preferred radicals for $R_G^5$ and $R_G^6$ are independently of one another hydrogen, an optionally substituted $C_1$-$C_6$-alkyl radical, in particular methyl and ethyl, an optionally substituted aryl radical, in particular optionally substituted phenyl or an optionally substituted arylalkyl radical, in particular an optionally substituted benzyl radical, and in each case both radicals $R_G^5$ and $R_G^6$ together can be an optionally substituted, fused, unsaturated or aromatic 3- to 10-membered carbocycle or heterocycle which can contain up to three different or identical heteroatoms O, N, S.

In particularly preferred radicals for $R_G^5$ and $R_G^6$, both radicals $R_G^5$ and $R_G^6$ together form an optionally substituted, fused, unsaturated or aromatic 3- to 6-membered carbocycle or heterocycle, for example selected from one of the following doubly bonded structural formulae:

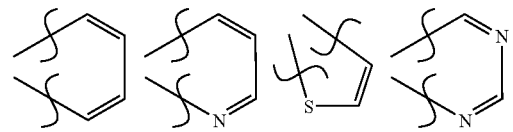

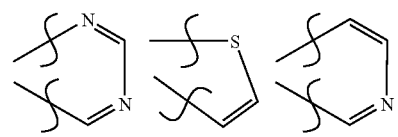

in particular selected from one of the following, doubly bonded structural formulae:

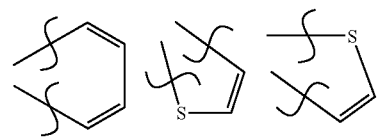

$W_G$ is a structural element selected from the group of structural elements of the formulae $I_{WG}^1$ to $I_{WG}^4$, where the dashed lines intersect the atomic bonds within the structural element G and the carbon atom substituted by $R_G^7$ and $R_G^8$ is bonded to $Y_G$.

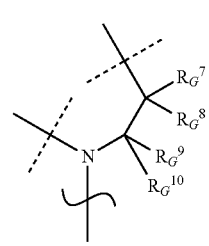

$I_{WG}^1$

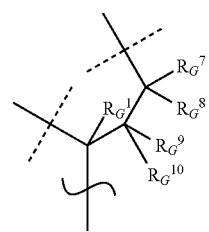

$I_{WG}^2$

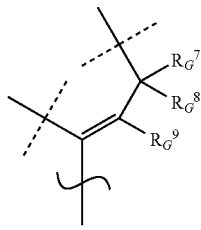

$I_{WG}^3$

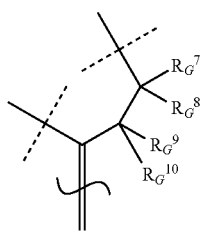

$I_{WG}^4$

In a preferred embodiment, $W_G$ is a structural element selected from the group of structural elements of the formulae $I_{WG}^1$, $I_{WG}^2$ and $I_{WG}^4$, in particular the structural element of the formula $IWG^2$.

$R_G^1$ in structural element $W_G$ is hydrogen, halogen, such as Cl, F, Br or I, a hydroxyl group or a branched or unbranched, optionally substituted $C_1$-$C_6$-alkyl radical, preferably $C_1$-$C_4$-alkyl or $C_1$-$C_4$-alkoxy radical such as in each case described above for $R_L^1$.

Preferred radicals for $R_G^1$ are hydrogen, hydroxyl and optionally substituted $C_1$-$C_4$-alkyl or $C_1$-$C_4$-alkoxy radicals.

Particularly preferred radicals for $R_G^1$ are hydrogen and carboxyl-substituted $C_1$-$C_4$-alkyl or $C_1$-$C_4$-alkoxy radicals, in particular the radicals —$CH_2COOH$ or —O—$CH_2COOH$.

$R_G^7$, $R_G^8$, $R_G^9$ and $R_G^{10}$ in structural element G are independently of one another hydrogen, a hydroxyl group, CN, halogen, such as F, Cl, Br, I, a branched or unbranched, optionally substituted $C_1$-$C_6$-alkyl radical, such as optionally substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, $C_2$-$C_6$-alkenyl radical, such as optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propeny-1 or 1-ethyl-2-methyl-2-propenyl, $C_2$-$C_6$-alkynyl radical, such as optionally substituted ethynyl, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, an optionally substituted $C_3$-$C_7$-cycloalkyl radical, such as optionally substituted cyclopropyl, cyclobutyl, cyclopentyl, cyclohexyl or cycloheptyl, $C_3$-$C_7$-heterocycloalkyl radical, such as optionally substituted aziridinyl, diaziridinyl, oxiranyl, oxaziridinyl, oxetanyl, thiiranyl, thietanyl, pyrrolidinyl, piperazinyl, morpholinyl, piperidinyl, tetrahydrofuranyl, tetrahydropyranyl, 1,4-dioxanyl, hexahydroazepinyl, oxepanyl, 1,2-oxathiolanyl or oxazolidinyl, $C_3$-$C_7$-heterocycloalkenyl radical, such as optionally substituted azirinyl, diazirinyl, thiirenyl, thietyl, pyrrolinyls, oxazolinyls, azepinyl, oxepanyl, α-pyranyl, β-pyranyl, γ-pyranyl, dihydropyranyls, 2,5-dihydropyrrolinyl or 4,5-dihydrooxazolyl, a branched or unbranched, optionally substituted $C_1$-$C_4$-alkylene-$C_3$-$C_7$-cycloalkyl radical, which is composed, for example, of branched or unbranched $C_1$-$C_4$-alkylene radicals such as methylene, ethylene, propylene, n-butylene, isobutylene or t-butylene and, for example, the abovementioned $C_3$-$C_7$-cycloalkyl radicals, a branched or unbranched optionally substituted $C_1$-$C_4$-alkylene-$C_3$-$C_7$-heterocycloalkyl or $C_1$-$C_4$-alkylene-$C_3$-$C_7$-heterocycloalkenyl radical, which is composed of optionally substituted $C_1$-$C_4$-alkylene radicals, such as methylene, ethylene, propylene, n-butylene, isobutylene or t-butylene and, for example, the above-mentioned $C_3$-$C_7$-heterocycloalkyl or $C_3$-$C_7$-heterocycloalkenyl radicals, the radicals being preferred which in the cyclic moiety contain one or two heteroatoms selected from the group consisting of N, O and S and up to two double bonds, a branched or unbranched, optionally substituted radical $C_1$-$C_4$-alkylene-O—$R_G^{11}$, $C_1$-$C_4$-alkylene-CO—OR-$G^{11}$, $C_1$-$C_4$-alkylene-O—CO—$R_G^{11}$, $C_1$-$C_4$-alkylene-CO—$R_6^{11}$, $C_1$-$C_4$-alkylene-SO$_2$—NR$_G^{12}$R$_G^{13}$, $C_1$-$C_4$-alkylene-CO—NR$_G^{12}$, $R_G^3$, $C_1$-$C_4$-alkylene-O—CO_NR$_G^{12}$R$_G^{13}$, $C_1$-$C_4$-alkylene-NR$_G^{12}$R$_G^{13}$, $C_1$-$C_4$-alkylene-SR$_G^{11}$ or $C_1$-$C_4$-alkylene-SO—$R_G^{11}$ which is composed of branched or unbranched, optionally substituted $C_1$-$C_4$-alkylene radicals, such as methylene, ethylene, propylene, n-butylene, isobutylene or t-butylene, the corresponding groups —O—, —CO—, —S—, —N and the terminal radicals $R_G^{11}$, $R_G^{12}$ and $R_G^{13}$ described below, an optionally substituted aryl radical, preferably optionally substituted phenyl, 1-naphthyl or 2-naphthyl, arylalkyl radical, preferably optionally substituted benzyl or ethylenephenyl (homobenzyl), hetaryl radical, preferably optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl or triazinyl or their fused derivatives such as indazolyl, indolyl, benzothiophenyl, benzofuranyl, indolinyl, benzimidazolyl, benzothiazolyl, benzoxazolyl, quinolinyl or isoquinolinyl, hetarylalkyl radical, preferably optionally substituted —$CH_2$-2-pyridyl, —$CH_2$-3-Pyridyl, —$CH_2$-4-pyridyl, —$CH_2$-2-thienyl, —$CH_2$-3-thienyl, —$CH_2$-2-thiazolyl, —$CH_2$-4-thiazolyl, —$CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, 10-$CH_2$—$CH_2$-2-thiazolyl, —$CH_2$—$CH_2$-4-thiazolyl or —$CH_2$—$CH_2$-5-thiazolyl or a radical —S—$R^{11}$, —SO—$R_G^{11}$, —$SO_2$—$R_G^{11}$, —CO—$OR_G^{11}$, —O—CO—$R_G^{11}$, —O—CO—$NR_G^{12}R_G^{13}$, —$SO_2$—$NR_G^{12}R_G^{13}$, —CO—$NR_G^{12}R_G^{13}$, —$NR_G^{12}R_G^{13}$, CO—$R_G^{11}$.

Further, two radicals $R_G^7$ and $R_G^9$ or $R_G^8$ and $R_G^{10}$ or $R_G^7$ and $R_G^8$ or $R_G^9$ and $R_G^1O$ can in each case independently of one another together form an optionally substituted, saturated or unsaturated, nonaromatic, 3- to 7-membered carbocycle or heterocycle which can contain up to 3 heteroatoms selected from the group consisting of O, N, S and up to two double bonds.

Preferred radicals for $R_G^7$, $R_G^8$, $R_G^9$ and $R_G^{10}$ in the structural element G are independently of one another hydrogen, halogen, in particular a branched or unbranched, optionally substituted $C_1$-$C_6$-alkyl, or $C_2$-$C_6$-alkynyl radical, a branched or unbranched, optionally substituted radical $C_1$-$C_4$-alkylene-$OR_G^{11}$, $C_1$-$C_4$-alkylene-CO—$OR$-$_G^{11}$, $C_1$-$C_4$-alkylene-O—CO—$R_G^{11}$, $C_1$-$C_4$-alkylene-CO—$NR_G^{12}R_G^{13}$, $C_1$-$C_4$-alkylene-O—CO—$NR_G^{12}R_G^{13}$, a radical —O—$R_G^{11}$, —CO—$OR_G^{11}$, —O—CO—$R_G^{11}$, —O—CO—$NR_G^{12}R_G^{13}$, —CO—$NR_G^{12}R_G$-13, —$NR_G^{12}R_G^{13}$ or CO—$R_G^{11}$, an optionally substituted aryl, hetaryl or arylalkyl radical, as described above in each case.

Particularly preferred radicals for $R_G^7R_G^8$, $R_G^9$ and $R_G^{10}$ in the structural element G are independently of one another hydrogen, F, a radical —CO—$OR_G^{11}$, —CO—$NR_G^{12}R_G^{13}$, or an optionally substituted aryl radical, as described above in each case.

A branched or unbranched, optionally substituted $C_1$-$C_3$-alkyl radical for $R_G^{11}$, $R_G^{12}$ and $R_G^{13}$ is understood as meaning independently of one another, for example, the $C_1$-$C_6$-alkyl radicals mentioned above for $R_G^1$, plus the radicals heptyl and octyl.

Preferred substituents of the branched or unbranched, optionally substituted $C_1$-$C_8$-alkyl radicals for $R_G^{11}$, $R_G^{12}$ and $R_G^{13}$ independently of one another are the radicals halogen, hydroxyl, $C_1$-$C_4$-alkoxy, —CN, —COOH and —CO—O—$C_1$-$C_4$-alkyl.

A branched or unbranched, optionally substituted $C_2$-$C_6$-alkenyl, $C_2$-$C_6$-alkynyl or $C_1$-$C_4$-alkylene-$C_3$-$C_7$-cycloalkyl radical, an optionally substituted $C_3$-$C_7$-cycloalkyl, aryl, arylalkyl, hetaryl or hetarylalkyl radical for $R_G^{11}$, $R_G^{12}$ and $R_G^{13}$ independently of one another is understood as meaning, for example, the corresponding radicals mentioned above for $R_G^1$.

Preferred branched or unbranched, optionally substituted —$C_1$-$C_8$-alkylene-$C_1$-$C_4$-alkoxy radicals for $R_G^{11}$, $R_G^{12}$ and $R_G^{13}$ are independently of one another methoxymethylene, ethoxymethylene, t-butoxymethylene, methoxyethylene or ethoxyethylene.

Preferred branched or unbranched, optionally substituted mono- and bisalkylaminoalkylene or acylaminoalkylene radicals for $R_G^{11}$, $R_G^{12}$ and $R_G^{13}$ are independently of one another branched or unbranched, optionally substituted radicals —$C_1$-$C_4$-alkylene-NH($C_1$-$C_4$-alkyl), —$C_1$-$C_4$-alkylene-N($C_1$-$C_4$-alkyl)$_2$ or —$C_1$-$C_4$-alkylene-NH—CO—$C_1$-$C_4$-alkyl.

Preferred optionally substituted heterocycloalkyl, heterocycloalkenyl, $C_1$-$C_4$alkyleneheterocycloalkyl or $C_1$-$C_4$-alkyleneheterocycloalkenyl radicals for $R_G^{11}$, $R_G^{12}$ and $R_G^{13}$ are independently of one another the $C_3$-$C_7$-heterocycloalkyl, $C_3$-$C_7$-heterocycloalkenyl, $C_1$-$C_4$-alkylene-$C_3$-$C_7$-heterocycloalkyl or $C_1$-$C_4$-alkylene-$C_3$-$C_7$-heterocycloalkenyl radicals described above for $R_G^1$.

Particularly preferred, optionally substituted heterocycloalkyl, heterocycloalkenyl, $C_1$-$C_4$-alkyleneheterocycloalkyl or $C_1$-$C_4$-alkyleneheterocycloalkenyl radicals for $R_G^{11}$, $R_G^{12}$ and $R_G^{13}$ are independently of one another the $C_3$-$C_7$-heterocycloalkyl, $C_3$-$C_7$-heterocycloalkenyl, $C_1$-$C_4$-alkylene-$C_3$-$C_7$-heterocycloalkyl or $C_1$-$C_4$-alkylene-$C_3$-$C_7$-heterocycloalkenyl radicals described above for $R_G^1$, one or two heteroatoms being selected from the group consisting of N, O and S and up to two double bonds being contained in the cyclic moiety.

Further, $R_G^{12}$ and $R_G^{13}$ can independently of one another be a radical —$SO_2$—$R_G^{11}$, —CO—O—$R_G^{11}$, —CO—$NR_G^{11}R_G^{11*}$ or —CO—$R_G^{11}$, $R_G^{11*}$ being a radical $R_G^{11}$ which is independent of $R_G^{11}$.

Furthermore, both radicals $R_G^{12}$ and $R_G^{13}$ can together form a 5- to 7-membered, to preferably saturated nitrogen-containing carbocycle, in the sense of a cyclic amine structure, such as N-pyrrolidinyl, N-piperidinyl, N-hexahydroazepinyl, N-morpholinyl or N-piperazinyl, where in the case of heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

Particularly preferred radicals for $R_G^{11}$ are hydrogen or an optionally substituted $C_1$-$C_4$-alkyl or aryl radical.

Particularly preferred radicals for $R_G^{12}$ and $R_G^{13}$ are independently of one another hydrogen or an optionally substituted $C_1$-$C_4$-alkyl radical.

Preferred structural elements G are composed of at least one preferred radical of the structural element G, while the remaining radicals are widely variable.

Particularly preferred structural elements G are composed of the preferred radicals of the structural element G.

Very particularly preferred structural elements G are composed of the particularly preferred radicals of the structural element G.

Structural element B is understood as meaning a structural element comprising at least one atom which under physiological conditions can form hydrogen bridges as a hydrogen acceptor, at least one hydrogen acceptor atom having a distance of 4 to 15 atom bonds to structural element G along the shortest possible route along the structural element skeleton. The arrangement of the structural skeleton of structural element B is widely variable.

Suitable atoms which under physiological conditions can form hydrogen bridges as hydrogen acceptors are, for example, atoms having Lewis base properties, such as the heteroatoms nitrogen, oxygen or sulfur.

Physiological conditions is understood as meaning a pH which prevails at the site in a body at which the ligands interact with the receptors. In the present case, the physiological conditions have a pH of, for example, 5 to 9.

In a preferred embodiment, structural element B is a structural element of the formula IB where A and E have the following meanings:

A is a structural element selected from the group:

a 4- to 8-membered monocyclic saturated, unsaturated or aromatic hydrocarbon which can contain up to 4 heteroatoms selected from the group O, N and S, where, in each case independently of one another, the ring nitrogen optionally contained or the carbons can be substituted, with the proviso that at least one heteroatom selected from the group O, N and S contained in the structural element A, or a 9- to 14-membered polycyclic, saturated, unsaturated or aromatic hydrocarbon which can contain up to 6 heteroatoms selected from the group N, O and S, where, in each case independently of one another, the ring nitrogen optionally contained or the carbons can be substituted, with the proviso that at least one heteroatom selected from the group O, N and S is contained in the structural element A, a radical

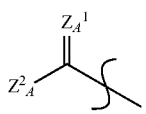

where $Z_A 1$ is oxygen, sulfur or optionally substituted nitrogen and $Z_A 2$ is optionally substituted nitrogen, oxygen or sulfur, or a radical

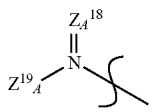

where $R_A^{18}$, $R_A^{19}$ independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl-, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$OR_G^{11}$, —C0-$NR^{11}R_G^{11*}$ or —CO—$R_G^{11}$ and E is a spacer structural element which covalently bonds the structural element A to the structural element G, where the number of atom bonds along the shortest possible route along the structural element skeleton E is 3 to 14.

In a particularly preferred embodiment, the structural element A is a structural element selected from the group of structural elements of the formulae $I_A 1$ to $I_A^{18}$,

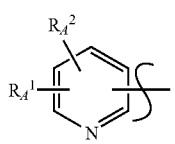 $I_A^1$

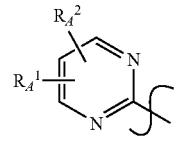 $I_A^2$

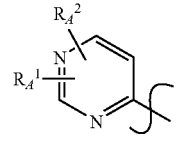 $I_A^3$

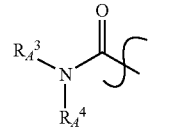 $I_A^4$

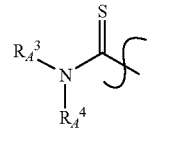 $I_A^5$

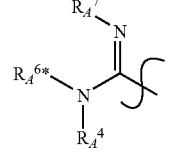 $I_A^6$

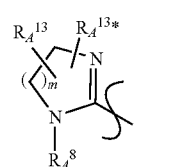 $I_A^7$

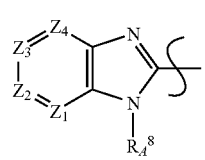 $I_A^8$

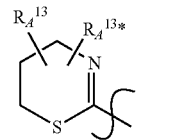 $I_A^9$

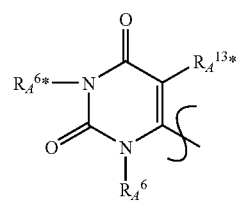 $I_A^{10}$

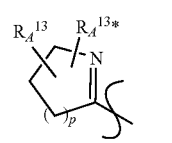 $I_A^{11}$

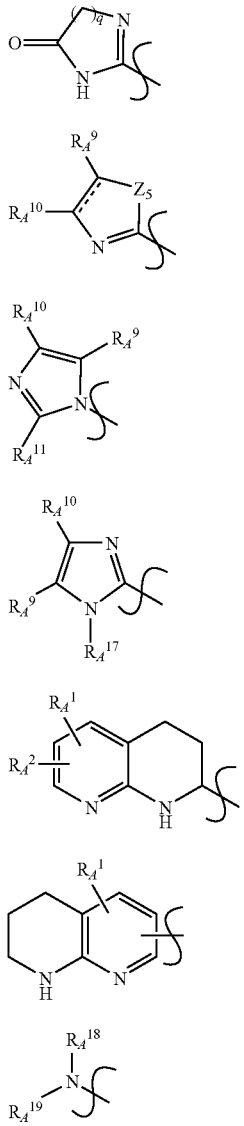

where
m, p, q independently of one another are 1, 2 or 3, independently of one another are hydrogen, CN, halogen, a branched or unbranched, optionally substituted $C_1$-$C_{16}$-alkyl or CO—$C_1$-$C_6$-alkyl radical or an optionally substituted aryl, arylalkyl, hetaryl, hetarylalkyl or $C_3$-$C_7$-cycloalkyl radical or a radical CO—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ or both radicals $R_A^1$ and $R_A^2$ together are a fused, optionally substituted, 5- or 6-membered, unsaturated or aromatic carbocycle or heterocycle which can contain up to three heteroatoms selected from the group O, N, and S, $R_A^{13}$, $R_A^{13*}$ independently of one another are hydrogen, CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_A^{14}$, O—$R_A^{14}$, S—$R_A^{14}$, $NR_A^{15}R_A^{15}$, $SO_2$—$NR_A^1$-5$R_A^{16}$ or CO—$NR_A^{15}R_A^{16}$, where $R_A^{14}$ is hydrogen, a branched or unbranched, optionally substituted $C_1$-$C_6$-alkyl, alkylene-$C_1$-$C_4$-alkoxy, $C_2$-$C_6$-alkenyl, $C_2$-$C_6$-alkynyl or $C_1$-$C_6$-alkylene-$C_3$-$C_7$-cycloalkyl radical or an optionally substituted $C_3$-$C_7$-cycloalkyl, aryl, arylalkyl, hetaryl or hetarylalkyl radical, $R_A^{15}$, $R_A^{16}$, independently of one another are hydrogen, a branched or unbranched, optionally substituted $C_1$-$C_6$-alkyl, CO—$C_1$-$C_6$-alkyl, $SO_2$—$C_1$-$C_6$-alkyl, COO—$C_1$-$C_6$-alkyl, CO—NH—$C_1$-$C_6$-alkyl, arylalkyl, COO-alkylenearyl, $SO_2$-alkylenearyl, CO—NH-alkylenearyl, CO—NH-alkylenehetaryl or hetarylalkyl radical or an optionally substituted $C_3$-$C_7$-cycloalkyl, aryl, CO-aryl, CO—NH-aryl, $SO_2$-aryl, hetaryl, CO—NH-hetaryl or Co-hetaryl radical, $R_A^3$, $R_A^4$ independently of one another are hydrogen, —(CH$_2$)$_n$—(X$_A$)$_j$—$R_A^{12}$, or both radicals together are a 3- to 8-membered, saturated, unsaturated or aromatic N-heterocycle which can additionally contain two further, identical or different heteroatoms O, N or S, where the cycle is optionally substituted or a further, optionally substituted, saturated, unsaturated or aromatic cycle can be fused to this cycle, where n is 0, 1, 2 or 3, j is 0 or 1, $X_A$ is —CO—, —CO—N($R_x^1$)—, —N($R_x^1$)—CO—, —N($R_x^1$)—CO—N($R_x^{1*}$)—, —N($R_x^1$)—CO—O—, O, S, $SO_2$—, —CO—O—, —O—CO—, —O—CO—N($R_x^1$)—, —N($R^{11}$)— or —N($R_x^1$)—$SO_2$—, $R_A^{12}$ is hydrogen, a branched or unbranched, optionally substituted $C_1$-$C_6$-alkyl radical, an optionally $C_1$-$C_4$-alkyl- or aryl-substituted $C_2$-$C_6$-alkynyl or $C_2$-$C_6$-alkenyl radical or a 3- to 6-membered, saturated or unsaturated heterocycle, substituted by up to three identical or different radicals, which can contain up to three different or identical heteroatoms O, N, S, a $C_3$-$C_7$-cycloalkyl, aryl or hetaryl radical, where two radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_A^{12}$, together with $RX^1$ or $RX1*$ forms a saturated or unsaturated $C_3$-$C_7$-heterocycle which can optionally contain up to two further heteroatoms selected from the group O, S and N, $R_x^1$, $R_x^{1*}$ independently of one another are hydrogen, a branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl or $SO_2$—$C_1$-$C_6$-alkyl radical or an optionally substituted $C_3$-$C_7$-cycloalkyl, aryl, arylalkyl, CO—O-alkylenearyl, CO-alkylenearyl, CO-aryl, $SO_2$-aryl, hetaryl, CO-hetaryl or $SO_2$-alkylenearyl radical, $R_A^6$, $R_A^{6*}$ are hydrogen, a branched or unbranched, optionally substituted $C_1$-$C_4$-alkyl, —CO—O—$C_1$-$C_4$-alkyl, arylalkyl, —CO—O-alkylenearyl, —CO—O-allyl, —CO—$C_1$-$C_4$-alkyl, —CO-alkylenearyl, $C_3$-$C_7$-cycloalkyl or —CO-allyl radical or in structural element $I_A^7$ both radicals $R_A^6$ and $R_A^{6*}$ together are an optionally substituted, saturated, unsaturated or aromatic heterocycle which, in addition to the ring nitrogen, can contain up to two further different or identical heteroatoms O, N, S, $R_A^7$ is hydrogen, —OH, —CN, —CONH$_2$, a branched or unbranched, optionally substituted $C_1$-$C_4$-alkyl, $C_1$-$C_4$-alkoxy, $C_3$-$C_7$-cycloalkyl or —O—CO—$C_1$-$C_4$-alkyl radical, or an optionally substituted arylalkyl, —O-alkylenearyl, —O—CO-aryl, —O—CO-alkylenearyl or —O—CO-allyl radical, or both radicals $R_A^6$ and $R_A^7$ together are an optionally substituted, unsaturated or aromatic heterocycle which, in addition to the ring nitrogen, can contain up to two further different or identical heteroatoms O, N, S, $R_A^8$ is hydrogen, a branched or unbranched, optionally substituted $C_1$-$C_4$-alkyl, CO—$C_1$-$C_4$-alkyl, $SO_2$—$C_1$-$C_4$-alkyl or CO—O—$C_1$-$C_4$-alkyl radical or an optionally substituted aryl, CO-aryl, $SO_2$-aryl, CO—O-aryl, CO-alkylenearyl, $SO_2$-alkylenearyl, CO—O-alkylenearyl or alkylenearyl radical, $R_A^9$, $R_A^{10}$ independently of one another are hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_A^{14}$, O—$R_A^{14}$, S—$R_A^{14}$, $NR_A^{15}R_A^{16}$, $SO_2$—$NR_A^{15}R_A^{16}$ or CO—$NR_A^{15}R_A$.sup-.16, or both radicals $R_A^9$ and $R_A^{10}$ together in structural element $I_A^{14}$ are a 5- to 7-membered saturated, unsaturated or aromatic carbocycle or heterocycle which can contain up to three different or identical heteroatoms O, N, S and is optionally substituted by up to three identical or different radicals, $R_A^{11}$ is hydrogen, —CN, halogen, a branched or unbranched, optionally substituted $C_1$-$C_6$-alkyl radical or an optionally substituted aryl, arylalkyl, hetaryl, $C_3$-$C_7$-cycloalkyl radical or a radical CO-o-$R_A^{14}$, O—$R_A^{14}$, S—$R_A^{14}$, $NR_A^{15}R_A^{16}$, $SO_2$—$NR_A^1$-$5R_A^{16}$ or CO—$NR_A^{15}R_A^{16}$, $R_A^{17}$ is hydrogen or, in structural element $I_A^{16}$, both radicals $R_A^9$ and $R_A^{17}$ together are a 5- to 7-membered saturated, unsaturated or aromatic heterocycle which, in addition to the ring nitrogen, can contain up to three different or identical heteroatoms O, N, S and is optionally substituted by up to three identical or different radicals, $R_A^{18}$, $R_A^{19}$ independently of one another are hydrogen, a branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl-, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G$-11, —CO—$ORG^{11}$, —CO—$NR_G^{11}R_G^{11*}$ or —CO—$R_G^{11}$ which is independent of $R_G^{11}$ $Z^1$, $Z^2$, $Z^3$, $Z^4$, independently of one another are nitrogen, C—H, C-halogen or a branched or unbranched, optionally substituted C—$C_1$-$C_4$-alkyl or C—$C_1$-$C_4$-alkoxy radical, $Z^5$ is $NR_A^8$, oxygen or sulfur.

In a further very particularly preferred embodiment, the structural element A is a structural element of the formula $I_A^1 I_A^4$, $I_A^7$, $I_A^8$ or $I_A^9$.

A branched or unbranched, optionally substituted $C_1$-$C_6$-alkyl radical for $R_A^1$ or $R_A^2$ independently of one another is understood as meaning, for example, the corresponding radicals described above for $R_G^1$, preferably methyl or trifluoromethyl.

For $R_A^1$ or $R_A^2$ in the structural elements $I_A^1$, $I_A^2$, $I_A^3$ and $I_A^{17}$ the branched or unbranched, optionally substituted radical CO—$C_1$-$C_6$-alkyl is composed, for example, of the group CO and the branched or unbranched, optionally substituted $C_1$-$C_6$-alkyl radicals described above for $R_A^1$ or $R_A^2$.

Optionally substituted hetaryl, hetarylalkyl, aryl, arylalkyl or $C_3$-$C_7$-cycloalkyl radicals for $R_A^1$ or $R_A^2$ independently of one another are understood as meaning, for example, the corresponding radicals described above for $R_G^7$.

For $R_A^1$ or $R_A^2$, the optionally substituted radicals Co—O—$R_A^{14}$, O—$R_A^{14}$, S—$R_A^{14}$, $NR_A^{15}R_A^{16}$, CO—$NR_A^{15}R_A^{16}$ or $SO_2NR_A^{15}R_A^{16}$ are composed, for example, of the groups CO—O, O, S, N, CO—N or $SO_2$—N and the radicals $R_A^{14}$, $R_A^{15}$ or $R_A^{16}$ described in greater detail below.

Further, both radicals $R_A^1$ and $R_A^2$ can together form a fused, optionally substituted, 5- or 6-membered, unsaturated or aromatic carbocycle or heterocycle which can contain up to three heteroatoms selected from the group consisting of O, N and S.

$R_A^{13}$ and $R_A^{13*}$ are independently of one another hydrogen, CN, halogen, such as fluorine, chlorine, bromine or iodine, a branched or unbranched, optionally substituted $C_1$-$C_6$-alkyl radical, such as described above for $R_G^1$, preferably methyl or trifluoromethyl or an optionally substituted aryl, arylalkyl, hetaryl or $C_3$-$C_7$-cycloalkyl radical or a radical Co—O—$R_A^{14}$, O—$R_A^{14}$, S—$R_A^{14}$, $NR_A^{15}R_A^{16}$, $SO_2NR_A^{15}R_A^{16}$ or CO—$NR_A^{15}R_A^{16}$ as in each case described above for $R_A^1$.

Preferred radicals for $R_A^{13}$ and $R_A^{13*}$ are the radicals hydrogen, F, Cl, a branched or unbranched, optionally substituted $C_1$-$C_6$-alkyl radical, optionally substituted aryl or arylalkyl or a radical Co—O—$R_A^{14}$, O—$R_A^{14}$, $NR_A^{15}R_A^{16}$, $SO_2$—$NR_A^{15}R_A^{16}$ or CO—$NR_A^{15}R_A^{16}$.

A branched or unbranched, optionally substituted $C_1$-$C_6$-alkyl, $C_3$-$C_7$-cycloalkyl, alkylenecycloalkyl, alkylene-$C_1$-$C_4$-alkoxy, $C_2$-$C_6$-alkenyl or $C_2$-$C_6$-alkynyl radical for $R_A^{14}$ in structural element A is understood as meaning, for example, the corresponding radicals described above for $R_G^7$.

Optionally substituted aryl, arylalkyl, hetaryl or alkylhetaryl radicals for $R_A^{14}$ in structural element A are understood as meaning, for example, the corresponding radicals described above for $R_G^7$.

Preferred radicals for $R_A^{14}$ are hydrogen, a branched or unbranched, optionally substituted $C_1$-$C_6$-alkyl radical and optionally substituted benzyl.

A branched or unbranched, optionally substituted $C_1$-$C_6$-alkyl or arylalkyl radical or an optionally substituted $C_3$-$C_1$-cycloalkyl, aryl, hetaryl or hetarylalkyl radical for $R_A^{15}$ or $R_A^{16}$ independently of one another is understood as meaning, for example, the corresponding radicals described above for $R_A^{14}$.

The branched or unbranched, optionally substituted CO—$C_1$-$C_6$-alkyl, $SO_2$—$C_1$-$C_6$-alkyl, COO—$C_1$-$C_6$-alkyl, CO—NH—$C_1$-$C_6$-alkyl, COO-alkylenearyl, CO—NH-alkylenearyl, CO—NH-alkylenehetaryl or $SO_2$alkylenearyl radicals or the optionally substituted CO-aryl, $SO_2$-aryl, CO—NH-aryl, CO—NH-hetaryl or CO-hetaryl radicals for $R_A^{15}$ or $R_A^{16}$ are composed, for example, of the corresponding groups —CO—, —$SO_2$—, —CO—O—, —CO—NH— and the corresponding branched or unbranched, optionally substituted $C_1$-$C_6$-alkyl, hetarylalkyl or arylalkyl radicals or the corresponding optionally substituted aryl or hetaryl radicals described above.

A radical —$(CH_2)_n$—$(X_A)_j$—$R_A^{12}$ for $R_A^3$ or $R_A^4$ independently of one another is understood as meaning a radical which is composed of the corresponding radicals —$(CH_2)_n$—, $(XA)_j$ and $R_A^{12}$. Here, n can be: 0, 1, 2 or 3 and j can be: 0 or 1.

$X_A$ is a doubly bonded radical selected from the group consisting of —CO—, —CO—$N(R_x^1)$—, —$N(R_x^1)$—CO—, —$N((R_x^1)*)$—, —$N(R_x^1)$—CO—O—, —O—, —S—, —$SO_2$—, —$SO_2$—$N(R_x^1)$—, —$SO_2$—O—, —CO—O—, —OCO—, —O—CO—$N((R_x^1))$—, $N(R_x^1)$— or $N((R_x^1))SO_2$—.

$R_A^{12}$ is hydrogen,
a branched or unbranched, optionally substituted $C_1$-$C_6$-alkyl radical, as described above for $R_G^7$,
a $C_2$-$C_6$-alkynyl or $C_2$-$C_6$-alkenyl radical optionally substituted by $C_1$-$C_4$-alkyl or aryl,
or a 3- to 6-membered, saturated or unsaturated heterocycle which is substituted by up to three identical or different radicals and can contain up to three different or identical heteroatoms O, N, S, such as optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4-thiadiazolyl), 2-(1,3,4)-oxadiazolyl, 3-isoxazolyl, 4-isoxazolyl, 5-isoxazolyl, triazinyl.

Further, $R_A^{12}$ and $Rx^1$ or $RX^{1*}$ can together form a saturated or unsaturated $C_3$-$C_7$-heterocycle which can optionally contain up to two further heteroatoms selected from the group consisting of O, S and N.

Preferably, the radical $R_A^{12}$ together with the radical $R_x^1$ or $R_x^{1*}$ forms a cyclic amine as the $C_3$-$C_7$-heterocycle in the case where the radicals are bonded to the same nitrogen atom, such as N-pyrrolidinyl, N-piperidinyl, N-hexahydroazepinyl, N-morpholinyl or N-piperazinyl, where in heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

A branched or unbranched, optionally substituted $C_1$-$C_6$-alkyl, $C_2$-$C_{12}$-alkynyl, preferably $C_2$-$C_6$-alkynyl or $C_2$-$C_6$-alkenyl radical, an optionally substituted $C_3$-$C_7$-cycloalkyl, aryl, arylalkyl or hetaryl radical for $Rx^1$ and $R_x^{1*}$ independently of one another is understood as meaning, for example, the corresponding radicals described above for $R_G^7$.

Preferred branched or unbranched, optionally substituted $C_1$-$C_6$-alkoxyalkyl for $R_x^1$ and $R_x^{1*}$ are independently of one another methoxymethylene, ethoxymethylene, t-butoxymethylene, methoxyethylene or ethoxyethylene.

Preferred branched or unbranched, optionally substituted radicals CO—$C_1$-$C_6$-alkyl, CO—O—$C_1$-$C_6$-alkyl, $SO_2$—$C_1$-$C_6$-alkyl, CO—O-alkylenearyl, CO-alkylenearyl, CO-aryl, $SO_2$-aryl, CO-hetaryl or $SO_2$-alkylenearyl are preferably composed of the $C_1$-$C_6$-alkyl, arylalkyl, aryl or hetaryl radicals and the radicals —CO—, —O—, —$SO_2$— described above.

Preferred radicals for $R_x^1$ and $R_x^{1*}$ are independently of one another hydrogen, methyl, cyclopropyl, allyl and propargyl.

$R_A^3$ and $R_A^4$ can further together form a 3- to 8-membered saturated, unsaturated or aromatic N heterocycle which can additionally contain two further, identical or different heteroatoms O, N or S, where the cycle can be optionally substituted or a further, optionally substituted, saturated, unsaturated or aromatic cycle can be fused to this cycle, $R_A^5$ is a branched or unbranched, optionally substituted $C_1$-$C_6$-alkyl, arylalkyl, $C_1$-$C_4$-alkyl-$C_3$-$C_7$-cycloalkyl or $C_3$-$C_7$-cycloalkyl radical or an optionally substituted aryl, hetaryl, heterocycloalkyl or heterocycloalkenyl radical, such as described above for $R_G^7$.

$R_A^6$ and $R_A^{6*}$ are independently of one another hydrogen, a branched or unbranched, optionally substituted $C_1$-$C_4$-alkyl radical, such as optionally substituted methyl, ethyl, propyl, 1-methylethyl, butyl, 1-methylpropyl, 2-methylpropyl or 1,1-dimethylethyl,
—CO—O—$C_1$-$C_4$-alkyl or —CO—$C_1$-$C_4$-alkyl radical such as composed of the group —CO—O— or —CO— and the $C_1$-$C_4$-alkyl radicals described above,
arylalkyl radical, as described above for $R_G^7$,
—CO—O-alkylenearyl or —CO-alkylenearyl radical such as composed of the group —CO—O— or —CO— and the arylalkyl radicals described above,
—CO—O-allyl or —CO-allyl radical, or $C_3$-$C_7$-cycloalkyl radical, such as described above for $R_G^7$.

Further, both radicals $R_A^6$ and $R_A^{6*}$ in structural element $I_A^7$ can together form an optionally substituted, saturated, unsaturated or aromatic heterocycle which, in addition to the ring nitrogen, can contain up to two further different or identical heteroatoms O, N, S.

$R_A^7$ is hydrogen, —OH, —CN, —$CONH_2$, a branched or unbranched, optionally substituted $C_1$-$C_4$-alkyl radical, for example as described above for $R_A^6$, $C_1$-$C_4$-alkoxy, arylalkyl or $C_3$-$C_7$-cycloalkyl radical, for example as described above for $R_L^{14}$, a branched or unbranched, optionally substituted —O—CO—$C_1$-$C_4$-alkyl radical, which is composed of the group —O—CO— and, for example, of the $C_1$-$C_4$-alkyl radicals mentioned above or an optionally substituted —O-alkylenearyl, —O—CO-aryl, —O—CO-alkylenearyl or —O—CO-allyl radical which is composed of the groups —O— or —O—CO— and, for example, of the corresponding radicals described above for $R_G^7$.

Further, both radicals $R_A^6$ and $R_A^7$ can together form an optionally substituted unsaturated or aromatic heterocycle which, in addition to the ring nitrogen, can contain up to two further different or identical heteroatoms O, N, S.

For $R_A^8$ in structural element A, a branched or unbranched, optionally substituted $C_1$-$C_4$-alkyl radical or an optionally substituted aryl or arylalkyl radical is understood as meaning, for example, the corresponding radicals described above for $R_A^{15}$, where the radicals CO—$C_1$-$C_4$-alkyl, $SO_2$—$C_1$-$C_4$-alkyl, CO—O—$C_1$-$C_4$-alkyl, CO-aryl, $SO_2$-aryl, CO—O-aryl, CO-alkylenearyl, $SO_2$-alkylenearyl or CO—O-alkylenearyl are composed analogously to the other composed radicals of the group consisting of CO, $SO_2$ and COO and, for example, of the corresponding $C_1$-$C_4$-alkyl, aryl or arylalkyl radicals described above for $R_A^{15}$, and these radicals can be optionally substituted.

In each case, for $R_A^9$ or $R_A^{10}$, a branched or unbranched, optionally substituted $C_1$-$C_6$-alkyl radical or an optionally substituted aryl, arylalkyl, hetaryl or $C_3$-$C_7$-cycloalkyl radical independently of one another is understood as meaning, for example, the corresponding radicals described above for $R_A^{14}$, preferably methyl or trifluoromethyl.

In each case, for $R_A^9$ or $R_A^{10}$, a radical CO—O—$R_A^{14}$, O—$R_A^{14}$, S—$R_A^{14}$, $SO_2$—$NR_A^{15}R_A^{16}$, $NR_A^{15}R_A^{16}$ or CO—$NR_A^{15}R_A^{16}$ independently of one another is understood as meaning, for example, the corresponding radicals described above for $R_A^{13}$.

Further, both radicals $R_A^9$ and $R_A^{10}$ together in structural element $I_A^{14}$ can form a 5- to 7-membered saturated, unsaturated or aromatic carbocycle or heterocycle, which can contain up to three different or identical heteroatoms O, N, S and is optionally substituted by up to three identical or different radicals.

Substituents in this case are in particular understood as meaning halogen, CN, a branched or unbranched, optionally substituted $C_1$-$C_4$-alkyl radical, such as methyl or trifluoromethyl or the radicals O—$R_A^{14}$, S—$R_A^{14}$, $NR_A^{15}R_A$-16, CO—$NR_A^{15}R_A^{16}$ or —$((R_A^8)HN)C$=$NR$.sub.-$A^7$.

A branched or unbranched, optionally substituted $C_1$-$C_6$-alkyl radical or an optionally substituted aryl, arylalkyl, hetaryl, $C_3$-$C_7$-cycloalkyl radical or a radical CO—O—$R_A^{14}$, $NR_A^{15}R_A^{16}$, $SO_2$—$NR_A^{15}R_A^{16}$ or CO—$NR_A^{15}R_A^{16}$ for $R_A^{11}$ is understood, for example, as meaning the corresponding radicals described above for $R_A^9$.

Further, in structural element $I_A^{16}$, both radicals $R_A^9$ and $R_A^{17}$ together can form a 5- to 7-membered saturated, unsaturated or aromatic heterocycle which, in addition to the ring nitrogen, can contain up to three different or identical heteroatoms O, N, S and is optionally substituted by up to three identical or different radicals.

A branched or unbranched, optionally substituted $C_1$-$C_8$-alkyl, $C_2$-$C_6$-alkenyl, $C_2$-$C_6$-alkynyl, $C_1$-$C_5$-alkylene-$C_1$-$C_4$-alkoxy, mono- and bisalkylaminoalkylene or acylaminoalkylene radical or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkyleneheterocycloalkyl, $C_1$-$C_4$-alkyleneheterocycloalkenyl or hetarylalkyl radical, or a radical —$SO_2$—$R_G^{11}$, —CO—$OR_G^{11*}$ or —CO—$R_G^1$ for $R_A^{18}$ and $R_A^{19}$ independently of one another is understood as meaning, for example, the radicals described above for $R_G^{12}$, preferably hydrogen or a branched or unbranched, optionally substituted $C_1$-$C_8$-alkyl radical.

$Z^1$, $Z^2$, $Z^3$, $Z^4$ are independently of one another nitrogen, C—H, C-halogen, such as C—F, C—Cl, C—Br or C—I or a branched or unbranched, optionally substituted C—$C_1$-$C_4$-alkyl radical which is composed of a carbon radical and, for example, a $C_1$-$C_4$-alkyl radical described above for $R_A^6$ or a branched or unbranched optionally substituted C—$C_1$-$C_4$-alkoxy radical which is composed of a carbon radical and, for example, a $C_1$-$C_4$-alkoxy radical described above for $R_A^7$.

$Z^5$ is oxygen, sulfur or a radical $NR_A^8$.

Preferred structural elements A are composed of at least one preferred radical of the radicals belonging to the structural element A, while the remaining radicals are widely variable.

Particularly preferred structural elements A are composed of the preferred radicals of the structural element A.

In a preferred embodiment, the spacer structural element E is understood as meaning a structural element that consists of a branched or unbranched aliphatic $C_2$-$C_{30}$-hydrocarbon radical which is optionally substituted and contains heteroatoms and/or of a 4- to 20-membered aliphatic or aromatic mono- or polycyclic hydrocarbon radical which is optionally substituted and contains heteroatoms.

In a further preferred embodiment, the spacer structural element E is composed of two to four substructural elements, selected from the group consisting of $E^1$ and $E^2$, where the sequence of linkage of the substructural elements is arbitrary and $E^1$ and $E^2$ have the following meanings:

$E^1$ is a substructural element of the formula $I_{E1}$

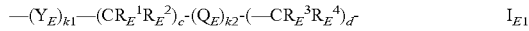   $I_{E1}$ and $E^2$ is a substructural element of the formula $I_{E2}$

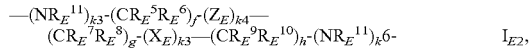   $I_{E2}$ where c, d, f, g, h independently of one another are 0, 1 or 2, k1, k2, k3, k4, k5, k6 independently of one another are 0 or 1, XE, QE independently of one another are an optionally substituted 4- to 11-membered mono- or polycyclic, aliphatic or aromatic hydrocarbon which can contain up to 6 double bonds and up to 6 identical or different heteroatoms selected from the group N, O and S, where the ring carbons and/or the ring nitrogens can optionally be substituted, YE, ZE independently of one another are CO, CO—$NR_E^{12}$, $NR_E^{12}$-CO, sulfur, SO, $SO_2$, $SO_2$—$NR_E^{12}$, $NR_E^{12}$-$SO_2$, CS, CS—$NR_E^{12}$, $NR_E^{12}$-CS, CS—O, O—CS, CO—O, O—CO, oxygen, ethynylene, $CR_E^{13}$-O—CR.sub.-$E^{14}$, C(=$CR_E^{13}R_E^{14}$), $CR_E^{13}$=$CR_E^{14}$, —$CR_E^{13}(CR_E^{15})$—$CHR_E^{14}$- or —$CHR_E^{13}$-$CR_E^{14}(OR_E^{15})$-, $R_E^1$, $R_E^2$, $R_E^3$, $R_E^4$, $R_E^5$, $R_E^6$, $R_E^7$, $R_E^8$, $R_E^9$, $R_E^{19}$ independently of one another are hydrogen, halogen, a hydroxyl group, a branched or unbranched, optionally substituted $C_1$-$C_6$-alkyl, $C_2$-$C_6$-alkenyl, $C_2$-$C_6$-alkynyl or alkylenecycloalkyl radical, a radical —$(CH_2)$—$(W_E)$.sub.z-$R_E^{17}$, an optionally substituted $C_3$-$C_7$-cycloalkyl, aryl, arylalkyl, hetaryl or hetarylalkyl radical or independently of one another in each case two radicals $R_E^1$ and $R_E^2$ or $R_E^3$ and $R_E^4$ or $R_E^5$ and $R_E^6$ or $R_E^7$ and $R_E^8$ or $R_E^9$ and $R_E^{10}$ together are a 3- to 7-membered, optionally substituted, saturated or unsaturated carbocycle or heterocycle which can contain up to three heteroatoms selected from the group O, N and S, x is 0, 1, 2, 3 or 4, z is 0 or 1, $W_E$ is —CO—, —CO—$N(R_W^2)$—, —$N(R_W^2)$—CO—, —$N(R_W^2)$—CO—$N(R_W^2)$—, —$N(R_W^2)$—CO—O—, —O—, —S—, —$SO_2$—, —$SO_2$—$N(R_W^2)$—, —$SO_2$—O—, —CO—O—, —O—CO—, —O—CO—$N(R_W^2)$—, —$NR_W^2$— or —$N(R_W^2)$—$SO_2$—, $R_W^2$, $R_W^{2*}$ independently of one another are hydrogen, a branched or unbranched, optionally substituted $C_1$-$C_6$-alkyl, $C_2$-$C_6$-alkenyl, $C_2$-$C_8$-alkynyl, CO—$C_1$-$C_6$-alkyl, CO—O—C, $C_1$-$C_6$-alkyl or $SO_2$—$C_1$-$C_6$-alkyl radical or an optionally substituted hetaryl, hetarylalkyl, arylalkyl, $C_3$-$C_7$-cycloalkyl, CO—O-alkylenearyl, CO-alkylenearyl, CO-aryl, $SO_2$-aryl, CO-hetaryl or $SO_2$-alkylenearyl radical, $R_E^{17}$ is hydrogen, a hydroxyl group, CN, halogen, a branched or unbranched, optionally substituted $C_1$-$C_6$-alkyl radical, an optionally substituted $C_3$-$C_7$-cycloalkyl, aryl, hetaryl or arylalkyl radical, a $C_2$-$C_6$-alkynyl or $C_2$-$C_6$-alkenyl radical optionally substituted by $C_1$-$C_4$alkyl or aryl, an optionally substituted $C_6$-$C_{12}$-bicycloalkyl, $C_1$-$C_6$-alkylene-$C_6$-$C_{12}$-bicycloalkyl, $C_7$-$C_{20}$-tricycloalkyl or $C_1$-$C_6$-alkylene-$C$-$_7$—$C_2$0-tricycloalkyl radical, or a 3- to 8-membered, saturated or unsaturated heterocycle substituted by up to three identical or different radicals, which can contain up to three different or identical heteroatoms O, N, S, where two radicals together can be a fused, saturated, unsaturated or aromatic carbocycle or heterocycle which can contain up to three different or identical heteroatoms O, N, S and the cycle can optionally be substituted or a further, optionally substituted, saturated, unsaturated or aromatic cycle can be fused to this cycle, or the radical $R_E^{17}$ forms, together with $R_W^2$ or $R_W^{2*}$ a saturated or unsaturated $C_3$-$C_7$-heterocycle which can optionally contain up to two further heteroatoms selected from the group O, S and N, $R_E^{11}$, $R_E^{11*}$ independently of one another are hydrogen, a branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl, CO—$C_1$-$C_6$-alkyl, CO—O—$C_1$-$C_6$-alkyl, CO—NH—$C_1$-$C_6$-alkoxyalkyl, CO—NH—$C_1$-$C_6$-alkyl or $SO_2$—$C_1$-$C_6$-alkyl radical or an optionally substituted hetaryl, arylalkyl, $C_3$-$C_7$-cycloalkyl, CO—O-alkylenearyl, CO—NH-alkylenearyl, CO-alkylenearyl, CO-aryl, CO—NH-aryl, $SO_2$-aryl, CO-hetaryl, $SO_2$-alkylenearyl, $SO_2$-hetaryl or $SO_2$-alkylenehetaryl radical, $R_E^{12}$ is hydrogen, a branched or unbranched, optionally substituted $C_1$-$C_6$-alkyl, $C_2$-$C_6$-alkenyl, $C_2$-$C_8$-alkynyl radical, an optionally substituted $C_3$-$C_1$-cycloalkyl, hetaryl, arylalkyl or hetarylalkyl radical or a radical CO—$R_E^{16}$, COO$R_E^{16}$ or $SO_2$—$R_E^{16}$, $R_E^{13}$, $R_E^{14}$ independently of one another are hydrogen, a hydroxyl group, a branched or unbranched, optionally substituted $C_1$-$C_6$-alkyl, $C_1$-$C_4$-alkoxy, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_E^{15}$ is hydrogen, a branched or unbranched, optionally substituted $C_1$-$C_6$-alkyl, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, $R_E^{16}$ is hydrogen, a hydroxyl group, a branched or unbranched, optionally substituted $C_1$-$C_6$-alkyl, $C_2$-$C_6$-alkenyl, $C_2$-$C_6$-alkynyl or $C_1$-$C_5$-alkylene-$C_1$-$C_4$-alkoxy radical, or an optionally substituted aryl, heterocycloalkyl, heterocycloalkenyl, hetaryl, $C_3$-$C_7$-cycloalkyl, $C_1$-$C_4$-alkylene-$C_3$-$C_7$-cycloalkyl, arylalkyl, $C_1$-$C_4$-alkylene-$C_3$-$C_7$-heterocycloalkyl, $C_1$-$C_4$-alkylene-$C_3$-$C_7$-heterocycloalkenyl or hetarylalkyl radical.

The coefficient c is preferably 0 or 1, the coefficient d is preferably 1 or 2, the coefficients f, g, h independently of one another are preferably 0 or 1 and $K^6$ is preferably 0.

An optionally substituted 4- to 11-membered mono- or polycyclic aliphatic or aromatic hydrocarbon which can contain up to 6 double bonds and up to 6 identical or different heteroatoms selected from the group consisting of N, O, S, where the ring carbons or ring nitrogens can optionally be substituted, for $Q_E$ and $X_E$ independently of one another is preferably understood as meaning optionally substituted arylene, such as optionally substituted phenylene or naphthylene, or optionally substituted hetarylene such as the radicals

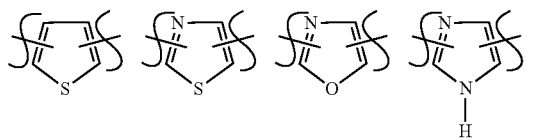

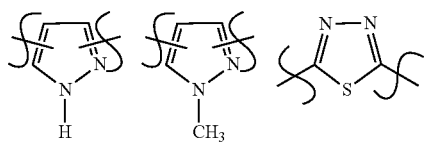

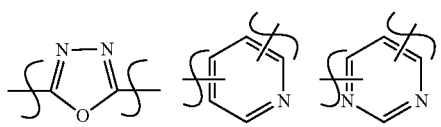

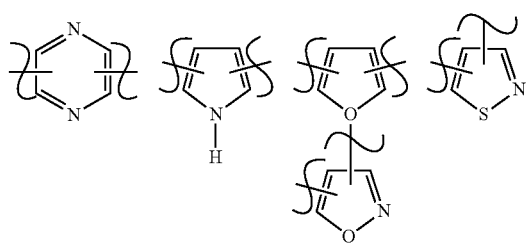

and their substituted or fused derivatives, or radicals of the formulae $I_E^1$ to $I_E^{11}$,

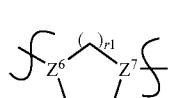
$I_E^1$

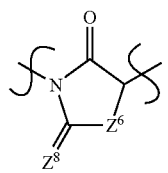
$I_E^2$

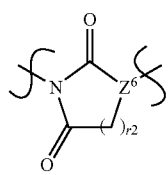
$I_E^3$

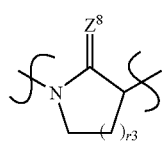
$I_E^4$

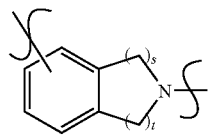
$I_E^5$

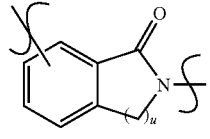
$I_E^6$

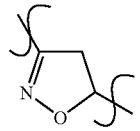
$I_E^7$

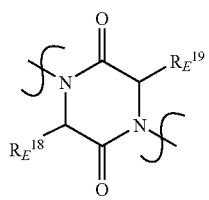
$I_E^8$

-continued

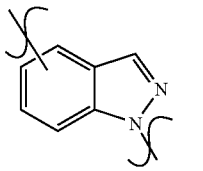
$I_E^9$

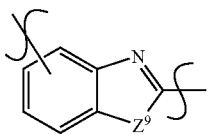
$I_E^{10}$

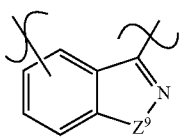
$I_E^{11}$ where the incorporation of the radicals can take place in both orientations. Aliphatic hydrocarbons are understood as meaning, for example, saturated and unsaturated hydrocarbons.

$Z^6$ and $Z^7$ are independently of one another CH or nitrogen.
$Z^8$ is oxygen, sulfur or NH,
$Z^9$ is oxygen, sulfur or $NR_E^{20}$.
r1, r2, r3 and t are independently of one another 0, 1, 2 or 3.
s and u are independently of one another 0, 1 or 2.

Particularly preferably, XE and QE independently of one another are optionally substituted phenylene, a radical

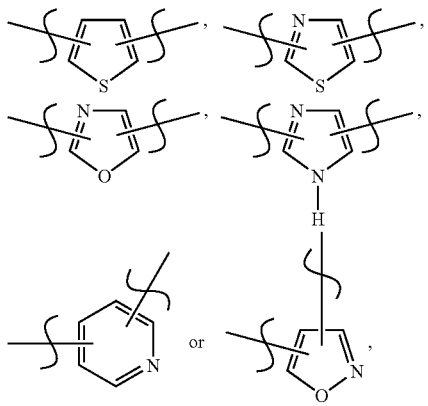

and their substituted or fused derivatives, or radicals of the formulae $IE^1$, $IE^2$, $IE^3$, $IE^4$ and $IE^7$, where the incorporation of the radicals can take place in both orientations.

$RE^{18}$ and $RE^{19}$ are independently of one another hydrogen, —$NO_2$, —$NH_2$, —CN, —COOH, a hydroxyl group, halogen, a branched or unbranched, optionally substituted $C_1$-$C_6$-alkyl, $C_1$-$C_4$-alkoxy, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical, as in each case described above.

$RE^{20}$ is, independently of one another, hydrogen, a branched or unbranched, optionally substituted $C_1$-$C_6$-alkyl, $C_1$-$C_6$-alkoxyalkyl, $C_3$-$C_{12}$-alkynyl, CO—$C_1$-$C_6$-alkyl, CO—O—$C_1$-$C_6$-alkyl or $SO_2$—$C_1$-$C_6$-alkyl radical or an optionally substituted $C_3$-$C_7$-cycloalkyl, aryl, arylalkyl, CO—O-alkylenearyl, CO-alkylenearyl, CO-aryl, $SO_2$-aryl, hetaryl, CO-hetaryl or $SO_2$-alkylenearyl radical, preferably hydrogen or a branched or unbranched, optionally substituted $C_1$-$C_6$-alkyl radical.

YE and ZE are independently of one another CO, CO—$NRE^{12}$, $NRE^{12}$-CO, sulfur, SO, $SO_2$, $SO_2$—$NRE^{12}$, $NRE^{12}$-$SO_2$, CS, CS—$NRE^{12}$, $NRE^{12}$-CS, CS—O, O—CS, CO—O, O—CO, oxygen, ethynylene, $CRE^{13}$-O—$CRE^{14}$, C(=$CRE^{13}RE^{14}$), $CRE^{13}$=$CRE^{14}$, —$CRE^{13}(ORE^{15})$—$CHRE^{14}$-14 or —$CHRE^{13}CRE^{14}(ORE^{15})$-, preferably CO, $SO_2$ and oxygen.

$RE^{12}$ is hydrogen, a branched or unbranched, optionally substituted $C_1$-$C_6$-alkyl, $C_2$-$C_6$-alkenyl or $C_2$-$C_8$-alkynyl radical or an optionally substituted $C_3$-$C_7$-cycloalkyl, hetaryl, arylalkyl or hetarylalkyl radical, such as correspondingly described above for $RG^7$ or a radical CO-$RE^{16}$, COO$RE^{16}$ or $SO_2$—$RE^{16}$, preferably hydrogen, methyl, allyl, propargyl and cyclopropyl.

A branched or unbranched, optionally substituted $C_1$-$C_6$-alkyl, $C_2$-$C_6$-alkenyl or $C_2$-$C_6$-alkynyl radical or an optionally substituted $C_3$-$C_7$-cycloalkyl, aryl, arylalkyl, hetaryl or hetarylalkyl radical for $RE^{13}$, $RE^{14}$ or $RE^{15}$ independently of one another is understood as meaning, for example, the corresponding radicals described above for $RG^7$.

A branched or unbranched, optionally substituted $C_1$-$C_4$-alkoxy radical for $RE^{13}$ or $RE^{14}$ independently of one another is understood as meaning, for example, the $C_1$-$C_4$-alkoxy radicals described above for $RA^{14}$.

Preferred alkylenecycloalkyl radicals for $RE^{13}{}_1RE^{14}$ or $RE^{15}$ independently of one another are, for example, the $C_1$-$C_4$-alkylene-$C_3$-$C_7$-cycloalkyl radicals described above for $RG^7$.

A branched or unbranched, optionally substituted $C_1$-$C_6$-alkyl, $C_2$-$C_6$-alkenyl, $C_2$-$C_6$-alkynyl or $C_1$-$C_5$-alkylene-$C_1$-$C_4$-alkoxy radical, or an optionally substituted aryl, heterocycloalkyl, heterocycloalkenyl, hetaryl, $C_3$-$C_7$-cycloalkyl, $C_1$-$C_4$-alkylene-$C_3$—C.sub.7-cycloalkyl, arylalkyl, $C_1$-$C_4$-alkylene-$C_3$-$C_7$-heterocycloalkyl, $C_1$-$C_4$-alkylene-$C_3$-$C_7$-heterocycloalkenyl or hetarylalkyl radical for $RE^{16}$ is understood as meaning, for example, the corresponding radicals described above for $RG^{11}$.

A branched or unbranched, optionally substituted $C_1$-$C_6$-alkyl, $C_2$-$C_6$-alkenyl, $C_2$-$C_6$-alkynyl or alkylenecycloalkyl radical or an optionally substituted $C_3$-$C_7$-cycloalkyl, aryl, arylalkyl, hetaryl or hetarylalkyl radical for $RE^1$, $RE^2$, $RE^3$, $RE^4$, $RE^5$, $RE^6$, $RE^7$, $RE^8$, $RE^9$ or $RE^{10}$ independently of one another is understood as meaning, for example, the corresponding radicals mentioned above for $RG^7$.

Further, two radicals $RE^3$ and $RE^4$ or $RE^5$ and $RE^6$ or $RE^7$ and $RE^8$ or $RE^9$ and $RE^{10}$ can in each case independently of one another together form a 3- to 7-membered, optionally substituted, saturated or unsaturated carbo- or heterocycle which can contain up to three heteroatoms from the group consisting of O, N and S.

The radical —$(CH2)x$-(WE)$Z$—$RE^{17}$ is composed of a CO—$C_4$-alkylene radical, optionally a bonding element WE selected from the group —CO—, —N($R^{12}$)—CO—, —N($RW^2$)—CO—N($RW^{2*}$)—, —N($R^2$)—CO—O—, O—S—, —$SO_2$—, —$SO_2$—N($RW^2$)—, —$SO_2$—O, —CO—O—, —O—CO—O—CO—N($RW^2$)—, —N($RW^2$)— or —N($RW^2$)—$SO_2$—, preferably selected from the group —CO—N($RW^2$)—, —N($RW^2$)—CO—, —O—, —$SO_2$N($RW^2$)—, —N($RW^2$)— or —N($RW^2$)—$SO_2$—, and the radical $RE^{17}$, where $RW^2$ and $RW^{2*}$ independently of one another are hydrogen, a branched or unbranched, optionally substituted $C_1$-$C_6$-alkyl, $C_2$-$C_6$-alkenyl, $C_2$-$C_8$-alkynyl, CO—$C_1$-$C_6$-alkyl, CO—O—$C_1$-$C_6$- alkyl or $SO_2$—$C_1$-$C_6$-alkyl radical or an optionally substituted hetaryl, hetarylalkyl, arylalkyl, $C_3$-$C_7$-cycloalkyl, CO—O-alkylenearyl, CO-alkylenearyl, CO-aryl, $SO_2$-aryl, CO-hetaryl or $SO_2$-alkylenearyl radical, preferably independently of one another are hydrogen, methyl, cyclopropyl, allyl, propargyl, and $RE^{17}$ is hydrogen, a hydroxyl group, CN, halogen, a branched or unbranched, optionally substituted $C_1$-$C_6$-alkyl radical, an optionally substituted $C_3$-$C_7$-cycloalkyl, aryl, hetaryl or arylalkyl radical, a $C_2C_6$alkynyl or $C_2$-$C_6$-alkenyl radical optionally substituted by $C_1$-$C_4$alkyl or aryl, an optionally substituted $C_6$-$C_{12}$-bicycloalkyl, $C_1$-$C_6$-alkylene-$C_6$-$C_{12}$-bicycloalkyl, $C_7$-$C_{20}$-tricycloalkyl or $C_1$-$C_6$-alkylene-$C_7$-C-20-tricycloalkyl radical, or a 3- to 8-membered, saturated or unsaturated heterocycle which is substituted by up to three identical or different radicals and can contain up to three different or identical heteroatoms O, N, S, where two radicals together can be a fused, saturated, unsaturated or aromatic carbocycle or heterocycle which can contain up to three different or identical heteroatoms O, N, S, and the cycle can be optionally substituted or a further, optionally substituted, saturated, unsaturated or aromatic cycle can be fused to this cycle, such as optionally substituted 2-pyridyl, 3-pyridyl, 4-pyridyl, 2-furyl, 3-furyl, 2-pyrrolyl, 3-pyrrolyl, 2-thienyl, 3-thienyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 2-(1,3,4-thiadiazolyl), 2-(1,3,4)-oxadiazolyl, 3-isoxazolyl, 4-isoxazolyl, 5-isoxazolyl or triazinyl.

Further, $RE^{17}$ and $RW^2$ or $RW^{2*}$ can together form a saturated or unsaturated $C_3$-$C_7$-heterocycle which can optionally contain up to two further heteroatoms selected from the group consisting of O, S and N.

Preferably, the radicals $RE^{17}$ and $RW^2$ or $RW^{2*}$ together form a cyclic amine as the $C_3$-$C_7$-heterocycle in the case where the radicals are bonded to the same nitrogen atom, such as N-pyrrolidinyl, N-piperidinyl, N-hexahydroazepinyl, N-morpholinyl or N-piperazinyl where in heterocycles which carry free amine protons, such as N-piperazinyl, the free amine protons can be replaced by customary amine protective groups, such as methyl, benzyl, Boc (tert-butoxycarbonyl), Z (benzyloxycarbonyl), tosyl, —$SO_2$—$C_1$-$C_4$-alkyl, —$SO_2$-phenyl or —$SO_2$-benzyl.

Preferred radicals for $RE^1$, $RE^2$, $RE^3$, $RE^4$, $RE^5$, $RE^6$, $RE^7$, $RE^8$, $RE^9$ or $RE^{10}$ are independently of one another hydrogen, halogen, a branched or unbranched, optionally substituted $C_1$-$C_6$-alkyl radical, optionally substituted aryl or the radical —$(CH_2)x$-$(WE)z$—$RE^{17}$.

Particularly preferred radicals for $RE^1$, $RE^2$, $RE^3$, $RE^4$, $RE^5$, $RE^6$, $RE^7$, $RE^8$, $RE^9$ or $RE^{10}$ are independently of one another hydrogen, F, a branched or unbranched, optionally substituted $C_1$-$C_4$-alkyl radical, in particular methyl.

A branched or unbranched, optionally substituted $C_1$-$C_6$-alkyl, $C_1$-$C_6$-alkoxyalkyl, $C_2$-$C_6$-alkenyl, $C_2$-$C_{12}$-alkynyl or arylalkyl radical or an optionally substituted aryl, hetaryl or $C_3$-$C_1$-cycloalkyl for $RE^{11}$ and $RE^{11*}$ in structural element E independently of one another is understood as meaning, for example, the corresponding radicals described above for $RG^7$.

The branched or unbranched, optionally substituted radicals CO—$C_1$-$C_6$-alkyl, CO—O—$C_1$-$C_6$-alkyl, CO—NH—$C_1$-$C_6$-alkoxalkyl, CO—NH—$C_1$-$C_6$-alkyl or $SO_2$—$C_1$-$C_6$-alkyl radical or the optionally substituted radicals Co—O-alkylenearyl, CO—NH-alkylenearyl, CO-alkylenearyl, CO-aryl, CO—NH-aryl, $SO_2$-aryl, CO-hetaryl, $SO_2$-alkylenearyl, $SO_2$-hetaryl or $SO_2$-alkylenehetaryl for $RE^{11}$ and $RE^{11*}$ independently of one another are composed, for example, of the corresponding groups CO, COO, CONH or $SO_2$ and the corresponding radicals mentioned above.

Preferred radicals for $RE^{11}$ or $RE^{11*}$ are independently of one another hydrogen, a branched or unbranched, optionally substituted $C_1$-$C_6$-alkyl, $C_1$-$C_6$-alkoxy, $C_2$-$C_6$-alkenyl, $C_2$-$C_{12}$-alkynyl or arylalkyl radical, or an optionally substituted hetaryl or $C_3$-$C_7$-cycloalkyl radical.

Particularly preferred radicals for $RE^{11}$ or $RE^{11*}$ are hydrogen, methyl, cyclopropyl, allyl or propargyl.

In a particularly preferred embodiment of structural element $E_1$, structural element $E_1$ is a radical —$CH_2$—$CH_2$—CO—$CH_2$—$CH_2$—$CH_2$—CO— or a $C_1$-$C_5$-alkylene radical.

In a particularly preferred embodiment of structural element E, the spacer structural element E used is a structural element of the formula $I_{E1E2}$ $$\text{-}E_2\text{-}E_1\text{-} \qquad\qquad I_{E1E2}$$

where the structural elements $E_2$ and $E_1$ have the meanings described above.

Preferred structural elements E are composed of at least one preferred radical of the radicals belonging to structural element E, while the remaining radicals are widely variable.

Particularly preferred structural elements E are composed of the preferred radicals of structural element E.

Preferred structural elements B are composed either of the preferred structural element A, while E is widely variable or of the preferred structural element E, while A is widely variable.

The compounds of the formula I, and also the intermediates for their preparation, can have one or more asymmetric substituted carbon atoms. The compounds can be present as pure enantiomers or pure diastereomers or as a mixture thereof. The use of an enantiomerically pure compound as the active compound is preferred.

The compounds of the formula I can also be present in other tautomeric forms.

The compounds of the formula I can also be present in the form of physiologically tolerable salts.

The compounds of the formula I can also be present as prodrugs in a form in which the compounds of the formula I are liberated under physiological conditions. By way of example, reference may be made here to the group T in structural element L, which in some cases contains groups which are hydrolyzable to the free carboxylic acid group under physiological conditions. Derivatized structural elements B or A are also suitable which liberate the structural element B or A respectively under physiological conditions.

In preferred compounds of the formula I, in each case one of the three structural elements B, G or L has the preferred range, while the remaining structural elements are widely variable.

In particularly preferred compounds of the formula I, in each case two of the three structural elements B, G or L have the preferred range, while the remaining structural elements are widely variable.

In very particularly preferred compounds of the formula I, in each case all three structural elements B, G or L have the preferred range, while the remaining structural element is widely variable.

Preferred compounds of the formula I contain, for example, the preferred structural element G, while the structural elements B and L are widely variable.

In particularly preferred compounds of the formula I, for example, B is replaced by the structural element A-E- and the compounds contain, for example, the preferred structural element G and the preferred structural element A, while the structural elements E and L are widely variable.

Further particularly preferred compounds of the formula I contain, for example, the preferred structural element G and the preferred structural element A, while the structural elements E and L are widely variable.

Very particularly preferred compounds of the formula I in which A-E- is B— are listed below, the number before the text block being the number of an individualized compound of the formula I, and in the text block A-E-G-L the abbreviations being separated by a bonding dash in each case for an individual structural element A, E, G or L and the meaning of the abbreviations of the structural elements being explained after the table.

No. A-E-G-L
1 bhs-dibema2-mmophec-es
2 gua-mepipe2-phec-es
3 gua-35thima2-4-phaz-es
4 bhs-apma2-pclphec-es gua-a23thima2-4-bec-es
6 bim-dibema2-4-bec-es
7 2py-bam2-pipmaz-es
8 bim-bam2-mmphec-es
9 2py-a23thima2-thec-es gua-pipa2-4-pec-es
11 dhim-35thima2-thec-es
12 gua-a24thima2-amaz-es
13 bim-pyma2-phec-es
14 gua-a24thima2-3bzlaz-es bhs-inda2-thec-es
16 2py-a24thima2-3bec-nes
17 gua-a24thima2-phaz-es
18 gua-bam2-pymaz-es
19 gua-me35thima2-phec-es
2py-dibema2-4-pec-es
21 bhs-35thima2-thec-gs
22 bhs-aaf-3bec-es
23 im-35thima2-thec-es
24 bhs-a23thima2-31pec-es bim-pipa2-4-pec-es
26 bhs-mea2-thec-es
27 gua-dibema2-7 cmc-es
28 2py-apma2-phaz-es
29 bhs-apma2-7 cmc-es thpyrn-bam2-4-pec-es
31 bim-me35thima2-4-pec-es
32 bim-a24thima2-3bec-es
33 bhs-me42thiaz2-phaz-es
34 2py-42thiaz2-thec-es
2py-pipa2-cpec-es
36 bim-35thima2-pyrnaz-es
37 bhs-a23thima2-3bec-es
38 2py-apma2-ppec-es
39 bhs-35thima2-pclphec-es
40 2py-buta-3bec-es
41 bim-a23thima2-7 cmc-gs
42 bhs-hexa-thec-es
43 bim-a23thima2-4-pec-f2es
44 2py-35thima2-7 cmc-es
45 gua-chex2-4-pec-es
46 bhs-edia2-thec-es
45 47 bhs-bam2-phaz-es
48 amim-35thima2-3bec-es
49 clim-apma2-3bec-es
50 gua-pipa2-phec-mals
51 am2py-a24thima2-thec-es
52 bhs-apma2-phaz-gs
53 2py-inda2-thec-es
54 bim-35thima2-mmophec-es
55 2py-inda2-3bec-es
56 2py-mepipe2-thec-es
57 bim-bam2-thec-es
58 bim-bam2-4-phaz-es
59 2py-apma2-3bec-es
60 bhs-a24thima2-pmophec-es
61 bim-dibema2-thec-es
62 mam2py-a24thima2-phaz-es
63 2py-meat-3bec-es
64 bim-penta-4-pec-es
65 gua-prodia2-7 cmc-es
66 bhs-dibema2-cpec-es
67 2py-hexa-phaz-es
68 gua-apma2-31pec-es
69 bim-apma2-phec-ms
70 gua-35thima2-phec-ps
71 bim-pipa2-3bec-es
72 gua-a23thima2-phec-es
73 2py-42thiaz2-phaz-es
74 bim-me35thima2-7 cmc-es
75 bhs-bam2-mpphec-es
76 gua-dibema2-thec-es
77 clim-bam2-thec-es
78 dimethpym-a23thima2-thec-es
79 gua-dibema2-4-pec-es
80 bhs-apma2-3bzlaz-es
81 gua-a24thima2-4-pec-es
82 bhs-pyma2-phaz-es
83 gua-apma2-7 cmc-es
84 bhs-a23thima2-4-phaz-es
85 bhs-penta-3bec-es
86 gua-aof-7 cmc-es
87 2py-a23thima2-phaz-ms
88 bim-dibema2-phaz-es
40 89 bim-35thima2-phec-as
90 bim-apma2-cpec-es
91 bhs-pipa2-3bec-nes
92 2py-pipa2-mmophec-es
93 bhs-35thima2-3bec-es
45 94 bhs-dibema2-phaz-es
95 gua-pipa2-3bec-es
96 bim-pipa2-phec-es
97 gua-42thiaz2-phec-es
98 pippy-a24thima2-4-pec-es
99 2py-35thima2-thec-es
100 2py-bam2-7 cmc-es
101 2py-35thima2-pmophec-es
102 bhs-dibema2-thec-es
103 bim-aof-4-pec-es
104 bim-hexa-phec-es
105 2py-a24thima2-7 cmc-es
106 gua-a24thima2-phec-gs
107 gua-me25thima2-7 cmc-es
108 clim-a24thima2-7 cmc-es
109 gua-apma2-4-pec-es
110 bim-35thima2-cpec-es
111 2py-me3 5thima2-thec-es
112 bhs-a24thima2-dbc-es
113 bim-bam2-4-pec-es
114 amim-a24thima2-4-pec-es
115 2py-dibema2-amec-es
116 2py-a23thima2-dbc-es
117 bim-bam2-4-pec-ps
118 2py-ba m2-mmophec-es
119 bim-apma2-3bec-es
120 bhs-pdagk-thec-es
121 gua-42thiaz2-7 cmc-es 122 gua-a23thima2-thec-es
123 bim-apma2-4-pec-es
124 thpym-35thima2-phec-es
125 bim-bam2-7 cmc-es
126 mam2py-bam2-4-pec-es
127 bhs-edia2-3bec-es
128 bhs-a23thima2-amec-es
129 gua-dibema2-3bec-es
130 bim-me42thiaz2-7 cmc-es
131 bhs-a23thima2-phec-es
132 bim-dibema2-mpphec-es
133 2py-prodia2-thec-es
134 bhs-bam2-mophaz-es
135 bhs-a24thima2-7 cmc-es
136 im-dibema2-4-pec-es
137 imhs-a24thima2-thec-es
138 bhs-a24thima2-dmaphec-es
139 2py-pipa2-dmaphec-es
140 2py-a24thima2-4-pec-es
141 2py-dibema2-7 cmc-es
142 bhs-apma2-phaz-es
143 gua-pipa2-mophaz-es
144 dhim-dibema2-4-pec-es
145 gua-pipa2-mpphec-es
146 bim-a23thima2-4-pec-es
147 2py-dibema2-4-phaz-es
148 bim-42thiaz2-4-pec-es
149 am2py-dibema2-3bec-es
150 bim-pipa2-7 cmc-es
151 gua-bam2-dmaphec-es
152 bhs-pipa2-amec-es
153 2py-apma2-mpphec-es
154 2py-hexa-3bec-es
155 bim-apma2-7 cmc-es
156 bim-a23thima2-pclphec-es
157 gua-a24thima2-pclphec-es
158 bim-a23thima2-phec-es
159 bim-a24thima2-4-pec-es
160 bhs-a23thima2-7 cmc-es
161 dimethpym-dibema2-phaz-es
162 2py-me25thima2-3bec-es
163 bhs-aof thec-es
164 gua-dibema2-phec-f2es
165 amim-a23thima2-phec-es
166 2py-bam2-pclphec-es
167 bhs-pyma2-thec-es
168 2py-a24thima2-3bec-es
169 bim-bam2-phec-es
170 bim-35thima2-7 cmc-es
171 bhs-35thima2-pipmaz-es
172 bim-prodia2-phec-es
173 bim-35thima2-phec-es
174 gua-edia3-4-pec-es
175 gua-a23thima2-ppec-es
176 gua-pipeme2-phec-es
177 gua-dibema2-phaz-es
178 2py-bam2-3bec-es
179 bhs-bam2-3bec-mals
180 mam2py-apma2-7 cmc-es
181 bhs-bam2-pmophec-es
182 gua-bam2-7 cmc-es
183 gua-buta-phec-es
184 bim-pyma2-7 cmc-es 185 2py-pipa2-thec-ms
186 bhs-dibema2-dmaphec-es
187 bim-a24thima2-ppec-es
188 am2py-barn2-7 cmc-es
189 bim-buta-7 cmc-es
190 im pipa2-phec-es
191 gua-dibema2-4-pec-gs
192 2py-buta-thec-es
193 2py-pipa2-7 cmc-es
194 2py-apma2-phec-es
195 bim-pipa2-phec-gs
196 bim-me25thima2-phec-es
197 2py-pyma2-3bec-es
198 gua-barn2-pmophec-es
199 gua-35thima2-4-pec-es
200 2py-pipeme2-thec-es
201 bhs-35thima2-phaz-f2es
202 bhs-edia3-phaz-es
203 2py-apma2-thec-pms
204 im apma2-phaz-es
205 bim-chex2-phec-es
206 bhs-35thima2-4-pec-es
207 gua-a23thima2-phaz-es
208 2py-me25thima2-phaz-es
209 2py-a23thima2-pmophec-es
210 bhs-chex2-3bec-es
211 2py-dibema2-3lpec-es
212 2py-bam2-phec-es
213 bhs-dibema2-phec-es
214 bim-a24thima2-thec-es
215 bim-pipa2-thec-es
216 bhs-buta-phaz-es
217 bhs-mepipe2-phaz-es
218 gua-buta-4-pec-es
219 am2py-a23thima2-phaz-es
220 gua-bam2-thec-es
221 gua-pdagk-4-pec-es
222 bim-pdagk-phec-es
223 2py-35thima2-phec-es
224 gua-35thima2-7 cmc-es
225 gua-bam2-3bec-es
226 bhs-bam2-3bec-es
227 gua-a23thima2-7 cmc-es
228 bhs-aepi2-thec-es
229 clim-pipa2-7 cmc-es
230 2py-a23thima2-3bec-es
231 bim-a23thima2-3bzlaz-es
232 bhs-pipa2-3bec-es
233 bim-pipa2-mmphec-es
234 clim-dibema2-phec-es
235 bhs-aepi2-3bec-es
236 2py-apma2-4-pec-es
237 dhim-a23thima2-7 cmc-es
238 bim-pipa2-pclphec-es
239 gua-mepipe2-7 cmc-es
240 gua-35thima2-3lpec-es
241 bhs-chex2-thec-es
242 bim-inda2-7 cmc-es
243 bhs-pipa2-phaz-es
244 imhs-pipa2-thec-es
245 gua-apma2-4-phaz-es
246 gua-me25thima2-4-pec-es
247 gua-35thima2-phec-es
248 bim-pipa2-amaz-es
249 2py-a24thima2-4-phaz-es
250 2py-me42thiaz2-3bec-es
251 imhs-apma2-phec-es
252 bhs-pipeme2-thec-es
253 dhim-a24thima2-phec-es
254 2py-a23thima2-7 cmc-es
255 2py-pipa2-pymaz-es
256 2py-me35thima2-3bec-es 257 bim-apma2-7 cmc-as
258 bhs-35thima2-amaz-es
259 mam2py-dibema2-thec-es
260 dimethpym-apma2-4-pec-es
261 bhs-bam2-4-bec-es
262 2py-a23thima2-cpec-es
263 mam2py-35thima2-phec-es
264 am2py-apma2-phec-es
265 gua-a23thima2-4-pec-es
266 bim-a24thima2-phec-es
267 2py-pipa2-thec-es
268 2py-dibema2-thec-es
269 pippy-pipa2-4-pec-es
270 bim-dibema2-7 cmc-es
271 bim-dibema2-phec-es
272 gua-pdagk-7 cmc-es
273 bhs-35thima2-thec-es
274 bhs-a23thima2-mmphec-es
275 bhs-a23thima2-thec-nes
276 bim-me25thima2-7 cmc-es
277 2py-a24thima2-phec-es
278 gua-bam2-dbc-es
279 amim-dibema2-7 cmc-es
280 2py-a23thima2-4-pec-es
281 thpym-dibema2-thec-es
282 2py-pipa2-phec-es
283 bhs-a24thima2-pymaz-es
284 gua-dibema2-amaz-es
285 dhim-bam2-3bec-es
286 gua-bam2-7 cmc-ms
287 bhs-edia3-thec-es
288 bim-a24thima2-phec-mals
289 bim-a24thima2-mophaz-es
290 gua-dibema2-phec-es
291 bhs-pipa2-4-pec-es
292 bhs-apma2-pipmaz-es
293 gua-dibema2-pipmaz-es
294 gua-aepi2-4-pec-es
295 gua-pipa2-ppec-es
296 bim-mea2-7 cmc-es
297 gua-pipa2-pmophec-es
298 imhs-bam2-7 cmc-es
299 gua-a24thima2-7 cmc-f2es
300 thpym-a23thima2-3bec-es
301 bim-mepipe2-7 cmc-es
302 thpym-pipa2-phaz-es
303 bim-aaf-7 cmc-es
304 bim-edia3-phec-es 305 2py-a24thima2-thec-es
306 bim-pipa2-phaz-es
307 dimethpym-bam-phec-es
308 bim-a24thima2-phaz-es
309 bhs-bam2-phaz-pms
310 2py-35thima2-3bec-es
311 2py-35thima2-mophaz-es
312 gua-apma2-phaz-es
313 bim-apma2-phaz-es
314 gua-35thima2-7 cmc-nes
315 bhs-pipa2-phec-es
316 bhs-mepipe2-3bec-es
317 gua-pipa2-phaz-es
318 2py-a23thima2-phec-es
319 2py-pipa2-4-pec-es
320 gua-apma2-mmphec-es
321 2py-apma2-7 cmc-es
322 gua-a24thima2-phec-es
323 bhs-a23thima2-4-pec-es
324 bim-35thima2-phaz-es
325 bim-pipeme2-7 cmc-es
326 bhs-42thiaz2-3bec-es
327 pippy-a23thima2-phec-es
328 2py-aof thec-es
329 2py-pdagk-phaz-es
330 gua-aepi2-7 cmc-es
331 dimethpym-pipa2-3bec-es
332 gua-35thima2-amec-es
333 bhs-inda2-phaz-es
334 2py-pipeme2-3bec-es
335 gua-apma2-4-pec-nes
336 gua-edia2-4-pec-es
337 gua-a24thima2-phec-es
338 gua-apma2-3bec-es
339 gua-aaf-phec-es
340 gua-apma2-thec-es
341 bim-apma2-pymaz-es
342 im a24thima2-phec-es
343 2py-a24thima2-amec-es
344 bim-pdagk-7 cmc-es
345 bim-pipa2-3bzlaz-es
346 2py-mea2-phaz-es
347 amim-bam-phaz-es
348 2py-pipa2-3bec-es
349 dhim-apma2-phaz-es
350 2py-35thima2-4-pec-es
351 bhs-aof-3bec-es
352 2py-dibema2-phaz-nes
353 gua-a24thima2-3bec-es
354 bhs-dibema2-pymaz-es
355 bim-a24thima2-4-bec-es
356 bhs-bam2-4-pec-es
357 bim-35thima2-thec-es gua-penta-phec-es
358 bim-buta-4-pec-es
359 bhs-apma2-amaz-es
360 dimethpym-a24thima2-3bec-es
361 gua-a2-3thima2-7 cmc-mals
362 gua-dibema2-3bzlaz-es
363 2py-edia2-3bec-es
364 2py-aaf-thec-es
364 gua-a24thima2-7 cmc-es
365 2py-diberna2-nunphee-es
366 hs-apma2-3bee-es
367 im-dibema2-ppec-es
368 ua-35thima2-phaz-es
369 py-me42thisz2-thec-es
370 im-35thima2-dbc-es
371 hs-prodia2-3bee-es
372 ua-35thima2-mmphec-es
373 hs-hexa-3bec-es
374 hs-penta-phaz-es
375 him-pipa2-phec-es
376 ua-bam2-phec-es
377 dhim-pipa2-phec-es
378 gua-bam2-phec-es
379 2py-apma2-phaz-mals
380 bim-apma2-dbc-es
381 gua-inda2-phec-es
382 2py-bam2-thec-es
383 gua-pipa2-4-bec-es
384 am2py-35thima2-4-pee-es
385 bim-a24thima2-mpphec-es
386 2py-35thima2-4-bec-es
387 bhs-pipa2-7 cmc-es
388 amim-pipa2-4-pec-es
389 bhs-apma2-4-pec-es
390 gua-a23thima2-phee-pms 391 bim-35thima2-4-pec-es
392 bhs-a24thima2-thec-es
393 thpym-a24thima2-phaz-es
394 bim-mea2-phec-es
395 bim-a23thima2-thec-es
396 pippy-apma2-thec-es
397 2py-35thima2-ppec-es
398 im a23thima2-7 cmc-es
399 gua-mea2-4-pec-es
400 gua-edia2-7 cmc-es
401 mam2py-pipa2-phaz-es
402 bhs-apma2-3bec-f2es
403 bim-aepi2-phec-es
404 2py-aepi2-phaz-es
405 2py-35thima2-thec-mals
406 2py-bam2-phaz-es
407 am2py-pipa2-thec-es
408 bhs-bam2-ppec-es
409 2py-dibema2-thec-ps
410 gua-pipa2-7 cmc-es
411 gua-bam2-4-pec-as
412 bhs-apma2-thec-es
413 clim-35thima2-phaz-es
414 2py-bam2-amaz-es
415 bhs-pipa2-phaz-ps
416 gua-bam2-phaz-es
417 bhs-apma2-mmophec-es
418 gua-a24thima2-thec-es
419 gua-chex2-7 cmc-es
420 2py-penta-thec-es
421 2py-edia2-phaz-es
422 gua-pipa2-phec-es
423 bim-chex2-4-pec-es
424 gua-dibema2-mmophec-es
425 2py-35thima2-phaz-es
426 bim-dibema2-mophaz-es
427 bim-me42thiaz2-4-pec-es
428 2py-pyma2-phaz-es
429 bhs-a24thima2-3bec-es
430 2py-Penta-phaz-es
431 bim-dibema2-pmophec-es
432 gua-pipa2-4-pec-pms
433 bim-a23thima2-nunophec-es
434 2py-dibema2-phec-es
435 gua-a24thima2-pipmaz-es
436 bim-apma2-phec-es
437 bhs-pipa2-mpphec-es
438 gua-a23thima2-3bec-es
439 bim-a23thima2-amaz-es
440 bhs-dibema2-4-pec-es
441 imhs-35thima2-4-pec-es
442 imhs-a23thima2-phaz-es
443 bim-bam2-phec-nes
444 bhs-dibema2-3bec-es
445 bhs-a24thima2-phaz-es
446 gua-apma2-7 cmc-ps
447 amim-apma2-thec-es
448 bim-edia3-7 cmc-es
449 gua-bam2-cpec-es
450 gua-inda2-4-pec-es
451 gua-edia3-phec-es
452 2py-pipa2-dbc-es
453 2py-a24thima2-mmphec-es
454 bim-pipa2-pipmaz-es
455 2py-a23thima2-dmaphec-es
456 bim-a23thima2-3bec-es
457 2py-pdagk-3bec-es
458 bim-dibema2-3bec-es
459 bim-apma2-thec-es
460 2py-bam2-4-pec-es
461 bhs-me35thima2-3bec-es
462 gua-35thima2-3bec-es
463 pippy-35thima2-3bec-es
464 2py-bam2-3bec-gs
465 2py-bam2-3bzlaz-es
466 bhs-pipeme2-phaz-es
467 bim-mepipe2-4-pec-es
468 bhs-dibema2-thec-as
469 2py-apma2-thec-es
470 bim-35thima2-3bec-es
471 bhs-me35thima2-phaz-es
472 bim-prodia2-4-pec-es
473 bhs-mea2-phaz-es
474 gua-a24thima2-mmophec-es
475 gua-pipeme2-4-pec-es
476 bim-a23thima2-phaz-es
477 gua-prodia2-phec-es
478 gua-dibema2-pclphec-es
479 bhs-Raf-phaz-es
480 2py-chex2-phaz-es
481 bim-35thima2-dmaphec-es
482 imhs-dibema2-3bec-es
483 2py-bam2-thec-f2es
484 bhs-35thima2-phec-es
485 bim-a23thima2-7 cmc-es
486 bhs-apma2-phec-es
487 bim-apma2-pmophec-es
488 bim-dibema2-7 cmc-pms
489 gua-35thima2-thec-es
490 bhs-pipa2-4-phaz-es
491 2py-dibema2-phaz-es
492 bim-apma2-dmaphec-es
493 bim-edia2-phec-es
494 2py-dibema2-3bec-es
495 bhs-35thima2-mmphec-es
496 gua-apma2-phec-es
497 bim-bam2-amec-es
498 gua-apma2-amec-es
499 bhs-35thima2-7 cmc-es
500 bhs-me25thima2-thec-es
501 bhs-dibema2-7 cmc-es
502 gua-hexa-4-pec-es
503 bim-bam2-3bec-es
504 bhs-pipa2-31pec-es
505 2py-apma2-4-bec-es
506 dimethpym-35thima2-7 cmc-es
507 bhs-bam2-phec-es
508 bhs-dibema2-3bec-ms
509 bhs-35thima2-3bzlaz-es
510 gua-penta-7 cmc-es
511 bhs-a23thima2-thec-es
512 clim-a23thima2-4-pec-es
513 bhs-me42thinz2-3bec-es
514 bhs-35thima2-phaz-es
515 bhs-a24thima2-4-pec-es
516 bhs-a23thima2-phaz-es
517 bhs-bam2-thec-es
518 2py-35thima2-mpphec-es
519 bhs-dibema2-dbc-es
520 2py-35thima2-3bec-pms
521 2py-a24thima2-phaz-es
522 gua-aaf-7 cmc-es
523 gua-me42thiaz2-phec-es
524 bim-a23thima2-pipmaz-es 525 bim-a24thima2-7 cmc-es
526 im-bam2-3bec-es
527 bhs-a24thima2-cpec-es
528 bim-bam2-phaz-es
529 2py-apma2-mophaz-es
530 bim-pipa2-7 cmc-f2es
531 gua-a23thima2-mpphec-es
532 2py-a23thima2-3bec-as
533 gua-pyma2-4-pec-es
534 2py-pipa2-phaz-es
535 2py-edia3-3bec-es
536 mam2py-a23thima2-3bec-es
537 2py-a24thima2-31pec-es
538 2py-aof-phaz-es
539 gua-hexa-7 cmc-es
540 bhs-a23thima2-3bec-ps
541 bim-a24thima2-4-pec-pms
542 bim-aaf-4-pec-es
543 bhs-pipa2-thec-es
544 pippy-dibema2-7 cmc-es
545 gua-pipa2-thec-es
546 bhs-bam2-7 cmc-es
547 gua-bam2-4-pec-es
548 bim-aepi2-4-pec-es
549 2py-prodia2-phaz-es
550 2py-a23thima2-phaz-es
551 bim-35thima2-4-pec-ms
552 bim-dibema2-4-pec-mals
553 bhs-a24thima2-thec-ms
554 bim-42thiaz2-phec-es
555 2py-a24thima2-phaz-ps
556 bim-aof-phec-es
557 2py-a23thima2-pymaz-es
558 gua-a23thima2-mophaz-es
559 thpym-apma2-7 cmc-es
560 bim-bam2-31pec-es
561 pippy-bam2-phaz-es
562 im-dibema2-4-pec-es In the above list, the following abbreviations are used for the structural units A, E, G and L.

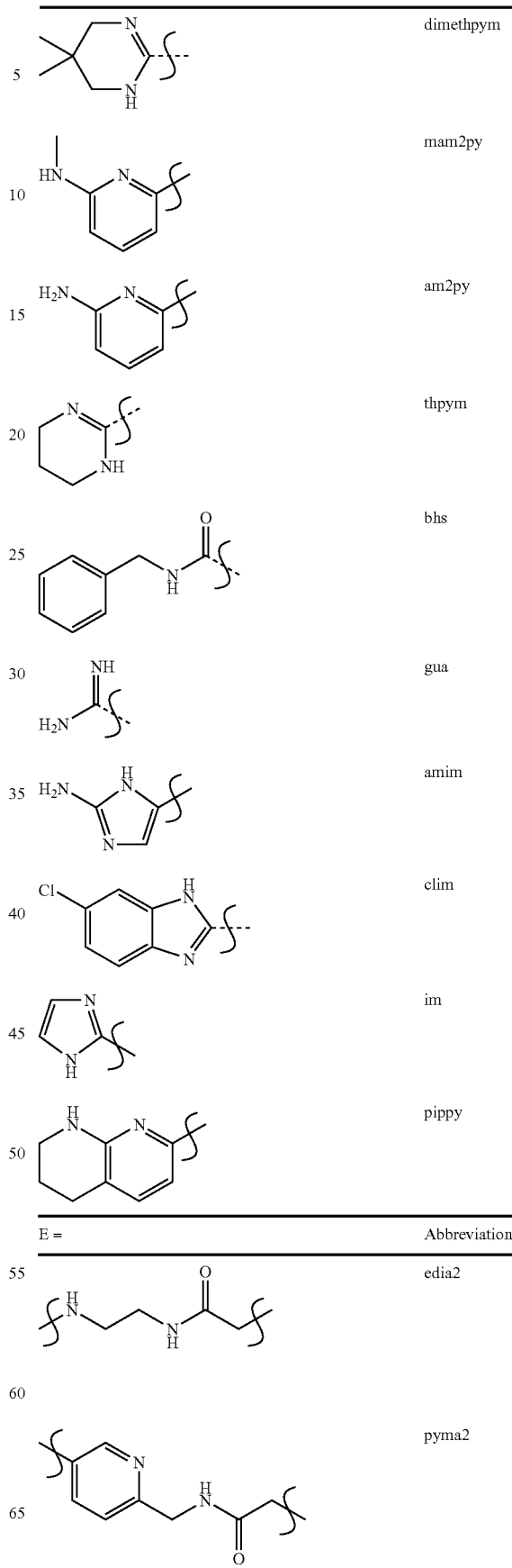

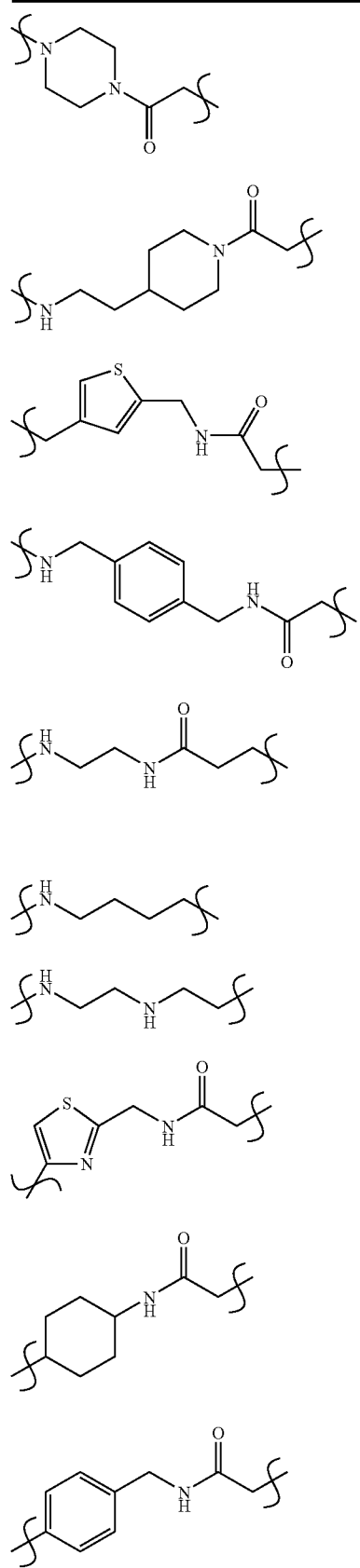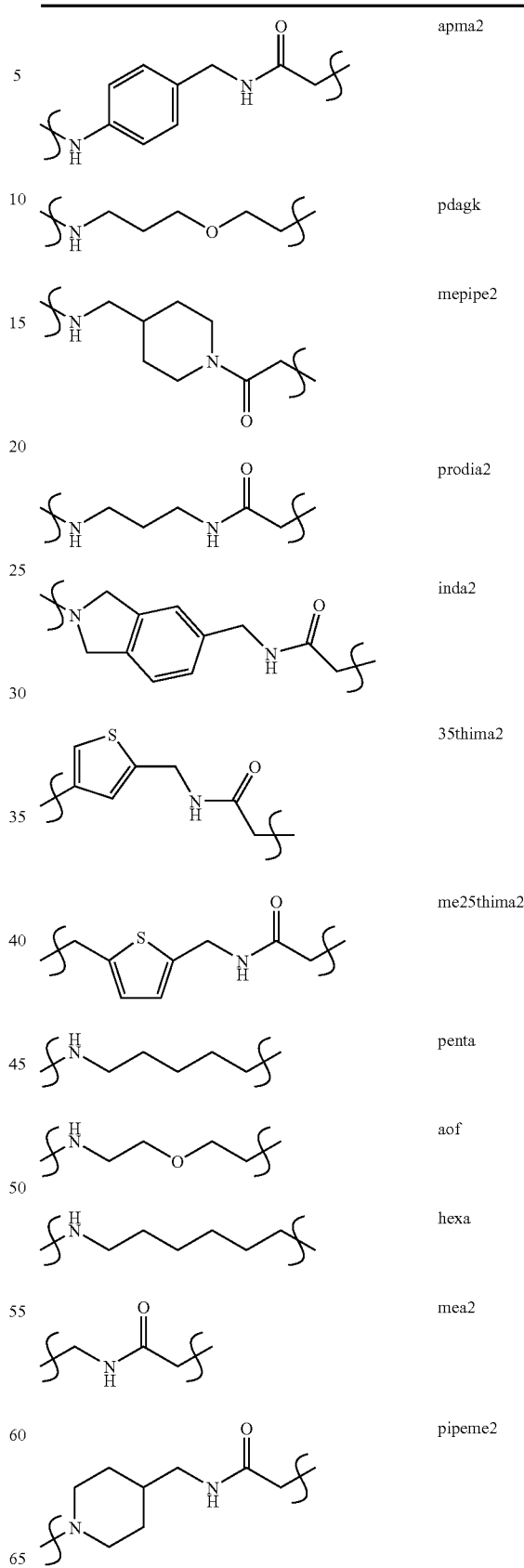

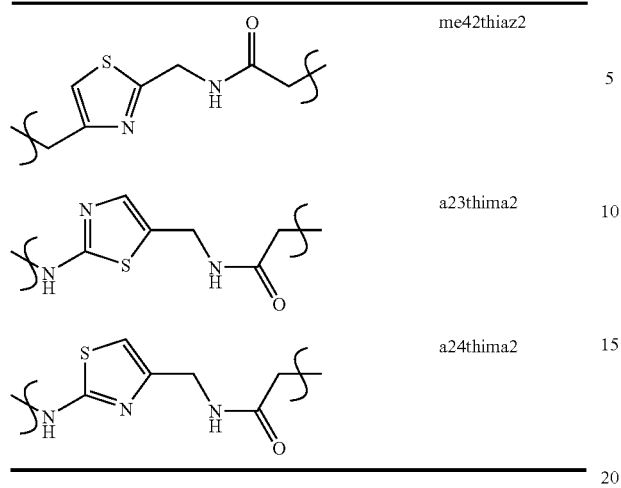
me42thiaz2
a23thima2
a24thima2
The bond from structural element G to structural unit L should be understood as meaning a double bond in the compound where L=as.
| G = | Abbreviation |
|---|---|
| 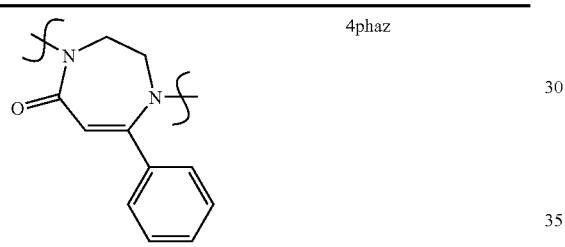 | 4phaz |
| | 3bzlaz |
| 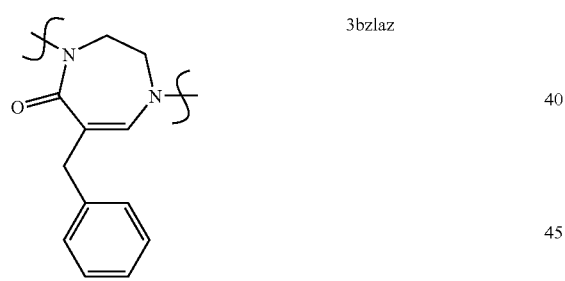 | mophaz |
| 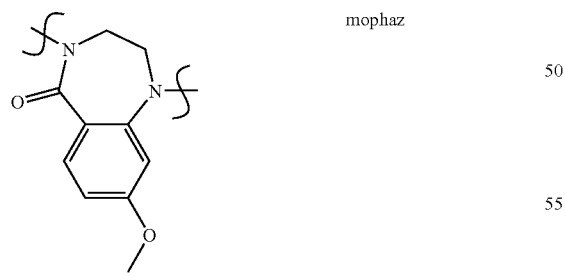 | pipmaz |
| 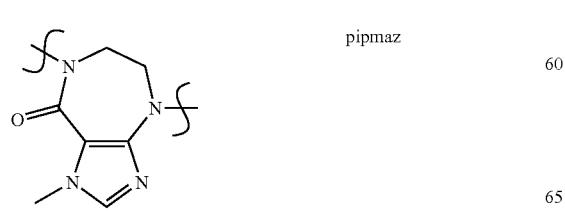 | |
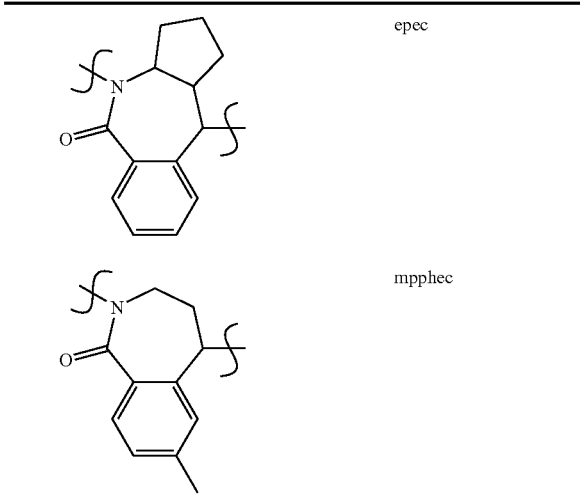 epec
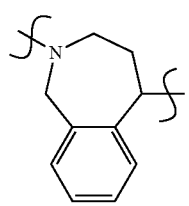 mpphec
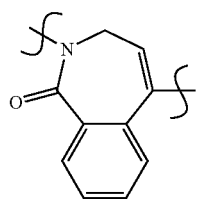 amec
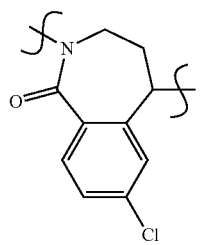 dbc
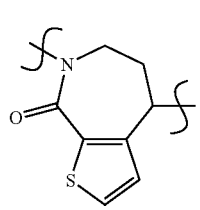 pclphec
thec
mmophec
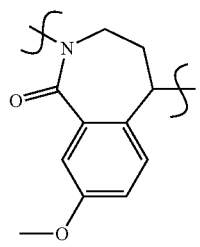

| | |
|---|---|
| 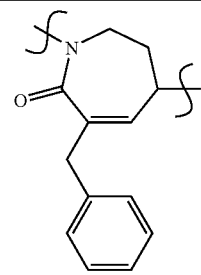 3bec | 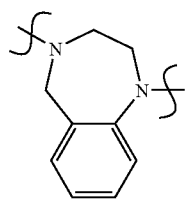 amaz |
| 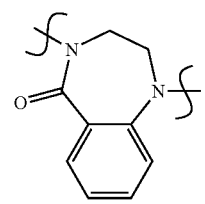 phaz | 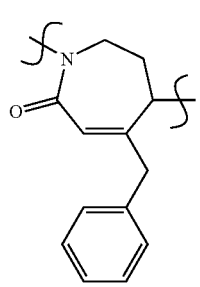 4bec |
| 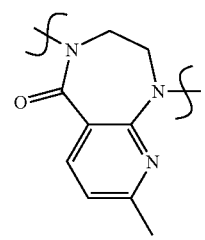 pymaz | 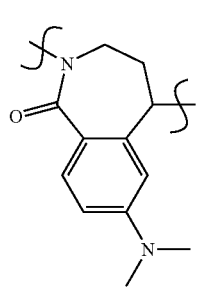 dmaphec |
| 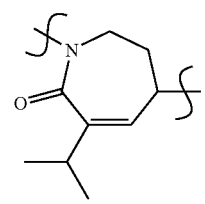 3ipec | 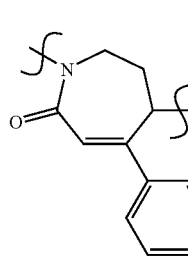 4pec |
| 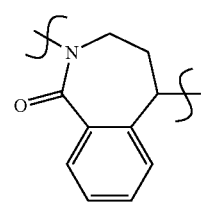 phec | 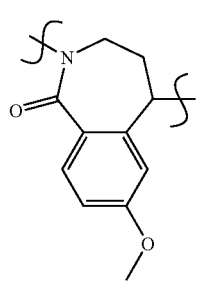 pmophec |
| 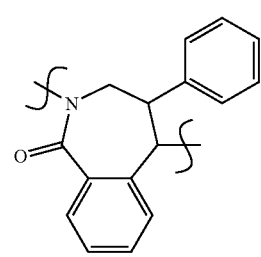 ppec | 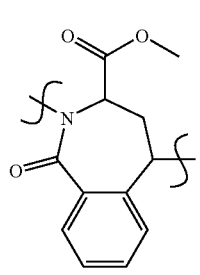 7cmc |
| 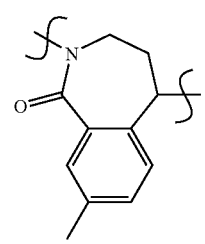 mmphec | |

-continued

| L = | Abbreviation |
|---|---|
| 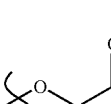 | es |
| 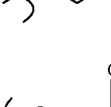 | gs |
| 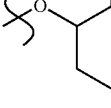 | pms |
| 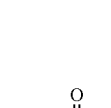 | f2es |
| 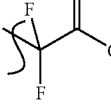 | mals |
| 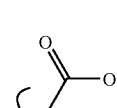 | ps |
| 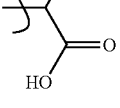 | ms |
| 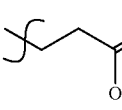 | nes |
| | as |

The compounds of the formula I and the starting substances used for their preparation can generally be prepared by methods of organic chemistry known to the person skilled in the art, such as are described in standard works such as Houben-Weyl (ed.), "Methoden der Organischen Chemie" [Methods of Organic Chemistry], Thieme-Verlag, Stuttgart, Taylor (ed.), "The Chemistry of Heterocyclic Compounds", Wiley & to Sons, New York, or March "Advanced Organic Chemistry", 4th Edition, Wiley & Sons. Further methods of preparing specific functional groups are also described in R. Larock, "Comprehensive Organic Transformations", Weinheim 1989, in particular the preparation of alkenes, alkynes, halides, amines, ethers, alcohols, phenols, aldehydes, ketones, nitrites, carboxylic acids, esters, amides and acid chlorides.

Inhibitors of Integrin $\alpha_v\beta_6$

The invention relates to novel integrin inhibitors of the formula I

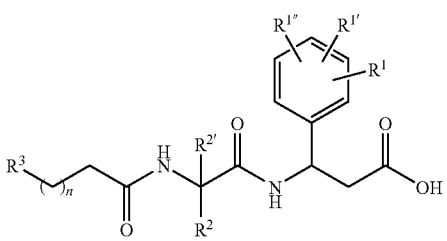

in which
$R^1$, $R^{1'}$ and $R^{1''}$ are H, A, Ar, Het', Hal, $NO_2$, CN, $OR^4$, COA, NHCOA, NH(CHO), $NR^4$, $COOR^4$ or $CONHR^4{}_2$,
$R^2$ is A, Ar, $(CH_2)_mXA$, $(CH_2)_mOH$, $(CH_2)_mNH_2$, $(CH_2)_m$ NHA, $(CH_2)_mNA_2$, $(CH_2)_mNHCOA$, $(CH_2)NO_2$, $(CH_2)$ $COOR^1$, $(CH_2)_mCONH_2$, $(CH_2)_mX(CH_2)_oAr$, $(CH2)_mX$ $(CH_2)_oCHAr_2$, $(CH_2)_mX(CH_2)_oCAr_3$, $(CH_2)_mXCOYA$, $(CH_2)_mXCOY(CH_2)_oAr$, $(CH_2)_mX$ $(CH_2)Het'$, $(CH_2)_mX$ $(CH_2)CHHet'_2$, $(CH_2)_mX(CH_2)_oCHet^1{}_3$, $(CH_2)_mX(CH_2)_o$ YA, $(CH_2)_mX$ $(CH_2)_mNHCOA$, $(CH_2)_mNHCONHR^{2'}$, $(CH_2)_mCH_2A$, $|(CH_2)_mCHA_2$, $(CH_2)_mCA_3$, $(CH_2)_mAr$, $(CH_2)_mCHAr_2$, $(CH_2)_mCAr_3$, $(CH_2)_mHet'$, $(CH_2)_mCH$-$Het^1{}_2$, $(CH_2)_mChet'_3$, $(CH_2)_m$cycloalkyl, $(CH_2)_m$—NH—C(=NH)—$NH_2$ or $(CH_2)_m$—(HN=) C—$NH_2$,
where X and Y, independently of one another, may be S, O, S=O, $SO_2$ or NH, where, if $R^2$=$(CH_2)_mXCOYA$ or $(CH_2)_mXCOY$ $(CH_2)_oAr$, X and Y cannot be S=O or $SO_2$,
$R^{2'}$ is H or A,
$R^2$ and $R^{2'}$ together may alternatively be —$(CH_2)_p$—, 0
$R^3$ is $H_2N$—C(=NH)—, $H_2N$—C(=NH)—NH—, A-C(=NH)—NH—, $Het^2$- or $Het^2$-NH—, where the primary amino groups may also be provided with conventional amino-protecting groups,
$R^4$ is II, A, Het', Hal, $NO_2$ or CN,
A is alkyl having from 1 to 8 carbon atoms,
Ar is phenyl, naphthyl, anthranyl or biphenyl, each of which is unsubstituted or monosubstituted or polysubstituted by Hal, A, OA, OH, CO-A, CN, COOA, COOH, $CONH_2$, CONHA, $CONA_2$, $CF_3$, $OCF_3$ or $NO_2$,
$Het^1$ is an aromatic monocyclic or bicyclic heterocyclic radical having from 1 to 3 N, O and/or S atoms, which may be unsubstituted or monosubstituted or disubstituted by F, Cl, Br, A, OA, SA, $OCF_3$, —CO-A, CN, COOA, $CONH_2$, CONHA, $CONA_2$, $NA_2$ or $NO_2$,
$Het^2$ is a monocyclic or bicyclic heterocyclic radical having from 1 to 4 N atoms, which may be unsubstituted or mono substituted or disubstituted by $NH_2$ or NHA,
m is 0, 1, 2, 3, 4, 5, 6 or 8,
n is 1, 2, 3, 4, 5 or 6,
o is 0, 1, 2 or 3,
p is 2, 3, 4 or 5,
to their stereoisomers, and to their physiologically acceptable salts and solvates.

The invention relates to novel peptides, of the formula I (SEQ ID NO: 4)

$$R^1\text{-Arg-X-Asp-Leu-Asp-Ser-Leu-Arg-}R^{2\prime} \qquad \text{I}$$

in which
$R^1$ denotes H, acetyl or acyl and
$R^2$ denotes —OH, $OR^3NH_2$, $NHR^3$, $N(R^3)_2$
$R^3$ denotes alkyl, aralkyl, aryl, Het and
X denotes an amino acid of the formula II

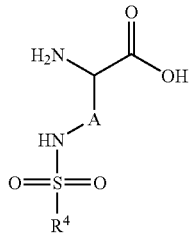

in which
A denotes $(CH2)_n$
$R^4$ denotes H, alkyl, aralkyl or aryl, and
n denotes 1, 2, 3, 4, 5 or 6,
and the amino acid of the formula II is bonded to the adjacent Arg via a peptide bond of the α-amino group and to the a-amino group of the adjacent Asp via a peptide bond of the α-carboxyl group.

The present invention also relates to the pharmaceutically usable pro-drugs, derivatives, solvates and stereoisomers of the compounds of the formula I and the salts thereof, including mixtures thereof in all ratios.

The invention relates, in particular, to peptidic compounds selected from the group of the formulae Ia)-Io)

```
                                              (SEQ ID NO: 6)
Ia) Ac-Arg-Dap(Psa)-Asp-Leu-Asp-Ser-Leu-Arg-NH2, (SEQ ID NO: 7)
Ib) Ac-Arg-Dap(F5-PSA)-Asp-Leu-Asp-Ser-Leu-Arg-
NH2,
                                              (SEQ ID NO: 8)
Ic) Ac-Arg-Dap(2-NO2-PSA)-Asp-Leu-Asp-Ser-Leu-Arg-
NH2,
                                              (SEQ ID NO: 9)
Id) Ac-Arg-Dap(4-NO2-PSA)-Asp-Leu-Asp-Ser-Leu-Arg-
NH2,
                                              (SEQ ID NO: 10)
Ie) Ac-Arg-Dap(2,4-NO2-PSA)-Asp-Leu-Asp-Ser-Leu-
Arg-NH2,
                                              (SEQ ID NO: 11)
If) Ac-Arg-Dap(6-OMe-PSA)-Asp-Leu-Asp-Ser-Leu-Arg-
NH2,
                                              (SEQ ID NO: 12)
Ig) Ac-Arg-Dap(2-CF3-PSA)-Asp-Leu-Asp-Ser-Leu-Arg-
NH2,
                                              (SEQ ID NO: 13)
Ih) Ac-Arg-Dap(3-CF3-PSA)-Asp-Leu-Asp-Ser-Leu-Arg-
NH2,
                                              (SEQ ID NO: 14)
Ii) Ac-Arg-Dap(Me5-PSA)-Asp-Leu-Asp-Ser-Leu-Arg-
NH2,
                                              (SEQ ID NO: 15)
Ij) Ac-Arg-Dap(4-tBu-PSA)-Asp-Leu-Asp-Ser-Leu-Arg-
NH2,
                                              (SEQ ID NO: 16)
Ik) Ac-Arg-Dap(BSA)-Asp-Leu-Asp-Ser-Leu-Arg-NH2, (SEQ ID NO: 17)
Il) Ac-Arg-Dap(iPrs)-Asp-Leu-Asp-Ser-Leu-Arg-NH2, (SEQ ID NO: 18)
Im) Ac-Arg-Dap(1-Nap)-Asp-Leu-Asp-Ser-Leu-Arg-NH2, (SEQ ID NO: 19)
In) Ac-Arg-Dap(2-Nap)-Asp-Leu-Asp-Ser-Leu-Arg-NH2, (SEQ ID NO: 20)
Io) Ac-Arg-Dap(4-Ph-Psa)-Asp-Leu-Asp-Ser-Leu-Arg-
NH2,
``` and pharmaceutically usable prodrugs, derivatives, solvates and stereoisomers thereof, and salts thereof, including mixtures thereof in all ratios, where the abbreviations used in brackets in the formulae Ia)-Io) stand for the following radicals:

| | |
|---|---|
| Psa | phenylsulfonyl radical |
| F5-PSA | pentafluorophenylsulfonyl radical |
| 2-NO$_2$-PSA | 2-nitrophenylsulfonyl radical |
| 4-NO$_2$-PSA | 4-nitrophenylsulfonyl radical |
| 2,4-NO$_2$-PSA | 2,4-dinitrophenylsulfonyl radical |
| 6-OMe-PSA | 6-methoxyphenylsulfonyl radical |
| 2-CF$_3$-PSA | 2-trifluoromethylphenylsulfonyl radical |
| 3-CF$_3$-PSA | 3-trifluoromethylphenylsulfonyl radical |
| Me$_5$-PSA | pentamethylphenylsulfonyl radical |
| 4-tBu-PSA | 4-tert-butylphenylsulfonyl radical |
| Bsa | benzylsulfonyl radical |
| iPrs | isopropylsulfonyl radical |
| 1-Nap | 1-naphthylsulfonyl radical |
| 2-Nap | 2-naphthylsulfonyl radical |
| 4-Ph-Psa | 4-phenylphenylsulfonyl radical |

The abbreviations mentioned above and below for amino acid radicals stand for the radicals of the following amino acids:

| | |
|---|---|
| Asp or D | aspartic acid |
| Arg or R | arginine |
| Dap | 2,3-diaminopropionic acid |
| Leu or L | leucine |
| Ser or S | serine |
| Thr or T | threonine |

Furthermore, the following abbreviations above and below have the following meanings:

| | |
|---|---|
| Ac | acetyl |
| BOC | tert-butoxycarbonyl |
| BSA | bovine serum albumin |
| CBZ or Z | benzyloxycarbonyl |
| DCCI | dicyclohexylcarbodiimide |
| DCM | dichloromethane |
| DIEA | diisopropylamine |
| DMA | N,N-dimethylacetamide |
| DMF | dimethylformamide |
| EDCI | N-ethyl-N,N'-(dimethylaminopropyl)carbodiimide |
| Et | ethyl |
| FCA | fluoresceincarboxylic acid |
| FITC | fluorescein isothiocyanate |
| Fmoc | 9-fluorenylmethoxycarbonyl |
| Fmoc-Dap(ivDde) | N-α-Fmoc-N-γ-1-(4,4-dimethyl-2,6-dioxocyclohex-1-yli-dene)-3-methylbutyldiaminopropionic acid |
| FTH | fluoresceinthiourea |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| NMP | N-methylpyrrolidone |
| HONSu | N-hydroxysuccinimide |
| OBut | tert-butyl ester |

| | |
|---|---|
| Oct | octanoyl |
| OMe | methyl ester |
| OEt | ethyl ester |
| Pbf | 2,2,4,6,7-pentamethyldihydrobenzofuran-5-sulfonyl |
| Pmc | 2,2,5,7,8-pentamethylchroman-6-sulfonyl |
| POA | phenoxyacetyl |
| Sal | salicyloyl |
| TBS++ | Tris buffered saline with divalent cations |
| TBSA | TBS + BSA |
| TBTU | 2-(1H-benzotriazol-1-yl)-1,1,3-tetramethyluronium tetrafluoroborate |
| TFA | trifluoroacetic acid |
| TIS | triisopropylamine |
| Trt | trityl(triphenylmethyl). |

If the above-mentioned amino acids can occur in a plurality of enantiomeric forms, all these forms and also mixtures thereof (for example the DL forms) are included above and below. Furthermore, the amino acids may be provided with corresponding protecting groups known per se.

As evidenced by the continuing research in integrin antagonists and by the shortcomings of the compounds and methods of the art, there still remains a need for small-molecule, non-peptidic selective $\alpha_v\beta_3$ and/or $\alpha_v\beta_s$ antagonists that display decreased side-effects, improved potency, pharmacodynamic and pharmacokinetic properties, such as oral bioavailability and duration of action, over already described compounds. Such compounds would prove to be useful for the treatment, prevention, or suppression of various pathologies enumerated above that are mediated by $\alpha_v\beta_3$ and/or $\alpha_v\beta_s$ receptor binding and cell adhesion and activation.

In one embodiment, the present invention comprises a class of biphenyl integrin antagonists.

The present invention relates to a class of compounds represented by the Formula I:

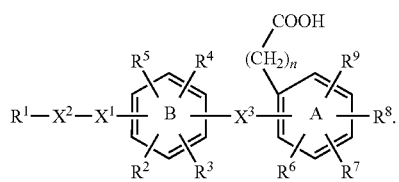

I or a pharmaceutically acceptable salt, ester or tautomer thereof, wherein:
A and B are phenyl;
n is an integer from 1 to 3;
$X^1$ is selected from O, NR, S, SO, $SO_2$, CHR and $CH_2$, wherein:
  R is selected from the group consisting of hydrogen, aryl, and heterocyclyl;
$X^2$ is selected from the group consisting of alkyl, alkylamino, aminoalkyl, alkylaminoalkyl, alklthio, thioalkyl, alkylthioalkyl, alkylsulfonyl, sulfonylalkyl, alkylsulfonylalkyl, oxyalkyl, alkoxyalkyl, and alkoxy;
$X^3$ is $C_1$-$C_6$ alkyl;
$R^1$ is selected from the group consisting of pyridinyl and napthyridinyl, wherein;
  either is optionally substituted with a substituent selected from the group consisting of hydrogen, alkyl, halo, and amino;
$R^2$, $R^3$, $R^4$, $R^5$, $R^6$, $R^7$, $R^8$ and $R^9$ are independently selected from the group consisting of hydrogen, alkyl, alkenyl, alkoxy, alkoxyalkyl, alkoxycarbonylalkyl, alkylamino, alkylcarbonyl, alkylheteroaryl, alkylsulfonylalkyl, alkylthio, alkynyl, aminocarbonylalkyl, cyano, dialkylamino, halo, haloalkoxy, haloalkyl, hydroxy and hydroxyalkyl; and
$X^3$ is independently meta- or para- to the $X^1$ of the B ring, and wherein further $X^3$ is ortho-, meta-, or para- to the carboxylic acid chain of the A ring.

In another embodiment, the invention comprises pharmaceutical compositions comprising compounds of the Formula I. Such compounds and compositions are useful in selectively inhibiting or antagonizing the $\alpha_v\beta_3$ and/or $\alpha_v\beta_s$ integrins and therefore in another embodiment the present invention relates to a method of selectively inhibiting or antagonizing the $\alpha_v\beta_3$ and/or $\alpha_v\beta_s$ integrin.

In another embodiment, the invention provides methods of treating or inhibiting pathological conditions associated therewith such as osteoporosis, humoral hypercalcemia of malignancy, Paget's disease, rumor metastasis, solid tumor growth (neoplasia), angiogenesis, including tumor angiogenesis, retinopathy including macular degeneration and diabetic retinopathy, arthritis including rheumatoid arthritis and osteoarthritis, periodontal disease, psoriasis, smooth muscle cell migration and restenosis in a mammal in need of such treatment. Additionally, such pharmaceutical agents are useful as antiviral agents and antimicrobials. The compounds of the present invention may be used alone or in combination with other pharmaceutical agents.

The compounds of this invention are 1) $\alpha_v\beta_3$ integrin antagonists; or 2) $\alpha_v\beta_s$ integrin antagonists; or 3) mixed or dual $\alpha_v\beta_3/\alpha\beta_s$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_s$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, Immoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_v\beta_3$ and/or $\alpha_v\beta_s$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious. Therefore, compounds of the present invention which selectively inhibit the $\alpha_v\beta_3$ integrin as opposed to the $\alpha_v\beta_6$ integrin have reduced side-effects associated with inhibition of the $\alpha_v\beta_6$ integrin.

The present invention relates to a class of compounds represented by the Formula I.

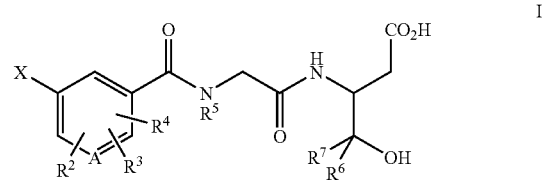

I or a pharmaceutically acceptable salts thereof wherein X is

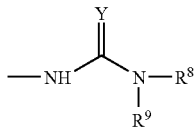

Y is selected from the group consisting of N—$R^1$, O, and S;

A is N or C;

$R^1$ is selected from the group consisting of H, alkyl, aryl, hydroxy, alkoxy, cyano, nitro, amino, alkenyl, alkynyl, amino, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^1$ taken together with $R^8$ forms a 4-12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or $R^1$ taken together with $R^8$ forms a 5 membered heteroaromatic ring optionally substituted with one or more substituent selected from lower alkyl, phenyl and hydroxy; or $R^1$ taken together with $R^8$ forms a 5 membered heteroaromatic ring fused with a phenyl group;

$R^8$ (when not taken together with $R^1$) and $R^9$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxycarbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

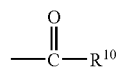

wherein $R^{10}$ is defined as above; or $NR^8$ and $R^9$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

or

X is

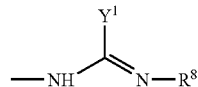

wherein $Y^1$ is selected from the group consisting of alkyl, cycloalkyl, bicycloalkyl, aryl, monocyclic heterocycles, alkyl optionally substituted with aryl which can also be optionally substituted with one or more substituent selected from halogen, haloalkyl, alkyl, nitro, hydroxy, alkoxy, aryloxy, aryl, or fused aryl, aryl optionally substituted with one or more substituent selected from halogen, haloalkyl, hydroxy, alkoxy, aryloxy, aryl, fused aryl, nitro, methylenedioxy, ethylenedioxy, or alkyl, alkynyl, alkenyl, —S—$R^{11}$ and —$OR^{11}$ wherein $R^{11}$ is selected from the group consisting of H, alkyl, aralkyl, aryl, alkenyl, and alkynyl, or $R^{11}$ taken together with $R^8$ forms a 4-12 membered mononitrogen and monosulfur or monooxygen containing heterocyclic ring optionally substituted with lower alkyl, hydroxy, keto, phenyl, carboxyl or carboxyl ester, and fused phenyl, or $R^{11}$ taken together with $R^8$ is thiazole, oxazole, benzoxazole, or benzothiazole;

$R^8$ is defined as above; or $Y^1$ (when $Y^1$ is carbon) taken together with $R^6$ forms a 4-12 membered mononitrogen or dinitrogen containing ring optionally substituted with alkyl, aryl, keto or hydroxy; or X is

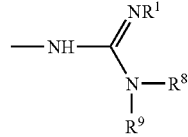

wherein R¹ and R⁸ taken together form a 5-8 membered dinitrogen containing heterocycle optionally substituted with one or more substituent selected from the group consisting of lower alkyl, hydroxy, keto, phenyl, or carboxyl derivatives; and R⁹ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or X is

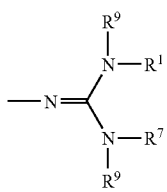

wherein R¹ and R⁸ taken together form a 5-8 membered dinitrogen containing heterocycle optionally substituted with hydroxy, keto, phenyl, or alkyl; and R⁹ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

R², R³ and R⁴ are independently selected from one or more substituent selected from the group consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above; R⁵, R⁶ and R⁷ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

The compounds according to Formula I can exist in various isomers, enantiomers, tautomers, racemates and polymorphs, and all such forms are meant to be included.

It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_v\beta_3$ and/or $\alpha_v\beta_5$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious. Therefore, compounds of the present invention which selectively inhibit the $\alpha_v\beta_3$ integrin as opposed to the $\alpha_v\beta_6$ integrin have reduced side-effects associated with inhibition of the $\alpha_v\beta_6$ integrin.

The present invention relates to a class of compounds represented by the Formula I.

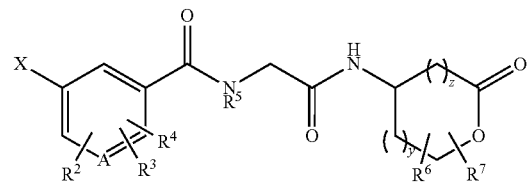

or a pharmaceutically acceptable salts thereof wherein

X is

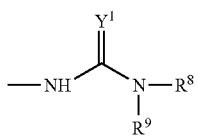

Y is selected from the group consisting of N—R$^1$, O, and S;

y and z are independently selected from an integer selected form 0, 1, 2 and 3;

A is N or C;

R$^1$ is selected from the group consisting of H, alkyl, aryl, hydroxy, alkoxy, cyano, nitro, amino, alkenyl, alkynyl, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or R$^1$ taken together with R$^8$ forms a 4-12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or R$^1$ taken together with R$^8$ forms a 5 membered heteroaromatic ring optionally substituted with one or more substituent selected from lower alkyl, phenyl and hydroxy; or R$^1$ taken together with R$^8$ forms a 5 membered heteroaromatic ring fused with a phenyl group;

R$^8$ (when not taken together with R$^1$) and R$^9$ are independently selected from the group consisting of 11, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxycarbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —SO$_2$R$^{19}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

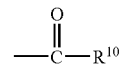

wherein R$^{10}$ is defined as above; or

NR$^8$ and R$^9$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S; or X is

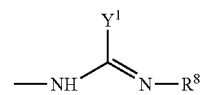

wherein Y' is selected from the group consisting of alkyl, cycloalkyl, bicycloalkyl, aryl, monocyclic heterocycles, alkyl optionally substituted with aryl which can also be optionally substituted with one or more substituent selected from halo, haloalkyl, alkyl, nitro, hydroxy, alkoxy, aryloxy, aryl, or fused aryl, aryl optionally substituted with one or more substituent selected from halo, haloalkyl, hydroxy, alkoxy, aryloxy, aryl, fused aryl, nitro, methylenedioxy, ethylenedioxy, or alkyl, alkynyl, alkenyl, —S—R$^{11}$ and —OR$^{11}$ wherein R$^{11}$ is selected from the group consisting of H, alkyl, aralkyl, aryl, alkenyl, and alkynyl, or R$^1$ taken together with R$^8$ forms a 4-12 membered mononitrogen and monosulfur or monooxygen containing heterocyclic ring optionally substituted with lower alkyl, hydroxy, keto, phenyl, carboxyl or carboxyl ester, and fused phenyl, or R$^{11}$ taken together with R$^8$ is thiazole, oxazole, benzoxazole, or benzothiazole;

R$^8$ is defined as above; or

Y$^1$ (when Y$^1$ is carbon) taken together with R$^8$ forms a 4-12 membered mononitrogen or dinitrogen containing ring optionally substituted with alkyl, aryl, keto or hydroxy;

X is

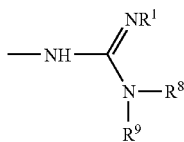

wherein $R^1$ and $R^8$ taken together form a 5-8 membered dinitrogen containing heterocycle optionally substituted with one or more substituent selected from the group consisting of lower alkyl, hydroxy, keto, phenyl, or carboxyl derivatives; and $R^9$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or X is

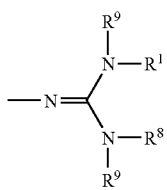

wherein $R^1$ and $R^8$ taken together form a 5-8 membered dinitrogen containing heterocycle optionally substituted with hydroxy, keto, phenyl, or alkyl; and $R^9$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

$R^2$, $R^3$ and $R^4$ are independently selected from one or more substituent selected from the group consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above;

$R^5$, $R^6$ and $R^7$ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

The compounds according to Formula I can exist in various isomers, enantiomers, tautomers, racemates and polymorphs, and all such forms are meant to be included.

It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_3$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Further, it has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and $\alpha_v\beta_8$ may play a role in the regulation of growth in the human pathway. Therefore, compounds which selectively inhibit the $\alpha_v\beta_3$ integrin as opposed to the $\alpha_v\beta_6$ and/or the $\alpha_v\beta_8$ integrin have reduced side-effects associated with inhibition of the $\alpha_v\beta_6$ and/or the $\alpha_v\beta_8$ integrin. It is therefore another object of the present invention to provide compounds that are selective antagonists of $\alpha_v\beta_3$ and/or $\alpha_v\beta_5$ as opposed to $\alpha_v\beta_6$, and it is yet another object of the present invention to provide compounds that are selective antagonists of CVD3 and/or $\alpha_v\beta_5$ as opposed to $\alpha_v\beta_8$.

The present invention relates to a class of compounds represented by the Formula 1.2

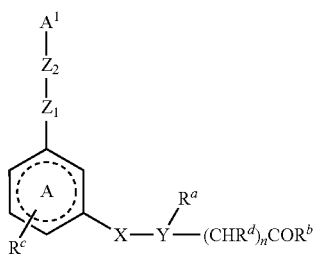

or a pharmaceutically acceptable salt thereof, wherein

is a 4-8 membered monocyclic or a 7-12 membered bicyclic ring, optionally containing 1 to 4 heteroatoms, selected from the group consisting of O, N or S; optionally saturated or unsaturated, optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, sulfone, sulfonamide, allyl, alkenyl, methylenedioxy, ethylenedioxy, alkynyl, carboxamide, cyano, and —(CH$_2$)$_n$ COR wherein n is 0-2 and R is hydroxy, alkoxy, alkyl or amino;

$A^1$ is a 5-9 membered monocyclic or 7-14 membered polycyclic heterocycle of the formula 4

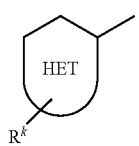

containing at least one nitrogen atom and optionally 1 to 4 heteroatoms or groups selected from O, N, S, SO$_2$ or CO; optionally saturated or unsaturated; optionally substituted by one or more Rk selected from the group consisting of hydroxy, alkyl, alkoxy, alkoxyalkyl, thioalkyl, haloalkyl, cyano, amino, alkylamino, halogen, acylamino, sulfonamide and —COR wherein R is hydroxy, alkoxy, alkyl or amino; 5

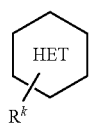

include the following heterocyclic ring systems containing at least one nitrogen atom:

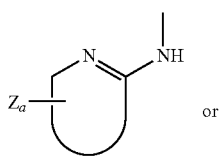

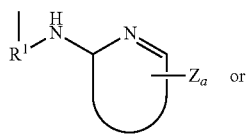

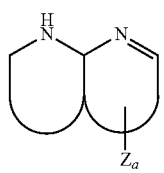

wherein $Z_a$ is H, alkyl, alkoxy, hydroxy, amine, alkylamine, dialkylamine, to carboxyl, alkoxycarbonyl, hydroxyalkyl, halogen or haloalkyl and $R^1$ is H, alkyl, alkoxyalkyl, acyl, haloalkyl or alkoxycarbonyl. More specifically some examples of embodiments include pyridylamino, imidazolylamino, morpholinopyridine, tetrahydronaphthyridine, oxazolylamino, thiazolylamino, pyrimidinylamino, quinoline, isoquinoline, tetrahydroquinoline, imidazopyridine, benzimidazole, pyridone or quinolone.

The following heteroaryls include the ring systems described above.

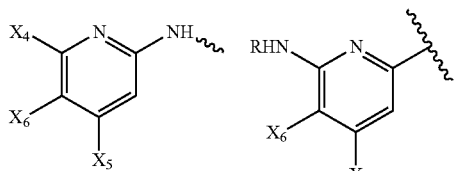

B = CH$_2$, O, CO, S CF$_2$, SO$_2$, NR
R' = OP, OH, H, Me n = 1 or 2

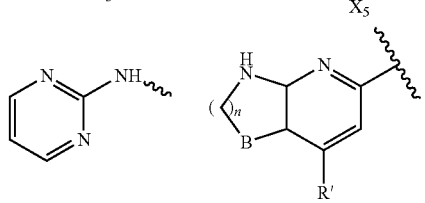

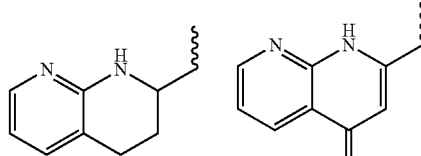

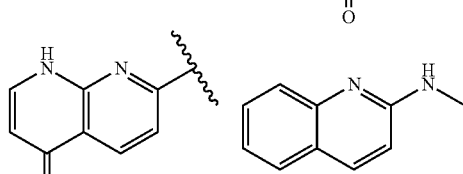

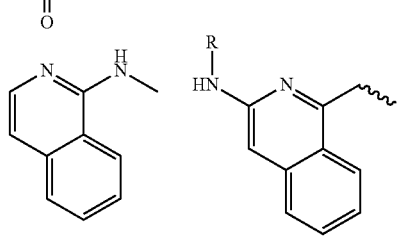

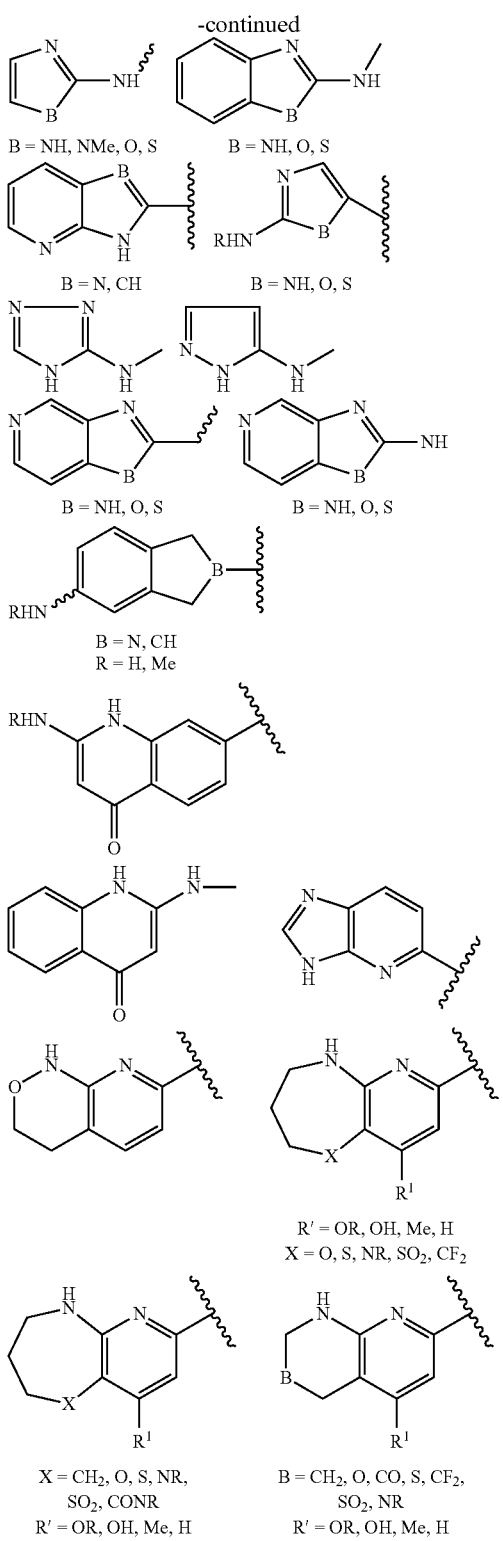

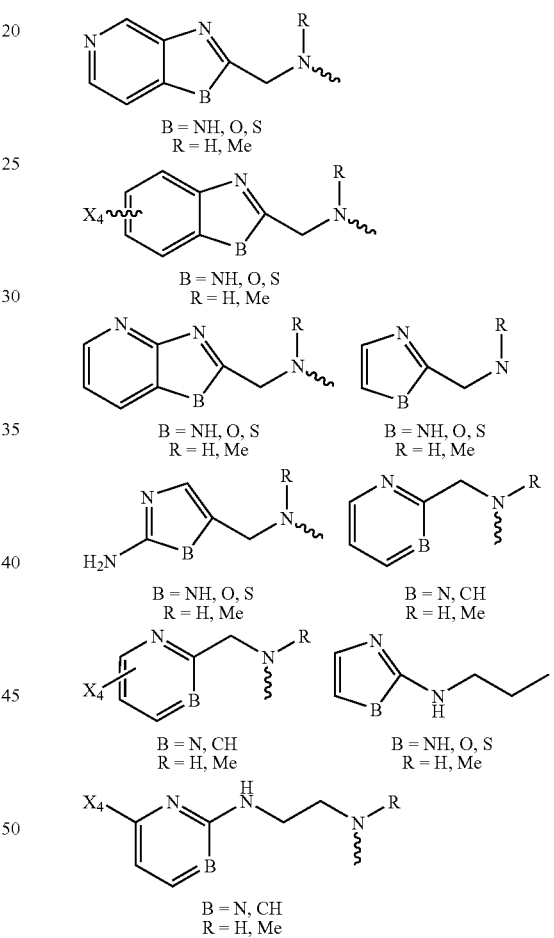

preferentially be H, alkyl, hydroxy, halogen, alkoxy and haloalkyl. Alternately, the pyridyl ring can be fused with a 4-8 membered ring, optionally saturated or unsaturated. Some examples of these ring systems include tetrahydronaphthyridine, quinoline, tetrahydroquinoline, azaquinoline, morpholinopyridine, imidazo-pyridine and the like. The monocyclic ring systems such as imidazole, thiazole, oxazole, pyrazole, and the like, may contain an amino or alkylamino substituent at any position within the ring.

In another embodiment of the present invention, when $Z_1$ of Formula I is CO or $SO_2$, the linkage $A^1$-$Z_2$ of Formula I includes the heterocycle derived ring systems such as: pyridine, imidazole, thiazole, oxazole, benzimidazole, imidazopyridine and the like.

Other heterocycles for $A^1$-$Z_2$ of the present invention include

For the pyridyl derived heterocycle, the substituents $X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups. In another embodiment of the invention, the substituents X4 and $X_5$ can be methyl, methoxy, amine, methylamine, trifluoromethyl, dimethylamine, hydroxy, chloro, bromo, fluoro and cyano. $X_6$ may wherein $X^4$ is as defined above.
or
$A^1$ is

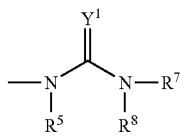

wherein $Y^1$ is selected from the group consisting of $N-R^2$, O, and S;

$R^2$ is selected from the group consisting of H; alkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxy ester, and fused phenyl;

or $R^2$ taken together with $R^7$ forms a 4-12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H and alkyl.

As evidenced by the continuing research in integrin antagonists and by the shortcomings of the compounds and methods of the art, there still remains a need for small-molecule, non-peptidic selective $\alpha_v\beta_3$ and/or $\alpha_v\beta_5$ antagonist that displays decreased side-effects, and improved potency, pharmacodynamic, and pharmacokinetic properties, such as oral bioavailability and duration of action, over already described compounds. Such compounds would prove to be useful for the treatment, prevention, or suppression of various pathologies enumerated above that are mediated by $\alpha_v\beta_3$ and/or $\alpha_v\beta_5$ receptor binding and cell adhesion and activation.

The compounds of the present invention further show greater selectivity for the $\alpha_v\beta_3$ and/or $\alpha_v\beta_5$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious (Huang et al., Am J Respir Cell Mol Biol 1998, 19(4): 636-42). Therefore, compounds of the present invention which selectively inhibit the $\alpha_v\beta_3$ integrin as opposed to the $\alpha_v\beta_6$ integrin have reduced side effects associated with inhibition of the $\alpha_v\beta_6$ integrin.

The compounds of the present invention comprise the R-isomers of the carbon of the beta amino acid. Other isomers may result from additional chiral centers, depending on the substitution of the parent structure.

The present invention relates to a class of compounds represented by the Formula I:

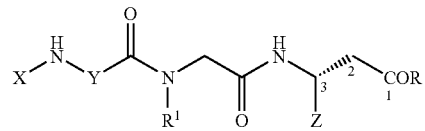

I or a pharmaceutically acceptable salt or tautomer thereof; wherein X has the structure of formula Ia:

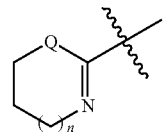

and wherein X is optionally substituted with one or more substituents independently selected from the group consisting of OH, alkyl, alkenyl, alkynyl, haloalkyl, alkylaryl, arylalkyl, alkoxy, dialkylamino, thioalkyl, cycloalkyl, CN, $NO_2$, and halogen;

or, in an alternative embodiment, X is a monocyclic heterocycle containing a N as shown, optionally substituted with one to ten, or alternatively 1-3, substituents independently selected from the group consisting of H, OH, alkyl, CN, $NO_2$, aminoalkyl, halogen, haloalkyl, and alkoxy;

Y is a six-membered aryl; or alternatively, a six-membered heterocycyl ring containing 1 to 2 heteroatoms, selected from the group consisting of O, N or S; wherein the six-membered ring is optionally substituted with one or more substitutents independently selected from the group consisting of OH, alkyl, alkoxy, $NO_2$, $NH_2$, CN, $NHCOCF_3$, $COCF_3$, haloalkyl, aryl, methylenedioxy, ethylenedioxy, heterocycyl, halogen, alkoxyalkyl, aminoalkyl, hydroxyalkyl, thioalkyl, alkylamino, arylamino, alkylsulfonamido, acyl, acylamino, alkylsulfone, sulfonamido, allyl, alkenyl, alkynyl, carboxamide, $NHCOCF_3$, and $-(CH_2)_mCOR^2$;

m is a number from 0 to 2;

$R^2$ is hydroxy, alkoxy, or amino;

Z is a 5 to 6-membered monocyclic, or a 9 to 12-membered bicyclic, aryl or heterocycyl ring; optionally containing 1 to 5 heteroatoms, selected from the group consisting of O, N or S; optionally saturated or unsaturated, optionally substituted with one or more substituents selected from the group consisting of alkyl, haloalkyl, aryl, heterocycyl, arylalkyl, aryloxy, phenethyl, arylsulfone, halogen, alkoxyalkyl, aminoalkyl, cycloalkyl, hydroxy, nitro, alkoxy, hydroxyalkyl, thioalkyl, amino, alkylamino, arylamino, alkylsulfonamido, acyl, acylamino, alkylsulfone, sulfonamido, allyl, alkenyl, methylenedioxy, ethylenedioxy, alkynyl, carboxamide, cyano, $NHCOCF_3$, and $-(CH_2)_mCOR^2$; wherein the aryl and heterocycyl substituents are also optionally substituted with one or more substituents selected from the group consisting of alkyl, cycloalkyl, haloalkyl, halogen, alkoxyalkyl, aminoalkyl, hydroxy, nitro, alkoxy, hydroxyalkyl, thioalkyl, amino, alkylamino, arylamino, alkylsulfonamido, acyl, acylamino, alkylsulfone, sulfonamido, allyl, alkenyl, methylenedioxy, ethylenedioxy, alkynyl, carboxamide, cyano, and $-(CH_2)_mCOR^2$;

Q is NH or $CH_2$;

R is selected from the group consisting of OH, alkoxy, and $NHR^3$;

$R^3$ is H or an alkyl group;

$R^1$ is H, CN, $NO_2$, acyl, haloalkyl, alkenyl, alkynyl, or alkyl;

n is 0, 1, or 2, and carbon atom 3 is in the (R) conformation.

It is another embodiment of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further embodies treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis and osteoarthritis, periodontal disease, psoriasis, smooth muscle cell migration and restenosis in a mammal in need of such treatment. Additionally, such pharmaceutical agents are useful as antiviral agents, and antimicrobials. The compounds of the present invention may be used alone or in combination with other pharmaceutical agents.

The compounds of this invention are 1) $\alpha_v\beta_3$ integrin antagonists; or 2) $\alpha_v\beta_5$ integrin antagonists; or 3) mixed or dual $\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_v\beta_3$ and/or $\alpha_v\beta_6$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious. Therefore, compounds of the present invention which selectively inhibit the $\alpha_v\beta_3$ integrin as opposed to the $\alpha_v\beta_6$ integrin have reduced side-effects associated with inhibition of the $\alpha_v\beta_6$ integrin.

The present invention relates to a class of compounds represented by the Formula I

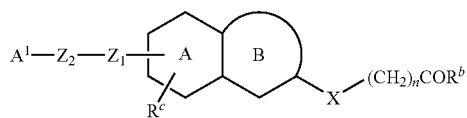

or a pharmaceutically acceptable salt thereof, wherein $A^1$ is a 5-9 membered monocyclic or 7-12 membered bicyclic heterocycle of the formula

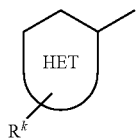

containing at least one nitrogen atom and optionally 1 to 3 heteroatoms, selected from the group consisting of O, N or S; optionally saturated or unsaturated; optionally substituted by one or more Rk selected from the group consisting of hydroxy, alkyl, cycloalkyl, alkoxy, alkoxyalkyl, thioalkyl, cyano, amino, alkylamino, halogen, acylamino, sulfonamide and —COR wherein R is hydroxy, alkoxy, alkyl or amino;

or $A^1$ is

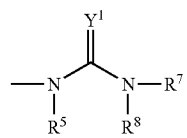

wherein $Y^1$ is selected from the group consisting of N—$R^2$, O, and S;

$R^2$ is selected from the group consisting of H; alkyl; cycloalkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl;

or $R^2$ taken together with $R^7$ forms a 4-12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, cycloalkyl and alkyl; 5

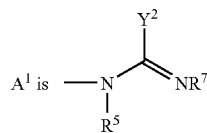

wherein Y² is selected from the group consisting of alkyl; cycloalkyl; bicycloalkyl; aryl; monocyclic heterocycles;

$Z_1$ is selected from the group consisting of $CH_2$, O, $CH_2O$, $NR_k$, CO, S, SO, CH(OH) and $SO_2$, wherein Rk is selected from H or lower alkyl;

$Z_2$ is a 1-5 carbon linker optionally containing one or more heteroatom selected from the group consisting of O, S and N; alternatively $Z_1$-$Z_2$ may further contain a carboxamide, sulfone, sulfonamide, alkenyl, alkynyl, or acyl group;

wherein the carbon and nitrogen atoms of $Z_1$-$Z_2$ are optionally substituted by alkyl, cycloalkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

n is an integer 0, 1 or 2;

$R^c$ is selected from the group consisting of hydrogen; alkyl; cycloalkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n COR$ wherein n is 0-2 and R is selected from hydroxy, alkoxy, alkyl and amino;

X is selected from the group consisting of O, CO, $SO_2$, $NR^m$ and $(CHR^p)_n$; wherein $R^p$ and $R^m$ are H or alkyl;

$R^b$ is $X_3$—$R^h$ wherein $X_3$ is selected from the group consisting of O, S and $NR^j$ wherein $R^h$ and $R^j$ are independently selected from the group consisting of H, alkyl, acyl, aryl, aralkyl and alkoxyalkyl; and It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrin(s) and therefore in another embodiment the present invention relates to a method of selectively inhibiting or antagonizing the $\alpha_v\beta_3$ and/or $\alpha_v\beta_5$ integrin(s). The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration including restenosis or atherosclerosis in a mammal in need of such treatment. Additionally, such pharmaceutical agents are useful as antiviral agents, antifungals and antimicrobials. The compounds of the present invention may be used alone or in combination with other pharmaceutical agents.

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Further, it has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and $\alpha_v\beta_8$ may play a role in the regulation of growth in the human pathway. Therefore, compounds which selectively inhibit the $\alpha_v\beta_3$ integrin as opposed to the $\alpha_v\beta_6$ and/or the $\alpha_v\beta_8$ integrin have reduced side-effects associated with inhibition of the $\alpha_v\beta_6$ and/or the $\alpha_v\beta_8$ integrin. It is therefore another object of the present invention to provide compounds that are selective antagonists of $\alpha_v\beta_3$ and/or $\alpha_v\beta_s$ as opposed to $\alpha_v\beta_6$, and it is yet another object of the present invention to provide compounds that are selective antagonists of $\alpha_v\beta_3$ and/or $\alpha_v\beta_5$ as opposed to $\alpha_v\beta_8$.

The present invention relates to a class of compounds represented by the Formula I

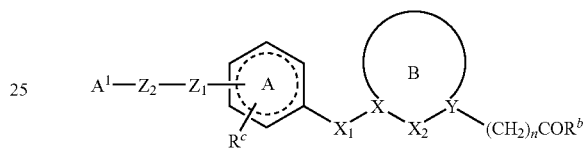

or a pharmaceutically acceptable salt thereof, wherein

is a 4-8 membered monocyclic ring or a 7-12 membered bicyclic ring, which ring is optionally saturated or unsaturated; which ring is optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, acylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)$. COR wherein n is 0-2 and R is hydroxy, alkoxy, alkyl or amino;

$A^1$ is a 5-9 membered monocyclic ring or 7-12 membered bicyclic heterocycle ring of the formula

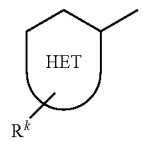

containing at least one nitrogen atom and optionally containing 1 to 4 heteroatoms, selected from the group consisting of O, N, S, $SO_2$ and CO; optionally saturated or unsaturated; optionally substituted by one or more Rk is selected from the group consisting of hydroxy, alkyl, alkoxy, alkoxyalkyl, thioalkyl, cyano, amino, alkylamino, haloalkyl, halogen, acylamino, sulfonamide and —COR wherein R is hydroxy, alkoxy, alkyl or amino;

or $A^1$ is

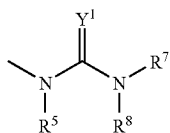

wherein $Y^1$ is selected from the group consisting of N—$R^2$, O, and S;

$R^2$ is selected from the group consisting of H; alkyl; aryl; hydroxy; alkoxy; cyano; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester;

or $R^2$ taken together with $R^7$ forms a 4-12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; aralkyl; amino; alkylamino; hydroxy; alkoxy; arylamino; amido; alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S; $R^5$ is selected from the group consisting of H, and alkyl;

or

A is

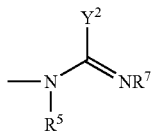

wherein Y is selected from the group consisting of alkyl; cycloalkyl; bicycloalkyl; aryl; monocyclic heterocycles;

$Z_1$ is selected from the group consisting of $CH_2$, $CH_2O$, O, NH, $NR_k$, CO, S, SO, CH(OH), and $SO_2$, wherein Rk is selected from H or lower alkyl;

$Z_2$ is a 1-5 carbon linker optionally containing one or more heteroatom selected from the group consisting of O, S and N; alternatively $Z_1$-$Z_2$ may further contain a carboxamide, sulfone, oxime, sulfonamide, alkenyl, alkynyl, or acyl group;

wherein the carbon and nitrogen atoms of $Z_1$-$Z_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

wherein $Z_2$-$Z_1$ is attached to

at the para or meta position relative to the $X_1$ substituent;

n is an integer 0, 1 or 2;

$R^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$—COR wherein n is 0-2 and R is selected from hydroxy, alkoxy, alkyl and amino;

$X_1$ is selected from the group consisting of —O—, CO, $SO_2$, $NR^m$ and $(CHR^p)_q$; wherein $R^m$ is H or alkyl; $R^p$ is H, alkyl, alkoxy or hydroxy and q is 0 or 1;

$X_2$ is selected from the group consisting of —$CHR^e$—, CO, $SO_2$, O, $NR^f$ and S;

$R^e$ is selected from the group consisting of H, alkyl, hydroxy and alkoxy; $R^f$ is H or alkyl;

X or Y are independently selected from the group consisting of —$CR^g$— or —N— wherein $R^g$ is selected from the group consisting of H, alkyl, haloalkyl, fluoro, alkoxyalkyl, alkynyl, aryl, heteroaryl, aralkyl, alkylsulfone, heteroaralkyl, hydroxy, alkoxy, hydroxyalkyl, and carboxyalkyl;

The group X—$X_2$—Y optionally contains a moiety selected from the group consisting of acyl, alkyl, amino, ether, thioether, sulfone, and olefin;

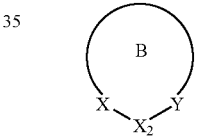

forms a 3-8 membered monocyclic ring system; or an 8-11 membered bicyclic system; optionally saturated or unsaturated; the monocyclic ring system optionally containing 1-2 heteroatoms selected from N, O and S; the bicyclic ring system optionally containing 1-4 heteroatoms selected from N, O, S or optionally containing the group such as $SO_2$ or CO); and optionally substituted with one or more substituent selected from the group consisting of alkyl, halogen, cyano, carboalkoxy, haloalkyl, alkoxyalkyl, alkylsulfone, aryl, heteroaryl, aralkyl, heteroaralkyl or alkoxy;

$R^b$ is $X_3$—$R^h$ wherein $X_3$ is selected from the group consisting of O, S and $NR^j$ wherein $R^h$ and $R^j$ are independently selected from the group consisting of H, alkyl, acyl, aryl, aralkyl and alkoxyalkyl; and and n is 0, 1 or 2.

It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrin(s) and therefore in another embodiment the present invention relates to a method of selectively inhibiting or antagonizing the $\alpha_v\beta_3$ and/or $\alpha_v\beta_5$ integrin(s). The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration including restenosis or atherosclerosis in a mammal in need of such treatment. Additionally, such pharmaceutical agents are useful as antiviral agents, antifungals and antimicrobials. The compounds of the present invention may be used alone or in combination with other pharmaceutical agents.

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_v\beta_3$ and/or $\alpha_v\beta_5$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious.

Therefore, compounds of the present invention which selectively inhibit the $\alpha_v\beta_3$ integrin as opposed to the $\alpha_v\beta_6$ integrin have reduced side-effects associated with inhibition of the $\alpha_v\beta$ $\alpha_v\beta_6$ integrin.

The present invention relates to a class of compounds represented by the Formula I.

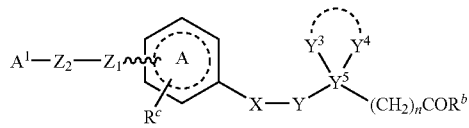

or a pharmaceutically acceptable salt thereof, wherein

is a 4-8 membered monocyclic or a 7-12 membered bicyclic ring, optionally saturated or unsaturated, optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, alkylsulfoxide, allyl, alkenyl, methylenedioxy, ethylenedioxy, alkynyl, carboxamide, cyano, and $-(CH_2)_n$, CUR wherein n is 0-2 and R is hydroxy, alkoxy, alkyl or amino;

$A^1$ is a 5-9 membered monocyclic or 7-12 membered bicyclic heterocycle of the formula

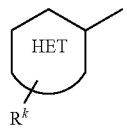

containing at least one nitrogen atom and optionally 1 to 3 additional heteroatoms, selected from the group consisting of O, N, S, CO, or $SO_2$ optionally saturated or unsaturated; optionally substituted by one or more Rk selected from the group consisting of hydroxy, alkyl, cycloalkyl, alkoxy, alkoxyalkyl, thioalkyl, cyano, amino, alkylamino, halogen, acylamino, sulfonamide and —COR wherein R is hydroxy, alkoxy, alkyl or amino;

or $A^1$ is

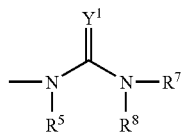

wherein $Y_1$ is selected from the group consisting of $N-R^2$, O, and S;

$R^2$ is selected from the group consisting of H; alkyl; cycloalkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl;

or $R^2$ taken together with $R^7$ forms a 4-12 membered heterocycle containing one or more heteroatom selected from O, N and S optionally unsaturated;

or $R^2$ taken together with $R^7$ forms a 5 membered heteroaromatic ring fused with an aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl, aryloxy, aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, hydroxy, alkoxy, cycloalkyl, and alkyl;

or

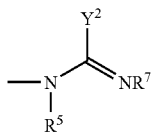

wherein Y² is selected from the group consisting of alkyl; cycloalkyl; bicycloalkyl; aryl; monocyclic heterocycles;

$Z_1$ is selected from the group consisting of $CH_2$, O, $CH_2O$, $NR_k$, CO, S, SO, CH(OH) and $SO_2$, wherein Rk is selected from H or lower alkyl;

$Z_2$ is a 1-5 carbon linker optionally containing one or more heteroatom selected from the group consisting of O, S and N; alternatively $Z_1$-$Z_2$ may further contain a carboxamide, sulfone, sulfonamide, alkenyl, alkynyl, or acyl group;

wherein the carbon and nitrogen atoms of $Z_1$-$Z_2$ are optionally substituted by alkyl, cycloalkyl, alkoxy, thioalkyl, alkylsulfone, aryl, arylsulfone, alkoxyalkyl, hydroxy, alkylamino, heteroaryl, alkenyl, alkynyl, carboxyalkyl, halogen, haloalkyl or acylamino;

n is an integer 1 or 2;

$R^c$ is selected from the group consisting of hydrogen, alkyl, heteroalkyl, cycloalkyl, heterocycloalkyl, halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$COR wherein n is 0-2 and R is selected from hydroxy, alkoxy, alkyl and amino;

X is selected from the group consisting of —$CHR^e$—, —$NR^f$—, —O—, —S—, —$SO_2$—, and —CO— wherein $R^e$ is H, lower alkyl, alkoxy, cycloalkyl, alkoxyalkyl, hydroxy, alkynyl, alkenyl, haloalkyl, thioalkyl or aryl; wherein when $R^e$ is hydroxy, the hydroxy group can optionally form a lactone with the carboxylic acid function of the chain; wherein $R^f$ is selected from the group consisting of H, alkyl, heteroalkyl, aryl, heteroaryl, aralkyl, arakylheteroaryl, and haloalkyl;

Y is selected from the group consisting of $(CH_2)_p$, —$CR^9$—, —$NR^9$, CO and $SO^2$, wherein $R^9$ is selected from the group consisting of H, alkyl, haloalkyl, alkoxyalkyl, alkynyl, aryl, heteroaryl, aralkyl, hydroxy, hydroxyalkyl, alkoxy, and carboxyalkyl; wherein p is 0 or 1;

optionally the group X—Y can contain a moiety selected from the group consisting of acyl, alkyl, sulfonyl, amino, ether, thioether, carboxamido, sulfonamido, aminosulfonyl and olefins;

$Y^3$ and $Y^4$ are independently selected from the group consisting of alkyl, haloalkyl, hydroxy, alkoxy, cyano, halogen, aralkyl, heteroaralkyl, alkoxyalkyl, hydroxyalkyl, aryloxyalkyl, alkylsulfone, alkene or alkyne; wherein the alkyl group optionally contains one or more heteroatoms selected from the group consisting of N, O, and S;

alternately, when $Y^3$ is an aryl or a heteroaryl, $Y^4$ may be an aryl, heteroaryl, alkene, alkyne, alkoxy, hydroxy, cyano, alkoxyalkyl or an alkylsulfone;

$Y^5$ is C;

Optionally, $Y^3$, $Y^4$ and $Y^5$ may form a sulfone ($SO_2$) group;

or $Y^3$ taken together with $Y^4$ forms a 3-8 membered monocyclic or a 7-11 membered bicyclic ring, optionally containing one or more double bonds, optionally containing one or more heteroatom or functional group selected from O, $NR^9$, S, CO or $SO_2$, optionally substituted with one or more substituent selected from the group consisting of alkyl, heteroalkyl, hydroxy, halogen, haloalkyl, alkoxy, alkyne, cyano, alkylsulfone, sulfonamide, aryl, heteroaryl, arakylaryl, heteroarakylarylcarboalkoxy and carboxyalkyl;

$R^b$ is $X_2$—$R^h$ wherein $X_2$ is selected from the group consisting of O, S and $NR^j$ wherein $R^h$ and $R^j$ are independently selected from the group consisting of H, alkyl, aryl, aralkyl, heteroalkyl, heteroaryl, heteroarakylaryl, acyl, and alkoxyalkyl;

It is another object of the invention to provide pharmaceutical compositions comprising compounds of the Formula I. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further involves treating or inhibiting pathological conditions associated therewith such as osteopbrosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. The compounds of the present invention may be used alone or in combination with other pharmaceutical agents.

The present invention as a first object provides compounds of the following formula (I)

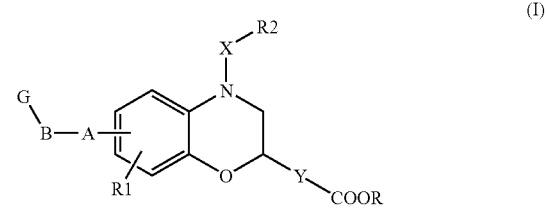

(I)

or a pharmaceutically acceptable salt, prodrug or ester thereof, wherein

G is selected from the group consisting of

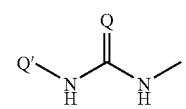

a)

wherein Q is NH or O and Q' is H, $C_1$-$C_6$ alkyl, phenyl, or phenyl-$C_1$-$C_4$-alkyl;

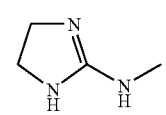

b)

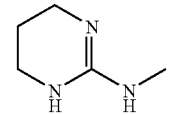

c)

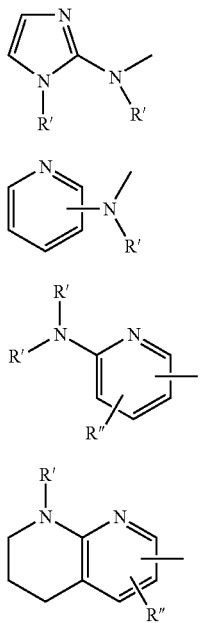

d)

e)

f)

g)

wherein R' and R" are independently H or $C_1$-$C_4$ alkyl;

B is a $C_1$-$C_4$ alkyl or a $C_2$-$C_4$ alkenyl;

A is $CH_2$, O, $S(O)_n$ wherein n is zero, 1 or 2, NH, a group $CON(R''')$ or $N(R''')CO$ wherein R''' is hydrogen or $CH_3$;

R1 is selected from the group consisting of H, $C_1$-$C_4$ alkyl, $C_1$-$C_4$ alkoxy, OH, halogen, and $CF_3$;

X is C=0 or completes a single bond;

R2 is selected from the group consisting of 1-1, $C_1$-$C_4$ alkyl, $C_3$-$C_7$ cycloalkyl, $C_1$-$C_4$-alkylcycloalkyl; aryl unsubstituted or optionally substituted by one to three substituents independently selected from halogen, $CF_3$, $C_1$-$C_4$ alkyl, hydroxy and $C_1$-$C_4$ alkoxy; aralkyl; and $C_5$-$C_7$ monocyclic heteroaryl ring containing one to three heteroatoms chosen from O, S, and N, unsubstituted or optionally substituted by one to three substituents independently selected from halogen, $CF_3$, $C_1$-$C_4$ alkyl, hydroxy and $C_1$-$C_4$ alkoxy;

Y is $(CH_2)_n$ wherein n is 1 or 2;

R is hydrogen, $C_1$-$C_6$ alkyl, $C_2$-$C_4$ alkenyl, $C_2$-$C_4$ alkynyl, aryl or aryl-$C_1$-$C_4$ alkyl.

With the proviso that m can not be 0 when G is:

a)

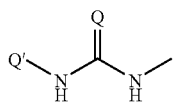

wherein Q' is H and Q is 0 and X is $(C=O)_m$.

The present invention includes within its scope all possible isomers, stereoisomers and optical isomers and their mixtures, and the bioprecursors or metabolites of the compounds of formula (I).

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

As evidenced by the continuing research in integrin antagonists and by the shortcomings of the compounds and methods of the art, there still remains a need for small-molecule, non-peptidic selective $\alpha_v\beta_3$ and/or $\alpha_v\beta_5$ antagonist that displays decreased side-effects, and improved potency, pharmacodynamic, and pharmacokinetic properties, such as oral bioavailability and duration of action, over already described compounds. Such compounds would prove to be useful for the treatment, prevention, or suppression of various pathologies enumerated above that are mediated by $\alpha_v\beta_3$ and/or $\alpha_v\beta_5$ receptor binding and cell adhesion and activation.

The compounds of this invention include 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, skeletal malignancy of breast cancer, osteoporosis, Paget's disease, humoral hypercalcemia of malignancy, retinopathy, macular degeneration, arthritis including rheumatoid, periodontal disease, smooth muscle cell migration, including restenosis and artherosclerosis, and microbial or viral diseases.

The compounds of the present invention can be used, alone or in combination with other therapeutic agents, in the treatment or modulation of various conditions or disease states described above.

In order to prevent bleeding side effects associated with the inhibition of $\alpha_v\beta_3$, it would be beneficial to have a high selectivity ratio of $\alpha_v\beta_3$ and $\alpha_v\beta_5$ over $\alpha_v\beta_3$. The compounds of the present invention include selective antagonists of $\alpha_v\beta_3$ over $\alpha_v\beta_3$.

The present invention relates to a class of compounds represented by Formula I

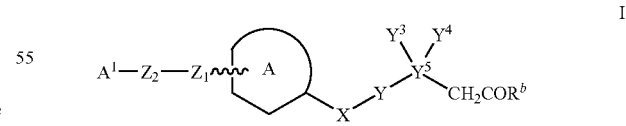

I or a pharmaceutically acceptable salt thereof, wherein

is a 4-8 membered monocyclic or a 7-12 membered bicyclic ring, containing 1 to 5 heteroatoms, selected from the group consisting of O, N or S; optionally saturated or unsaturated, optionally substituted with one or more substituents selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m$COR wherein m is 0-2 and R is hydroxy, alkoxy, alkyl or amino; with the proviso that when $Y^4$ in formula I is H, the ring A may not be an oxazole, with X—Y containing side-chain connected at the carbon-2 as in

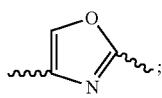

The ring A may further contain a carboxamide, sulfone, sulfonamide or an acyl group.

$A^1$ is a 5-9 membered monocyclic or 8-14 membered polycyclic heterocycle of the formula

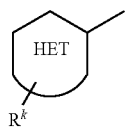

containing at least one nitrogen atom and optionally 1 to 4 heteroatoms or groups, selected from O, N, S, $SO_2$ or CO; optionally saturated or unsaturated; optionally substituted by one or more $R^k$ selected from the group consisting of hydroxy, alkyl, alkoxy, alkoxyalkyl, thioalkyl, haloalkyl, cyano, amino, alkylamino, halogen, acylamino, sulfonamide and —COR wherein R is hydroxy, alkoxy, alkyl or amino; or $A^1$ is

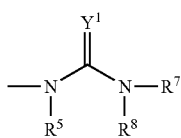

wherein $Y^1$ is selected from the group consisting of N—$R^2$, O, and S;

$R^2$ is selected from the group consisting of H; alkyl; aryl; hydroxy; alkoxy; cyano; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester; or $R^2$ taken together with $R^7$ forms a 4-12 membered heterocycle containing one or more heteroatom selected from O, N and S optionally unsaturated; or $R^2$ taken together with $R^7$ forms a 5 membered heteroaromatic ring fused with an aryl or heteroaryl ring;

$R^7$ (when not taken together with $R^2$) and $R^8$ are independently selected from the group consisting of H; alkyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; or $NR^7$ and $R^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H and alkyl; or
$A^1$ is

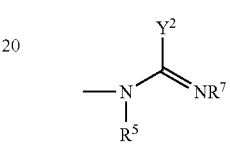

wherein $Y^2$ is selected from the group consisting of alkyl; cycloalkyl; bicycloalkyl; aryl; monocyclic heterocycles;

$Z_1$ is selected from the group consisting of $CH_2$, $CH_2O$, O, NH, CO, S, SO, CH(OH) and $SO_2$;

$Z_2$ is a 1-5 carbon linker optionally containing one or more heteroatom selected from the group consisting of O, S and N;

alternatively $Z_1$-$Z_2$ may further contain a carboxamide, sulfone, sulfonamide, alkenyl, alkynyl, or acyl group;

wherein the carbon and nitrogen atoms of $Z_1$-$Z_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

Additionally, $Z_1$-$Z_2$ may contain a 5- or 6-membered aryl or heteroaryl ring optionally substituted with $R^c$, wherein the heteroaryl ring may contain 1-3 heteroatoms selected from the group consisting of O, N and S; $R^c$ is selected from the group consisting of H, alkyl, haloalkyl, aryl, heteroaryl, halogen, alkoxyalkyl, aminoalkyl, hydroxy, alkoxy, carboxamide, or cyano.

X is selected from the group consisting of —$CHR^e$—, —$NR^f$—, —O—, —S—, —$SO_2$—, and —CO— wherein $R^e$ is H, lower alkyl, alkoxy, cycloalkyl, alkoxyalkyl, hydroxy, alkynyl, alkenyl, haloalkyl, thioalkyl or aryl; wherein when $R^e$ is hydroxy, the hydroxy group can optionally form a lactone with the carboxylic acid function of the chain; wherein $R^f$ is selected from the group consisting of H, alkyl, aryl, aralkyl, and haloalkyl;

Y is selected from the group consisting of $(CH_2)_p$, —$CHR^g$—, —$NR^g$—, CO and $SO_2$, wherein $R^g$ is selected from the group consisting of H, alkyl, haloalkyl, alkoxyalkyl, alkynyl, aryl, heteroaryl, aralkyl, hydroxy, alkoxy, and carboxyalkyl; wherein p is 0 or 1.

Optionally the group X—Y can contain a moiety selected from the group consisting of acyl, alkyl, sulfonyl, amino, ether, thioether, carboxamido, sulfonamido, aminosulfonyl and olefins;

$Y^3$ and $Y^4$ are independently selected from the group consisting of H, alkyl, haloalkyl, halogen, aryl, aralkyl, heteroaralkyl, heteroaryl, hydroxyalkyl, alkenes, and alkyne; wherein the alkyl chain may be straight or branched and optionally containing one or more heteroatoms selected from the group consisting of N, O, and S, and may further contain a sulfone, sulfonamide, nitrile, carboxamide, carboalkoxy or carboxyl group; wherein aryl and heteroaryl rings may be monocyclic or bicyclic optionally containing 1-5 heteroatoms and wherein said ring may be saturated or unsaturated, and such rings may optionally be substituted by one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m$COR wherein m is 0-2 and R is hydroxy, alkoxy, alkyl or amino; with the proviso that when $Y^3$ or $Y^4$ is H, $Y^5$ may be C or N, otherwise $Y^5$ is C; or $Y^3$ taken together with $Y^4$ forms a 3-8 membered monocyclic or a 7-11 membered bicyclic ring B,

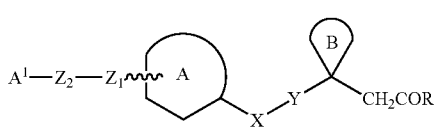

IA optionally containing one or more double bonds, optionally containing one or more heteroatom or functional group selected from O, $NR^5$, S, CO or $SO_2$, optionally substituted with one or more substituent selected from the group consisting of alkyl, hydroxy, halogen, haloalkyl, alkoxy, alkyne, cyano, alkylsulfone, sulfonamide, carboalkoxy and carboxyalkyl; or X taken together with $Y^3$ forms a 3-7 membered monocyclic ring C,

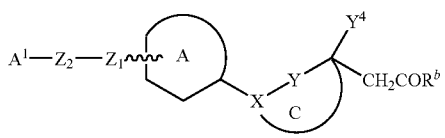

IB optionally containing one or more double bonds, optionally containing one or more heteroatom or functional group selected from O, $NR^g$, S, CO or $SO_2$, optionally substituted with one or more substituent selected from the group consisting of alkyl, halogen, alkoxy, haloalkyl, hydroxyalkyl, or alkoxyalkyl; and $R^b$ is $X_2$—$R^h$ wherein $X_2$ is selected from the group consisting of O, S and $NR^j$ wherein $R^h$ and $R^i$ are independently selected from the group consisting of H, alkyl, aryl, aralkyl, acyl and alkoxyalkyl.

The compounds of the present invention comprise novel heteroarylalkanoic integrin antagonists.

The present invention relates to the following compounds:

3-(3,5-ditert-butylphenyl)-4-{3-[3-(5,6,7,8-tetrahydro-1,8-naphthyridin-2-yl)propyl]-1,2,4-oxadiazol-5-yl}butanoic acid (TFA salt);

3-(3-tert-butyl-5-iodophenyl)-4-{3-[3-(5,6,7,8-tetrahydro-1,8-naphthyridin-2-yl)propyl]-1,2,4-oxadiazol-5-yl}butanoic acid;

3-(3-tert-butyl-5-bromophenyl)-4-{3-[3-(5,6,7,8-tetrahydro-1,8-naphthyridin-2-yl)propyl]-1,2,4-oxadiazol-5-yl}butanoic acid;

3-(5-tert-Butyl-2-hydroxyphenyl)-4-{3-[3-(5,6,7,8-tetrahydro-1,8-naphthyridin-2-yl)propyl]-1,2,4-oxadiazol-5-yl}butanoic acid;

3-[3,5-Ditert-butyl-2-(carboxymethoxy)phenyl]-4-{3-[3-(5,6,7,8-tetrahydro-1,8-naphthyridin-2-yl)propyl]-1,2,4-oxadiazol-5-yl}butanoic acid;

3-(5-tert-Butyl-2-methoxyphenyl)-4-{3-[3-(5,6,7,8-tetrahydro-1,8-naphthyridin-2-yl)propyl]-1,2,4-oxadiazol-5-yl}butanoic acid;

3-(3,5-Ditert-butyl-4-methoxyphenyl)-4-{3-[3-(5,6,7,8-tetrahydro-1,-8-naphthyridin-2-yl)propyl]-1,2,4-oxadiazol-5-yl}butanoic acid;

3-{3-tert-Butyl-5-[2,2,2-trifluoro-1-hydroxyl-(trifluoromethyl)ethyl]-phenyl}-4-{3-[3-(5,6,7,8-tetrahydro-1,8-naphthyridin-2-yl)propyl]-1,2,-4-oxadiazol-5-yl}butanoic acid;

3-(3,4-Dichlorophenyl)-4-{3-[3-(5,6,7,8-tetrahydro-1,8-naphthridin-2-yl)propyl]-1,2,4-oxadiazol-5-yl}butanoic acid trifluoroacetate;

3-(3-Fluoro-4-methylphenyl)-4-{3-[3-(5,6,7,8-tetrahydro-1,8-naphthyridin-2-yl)propyl]-1,2,4-oxadiazol-5-yl}butanoic acid hydrochloride;

3-(4-Phenoxyphenyl)-4-{3-[3-(5,6,7,8-tetrahydro-1,8-naphthyridin-2-yl)propyl]-1,2,4-oxadiazol-5-yl}butanoic acid trifluoroacetate;

3-(1-Benzofuran-2-yl)-4-{3-[3-(5,6,7,8-tetrahydro-1,8-naphthyridin-2-yl)propyl]-1,2,4-oxadiazol-5-yl}butanoic acid trifluoroacetate;

3-[4-(Benzyloxy)phenyl]4-{3-[3-(5,6,7,8-tetrahydro-1,8-naphthridin-2-yl)propyl]-1,2,4-oxadiazol-5-yl}butanoic acid trifluoroacetate;

3-[4-(Methylsulfonyl)phenyl]-4-{3-[3-(5,6,7,8-tetrahydro-1,8-naphthyridin-2-yl)propyl]-1,2,4-oxadiazol-5-yl}butanoic acid trifluoroacetate;

4-{3-[3-(5,6,7,8-Tetrahydro-1,8-naphthyridin-2-yl)propyl]-1,2,4-oxadiazol-5-yl}-3-[4-(trifluoromethoxy)phenyl]butanoic acid trifluoroacetate;

3-(3-Furyl)-4-{3-[3-(5,6,7,8-tetrahydro-1,8-naphthyridin-2-yl)propyl]-1,2,4-oxadiazol-5-yl}butanoic acid trifluoroacetate;

4-{3-[3-(5,6,7,8-Tetrahydro-1,8-naphthyridin-2-yl)propyl]-1,2,4-oxadiazol-5-yl}-3-thien-3-ylbutanoic acid trifluoroacetate;

3-(2,3-Dihydro-1,4-benzodioxin-6-yl)-4-{3-[3-(5,6,7,8-tetrahydro-1,-8-naphthyridin-2-yl)propyl]-1,2,4-oxadiazol-5-yl}butanoic acid hydrochloride;

4-{3-[3-(5,6,7,8-Tetrahydro-1,8-naphthyridin-2-yl)propyl]-1,2,4-oxadiazol-5-yl}-3-[3-(trifluoromethoxy)phenyl]butanoic acid hydrochloride;

4-{3-[3-(5,6,7,8-Tetrahydro-1,8-naphthyridin-2-yl)propyl]-1,2,4-oxa-yl}-3-(3,4,5-trifluorophenyl)butanoic acid hydrochloride;

3-(2,2-Difluoro-1,3-benzodioxol-5-yl)-4-{3-[3-(5,6,7,8-tetrahydro-1,-8-naphthyridin-2-yl)propyl]-1,2,4-oxadiazol-5-yl}butanoic acid hydrochloride;

3-[3-Fluoro-5-(trifluoromethyl)phenyl]4-{3-[3-(5,6,7,8-tetrahydro-1,-8-naphthyridin-2-yl)propyl]-1,2,4-oxadiazol-5-yl}butanoic acid hydrochloride;

3-(6-Methoxy-2-naphthyl)-4-{3-[3-(5,6,7,8-tetrahydro-1,8-naphthyridin-2-yl)propyl]-1,2,4-oxadiazol-5-yl}butanoic acid hydrochloride;

3-(6-Methoxypyridin-3-yl)-4-{3-[3-(5,6,7,8-tetrahydro-1,8-naphthyridin-2-yl)propyl]-1,2,4-oxadiazol-5-yl}butanoic acid;

3-(4-Cyanophenyl)-4-{3-[3-(5,6,7,8-tetrahydro-1,8-naphthyridin-2-yl-)propyl]-1,2,4-oxadiazol-5-yl}butanoic acid;

3-(3-Cyanophenyl)-4-{3-[3-(5,6,7,8-tetrahydro-1,8-naphthyridin-2-yl-)propyl]-1,2,4-oxadiazol-5-yl}butanoic acid;

3-benzyl-4-{3-[3-(5,6,7,8-tetrahydro-1,8-naphthyridin-2-yl)propyl]-1,2,4-oxadiazol-5-yl}butanoic acid trifluoroacetate;
3-(4-fluoro-3-methoxyphenyl)-4-{3-[3-(5,6,7,8-tetrahydro-1,8-naphthyridin-2-yl)propyl]-1,2,4-oxadiazol-5-yl}butanoic acid trifluoroacetate;
3-(3-Fluoro-5-methoxyphenyl)-4-{3-[3-(5,6,7,8-tetrahydro-1,8-naphthyridin-2-yl)propyl]-1,2,4-oxadiazol-5-yl}butanoic acid hydrochloride;
3-(2-Methyl-1,3-benzothiazol-5-yl)-4-{3-[3-(5,6,7,8-tetrahydro-1,8-naphthyridin-2-yl)propyl]-1,2,4-oxadiazol-5-yl}butanoic acid hydrochloride;
3-[2-(4-Chlorophenyl)-1,3-thiazol-5-yl]-4-{3-[3-(5,6,7,8-tetrahydro-1,8-naphthyridin-2-yl)propyl]-1,2,4-oxadiazol-5-yl}butanoic acid hydrochloride;
3-[2-(4-Methoxyphenyl)-1,3-thiazol-5-yl]4-{3-[3-(5,6,7,8-tetrahydro-1,8-naphthyridin-2-yl)propyl]-1,2,4-oxadiazol-5-yl}butanoic acid hydrochloride;
3-(2-Methyl-1,3-benzothiazol-5-yl)-4-{3-[3-(5,6,7,8-tetrahydro-1,8-naphthyridin-2-yl)propyl]-1,2,4-oxadiazol-5-yl}butanoic acid hydrochloride;
3-[2-(4-Fluorophenyl)-1,3-thiazol-5-yl]-4-{3-[3-(5,6,7,8-tetrahydro-1,8-naphthyridin-2-yl)propyl]-1,2,4-oxadiazol-5-yl}butanoic acid hydrochloride;
3-[2-(3,5-Difluorophenyl)-1,3-thiazol-5-yl]-4-{3-[3-(5,6,7,8-tetrahydro-1,8-naphthyridin-2-yl)propyl]-1,2,4-oxadiazol-5-yl}butanoic acid hydrochloride;
3-[2-(3,4-Difluorophenyl)-1,3-thiazol-5-yl]4-{3-[3-(5,6,7,8-tetrahydro-1,8-naphthyridin-2-yl)propyl]-1,2,4-oxadiazol-5-yl}butanoic acid hydrochloride;
3-[2-(2-Furyl)-1,3-thiazol-5-yl]4-{3-[3-(5,6,7,8-tetrahydro-1,8-naphthyridin-2-yl)propyl]-1,2,4-oxadiazol-5-yl}butanoic acid hydrochloride;
3-(3,4-Dimethoxyphenyl)-4-{3-[3-(5,6,7,8-tetrahydro-1,8-naphthyridin-2-yl)propyl]1,2,4-oxadiazol-5-yl}butanoic acid trifluoroacetate;
3-(3,5-Dimethoxyphenyl)-4-{3-[3-(5,6,7,8-tetrahydro-1,8-naphthyridin-2-yl)propyl]1,2,4-oxadiazol-5-yl}butanoic acid trifluoroacetate;
3-(3,5-Dichlorophenyl)-4-{3-[3-(5,6,7,8-tetrahydro-1,8-naphthyridin-2-yl)propyl]-1,2,4-oxadiazol-5-yl}butanoic acid trifluoroacetate;
3-(3,5-Difluorophenyl)-4-{3-[3-(5,6,7,8-tetrahydro-1,8-naphthyridin-2-yl)propyl]-1,2,4-oxadiazol-5-yl}butanoic acid trifluoroacetate;
3-(3-Fluoro-4-methoxyphenyl)-4-{3-[3-(5,6,7,8-tetrahydro-1,8-naphthyridin-2-yl)propyl]-1,2,4-oxadiazol-5-yl}butanoic acid trifluoroacetate;
4-{3-[3-(5,6,7,8-Tetrahydro-1,8-naphthyridin-2-yl)propyl]-1,2,4-oxadiazol-5-yl}-3-[4-(trifluoromethyl)phenyl]butanoic acid trifluoroacetate;
3-(2-Methyl-1,3-thiazol-5-yl)-4-{3-[3-(5,6,7,8-tetrahydro-1,8-naphthyridin-2-yl)propyl]-1,2,4-oxadiazol-5-yl}butanoic acid trifluoroacetate;
3-(1-Phenyl-1H-pyrazol-4-yl)-4-{3-[3-(5,6,7,8-tetrahydro-1,8-naphthyridin-2-yl)propyl]-1,2,4-oxadiazol-5-yl}butanoic acid trifluoroacetate;
3-(1-Benzofuran-6-yl)-4-{3-[3-(5,6,7,8-tetrahydro-1,8-naphthyridin-2-yl)propyl]-1,2,4-oxadiazol-5-yl}butanoic acid hydrochloride;
3-(2,3-dihydro-1-benzofuran-6-yl)-4-{3-[3-(5,6,7,8-tetrahydro-1,8-naphthyridin-2-yl)propyl]-1,2,4-oxadiazol-5-yl}butanoic acid hydrochloride;
3-(1,3-Benzodioxol-5-yl)-4-(3-{3-[(pyridin-2-ylamino)methyl]phenyl}-1,2,4-oxadiazol-5-yl)butanoic acid hydrochloride;
3-(7-Fluoro-1,3-benzodioxol-5-yl)-4-{3-[3-(5,6,7,8-tetrahydro-1,8-naphthyridin-2-yl)propyl]-1,2,4-oxadiazol-5-yl}butanoic acid trifluoroacetate;
3-(1,3-Benzoxazol-6-yl)-4-{3-[3-(5,6,7,8-tetrahydro-1,8-naphthyridin-2-yl)propyl]-1,2,4-oxadiazol-5-yl}butanoic acid hydrochloride;
3-(3-Methyl-1,2,4-oxadiazol-5-yl)-4-{3-[3-(5,6,7,8-tetrahydro-1,8-naphthyridin-2-yl)propyl]-1,2,4-oxadiazol-5-yl}butanoic acid trifluoroacetate;
3-(3-Ethyl-1,2,4-oxadiazol-5-yl)-4-{3-[3-(5,6,7,8-tetrahydro-1,8-naphthyridin-2-yl)propyl]-1,2,4-oxadiazol-5-yl}butanoic acid trifluoroacetate;
3-(3-Phenyl-1,2,4-oxadiazol-5-yl)-4-{3-[3-(5,6,7,8-tetrahydro-1,8-naphthyridin-2-yl)propyl]-1,2,4-oxadiazol-5-yl}butanoic acid trifluoroacetate;
[1-Benzoyl-4-{3-[3-(5,6,7,8-tetrahydro-1,8-naphthyridin-2-yl)propyl]-1,2,4-oxadiazol-5-yl}methyl)piperidin-4-yl]acetic acid trifluoroacetate;
[1-Benzoyl-4-({3-[4-(pyridin-2-ylamino)butyl]-1,2,4-oxadiazol-5-yl]-methyl)piperidin-4-yl}acetic acid trifluoroacetate;
[1-(tert-Butoxycarbonyl)-4-({3-[3-(5,6,7,8-tetrahydro-1,8-naphthyridin-2-yl)propyl]-1,2,4-oxadiazol-5-yl}methyl)piperidin-4-yl]acetic acid trifluoroacetate;
[1-(tert-Butoxycarbonyl)-4-({3-[4-(pyridin-2-ylamino)butyl]-1,2,4-oxadiazol-5-yl}methyl)piperidin-4-yl]acetic acid trifluoroacetate;
3-(4-Methylphenyl)-4-{3-[3-(5,6,7,8-tetrahydro-1,8-naphthyridin-2-yl)propyl]-1,2,4-oxadiazol-5-yl}butanoic acid trifluoroacetate;
3-(3-Chlorophenyl)-4-{3-[3-(5,6,7,8-tetrahydro-1,8-naphthyridin-2-yl)propyl]-1,2,4-oxadiazol-5-yl}butanoic acid hydrochloride;
3-(4-Methoxy-3-methylphenyl)-4-{3-[3-(5,6,7,8-tetrahydro-1,8-naphthyridin-2-yl)propyl]-1,2,4-oxadiazol-5-yl}butanoic acid hydrochloride;
3-[4-(Methylthio)phenyl]-4-{3-[3-(5,6,7,8-tetrahydro-1,8-naphthyridin-2-yl)propyl]-1,2,4-oxadiazol-5-yl}butanoic acid trifluoroacetate;
3-(1-Methyl-1H-indol-3-yl)-4-{3-[3-(5,6,7,8-tetrahydro-1,8-naphthyridin-2-yl)propyl]-1,2,4-oxadiazol-5-yl}butanoic acid trifluoroacetate;
3-(1,1'-Biphenyl-4-yl)-4-{3-[3-(5,6,7,8-tetrahydro-1,8-naphthyridin-2-yl)propyl]-1,2,4-oxadiazol-5-yl}butanoic acid hydrochloride;
3-(3-Bromophenyl)-4-{3-[3-(5,6,7,8-tetrahydro-1,8-naphthyridin-2-yl-)propyl]-1,2,4-oxadiazol-5-yl}butanoic acid trifluoroacetate;
3-(4-Bromophenyl)-4-{3-[3-(5,6,7,8-tetrahydro-1,8-naphthyridin-2-yl-)propyl]-1,2,4-oxadiazol-5-yl}butanoic acid hydrochloride;
3-(3-Phenoxyphenyl)-4-{3-[3-(5,6,7,8-tetrahydro-1,8-naphthyridin-2-yl)propyl]-1,2,4-oxadiazol-5-yl}butanoic acid trifluoroacetate;
3-[3-(Benzyloxy)phenyl]4-{3-[3-(5,6,7,8-tetrahydro-1,8-naphthyridin-2-yl)propyl]-1,2,4-oxadiazol-5-yl}butanoic acid hydrochloride;
3-(3-Bromo-4-methoxyphenyl)-4-{3-[3-(5,6,7,8-tetrahydro-1,8-naphthyridin-2-yl)propyl]-1,2,4-oxadiazol-5-yl}butanoic acid trifluoroacetate;
4-{3-[3-(5,6,7,8-Tetrahydro-1,8-naphthyridin-2-yl)propyl]-1,2,4-oxadiazol-5-yl}-3-(3,4,5-trimethoxyphenyl)butanoic acid trifluoroacetate;
3-(2-Naphthyl)-4-{3-[3-(5,6,7,8-tetrahydro-1,8-naphthyridin-2-yl)propyl]-1,2,4-oxadiazol-5-yl}butanoic acid hydrochloride;

3-(3-Nitrophenyl)-4-{3-[3-(5,6,7,8-tetrahydro-1,8-naphthyridin-2-yl-)propyl]-1,2,4-oxadiazol-5-yl}butanoic acid hydrochloride;

3-(3-Methylphenyl)-4-{3-[3-(5,6,7,8-tetrahydro-1,8-naphthyridin-2-yl)propyl]-1,2,4-oxadiazol-5-yl}butanoic acid hydrochloride;

3-(2-Furyl)-4-{3-[3-(5,6,7,8-tetrahydro-1,8-naphthyridin-2-yl)propyl]-1,2,4-oxadiazol-5-yl}butanoic acid hydrochloride;

3-(2-Methylphenyl)-4-{3-[3-(5,6,7,8-tetrahydro-1,8-naphthyridin-2-yl)propyl]-1,2,4-oxadiazol-5-yl}butanoic acid hydrochloride;

3-(1,3-benzodioxol-5-yl)-4-{3-[3-(3,4-dihydro-2,1-pyrido[3,2-b][1,4]-oxazin-6-yl)propyl]-1,2,4-oxadiazol-5-yl}butanoic acid, TFA;

4-{3-[3-(3,4-dihydro-2H-pyrido[3,2-b][1,4]oxazin-6-yl)propyl]-1,2,4-oxadiazol-5-yl}-3-(3,5-dimethoxyphenyl)butanoic acid, TFA;

3-Benzo[1,3]dioxol-5-yl-4-{3-[3-(6,7,8,9-tetrahydro-5-oxa-1,9-diaza-benzocyclohepten-2-yl)-propyl]-[1,2,4]oxadiazol-5-yl}-butyric acid;

3-(3-Fluoro-4-methoxyphenyl)-4-{3-[3-(6,7,8,9-tetrahydro-5-oxa-1,9-diaza-benzocyclohepten-2-yl)-propyl]-[1,2,4]oxadiazol-5-yl}-butyric acid;

3-(3,5-Difluorophenyl)-4-{3-[3-(6,7,8,9-tetrahydro-5-oxa-1,9-diaza-benzocyclohepten-2-yl)-propyl]-[1,2,4]oxadiazol-5-yl}-butyric acid;

3-(3,5-Dimethoxyphenyl)-4-{3-[3-(6,7,8,9-tetrahydro-5-oxa-1,9-diaza-benzocyclohepten-2-yl)-propyl]-[1,2,4]oxadiazol-5-yl}-butyric acid;

3-(2-Methylbenzothiazol-5-yl)-4-{3-[3-(6,7,8,9-tetrahydro-5-oxa-1,9-diaza-benzocyclohepten-2-yl)-propyl]-[1,2,4]oxadiazol-5-yl}-butyric acid;

3-(1,3-benzodioxol-5-yl)-4-{3-[3-(1,2,3,5-tetrahydropyrido[2,3-e][1-,4]oxazepin-8-yl)propyl]-1,2,4-oxadiazol-5-yl}butanoic acid, TFA;

3-(3,5-dimethoxyphenyl)-4-{3-[3-(1,2,3,5-tetrahydropyrido[2,3-e][1,4]oxazepin-8-yl)propyl]-1,2,4-oxadiazol-5-yl}butanoic acid, TFA;

3-(1,3-Benzodioxol-5-yl)-4-(3-{3-[6-(methylamino)pyridin-2-yl]propyl}-1,2,4-oxadiazol-5-yl)butanoic acid hydrochloride;

3-(3-Fluorophenyl)-4-(3-{3-[6-(methylamino)pyridin-2-yl]propyl}-1,2-,4-oxadiazol-5-yl)butanoic acid trifluoroacetate;

3-(1,3-benzodioxol-5-yl)-4-(3-{3-[6-(ethylamino)pyridin-2-yl]propyl-1,2,4-oxadiazol-5-yl}butanoic acid trifluoroacetate;

3-(3-Fluorophenyl)-4-(3-{3-[6-(methylamino)pyridin-2-yl]propyl-1,2,-4-oxadiazol-5-yl}butanoic acid trifluoroacetate;

3-(1,3-Benzodioxol-5-yl)-4-(3-{4-[(4-methylpyridin-2-yl)amino]butyl-}-1,2,4-oxadiazol-5-yl)butanoic acid;

3-(1,3-benzodioxol-5-yl)-4-(3-{4-[(6-methylpyridin-2-yl)amino]butyl-)-1,2,4-oxadiazol-5-yl)butanoic acid;

(2-{6-[2-(5,6,7,8-Tetrahydro-1,8-naphthyridin-2-yl)ethoxy]pyridin-3-yl}cyclopropyl)acetic acid;

3-Methyl-4-{6-[2-(5,6,7,8-tetrahydro-1,8-naphthyridin-2-yl)ethoxy]pyridin-3-yl}butanoic acid;

3-(1,3-benzodioxol-5-yl)-4-{5-[3-(5,6,7,8-tetrahydro-1,8-naphthyridin-2-yl)propyl]-1,3,4-oxadiazol-2-yl}butanoic acid trifluoroacetate;

3-(3-fluorophenyl)-4-{5-[3-(5,6,7,8-tetrahydro-1,8-naphthyridin-2-yl)propyl]-1,3,4-oxadiazol-2-yl}butanoic acid trifluoroacetate;

3-(3-Fluoro-4-methoxyphenyl)-4-{5-[3-(5,6,7,8-tetrahydro-1,8-naphthyridin-2-yl)propyl]-1,3,4-oxadiazol-2-yl}butanoic acid trifluoroacetate;

3-(3,5-Dimethoxyphenyl)-4-{5-[3-(5,6,7,8-tetrahydro-1,8-naphthyridin-2-yl)propyl]-1,3,4-oxadiazol-2-yl}butanoic acid trifluoroacetate;

3-(2-Methyl-1,3-thiazol-5-yl)-4-{5-[3-(5,6,7,8-tetrahydro-1,8-naphthyridin-2-yl)propyl]-1,3,4-oxadiazol-2-yl}butanoic acid trifluoroacetate;

3-(4-Fluorophenyl)-4-{5-[3-(5,6,7,8-tetrahydro-1,8-naphthyridin-2-yl)propyl]-1,3,4-oxadiazol-2-yl}butanoic acid trifluoroacetate;

3-(3,5-Difluorophenyl)-4-{5-[3-(5,6,7,8-tetrahydro-1,8-naphthyridin-2-yl)propyl]-1,3,4-oxadiazol-2-yl}butanoic acid trifluoroacetate;

3-(3,5-Difluorophenyl)-4-{5-[3-(5,6,7,8-tetrahydro-1,8-naphthyridin-2-yl)propyl]-1,3,4-thiadiazol-2-yl}butanoic acid trifluoroacetate;

3-(4-Fluorophenyl)-4-{5-[3-(5,6,7,8-tetrahydro-1,8-naphthyridin-2-yl-)propyl]-1,3,4-thiadiazol-2-yl}butanoic acid trifluoroacetate;

3-(2-Methyl-1,3-thiazol-5-yl)-4-{5-[3-(5,6,7,8-tetrahydro-1,8-naphthyridin-2-yl)propyl]-1,3,4-thiadiazol-2-yl}butanoic acid trifluoroacetate;

3-(1,3-Benzodioxol-5-yl)-4-{5-[3-(5,6,7,8-tetrahydro-1,8-naphthyridin-2-yl)propyl]-1,3,4-thiadiazol-2-yl}butanoic acid trifluoroacetate;

3-(1,3-benzodioxol-5-yl)-4-{3-[2-(5,6,7,8-tetrahydro-1,8-naphthyridin-2-yl)ethoxy]isoxazol-5-yl}butanoic acid;

3-(1,3-benzodioxol-5-yl)-4-{5-[3-(5,6,7,8-tetrahydro-1,8-naphthyridin-2-yl)propyl]-2H-tetraazol-2-yl}butanoic acid;

3-(1,3-benzodioxol-5-yl)-4-{5-[3-(5,6,7,8-tetrahydro-1,8-naphthyridin-2-yl)propyl]-1H-tetraazol-1-yl}butanoic acid;

3-(1,3-benzodioxol-5-yl)-4-{3-[2-(5,6,7,8-tetrahydro-1,8-naphthyridin-2-yl)ethoxy]-1H-pyrazol-5-yl}butanoic acid;

3-(1,3-benzodioxol-5-yl)-4-{3-[3-(4,5-dihydro-1H-imidazol-2-ylamino-) propoxy]isoxazol-5-yl}butanoic acid;

3-[2-(4-chlorophenyl)-1,3-thiazol-5-yl]4-{3-[2-(5,6,7,8-tetrahydro-1,8-naphthyridin-2-yl)ethoxy]isoxazol-5-yl}butanoic acid;

3-Benzo[1,3]dioxol-5-yl-4-{3-[2-(6,7,8,9-tetrahydro-5-oxa-1,9-diaza-benzocyclohepten-2-yl)-ethoxy]-isoxazol-5-yl}-butyric acid;

3-Benzo[1,3]dioxol-5-yl-4-{3-oxo-2-[2-(6,7,8,9-tetrahydro-5-oxa-1,9-diaza-benzocyclohepten-2-yl)-ethyl]-2,3-dihydro-isoxazol-5-yl}-butyric acid;

3-(1,3-benzodioxol-5-yl)-4-{3-[2-(3,4-dihydro-2H-pyrido[3,2-b][1,4]-oxazin-6-yl)ethoxy]isoxazol-5-yl}butanoic acid, TFA;

3-(1,3-benzodioxol-5-yl)-4-{2-[2-(3,4-dihydro-2H-pyrido[3,2-b][1,4]-oxazin-6-yl)ethyl]-3-oxo-2,3-dihydroisoxazol-5-yl}butanoic acid, TFA;

3-(1,3-benzodioxol-5-yl)-4-{3-[2-(1,2,3,5-tetrahydropyrido[2,3-e][1-,4]oxazepin-8-yl)ethoxy]isoxazol-5-yl}butanoic acid, TFA;

3-(1,3-benzodioxol-5-yl)-4-{3-oxo-2-[2-(1,2,3,5-tetrahydropyrido[2,-3-e][1,4]oxazepin-8-yl)ethyl]-2,3-dihydroisoxazol-5-yl}butanoic acid, TFA;

3-(1,3-benzodioxol-5-yl)-4-(3-{2-[5-(methoxymethyl)-6-(methylamino)-pyridin-2-yl]ethoxy}isoxazol-5-yl)butanoic acid, TFA;

3-(1,3-Benzodioxol-5-yl)-4-{3-[3-(5,5-dimethyl-5,6,7,8-tetrahydro-1-,8-naphthyridin-2-yl)propyl]-1,2,4-oxadiazol-5-yl}butanoic acid;

3-(1,3-benzodioxol-5-yl)-4-{3-[3-(1-methyl-1,2,3,4-tetrahydropyrido-[2,3-b]pyrazin-6-yl)propyl]-1,2,4-oxadiazol-5-yl}butanoic acid;
3-(2-methyl-1,3-benzothiazol-5-yl)-4-{3-[3-(1-methyl-1,2,3,4-tetrahydropyrido[2,3-b]pyrazin-6-yl)propyl]-1,2,4-oxadiazol-5-yl}butanoic acid;
3-(3-fluoro-4-methoxyphenyl)-4-{3-[3-(1-methyl-1,2,3,4-tetrahydropyrido[2,3-b]pyrazin-6-yl)propyl]-1,2,4-oxadiazol-5-yl}butanoic acid;
3-(6-methoxypyridin-3-yl)-4-{3-[3-(1-methyl-1,2,3,4-tetrahydropyrido[2,3-b]pyrazin-6-yl)propyl]-1,2,4-oxadiazol-5-yl}butanoic acid;
3-(1,3-benzodioxol-5-yl)-4-(3-{[2-(5,6,7,8-tetrahydro-1,8-naphthyridin-2-yl)ethyl]thio}-1H-1,2,4-triazol-5-yl)butanoic acid;
3-(1,3-benzodioxol-5-yl)-4-(1-methyl-5-{[2-(5,6,7,8-tetrahydro-1,8-naphthyridin-2-yl)ethyl]thio}-1H-1,2,4-triazol-3-yl)butanoic acid;
3-(1,3-benzodioxol-5-yl)-4-(4-methyl-5-{[2-(5,6,7,8-tetrahydro-1,8-naphthyridin-2-yl)ethyl]thio}4H-1,2,4-triazol-3-yl)butanoic acid;
3-(1,3-benzodioxol-5-yl)-4-{3-[2-(1-methyl-1,2,3,4-tetrahydropyrido-[2,3-b]pyrazin-6-yl)ethoxy]isoxazol-5-yl}butanoic acid;
3-(1,3-benzodioxol-5-yl)-4-(3-{2-[6-(methylamino)pyridin-2-yl]ethoxy}isoxazol-5-yl)butanoic acid; and
3-(6-methoxypyridin-3-yl)-4-{3-[2-(5,6,7,8-tetrahydro-1,8-naphthyridin-2-yl)ethoxy]isoxazol-5-yl}butanoic acid.

In another embodiment, the present invention may also include the following compounds:
3-methyl-4-(3-{3-[(pyridin-2-ylamino)methyl]phenyl}-1,2,4-oxadiazol-5-yl)butanoic acid;
3-methyl-4-(3-{4-[(pyridin-2-ylamino)methyl]phenyl}-1,2,4-oxadiazol-5-yl)butanoic acid;
3,3-dimethyl-4-{4-[4-(pyridin-2-ylamino)butyl]-1,3-thiazol-2-yl}butanoic acid;
[1-({3-[4-(pyridin-2-ylamino)butyl]-1,2,4-oxadiazol-5-yl}methyl)cyclopentyl]-acetic acid;
4-phenyl-4-{3-[4-(pyridin-2-ylamino)butyl]-1,2,4-oxadiazol-5-yl}-butanoic acid;
2-phenyl-4-{3-[4-(pyridin-2-ylamino)butyl]-1,2,4-oxadiazol-5-yl}-butanoic acid;
3,3-dimethyl-4-{3-[2-(2-methyl-5,6,7,8-tetrahydro-1,8-naphthyridin-3-yl)ethyl]-1,2,4-oxadiazol-5-yl}butanoic acid;
[1-({3-[2-(2-methyl-5,6,7,8-tetrahydro-1,8-naphthyridin-3-yl)ethyl]-1,2,4-oxadiazol-5-yl}methyl)cyclopentyl]acetic acid;
4-{3-[2-(2-methyl-5,6,7,8-tetrahydro-1,8-naphthyridin-3-yl)ethyl]-1-,2,4-oxadiazol-5-yl}4-phenylbutanoic acid;
4-{3-[2-(2-methyl-5,6,7,8-tetrahydro-1,8-naphthyridin-3-yl)ethyl]-1-,2,4-oxadiazol-5-yl}-2-phenylbutanoic acid;
4-{3-[2-(2-methyl-5,6,7,8-tetrahydro-1,8-naphthyridin-3-yl)ethyl]-1-,2,4-oxadiazol-5-yl}-2-phenylbutanoic acid;
3,3-dimethyl-4-{3-[3-(5,6,7,8-tetrahydro-1,8-naphthyridin-2-yl)propyl]-1,2,4-oxadiazol-5-yl}butanoic acid;
[1-({3-[3-(5,6,7,8-tetrahydro-1,8-naphthyridin-2-yl)propyl]-1,2,4-oxadiazol-5-yl}methyl)cyclopentyl]acetic acid;
4-phenyl-4-[3-[3-(5,6,7,8-tetrahydro-1,8-naphthyridin-2-yl)propyl]-1,2,4-oxadiazol-5-yl]butanoic acid;
2-phenyl-4-{3-[3-(5,6,7,8-tetrahydro-1,8-naphthyridin-2-yl)propyl]-1,2,4-oxadiazol-5-yl}butanoic acid;
3-(1,3-benzodioxol-5-yl)-4-{3-[3-(5,6,7,8-tetrahydro-1,8-naphthyridin-2-yl)propyl]-1,2,4-oxadiazol-5-yl}butanoic acid;
3-(1,3-benzodioxol-5-yl)-4-{3-[4-(pyridin-2-ylamino)butyl]-1,2,4-oxadiazol-5-yl}butanoic acid;
3-quinolin-3-yl-4-{3-[3-(5,6,7,8-tetrahydro-1,8-naphthyridin-2-yl)-propyl]-1,2,4-oxadiazol-5-yl}butanoic acid;
3-quinolin-3-yl 4-{3-[4-(pyridin-2-ylamino)butyl]-1,2,4-oxadiazol-5-yl}-butanoic acid;
3-(3-methoxyphenyl)-4-{3-[3-(5,6,7,8-tetrahydro-1,8-naphthyridin-2-yl)propyl]-1,2,4-oxadiazol-5-yl}butanoic acid;
3-(3-methoxyphenyl)-4-{3-[4-(pyridin-2-ylamino)butyl]-1,2,4-oxadiazol-5-yl}butanoic acid;
3-(4-methoxyphenyl)-4-{3-[3-(5,6,7,8-tetrahydro-1,8-naphthyridin-2-yl)propyl]-1,2,4-oxadiazol-5-yl}butanoic acid;
3-(4-methoxyphenyl)-4-{3-[4-(pyridin-2-ylamino)butyl]-1,2,4-oxadiazol-5-yl}butanoic acid;
3-(3-fluorophenyl)-4-{3-[3-(5,6,7,8-tetrahydro-1,8-naphthyridin-2-yl)propyl]-1,2,4-oxadiazol-5-yl}butanoic acid;
3-(3-fluorophenyl)-4-{3-[4-(pyridin-2-ylamino)butyl]-1,2,4-oxadiazol-5-yl}butanoic acid;
3-(4-fluorophenyl)-4-{3-[3-(5,6,7,8-tetrahydro-1,8-naphthyridin-2-yl)-propyl]-1,2,4-oxadiazol-5-yl}butanoic acid;
3-(4-fluorophenyl)-4-{3-[4-(pyridin-2-ylamino)butyl]-1,2,4-oxadiazol-5-yl}butanoic acid;
4-{3-[3-(5,6,7,8-tetrahydro-1,8-naphthyridin-2-yl)propyl]-1,2,4-oxadiazol-5-yl}-3-[3-(trifluoromethyl)phenyl]butanoic acid;
4-{3-[4-(pyridin-2-ylamino)butyl]-1,2,4-oxadiazol-5-yl}-3-[3-(trifluoro-methyl)-phenyl]butanoic acid;
3-(3-hydroxyphenyl)-4-{3-[3-(5,6,7,8-tetrahydro-1,8-naphthyridin-2-yl)propyl]-1,2,4-oxadiazol-5-yl}butanoic acid;
3-(3-hydroxyphenyl)-4-{3-[4-(pyridin-2-ylamino)butyl]-1,2,4-oxadiazol-5-yl}butanoic acid;
3-pyridin-3-yl-4-{3-[3-(5,6,7,8-tetrahydro-1,8-naphthyridin-2-yl)-propyl]-1,2,4-oxadiazol-5-yl}butanoic acid;
3-pyridin-3-yl-4-{3-[4-(pyridin-2-ylamino)butyl]-1,2,4-oxadiazol-5-yl}-butanoic acid;
3-phenyl-4-{3-[3-(5,6,7,8-tetrahydro-1,8-naphthyridin-2-yl)propyl]-1,2,4-oxadiazol-5-yl}butanoic acid;
3-phenyl-4-{3-[4-(pyridin-2-ylamino)butyl]-1,2,4-oxadiazol-5-yl}butanoic acid;
3-methyl-3-({3-[4-(pyridin-2-ylamino)butyl]-1,2,4-oxadiazol-5-yl]-m-ethyl)pentanoic acid;
[1-({3-[4-(pyridin-2-ylamino)butyl]-1,2,4-oxadiazol-5-yl}methyl)-cyclohexyl]acetic acid;
3-methyl-3-({3-[4-(pyridin-2-ylamino)butyl]-1,2,4-oxadiazol-5-yl]-methyl)-hexanoic acid;
3,4-dimethyl-3-({3-[4-(pyridin-2-ylamino)butyl]-1,2,4-oxadiazol-5-yl}methyl)-pentanoic acid;
3-ethyl-3-({3-[4-(pyridin-2-ylamino)butyl]-1,2,4-oxadiazol-5-yl}methyl)-pentanoic acid;
4-{3-[4-(pyridin-2-ylamino)butyl]-1,2,4-oxadiazol-5-yl}butanoic acid;
3-methyl-3-phenyl-4-{3-[4-(pyridin-2-ylamino)butyl]-1,2,4-oxadiazol-5-yl}butanoic acid;
3-Methyl-3-{3-[3-(5,6,7,8-tetrahydro-[1,8]naphthyridin-2-yl)-propyl-]-[1,2,4]oxadiazol-5-ylmethyl}-pentanoic acid;
3-Methyl-3-{3-[3-(5,6,7,8-tetrahydro-[1,8]naphthyridin-2-yl)-propyl-]-[1,2,4]oxadiazol-5-ylmethyl}-hexanoic acid;
3,4-Dimethyl-3-{3-[3-(5,6,7,8-tetrahydro-[1,8]naphthyridin-2-yl)-propyl]-[1,2,4]oxadiazol-5-ylmethyl}-pentanoic acid;
3-Ethyl-3-{3-[3-(5,6,7,8-tetrahydro-[1,8]naphthyridin-2-yl)-propyl]-[1,2,4]oxadiazol-5-ylmethyl}-pentanoic acid;
3-Methyl-3-phenyl-4-{3-[3-(5,6,7,8-tetrahydro-[1,8]naphthyridin-2-yl)-propyl]-[1,2,4]oxadiazol-5-yl}-butyric acid;

3-Phenyl-3-{3-[3-(5,6,7,8-tetrahydro-[1,8]naphthyridin-2-yl)-propyl-]-[1,2,4]oxadiazol-5-ylmethyl}-pentanoic acid;
3-Phenyl-3-{3-[3-(5,6,7,8-tetrahydro-[1,8]naphthyridin-2-yl)-propyl-]-[1,2,4]oxadiazol-5-ylmethyl}-hexanoic acid;
4-{3-[3-(5,6,7,8-Tetrahydro-[1,8]naphthyridin-2-yl)-propyl]-[1,2,4]-oxadiazol-5-yl}-butyric acid;
3-Methyl-3-pyridin-3-yl-4-{3-[3-(5,6,7,8-tetrahydro-[1,8]naphthyridin-2-yl)-propyl]-[1,2,4]oxadiazol-5-yl}-butyric acid;
(1-Acetyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid;
(1-{3-[3-(5,6,7,8-Tetrahydro-[1,8]naphthyridin-2-yl)propyl]-[1,2,4]-oxadiazol-5-ylmethyl}-cyclohexyl)-acetic acid;
3-Methyl-3-pyridin-3-yl-4-{3-[4-(pyridin-2-ylamino)butyl]-[1,2,4]oxadiazol-5-yl}-butyric acid;
4-(benzyloxy)-3-({3-[4-(pyridin-2-ylamino)butyl]-1,2,4-oxadiazol-5-yl}methyl)-butanoic acid;
4-[4-(N-pyridin-2-yl-beta-alanyl)piperazin-1-yl]butanoic acid;
4-{4-[3-(pyridin-2-ylamino)propyl]piperazin-1-yl}butanoic acid;
2-methyl-6-[3(2-pyridylamino)propoxy)-3-pyridinebutanoic acid;
β,β-dimethyl-3-[5-(2-pyridinylamino)pentyl]-1,2,4-oxadiazole-5-butanoic acid;
β,β-dimethyl-3-[4-(2-pyridinylamino)butyl]-1,2,4-oxadiazole-5-butanoic acid;
β,β-dimethyl-3-[[[2-(2-pyridinylamino)ethyl]thio]methyl]-1,2,4-oxadiazole-5-butanoic acid;
4-Carboxymethyl-4-{3-[3-(5,6,7,8-tetrahydro-[1,8]naphthyridin-2-yl)-propyl]-[1,2,4]oxadiazol-5-ylmethyl}-piperidine-1-carboxylic acid tert-butyl ester;
(1-Benzoyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid;
[4-{3-[3-(5,6,7,8-Tetrahydro-[1,8]naphthyridin-2-yl)-propyl]-[1,2,4-]oxadiazol-5-ylmethyl}-1-(2,2,2-trifluoro-acetyl)-piperidin-4-yl]-acetic acid;
4-(phenylthio)-3-({3-[4-(pyridin-2-ylamino)butyl]-1,2,4-oxadiazol-5-yl}methyl)butanoic acid;
4-(phenylthio)-3-({3-[3-(5,6,7,8-tetrahydro-1,8-naphthyridin-2-yl)propyl]-1,2,4-oxadiazol-5-yl}methyl)butanoic acid;
3-methyl-4-{3-[4-(pyridin-2-ylamino)butyl]-1,2,4-oxadiazol-5-yl}butanoic acid hydrochloride;
3-methyl-4-{3-[3-(5,6,7,8-tetrahydro-1,8-naphthyridin-2-yl)propyl]—1,2,4-oxadiazol-5-yl}butanoic acid;
((1S,2R)-2-{3-[3-(5,6,7,8-tetrahydro-1,8-naphthyridin-2-yl)propyl]-1,2,4-oxadiazol-5-yl}cyclopropyl)acetic acid;
((1S,2S)-2-{3-[3-(5,6,7,8-tetrahydro-1,8-naphthyridin-2-yl)propyl]-1,2,4-oxadiazol-5-yl}cyclopropyl)acetic acid;
3-Pyridin-3-yl-4-{5-[3-(5,6,7,8-tetrahydro-[1,8]naphthyridin-2-yl)-propyl]4H-[1,2,4]triazol-3-yl}-butyric acid;
3-Benzo[1,3]dioxol-5-yl-4-{5-[3-(5,6,7,8-tetrahydro-[1,8]naphthyridin-2-yl)-propyl]-tetrazol-2-yl}-butyric acid;
(2-{5-[3-(5,6,7,8-Tetrahydro-[1,8]naphthyridin-2-yl)-propyl]-[1,3,4-]oxadiazol-2-yl}-cyclopropyl)-acetic acid;
3-Phenyl-4-{5-[3-(5,6,7,8-tetrahydro-[1,8]naphthyridin-2-yl)-propyl-]-[1,3,4]oxadiazol-2-yl}-butyric acid;
3-(2,3-Dihydro-benzofuran-6-yl)-4-{5-[3-(5,6,7,8-tetrahydro-[1,8]naphthyridin-2-yl)-propyl]-[1,3,4]oxadiazol-2-yl}-butyric acid;
3-(3-Fluoro-phenyl)-4-{5-[3-(5,6,7,8-tetrahydro-[1,8]naphthyridin-2-yl)-propyl]-[1,3,4]oxadiazol-2-yl}-butyric acid;
3-Benzo[1,3]dioxol-5-yl-4-{5-[3-(5,6,7,8-tetrahydro-[1,8]naphthyridin-2-yl)-propyl]-[1,3,4]oxadiazol-2-yl}-butyric acid;
(2-{2-[3-(5,6,7,8-Tetrahydro-[1,8]naphthyridin-2-yl)-propyl]-2H-tetrazol-5-yl}-cyclopropyl)-acetic acid;
3-Phenyl-4-{2-[3-(5,6,7,8-tetrahydro-[1,8]naphthyridin-2-yl)-propyl-]-2H-tetrazol-5-yl}-butyric acid;
3-(2,3-Dihydro-benzofuran-6-yl)-4-{2-[3-(5,6,7,8-tetrahydro-[1,8]naphthyridin-2-yl)-propyl]-2H-tetrazol-5-yl}-butyric acid;
3-(2,3-Dihydro-benzofuran-6-yl)-4-{2-[3-(5,6,7,8-tetrahydro-[1,8]naphthyridin-2-yl)-propyl]-2H-tetrazol-5-yl}-butyric acid;
3-(3-Fluoro-phenyl)-4-{2-[3-(5,6,7,8-tetrahydro-[1,8]naphthyridin-2-yl)-propyl]-2,1-tetrazol-5-yl}-butyric acid;
3-Pyridin-3-yl-4-{2-[3-(5,6,7,8-tetrahydro-[1,8]naphthyridin-2-yl)-propyl]-2H-tetrazol-5-yl}-butyric acid;
3-Benzo[1,3]dioxol-5-yl-4-{2-[3-(5,6,7,8-tetrahydro-[1,8]naphthyridin-2-yl)-propyl]-2H-tetrazol-5-yl}-butyric acid;
(2-{5-[3-(5,6,7,8-Tetrahydro-[1,8]naphthyridin-2-yl)-propyl]-isoxazol-3-yl}-cyclopropyl)-acetic acid;
3-Phenyl-4-{5-[3-(5,6,7,8-tetrahydro-[1,8]naphthyridin-2-yl)-propyl-]-isoxazol-3-yl}-butyric acid;
3-(2,3-Dihydro-benzofuran-6-yl)-4-{5-[3-(5,6,7,8-tetrahydro-[1,8]naphthyridin-2-yl)-propyl]-isoxazol-3-yl}-butyric acid;
3-(3-Fluoro-phenyl)-4-{5-[3-(5,6,7,8-tetrahydro-[1,8]naphthyridin-2-yl)-propyl]-isoxazol-3-yl}-butyric acid;
3-Pyridin-3-yl-4-{5-[3-(5,6,7,8-tetrahydro-[1,8]naphthyridin-2-yl)-propyl]-isoxazol-3-yl}-butyric acid;
3-Benzo[1,3]dioxol-5-yl-4-{5-[3-(5,6,7,8-tetrahydro-[1,8]naphthyridin-2-yl)-propyl]-isoxazol-3-yl}-butyric acid;
3-(2,3-Dihydro-benzofuran-6-yl)-4-{3-[3-(5,6,7,8-tetrahydro-[1,8]naphthyridin-2-yl)-propyl]-isoxazol-5-yl}-butyric acid;
3-(3-Fluoro-phenyl)-4-{3-[3-(5,6,7,8-tetrahydro-[1,8]naphthyridin-2-yl)-propyl]-isoxazol-5-yl}-butyric acid;
3-Pyridin-3-yl-4-{3-[3-(5,6,7,8-tetrahydro-[1,8]naphthyridin-2-yl)-propyl]-isoxazol-5-yl}-butyric acid;
3-Benzo[1,3]dioxol-5-yl-4-{3-[3-(5,6,7,8-tetrahydro-[1,8]naphthyridin-2-yl)-propyl]-isoxazol-5-yl}-butyric acid;
3-Phenyl-4-{5-[3-(5,6,7,8-tetrahydro-[1,8]naphthyridin-2-yl)-propyl-]-1H-pyrazol-3-yl}-butyric acid;
3-(2,3-Dihydro-benzofuran-6-yl)-4-{5-[3-(5,6,7,8-tetrahydro-[1,8]naphthyridin-2-yl)-propyl]-1H-pyrazol-3-yl-butyric acid;
3-(3-Fluoro-phenyl)-4-{5-[3-(5,6,7,8-tetrahydro-[1,8]naphthyridin-2-yl-propyl]-1H-pyrazol-3-yl}-butyric acid;
3-Pyridin-3-yl-4-{5-[3-(5,6,7,8-tetrahydro-[1,8]naphthyridin-2-yl)-propyl]-1H-pyrazol-3-yl}-butyric acid;
3-Benzo[1,3]dioxol-5-yl-4-{5-[3-(5,6,7,8-tetrahydro-[1,8]naphthyridin-2-yl)-propyl]-1H-pyrazol-3-yl}-butyric acid;
(2-{3-[3-(5,6,7,8-Tetrahydro-[1,8]naphthyridin-2-yl)-propyl]-isoxazol-5-yl}-cyclopropyl)-acetic acid;
(2-{5-[3-(5,6,7,8-Tetrahydro-[1,8]naphthyridin-2-yl)-propyl]-1H-pyrazol-3-yl}-cyclopropyl)-acetic acid;
(2-{4-[3-(5,6,7,8-Tetrahydro-[1,8]naphthyridin-2-yl)-propyl]-thiazol-2-yl}-cyclopropyl)-acetic acid; 3-Phenyl-4-{4-[3-(5,6,7,8-tetrahydro-[1,-8]naphthyridin-2-yl)-propyl]-thiazol-2-yl}-butyric acid;

3-(2,3-Dihydro-benzofuran-6-yl)-4-{4-[3-(5,6,7,8-tetrahydro-[1,8]naphthyridin-2-yl)-propyl]-thiazol-2-yl}-butyric acid;

3-(3-Fluoro-phenyl)-4-{4-[3-(5,6,7,8-tetrahydro-[1,8]naphthyridin-2-yl)-propyl]-thiazol-2-yl}-butyric acid;

3-Pyridin-3-yl-4-{4-[3-(5,6,7,8-tetrahydro-[1,8]naphthyridin-2-yl)-propyl]-thiazol-2-yl}-butyric acid;

3-Benzo[1,3]dioxol-5-yl-4-{4-[3-(5,6,7,8-tetrahydro-[1,8]naphthyridin-2-yl)-propyl]-thiazol-2-yl}-butyric acid;

3-Phenyl-4-{3-[3-(5,6,7,8-tetrahydro-[1,8]naphthyridin-2-yl)-propyl-]-pyrazol-1-yl}-butyric acid;

3-(2,3-Dihydro-benzofuran-6-yl)-4-{3-[3-(5,6,7,8-tetrahydro-[1,8]naphthyridin-2-yl)-propyl]-pyrazol-1-yl}-butyric acid;

3-(3-Fluoro-phenyl)-4-{3-[3-(5,6,7,8-tetrahydro-[1,8]naphthyridin-2-yl)-propyl]-pyrazol-1-yl}-butyric acid;

3-Pyridin-3-yl-4-{3-[3-(5,6,7,8-tetrahydro-[1,8]naphthyridin-2-yl)-propyl]-pyrazol-1-yl}-butyric acid;

3-Pyridin-3-yl-4-{3-[3-(5,6,7,8-tetrahydro-[1,8]naphthyridin-2-yl)-propyl]-pyrazol-1-yl}-butyric acid;

3-Benzo[1,3]dioxol-5-yl-4-{3-[3-(5,6,7,8-tetrahydro-[1,8]naphthyridin-2-yl)-propyl]-pyrazol-1-yl}-butyric acid;

3-Phenyl-4-{4-[3-(5,6,7,8-tetrahydro-[1,8]naphthyridin-2-yl)-propyl-]-imidazol-1-yl}-butyric acid;

3-(2,3-Dihydro-benzofuran-6-yl)-4-{4-[3-(5,6,7,8-tetrahydro-[1,8]naphthyridin-2-yl)-propyl]-imidazol-1-yl}-butyric acid;

3-(3-Fluoro-phenyl)-4-{4-[3-(5,6,7,8-tetrahydro-[1,8]naphthyridin-2-yl)-propyl]-imidazol-1-yl}-butyric acid;

3-Pyridin-3-yl-4-{4-[3-(5,6,7,8-tetrahydro-[1,8]naphthyridin-2-yl)-propyl]-imidazol-1-yl}-butyric acid;

3-Benzo[1,3]dioxol-5-yl-4-{4-[3-(5,6,7,8-tetrahydro-[1,8]naphthylidine-2-yl)-propyl]-imidazol-1-yl}-butyric acid3-Phenyl-4-{3-[2-(5,6,7,8-tetrahydro-[1,8]naphthyridin-2-yl)-ethoxy]-isoxazol-5-yl}-butyric acid;

3-(2,3-Dihydro-benzofuran-6-yl)-4-{3-[2-(5,6,7,8-tetrahydro-[1,8]naphthyridin-2-yl)-ethoxy]-isoxazol-5-yl}-butyric acid;

3-(3-Fluoro-phenyl)-4-{3-[2-(5,6,7,8-tetrahydro-[1,8]naphthyridin-2-yl)-ethoxy]-isoxazol-5-yl}-butyric acid;

3-Pyridin-3-yl-4-{3-[2-(5,6,7,8-tetrahydro-[1,8]naphthyridin-2-yl)-ethoxy]-isoxazol-5-yl}-butyric acid;

3-Benzo[1,3]dioxol-5-yl-4-{3-[2-(5,6,7,8-tetrahydro-[1,8]naphthyridin-2-yl)-ethoxy]-isoxazol-5-yl}-butyric acid;

3-(3-Fluoro-phenyl)-4-{5-[2-(5,6,7,8-tetrahydro-[1,8]naphthyridin-2-yl)-ethoxy]-2H-pyrazol-3-yl}-butyric acid;

3-(2,3-Dihydro-benzofuran-6-yl)-4-{5-[2-(5,6,7,8-tetrahydro-[1,8]naphthyridin-2-yl)-ethoxy]-2H-pyrazol-3-yl}-butyric acid;

3-Phenyl-4-{5-[2-(5,6,7,8-tetrahydro-[1,8]naphthyridin-2-yl)-ethoxy-]-2H-pyrazol-3-yl}-butyric acid;

3-Pyridin-3-yl-4-{5-[2-(5,6,7,8-tetrahydro-[1,8]naphthyridin-2-yl)-ethoxy]-2H-pyrazol-3-yl}-butyric acid;

3-Benzo[1,3]dioxol-5-yl-4-{5-[2-(5,6,7,8-tetrahydro-[1,8]naphthyridin-2-yl)-ethoxy]-2H-pyrazol-3-yl}-butyric acid;

3-Phenyl-4-[4-(3-5,6,7,8-tetrahydro-[1,8]naphthyridin-2-yl-propionyl)-imidazol-1-yl]-butyric acid;

3-(2,3-Dihydro-benzofuran-6-yl)-4-[4-(3-5,6,7,8-tetrahydro-[1,8]naphthyridin-2-yl-propionyl imidazol-1-yl]-butyric acid;

3-(3-Fluoro-phenyl)-4-[4-(3-5,6,7,8-tetrahydro-[1,8]naphthyridin-2-yl-propionyl)-imidazol-1-yl]-butyric acid;

3-Pyridin-3-yl-4-[4-(3-5,6,7,8-tetrahydro-[1,8]naphthyridin-2-yl-propionyl)-imidazol-1-yl]-butyric acid;

3-Benzo[1,3]dioxol-5-yl-4-[4-(3-5,6,7,8-tetrahydro-[1,8]naphthyridin-2-yl-propionyl)-imidazol-1-yl]-butyric acid;

4-{4-[1-Hydroxy-3-(5,6,7,8-tetrahydro-[1,8]naphthyridin-2-yl)-propyl]-imidazol-1-yl}-3-phenyl-butyric acid;

3-(2,3-Dihydro-benzofuran-6-yl)-4-{4-[1-hydroxy-3-(5,6,7,8-tetrahydro-[1,8]naphthyridin-2-yl)-propyl]-imidazol-1-yl}-butyric acid;

3-(3-Fluoro-phenyl)-4-{4-[1-hydroxy-3-(5,6,7,8-tetrahydro-[1,8]naphthyridin-2-yl)-propyl]-imidazol-1-yl}-butyric acid;

4-{4-[1-Hydroxy-3-(5,6,7,8-tetrahydro-[1,8]naphthyridin-2-yl)-propyl]-imidazol-1-yl}-3-pyridin-3-yl-butyric acid;

4-{4-[1-Hydroxy-3-(5,6,7,8-tetrahydro-[1,8]naphthyridin-2-yl)-propyl]-imidazol-1-yl}-3-pyridin-3-yl-butyric acid;

4-{4-[3-Hydroxy-3-(5,6,7,8-tetrahydro-[1,8]naphthyridin-2-yl)-prop-1-ynyl]-imidazol-1-yl}-3-phenyl-butyric acid;

3-(2,3-Dihydro-benzofuran-6-yl)-4-{4-[3-hydroxy-3-(5,6,7,8-tetrahydro-[1,8]naphthyridin-2-yl)-prop-1-ynyl]-imidazol-1-yl}-butyric acid;

3-(3-Fluoro-phenyl)-4-{4-[3-hydroxy-3-(5,6,7,8-tetrahydro-[1,8]naphthyridin-2-yl)-prop-1-ynyl]-imidazol-1-yl}-butyric acid;

4-{4-[3-Hydroxy-3-(5,6,7,8-tetrahydro-[1,8]naphthyridin-2-yl)-prop-1-ynyl]-imidazol-1-yl}-3-pyridin-3-yl-butyric acid;

3-(2,3-Dihydro-benzofuran-6-yl)-4-{2-[3-(5,6,7,8-tetrahydro-[1,8]naphthyridin-2-yl)-propyl]-2H-tetrazol-5-yl}-butyric acid;

3-(3-Fluoro-phenyl)-4-{2-[3-(5,6,7,8-tetrahydro-[1,8]naphthyridin-2-yl)-propyl]-2H-tetrazol-5-yl}-butyric acid;

3-Pyridin-3-yl-4-{2-[3-(5,6,7,8-tetrahydro-[1,8]naphthyridin-2-yl)-propyl]-2H-tetrazol-5-yl}-butyric acid;

3-Benzo[1,3]dioxol-5-yl-4-{2-[3-(5,6,7,8-tetrahydro-[1,8]naphthyridin-2-yl)-propyl]-2H-tetrazol-5-yl}-butyric acid;

(2-{5-[3-(5,6,7,8-Tetrahydro-[1,8]naphthyridin-2-yl)-propyl]-isoxazol-3-yl}-cyclopropyl)-acetic acid;

3-Phenyl-4-{5-[3-(5,6,7,8-tetrahydro-[1,8]naphthyridin-2-yl)-propyl]-isoxazol-3-yl}-butyric acid;

3-(2,3-Dihydro-benzofuran-6-yl)-4-{5-[3-(5,6,7,8-tetrahydro-[1,8]naphthyridin-2-yl)-propyl]-isoxazol-3-yl}-butyric acid;

3-(3-Fluoro-phenyl)-4-{5-[3-(5,6,7,8-tetrahydro-[1,8]naphthyridin-2-yl)-propyl]-isoxazol-3-yl}-butyric acid;

3-Pyridin-3-yl-4-{5-[3-(5,6,7,8-tetrahydro-[1,8]naphthyridin-2-yl)-propyl]-isoxazol-3-yl}-butyric acid;

3-Benzo[1,3]dioxol-5-yl-4-{5-[3-(5,6,7,8-tetrahydro-[1,8]naphthyridin-2-yl)-propyl]-isoxazol-3-yl}-butyric acid;

3-(2,3-Dihydro-benzofuran-6-yl)-4-{3-[3-(5,6,7,8-tetrahydro-[1,8]naphthyridin-2-yl)-propyl]-isoxazol-5-yl}-butyric acid;

3-(3-Fluoro-phenyl)-4-{3-[3-(5,6,7,8-tetrahydro-[1,8]naphthyridin-2-yl)-propyl]-isoxazol-5-yl}-butyric acid;

3-Pyridin-3-yl-4-{3-[3-(5,6,7,8-tetrahydro-[1,8]naphthyridin-2-yl)-propyl]-isoxazol-5-yl}-butyric acid;

3-Benzo[1,3]dioxol-5-yl-4-{3-[3-(5,6,7,8-tetrahydro-[1,8]naphthyridin-2-yl)-propyl]-isoxazol-5-yl}-butyric acid;

3-Phenyl-4-{5-[3-(5,6,7,8-tetrahydro-[1,8]naphthyridin-2-yl)-propyl-]-1H-pyrazol-3-yl}-butyric acid;

3-(2,3-Dihydro-benzofuran-6-yl)-4-{5-[3-(5,6,7,8-tetrahydro-[1,8]naphthyridin-2-yl)-propyl]-1H-pyrazol-3-yl}-butyric acid;

3-(3-Fluoro-phenyl)-4-{5-[3-(5,6,7,8-tetrahydro-[1,8]naphthyridin-2-yl)-propyl]-1H-pyrazol-3-yl}-butyric acid;

3-Pyridin-3-yl-4-{5-[3-(5,6,7,8-tetrahydro-[1,8]naphthyridin-2-yl)-propyl]-1H-pyrazol-3-yl}-butyric acid;

3-Benzo[1,3]dioxol-5-yl-4-{5-[3-(5,6,7,8-tetrahydro-[1,8]naphthyridin-2-yl)-propyl]-1H-pyrazol-3-(3-yl}-butyric acid;

(2-{3-[3-(5,6,7,8-Tetrahydro-[1,8]naphthyridin-2-yl)-propyl]-isoxazol-5-yl}-cyclopropyl)-acetic acid;
(2-{5-[3-(5,6,7,8-Tetrahydro-[1,8]naphthyridin-2-yl)-propyl]-1H-pyrazol-3-yl}-cyclopropyl)-acetic acid;
(2-{4-[3-(5,6,7,8-Tetrahydro-[1,8]naphthyridin-2-yl)-propyl]-thiazol-2-yl}-cyclopropyl)-acetic acid;
3-Phenyl-4-{-[3-(5,6,7,8-tetrahydro-[1,8]naphthyridin-2-yl)-propyl]-thiazol-2-yl}butyric acid;
3-(2,3-Dihydro-benzofuran-6-yl)-4-{4-[3-(5,6,7,8-tetrahydro-[1,8]naphthyridin-2-yl)-propyl]-thiazol-2-yl}-butyric acid;
3-(3-Fluoro-phenyl)-4-{4-[3-(5,6,7,8-tetrahydro-[1,8]naphthyridin-2-yl)-propyl]-thiazol-2-yl}-butyric acid;
3-Pyridin-3-yl-4-{4-[3-(5,6,7,8-tetrahydro-[1,8]naphthyridin-2-yl)-propyl]-thiazol-2-yl}-butyric acid;
3-Benzo[1,3]dioxol-5-yl-4-{4-[3-(5,6,7,8-tetrahydro-[1,8]naphthyridin-2-yl)-propyl]-thiazol-2-yl}-butyric acid;
3-Phenyl-4-{3-[3-(5,6,7,8-tetrahydro-[1,8]naphthyridin-2-yl)-propyl-]-pyrazol-1-yl}-butyric acid;
3-(2,3-Dihydro-benzofuran-6-yl)-4-{3-[3-(5,6,7,8-tetrahydro-[1,8]naphthyridin-2-yl)-propyl]-pyrazol-1-yl}-butyric acid;
3-(3-Fluoro-phenyl)-4-{3-[3-(5,6,7,8-tetrahydro-[1,8]naphthyridin-2-yl)-propyl]-pyrazol-1-yl}-butyric acid;
3-Pyridin-3-yl-4-{3-[3-(5,6,7,8-tetrahydro-[1,8]naphthyridin-2-yl)-propyl]-pyrazol-1-yl}-butyric acid;
3-Pyridin-3-yl-4-{3-[3-(5,6,7,8-tetrahydro-[1,8]naphthyridin-2-yl)-propyl]-pyrazol-1-yl}-butyric acid;
3-Benzo[1,3]dioxol-5-yl-4-{3-[3-(5,6,7,8-tetrahydro-[1,8]naphthyridin-2-yl)-propyl]-pyrazol-1-yl}-butyric acid;
3-Phenyl-4-{4-[3-(5,6,7,8-tetrahydro-[1,8]naphthyridin-2-yl)-propyl-]-imidazol-1-yl}-butyric acid;
3-(2,3-Dihydro-benzofuran-6-yl)-4-{4-[3-(5,6,7,8-tetrahydro-[1,8]naphthyridin-2-yl)-propyl]-imidazol-1-yl}-butyric acid;
3-(3-Fluoro-phenyl)-4-{4-[3-(5,6,7,8-tetrahydro-[1,8]naphthyridin-2-yl)-propyl]-imidazol-1-yl}-butyric acid;
3-Pyridin-3-yl-4-{4-[3-(5,6,7,8-tetrahydro-[1,8]naphthyridin-2-yl)-propyl]-imidazol-1-yl}-butyric acid;
3-Benzo[1,3]dioxol-5-yl-4-{4-[3-(5,6,7,8-tetrahydro-[1,8]naphthyridin-2-yl)-propyl]-imidazol-1-yl}-butyric acid3-Phenyl-4-{3-[2-(5,6,7,8-tetrahydro-[1,8]naphthyridin-2-yl)-ethoxy]-isoxazol-5-yl}-butyric acid;
3-(2,3-Dihydro-benzofuran-6-yl)-4-{3-[2-(5,6,7,8-tetrahydro-[1,8]naphthyridin-2-yl)-ethoxy]-isoxazol-5-yl}-butyric acid;
3-(3-Fluoro-phenyl)-4-{3-[2-(5,6,7,8-tetrahydro-[1,8]naphthyridin-2-yl)-ethoxy]-isoxazol-5-yl}-butyric acid;
3-Pyridin-3-yl-4-{3-[2-(5,6,7,8-tetrahydro-[1,8]naphthyridin-2-yl)-ethoxy]-isoxazol-5-yl}-butyric acid;
3-Benzo[1,3]dioxol-5-yl-4-{3-[2-(5,6,7,8-tetrahydro-[1,8]naphthyridin-2-yl)-ethoxy]-isoxazol-5-yl}-butyric acid;
3-(3-Fluoro-phenyl)-4-{5-[2-(5,6,7,8-tetrahydro-[1,8]naphthyridin-2-yl)-ethoxy]-2H-pyrazol-3-yl}-butyric acid;
3-(2,3-Dihydro-benzofuran-6-yl)-4-{5-[2-(5,6,7,8-tetrahydro-[1,8]naphthyridin-2-yl)-ethoxy]-2H-pyrazol-3-yl}-butyric acid;
3-Phenyl-4-{5-[2-(5,6,7,8-tetrahydro-[1,8]naphthridin-2-yl)-ethoxy-]-2H-pyrazol-3-yl}-butyric acid;
3-Pyridin-3-yl-4-{5-[2-(5,6,7,8-tetrahydro-[1,8]naphthyridin-2-yl)-ethoxy]-2H-pyrazol-3-yl}-butyric acid;
3-Benzo[1,3]dioxol-5-yl-4-{5-[2-(5,6,7,8-tetrahydro-[1,8]naphthyridin-2-yl)-ethoxy]-2H-pyrazol-3-yl}-butyric acid;
3-Phenyl-4-[4-(3-5,6,7,8-tetrahydro-[1,8]naphthyridin-2-yl-propionyl)-imidazol-1-yl]-butyric acid;
3-(2,3-Dihydro-benzofuran-6-yl)-4-[4-(3-5,6,7,8-tetrahydro-[1,8]naphthyridin-2-yl-propionyl)-imidazol-1-yl]-butyric acid;
3-(3-Fluoro-phenyl)-4-[4-(3-5,6,7,8-tetrahydro-[1,8]naphthyridin-2-yl-propionyl)-imidazol-1-yl]-butyric acid;
3-Pyridin-3-yl-4-[4-(3-5,6,7,8-tetrahydro-[1,8]naphthyridin-2-yl-propionyl)-imidazol-1-yl]-butyric acid;
3-Benzo[1,3]dioxol-5-yl-4-[4-(3-5,6,7,8-tetrahydro-[1,8]naphthyridin-2-yl-propionyl)-imidazol-1-yl]-butyric acid;
4-{4-[1-Hydroxy-3-(5,6,7,8-tetrahydro-[1,8]naphthyridin-2-yl)-propyl]-imidazol-1-yl}-3-phenyl-butyric acid;
3-(2,3-Dihydro-benzofuran-6-yl)-4-{4-[1-hydroxy-3-(5,6,7,8-tetrahydro-[1,8]naphthyridin-2-yl)-propyl]-imidazol-1-yl}-butyric acid;
3-(3-Fluoro-phenyl)-4-{4-[1-hydroxy-3-(5,6,7,8-tetrahydro-[1,8]naphthyridin-2-yl)-propyl]-imidazol-1-yl}butyric acid;
4-{4-[1-Hydroxy-3-(5,6,7,8-tetrahydro-[1,8]naphthyridin-2-yl propyl]-imidazol-1-yl}-3-pyridin-3-yl-butyric acid;
4-{4-[1-Hydroxy-3-(5,6,7,8-tetrahydro-[1,8]naphthyridin-2-yl)-propyl]-imidazol-1-yl}-3-pyridin-3-yl-butyric acid;
4-{4-[3-Hydroxy-3-(5,6,7,8-tetrahydro-[1,8]naphthyridin-2-yl)-prop-1-ynyl]-imidazol-1-yl}-3-phenyl-butyric acid;
3-(2,3-Dihydro-benzofuran-6-yl)-4-{4-[3-hydroxy-3-(5,6,7,8-tetrahydro-[1,8]naphthyridin-2-A-prop-1-ynyl]-imidazol-1-yl}-butyric acid;
3-(3-Fluoro-phenyl)-4-{4-[3-hydroxy-3-(5,6,7,8-tetrahydro-[1,8]naphthyridin-2-yl)-prop-1-ynyl]-imidazol-1-yl}-butyric acid;
4-{4-[3-Hydroxy-3-(5,6,7,8-tetrahydro-[1,8]naphthyridin-2-yl)-prop-1-ynyl]-imidazol-1-yl}-3-pyridin-3-yl-butyric acid;
3-Benzo[1,3]dioxol-5-yl-4-{4-[3-hydroxy-3-(5,6,7,8-tetrahydro-[1,8]-naphthyridin-2-yl)-prop-1-ynyl]-imidazol-1-yl}-butyric acid;
4-{4-[3-Hydroxy-3-(5,6,7,8-tetrahydro-[1,8]naphthyridin-2-yl)-prop-1-ynyl]-pyrazol-1-yl}-3-phenyl-butyric acid;
3-(2,3-Dihydro-benzofuran-6-yl)-4-{4-[3-hydroxy-3-(5,6,7,8-tetrahydro-[1,8]naphthyridin-2-yl)-prop-1-ynyl]-pyrazol-1-yl}-butyric acid;
3-(3-Fluoro-phenyl)-4-{-[3-hydroxy-3-(5,6,7,8-tetrahydro-[1,8]-naphthyridin-2-yl)-prop-1-ynyl]-pyrazol-1-yl}-butyric acid;
4-{4-[3-Hydroxy-3-(5,6,7,8-tetrahydro-[1,8]naphthyridin-2-yl)-prop-1-ynyl]-pyrazol-1-yl}-3-pyridin-3-yl-butyric acid3-Benzo[1,3]dioxol-5-yl-4-{4-[3-hydroxy-3-(5,6,7,8-tetrahydro-[1,8]naphthyridin-2-yl)-prop-1-ynyl]-pyrazol-1-yl}-butyric acid4-{4-[3-Hydroxy-3-(5,6,7,8-tetrahydro-[1,8]naphthyridin-2-yl)-propenyl]-pyrazol-1-yl}-3-phenyl-butyric acid;
3-(2,3-Dihydro-benzofuran-6-yl)-4-{4-[3-hydroxy-3-(5,6,7,8-tetrahydro-[1,8]naphthyridin-2-yl)-propenyl]-pyrazol-1-yl}-butyric acid3-(3-Fluoro-phenyl)-4-{4-[3-hydroxy-3-(5,6,7,8-tetrahydro-[1,8]naphthyridin-2-yl)-propenyl]-pyrazol-1-yl}-butyric acid;
4-{4-[3-Hydroxy-3-(5,6,7,8-tetrahydro-[1,8]naphthyridin-2-yl)-propenyl]-pyrazol-1-yl}-3-pyridin-3-yl-butyric acid;
3-Benzo[1,3]dioxol-5-yl-4-{4-[3-hydroxy-3-(5,6,7,8-tetrahydro-[1,8]-naphthyridin-2-yl)-propenyl]-pyrazol-1-yl}-butyric acid;
3-Benzo[1,3]dioxol-5-yl-4-{4-[3-hydroxy-3-(5,6,7,8-tetrahydro-[1,8]-naphthyridin-2-yl)-propenyl]pyrazol-1-yl}-butyric acid;
4-{4-[3-Hydroxy-3-(5,6,7,8-tetrahydro-[1,8]naphthyridin-2-yl)-propenyl]-imidazol-1-yl}-3-phenyl-butyric acid;

3-(2,3-Dihydro-benzofuran-6-yl)-4-{4-[3-hydroxy-3-(5,6,7,8-tetrahydro-[1,8]naphthyridin-2-yl)-propenyl]-imidazol-1-yl}-butyric acid;
3-(3-Fluoro-phenyl)-4-{4-[3-hydroxy-3-(5,6,7,8-tetrahydro-[1,8]naphthyridin-2-yl)-propenyl]-imidazol-1-yl}-butyric acid;
4-{4-[3-Hydroxy-3-(5,6,7,8-tetrahydro-[1,8]naphthyridin-2-yl)-propenyl]-imidazol-1-yl}-3-pyridin-3-yl-butyric acid;
3-Benzo[1,3]dioxol-5-yl-4-{4-[3-hydroxy-3-(5,6,7,8-tetrahydro-[1,8]-naphthyridin-2-yl)-propenyl]-imidazol-1-yl}-butyric acid;
4-{4-[3-Hydroxy-3-(5,6,7,8-tetrahydro-[1,8]naphthyridin-2-yl)-propyl]-imidazol-1-yl}-3-phenyl-butyric acid;
3-(2,3-Dihydro-benzofuran-6-yl)-4-{4-[3-hydroxy-3-(5,6,7,8-tetrahydro-[1,8]naphthyridin-2-yl)-propyl]-imidazol-1-yl}-butyric acid;
3-(3-Fluoro-phenyl)-4-{4-[3-hydroxy-3-(5,6,7,8-tetrahydro-[1,8]naphthyridin-2-yl)-propyl]-imidazol-1-yl}-butyric acid;
4-{4-[3-Hydroxy-3-(5,6,7,8-tetrahydro-[1,8]naphthyridin-2-yl)-propy-imidazol-1-yl}-3-pyridin-3-yl-butyric acid;
3-Benzo[1,3]dioxol-5-yl]-{4-[3-hydroxy-3-(5,6,7,8-tetrahydro-[1,8]naphthyridin-2-yl)-propyl]-imidazol-1-yl}-butyric acid;
4-{4-[3-Hydroxy-3-(5,6,7,8-tetrahydro-[1,8]naphthyridin-2-yl)-propyl]-pyrazol-1-yl}-3-phenyl-butyric acid;
3-(2,3-Dihydro-benzofuran-6-yl)-4-(4-[3-hydroxy-3-(5,6,7,8-tetrahydro-[1,8]naphthyridin-2-yl)-propyl]-pyrazol-1-yl}-butyric acid;
3-(3-Fluoro-phenyl)-4-{4-[3-hydroxy-3-(5,6,7,8-tetrahydro-[1,8]naphthyridin-2-yl)-propyl]-pyrazol-1-yl}-butyric acid;
3-Benzo[1,3]dioxol-5-yl-4-{4-[3-hydroxy-3-(5,6,7,8-tetrahydro-[1,8]-naphthyridin-2-yl)-propyl]-pyrazol-1-yl}-butyric acid;
4-{4-[3-Hydroxy-3-(5,6,7,8-tetrahydro-[1,8]naphthyridin-2-yl)-propyl]-pyrazol-1-yl}-3-pyridin-3-yl-butyric acid;
3-(3-Fluoro-phenyl)-4-{4-[3-(5,6,7,8-tetrahydro-[1,8]naphthyridin-2-yl)-propenyl]-imidazol-1-yl}-butyric acid;
3-Phenyl-4-{4-[3-(5,6,7,8-tetrahydro-[1,8]naphthyridin-2-yl)-propenyl]-imidazol-1-yl}-butyric acid;
3-(2,3-Dihydro-benzofuran-6-yl)-4-{4-[3-(5,6,7,8-tetrahydro-[1,8]naphthyridin-2-yl)-propenyl]-imidazol-1-yl}-butyric acid;
3-Pyridin-3-yl-4-{4-[3-(5,6,7,8-tetrahydro-[1,8]naphthyridin-2-yl)-propenyl]-imidazol-1-yl}-butyric acid;
3-Benzo[1,3]dioxol-5-yl-4-{4-[3-(5,6,7,8-tetrahydro-[1,8]naphthyridin-2-yl)-propenyl]-imidazol-1-yl}-butyric acid;
3-Benzo[1,3]dioxol-5-yl-4-{4-[3-(5,6,7,8-tetrahydro-[1,8]naphthyridin-2-yl)-propenyl]-pyrazol-1-yl}-butyric acid;
3-Pyridin-3-yl-4-{4-[3-(5,6,7,8-tetrahydro-[1,8]naphthyridin-2-yl)-propenyl]-pyrazol-1-yl}-butyric acid;
3-Phenyl-4-{4-[3-(5,6,7,8-tetrahydro-[1,8]naphthyridin-2-yl)-propenyl]-pyrazol-1-yl}-butyric acid;
3-hydroxy-4-{3-[4-(pyridin-2-ylamino)butyl]-1,2,4-oxadiazol-5-yl}butanoic acid;
3-hydroxy-4-{3-[3-(5,6,7,8-tetrahydro-1,8-naphthyridin-2-yl)propyl]-1,2,4-oxadiazol-5-yl}butanoic acid;
3-Benzo[1,3]dioxol-5-yl-4-{3-[4-(1H-imidazol-2-ylamino)-butyl]-[1,2-,4]oxadiazol-5-yl}-butyric acid;
3-(3-Fluoro-phenyl)-4-{3-[4-(1H-imidazol-2-ylamino)-butyl]-[1,2,4]oxadiazol-5-yl}-butyric acid;
3-Benzo[1,3]dioxol-5-yl-4-{3-[4-(2H-pyrazol-3-ylamino)-butyl]-[1,2,-4]oxadiazol-5-yl}-butyric acid;

3-(3-Fluoro-phenyl)-4-{3-[4-(2H-pyrazol-3-ylamino)-butyl]-[1,2,4]oxadiazol-5-yl}-butyric acid;
3-Benzo[1,1]dioxol-5-yl-4-{3-[4-(3H-imidazol-4-ylamino)-butyl]-[1,2-,4]oxadiazol-5-yl}-butyric acid;
3-(3-Fluoro-phenyl)-4-{3-[4-(3H-imidazol-4-ylamino)-butyl]-[1,2,4]oxadiazol-5-yl}-butyric acid;
3-Benzo[1,3]dioxol-5-yl-4-{3-[3-(6-methylamino-pyridin-2-yl)-propyl-]-[1,2,4]oxadiazol-5-yl}-butyric acid;
3-(3-Fluoro-phenyl)-4-{3-[3-(6-methylamino-pyridin-2-yl)-propyl]-[1-,2,4]oxadiazol-5-yl}-butyric acid;
4-{3-[3-(6-Ethylamino-pyridin-2-yl)-propyl]-[1,2,4]oxadiazol-5-yl}-3-(3-fluoro-phenyl)-butyric acid;
3-(3-Fluoro-phenyl)-4-(3-{3-[6-(2-methoxy-ethylamino)-pyridin-2-yl]-propyl}-[1,2,4]oxadiazol-5-yl)-butyric acid;
3-(3-Fluoro-phenyl)-4-(3-{3-[6-(3-methoxy-propylamino)-pyridin-2-yl-]-propyl}-[1,2,4]oxadiazol-5-yl)-butyric acid;
3-(3-Fluoro-phenyl)-4-(3-{3-[6-(2,2,2-trifluoro-ethylamino)-pyridin-2-yl]-propyl}-[1,2,4]oxadiazol-5-yl)-butyric acid;
3-(3-Fluoro-phenyl)-4-{3-[3-(5-oxo-5,6,7,8-tetrahydro-[1,8]naphthyridin-2-yl)-propyl]-[1,2,4]oxadiazol-5-yl}-butyric acid;
4-{3-[3-(5,5-Dimethyl-5,6,7,8-tetrahydro-[1,8]naphthyridin-2-yl)-propyl]-[1,2,4]oxadiazol-5-yl}-3-(3-fluoro-phenyl)-butyric acid;
4-{3-[3-(5,5-Difluoro-5,6,7,8-tetrahydro-[1,8]naphthyridin-2-yl)-propyl]-[1,2,4]oxadiazol-5-yl}-3-(3-fluoro-phenyl)-butyric acid; and
3-(1,3-benzodioxol-5-yl)-4-{3-[(5,6,7,8-tetrahydro-1,8-naphthyridin-2-ylmethoxy)methyl]-1,2,4-oxadiazol-5-yl}butanoic acid.

In another embodiment of the present invention

is a heteroaryl substituted by one or more substituents selected from lower alkyl, alkynyl, alkenyl, halogen, alkoxy, hydroxy, cyano, amino, alkylamino, dialkylamino or methylsulfonamide. More specifically, some examples of heteroaryl include oxadiazole, pyridine, pyrimidine, imidazole, thiadiazole, triazole, tetrazole, pyrazole, isoxazole, and thiazole.

Other embodiments of

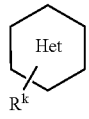

include the following heterocyclic ring systems containing at least one nitrogen atom:

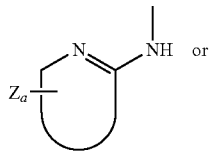

-continued

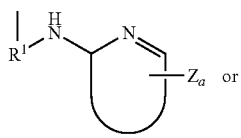
B3

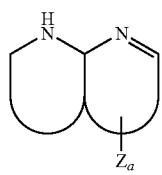
B4 wherein $Z_a$ is H, alkyl, alkoxy, hydroxy, amine, alkylamine, dialkylamine, carboxyl, alkoxycarbonyl, hydroxyalkyl, halogen or haloalkyl and $R^1$ is H, alkyl, alkoxyalkyl, acyl, haloalkyl or alkoxycarbonyl. More specifically some examples include pyridylamino, imidazolylamino, morpholinopyridine, tetrahydronaphthyridine, oxazolylamino, thiazolylamino, pyrimidinylamino, quinoline, tetrahydroquinoline, imidazopyridine, benzimidazole, pyridone or quinolone.

The following heteroaryls include the ring systems described above.

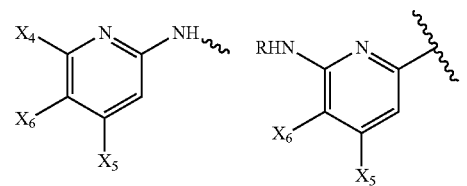

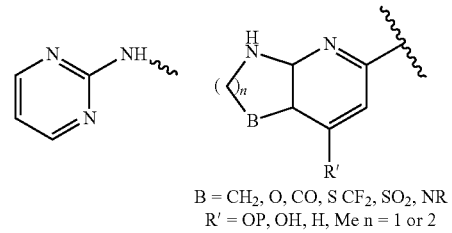

B = CH$_2$, O, CO, S CF$_2$, SO$_2$, NR
R' = OP, OH, H, Me n = 1 or 2

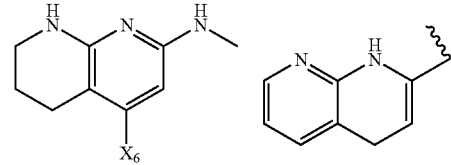

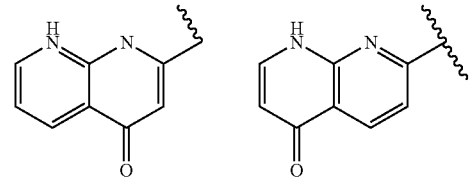

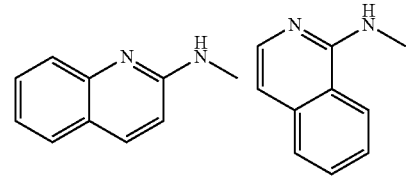

-continued

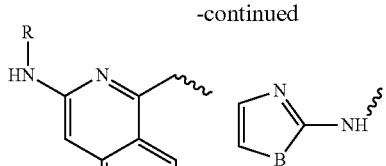

B = NH, NMe, O, S

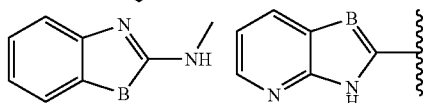

B = NH, O, S          B = N, CH

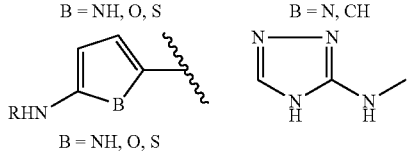

B = NH, O, S

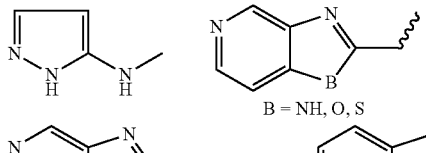

B = NH, O, S

B = NH, O, S          B = N, CH
                      R = H, Me

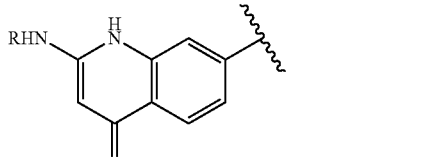

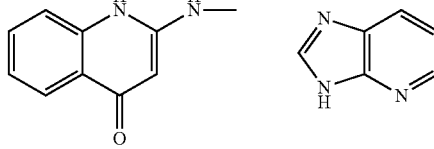

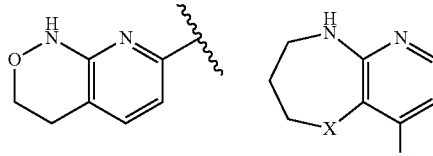

X = O, S, NR, SO$_2$, CF$_2$

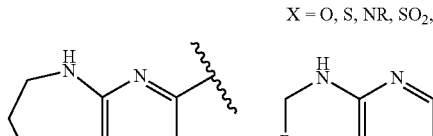

X = CH$_2$, O, S, NR,     B = CH$_2$, O, CO, S, CF$_2$, SO$_2$, NR
SO$_2$, CONR              R' = OR, OH, Me n = 1 or 2

For the pyridyl derived heterocycle, the substituents $X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups.

In another embodiment of the invention, the substituents $X_4$ and $X_5$ can be methyl, methoxy, amine, methylamine, trifluoromethyl, dimethylamine, hydroxy, chloro, bromo, fluoro and cyano. $X_6$ may preferentially be H, alkyl, hydroxy, halogen, alkoxy and haloalkyl. Alternately, the pyridyl ring can be fused with a 4-8 membered ring, optionally saturated or unsaturated. Some examples of these ring systems include tetrahydronaphthyridine, quinoline, tetrahydroquinoline, azaquinoline, morpholinopyridine, imidazopyridine and the like. The monocyclic ring systems such as imidazole, thiazole, oxazole, pyrazole, and the like, may contain an amino or alkylamino substituent at any position within the ring.

In another embodiment of the present invention, when $Z_1$ of Formula I is CO or $SO_2$, the linkage $A^1$-$Z_2$ of Formula I includes the heterocycle derived ring systems such as: pyridine, imidazole, thiazole, oxazole, benzimidazole, imidazopyridine and the like.

Other heterocycles for $A^1$-$Z_2$ of the present invention include

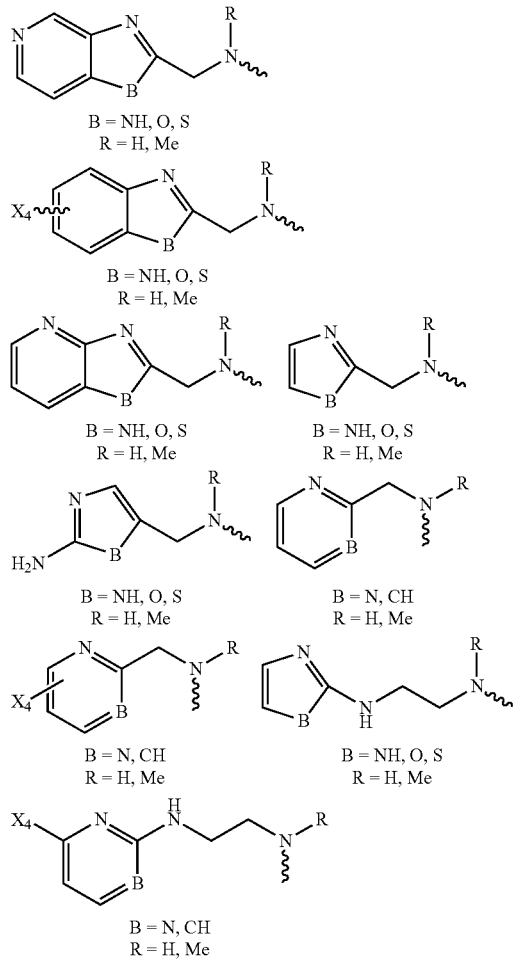

wherein $X_4$ is as defined above.

In another embodiment, $Y^3$ or $Y^4$ is an aryl or a heteroaryl group selected from phenyl, benzofuran, benzothiophene, indole, quinoline, isoquinoline, benzimidazole, benzoxazole, 1,3-benzodioxole, 1,4-benzodioxane, benzopyran, quinolone, imidazopyridine, tetrahydro-quinoline, benzotriazole, dihydroindole, dihydrobenzofuran, furan, thiophene, phenyl, oxazole, thiazole, isoxazole, pyrazole, imidazole, pyrrole, pyridine, pyrimidine, pyridone, triazole, thiadiazole and the like. The aryl system can be optionally substituted at one or more positions with alkyl, alkoxy, hydroxy, cyano, halogen or haloalkyl.

In another embodiment of the present invention, $Y^3$ or $Y^4$ may be an amine, alkylamine, acylamine, aminosulfone ($NHSO_2R$), arylamine, alkoxyalkylamine, aralkylamine, or heterocyclic amine.

In another embodiment of the present invention, $Y^3$ taken together with $Y^4$ forms a 3-8 membered monocyclic or a 7-11 membered bicyclic ring B,

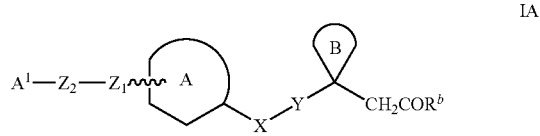

IA optionally containing one or more double bonds, optionally containing one or more heteroatoms or functional groups selected from O, $NR^g$, S, CO or $SO_2$, optionally substituted with one or more substituent selected from the group consisting of alkyl, haloalkyl, halogen, haloalkyl, alkoxy, alkyne, cyano, alkylsulfone, sulfonamide, carboalkoxy and carboxyalkyl; wherein $R^g$ is selected from the group consisting of H, alkyl, haloalkyl, alkoxyalkyl, aryl, heteroaryl, aralkyl, and carboxyalkyl.

In another embodiment of the present invention, X taken together with $Y^3$ forms a 3-7 membered monocyclic ring C,

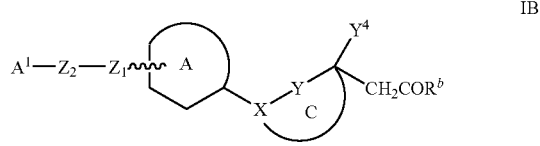

IB optionally containing one or more double bonds, optionally containing one or more heteroatom or functional group selected from O, $NR^g$, S, CO or $SO_2$, optionally substituted with one or more substituent selected from the group consisting of alkyl, halogen, alkoxy, haloalkyl, hydroxyalkyl, or alkoxyalkyl; wherein $R^g$ is selected from the group consisting of H, alkyl, haloalkyl, alkoxyalkyl, aryl, heteroaryl, aralkyl, and carboxyalkyl.

The invention further relates to pharmaceutical compositions containing therapeutically effective amounts of the compounds of Formula I.

The present invention as a first object provides novel non-peptide compounds having the following formula (I)

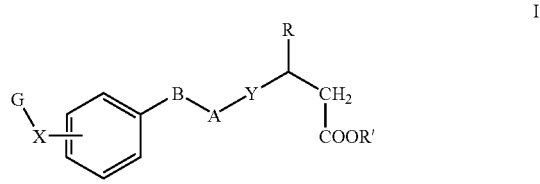

I wherein;

G is a group selected among:

a) 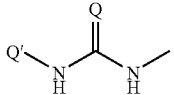

wherein Q is NH or O and Q' is H, $C_1$-$C_6$ alkyl, phenyl, or phenyl-$C_1$-$C_4$-alkyl;

b) 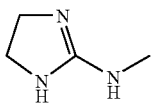

c) 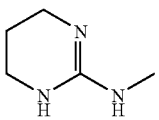

d) 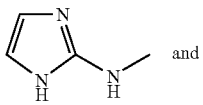 and e) 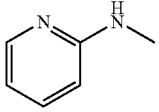

X is a direct linkage, $CH_2$—CONH, —$(CH_2)_m$,— or $(CH_2)_m$—X' wherein X' is O, S or NH and m is an integer of 1 to 4;

B is CONH, $CH_2$—CONH, a $C_2$-$C_4$ alkylene or $C_2$-$C_4$ alkenylene chain or —$(CH_2)_m$—X', wherein X' and m are as defined above;

A is a phenyl or pyridine ring, unsubstituted or optionally substituted by one to to three substituents chosen independently from halogen, $CF_3$, $C_1$-$C_4$ alkyl, OH and $C_1$-$C_4$ alkoxy;

Y is selected from O or $S(O)_n$ wherein n is zero, 1 or 2;

R is $C_1$-$C_6$ alkyl or a phenyl or $C_5$-$C_7$ monocyclic heteroaryl ring containing one to three heteroatoms chosen from O, S, and N, unsubstituted or optionally substituted by one to three substituents chosen independently from halogen, $CF_3$, $C_1$-$C_4$ alkyl, hydroxy and $C_1$-$C_4$ alkoxy;

R' is hydrogen, $C_1$-$C_6$ alkyl, $C_2$-$C_4$ alkenyl, $C_2$-$C_4$ alkynyl, aryl or aryl-$C_1$-$C_4$ alkyl;

and the pharmaceutically acceptable salts thereof.

The present invention includes within its scope all possible isomers, stereoisomers and optical isomers and their mixtures, and the metabolites and the metabolic precursors or bioprecursors of the compounds of formula (I).

A halogen atom is preferably chlorine or fluorine.

The alkyl, alkoxy, alkenyl and alkynyl groups and the alkylene and alkenylene chains may be branched or straight groups or chains, respectively.

A $C_5$-$C_7$ monocyclic heteroaryl ring is preferably a $C_5$-$C_6$ heteromonocyclic ring, in particular selected from pyridine, pyrazine, pyridazine, pyrimidine, thiophene, pyrrole, pyrazole, imidazole, oxazole and isoxazole.

An aryl group is, e.g., an aromatic $C_6$-$C_{20}$ mono- or polynuclear moiety, typically phenyl, unsubstituted or substituted by one to three substituents independently chosen from halogen, hydroxy, $CF_3$, $C_1$-$C_4$ alkyl and $C_1$-$C_4$ alkoxy.

Accordingly an aralkyl group is e.g. benzyl or phenethyl, in which the phenyl ring is optionally substituted by one to three substituents independently chosen from halogen, hydroxy, $CF_3$, $C_1$-$C_4$ alkyl and $C_1$-$C_4$ alkoxy.

A $C_2$-$C_4$ alkenyl group is preferably an allyl group.

A $C_1$-$C_6$ alkyl group is preferably a $C_1$-$C_4$ alkyl group.

A $C_1$-$C_4$ alkyl group is preferably a methyl or ethyl group.

A $C_2$-$C_4$ alkynyl group is preferably an ethynyl group.

A $C_1$-$C_4$ alkoxy group is preferably methoxy, ethoxy, propoxy and butoxy.

Examples of pharmaceutically acceptable salts of the compounds of the invention are either those with inorganic bases, such as sodium, potassium, calcium and aluminium hydroxides, or with organic bases, such as lysine, arginine, N-methyl-glucamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic and sulphuric acids and with organic acids, e.g. citric, tartaric, maleic, malic, fumaric, trifluoroacetic, methanesulphonic and ethanesulphonic acids.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are those wherein, in formula (I),

G is as defined above;

X is a direct linkage or $(CH_2)_m$—X', in which m is 1 or 2 and X' is as defined above;

B is CONH or CH=CH or $CH_2$—X', wherein X' is as defined above;

A is a phenyl ring unsubstituted or optionally substituted by one or two substituents selected from halogen, $CF_3$, $C_1$-$C_4$ alkyl, OH and $C_1$-$C_4$ alkoxy;

Y is as defined above;

R is a phenyl, pyridine, pyrazine, pyridazine, pyrimidine, thiophene, pyrrole, pyrazole, imidazole, oxazole or isoxazole ring, unsubstituted or optionally substituted by one or two substituents selected from halogen, $CF_3$, $C_1$-$C_4$ alkyl, OH and $C_1$-$C_4$ alkoxy;

R' is hydrogen, $C_1$-$C_6$ alkyl; and the pharmaceutically acceptable salts thereof.

A further class of preferred compounds of the invention are those wherein, in formula (I), G and Y are as defined above;

X is $CH_2$—CONH or $(CH_2)_m$—X, in which m and X are as defined above;

A is a phenyl or pyridine ring, unsubstituted or optionally substituted by one to three substituents chosen independently from halogen, $CF_3$, $C_1$-$C_4$ alkyl, OH and $C_1$-$C_4$ alkoxy;

B is CONH or $CH_2$—CONH;

R is a phenyl, pyridine, pyrazine, pyridazine, pyrimidine, thiophene, pyrrole, pyrazole, imidazole, oxazole or isoxazole ring, unsubstituted or optionally substituted by one or two substituents selected from halogen, $CF_3$, $C_1$-$C_4$ alkyl, OH and $C_1$-$C_4$ alkoxy;

R' is hydrogen, $C_1$-$C_6$ alkyl; and the pharmaceutically acceptable salts thereof.

Most preferred compounds of the invention are those wherein, in formula (I),

G and Y are as defined above;

X is a direct linkage or $(CH_2)_m$—X', in which m is 1 or 2 and X' is as defined above;

B is CONH or CH=CH or $CH_2$—X', wherein X' is as defined above;

A is a phenyl ring unsubstituted or optionally substituted by one or two substituents selected from halogen, $CF_3$, $C_1$-$C_4$ alkyl, OH and $C_1$-$C_4$ alkoxy;

R is a phenyl or pyridine ring, unsubstituted or optionally substituted by one or two substituents selected from halogen, $CF_3$, $C_4$-$C_4$ alkyl, OH and $C_1$-$C_4$ alkoxy;

R' is hydrogen, $C_1$-$C_6$ alkyl; and the pharmaceutically acceptable salts thereof.

Examples of specific preferred compounds according to the invention are the to following:

3-({2-[(3-{[amino(imino)methyl]amino}benzoyl)amino]phenyl}sulfanyl)-3-(3-pyridinyl)propanoic acid;
3-({3-[(3-{[amino(imino)methyl]amino}benzoyl)amino]phenyl}sulfanyl)-3-(3-pyridinyl)propanoic acid;
3-({4-[(3-{[amino(imino)methyl]amino}benzoyl)amino]phenyl}sulfanyl)-3-(3-pyridinyl)propanoic acid;
3-({2-[(3-{[(benzylamino)(imino)methyl]amino}benzoyl)amino]phenyl}sulfanyl)-3-(3-pyridinyl)propanoic acid;
3-({3-[(3-{[(benzylamino)(imino)methyl]amino}benzoyl)amino]phenyl}sulfanyl)-3-(3-pyridinyl)propanoic acid;
3-({4-[(3-{[(benzylamino)(imino)methyl]amino}benzoyl)amino]phenyl}sulfanyl)-3-(3-pyridinyl)propanoic acid;
3-{[2-({3-[(aminocarbonyl)amino]benzoyl}amino)phenyl]sulfanyl}-3-(3-pyridinyl)propanoic acid;
3-{[3-({3-[(aminocarbonyl)amino]benzoyl}amino)phenyl]sulfanyl}-3-(3-pyridinyl)propanoic acid;
3-{[4-({3-[(aminocarbonyl)amino]benzoyl}amino)phenyl]sulfanyl}-3-(3-pyridinyl)propanoic acid;
3-({2-[(3-{[(benzylamino)carbonyl]amino}benzoyl)amino]phenyl}sulfanyl)-3-(3-pyridinyl)propanoic acid;
3-({3-[(3-{[(benzylamino)carbonyl]amino}benzoyl)amino]phenyl}sulfanyl)-3-(3-pyridinyl)propanoic acid;
3-({4-[(3-{[(benzylamino)carbonyl]amino}benzoyl)amino]phenyl}sulfanyl)-3-(3-pyridinyl)propanoic acid;
3-[(2-{[3-(4,5-dihydro-1H-imidazo-2-ylamino)benzoyl]amino}phenyl)sulfanyl]-3-(3-pyridinyl)propanoic acid;
3-[(3-{[3-(4,5-dihydro-1H-imidazol-2-ylamino)benzoyl]amino}phenyl)sulfanyl]-3-(3-pyridinyl)propanoic acid;
3-[(4-{[3-(4,5-dihydro-1H-imidazo-2-ylamino)benzoyl]amino}phenyl)sulfanyl]-3-(3-pyridinyl)propanoic acid;
3-[(2-{[3-(1H-imidazol-2-ylamino)benzoyl]amino}phenyl)sulfanyl]-3-(-3-pyridinyl)propanoic acid;
3-[(3-{[3-(1H-imidazol-2-ylamino)benzoyl]amino}phenyl)sulfanyl]-3-(-3-pyridinyl)propanoic acid;
3-[(4-{[3-(1H-imidazol-2-ylamino)benzoyl]amino}phenyl)sulfanyl]-3-(-3-pyridinyl)propanoic acid;
3-(3-pyridinyl)-3-[(2-{[3-(2-pyridinylamino)benzoyl]amino}phenyl)sulfanyl]propanoic acid;
3-(3-pyridinyl)-3-[(3-{[3-(2-pyridinylamino)benzoyl]amino}phenyl)sulfanyl]propanoic acid;
3-(3-pyridinyl)-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-(3-pyridinyl)propanoic acid;
3-({3-[(4-{[amino(imino)methyl]amino}benzoyl)amino]phenyl}sulfanyl)-3-(3-pyridinyl)propanoic acid;
3-({4-[(4-{[amino(imino)methyl]amino}benzoyl)amino]phenyl}sulfanyl)-3-(3-pyridinyl)propanoic acid;
3-({2-[(4-{[(benzylamino)(imino)methyl]amino}benzoyl)amino]phenyl}sulfanyl)-3-(3-pyridinyl)propanoic acid;
3-({3-[(4-{[(benzylamino)(imino)methyl]amino}benzoyl)amino]phenyl}sulfanyl)-3-(3-pyridinyl)propanoic acid;
3-({4-[(4-{[(benzylamino)(imino)methyl]amino}benzoyl)amino]phenyl}sulfanyl)-3-(3-pyridinyl)propanoic acid;
3-{[2-({4-[(aminocarbony)amino]benzoyl}amino)phenyl]sulfanyl}-3-(3-pyridinyl)propanoic acid;
3-{[3-({4-[(aminocarbonyl)amino]benzoyl}amino)phenyl]sulfanyl}-3-(3-pyridinyl)propanoic acid;
3-{[4-({4-[(aminocarbonyl)amino]benzoyl}amino)phenyl]sulfanyl}-3-(3-pyridinyl)propanoic acid;
3-({2-[(4-{[(benzylamino)carbonyl]amino}benzoyl)amino]phenyl}sulfanyl)-3-(3-pyridinyl)propanoic acid;
3-({3-[(4-{[(benzylamino)carbonyl]amino}benzoyl)amino]phenyl}sulfanyl)-3-(3-pyridinyl)propanoic acid;
3-({4-[(4-{[(benzylamino)carbonyl]amino}benzoyl)amino]phenyl}sulfanyl)-3-(3-pyridinyl)propanoic acid;
3-[(2-{[4-(4,5-dihydro-1H-imidazol-2-ylamino)benzoyl]amino}phenyl)sulfanyl]-3-(3-pyridinyl)propanoic acid;
3-(3-{[4-(4,5-dihydro-1H-imidazol-2-ylamino)benzoyl]amino}phenyl)sulfanyl]-3-(3-pyridinyl)propanoic acid;
3-[(4-{[4-(4,5-dihydro-1H-imidazol-2-ylamino)benzoyl]amino}phenyl)sulfanyl]-3-(3-pyridinyl)propanoic acid;
3-[(2-{[4-(1H-imidazol-2-ylamino)benzoyl]amino}phenyl)sulfanyl]-3-(-3-pyridinyl)propanoic acid;
3-[(3-{[4-(1H-imidazol-2-ylamino)benzoyl]amino}phenyl)sulfanyl]-3-(-3-pyridinyl)propanoic acid;
3-[(4-{[4-(1H-imidazol-2-ylamino)benzoyl]amino}phenyl)sulfanyl]-3-(-3-pyridinyl)propanoic acid;
3-(3-pyridinyl)-3-[(2-{[4-(2-pyridinylamino)benzoyl]amino}phenyl)sulfanyl]propanoic acid;
3-(3-pyridinyl)-3-[(3-{[4-(2-pyridinylamino)benzoyl]amino}phenyl)sulfanyl]propanoic acid;
3-(3-pyridinyl)-3-[(4-{[4-(2-pyridinylamino)benzoyl]amino}phenyl)sulfanyl]propanoic acid;
3-({3-[(3-{[amino(imino)methyl]amino}benzoyl)amino]phenyl}sulfanyl)-3-phenylpropanoic acid;
3-({2-[(3-{[amino(imino)methyl]amino}benzoyl)amino]phenyl}sulfanyl)-3-phenylpropanoic acid;
3-({4-[(3-{[amino(imino)methyl]amino}benzoyl)amino]phenyl}sulfanyl)-3-phenylpropanoic acid;
3-({2-[(3-{[(benzylamino)(imino)methyl]amino}benzoyl)amino]phenyl}sulfanyl)-3-phenylpropanoic acid;
3-({3-[(3-{[(benzylamino)(imino)methyl]amino}benzoyl)amino]phenyl}sulfanyl)-3-phenylpropanoic acid;
3-({4-[(3-{[(benzylamino)(imino)methyl]amino}benzoyl)amino]phenyl}sulfanyl)-3-phenylpropanoic acid;
3-{[2-({3-[(aminocarbonyl)amino]benzoyl}amino)phenyl]sulfanyl}-3-phenylpropanoic acid;
3-{[3-({3-[(aminocarbonyl)amino]benzoyl}amino)phenyl]sulfanyl}-3-phenylpropanoic acid;
3-{[4-({3-[(aminocarbonyl)amino]benzoyl}amino)phenyl]sulfanyl}-3-phenylpropanoic acid;
3-({2-[(3-{[(benzylamino)carbonyl]amino}benzoyl)amino]phenyl}sulfanyl)-3-phenylpropanoic acid;
3-({3-[(3-{[(benzylamino)carbonyl]amino}benzoyl)amino]phenyl}sulfanyl)-3-phenylpropanoic acid;
3-({4-[(3-{[(benzylamino)carbonyl]amino}benzoyl)amino]phenyl}sulfanyl)-3-phenylpropanoic acid;
3-[(2-{[3-(4,5-dihydro-1H-imidazol-2-ylamino)benzoyl]amino}phenyl)sulfanyl]-3-phenylpropanoic acid;
3-[(3-{[3-(4,5-dihydro-1H-imidazol-2-ylamino)benzoyl]amino}phenyl)sulfanyl]-3-phenylpropanoic acid;
3-[(4-{[3-(4,5-dihydro-1H-imidazol-2-ylamino)benzoyl]amino}phenyl)sulfanyl]-3-phenylpropanoic acid;

3-[(2-{[3-(1H-imidazol-2-ylamino)benzoyl]amino}phenyl)
 sulfanyl]-3-phenylpropanoic acid;
3-[(3-{[3-(1H-imidazol-2-ylamino)benzoyl]amino}phenyl)
 sulfanyl]-3-phenylpropanoic acid;
3-[(4-{[3-(1H-imidazol-2-ylamino)benzoyl]amino}phenyl)
 sulfanyl]-3-phenylpropanoic acid;
3-phenyl-3-[(2-{[3-(2-pyridinylamino)benzoyl]
 amino}phenyl)sulfanyl]-propanoic acid;
3-phenyl-3-[(3-{[3-(2-pyridinylamino)benzoyl]
 amino}phenyl)sulfanyl]-propanoic acid;
3-phenyl-3-[(4-{[3-(2-pyridinylamino)benzoyl]
 amino}phenyl)sulfanyl]-propanoic acid;
3-({2-[(4-{[amino(imino)methyl]amino}benzoyl)amino]
 phenyl}sulfanyl)-3-phenylpropanoic acid;
3-({3-[(4-{[amino(imino)methyl]amino}benzoyl)amino]
 phenyl}sulfanyl)-3-phenylpropanoic acid;
3-({4-[(4-{[amino(imino)methyl]amino}benzoyl)amino]
 phenyl}sulfanyl)-3-phenylpropanoic acid;
3-({2-[(4-{[(benzylamino)(imino)methyl]amino}benzoyl)
 amino]phenyl}sulfanyl)-3-phenylpropanoic acid;
3-({3-[(4-{[(benzylamino)(imino)methyl]amino}benzoyl)
 amino]phenyl}sulfanyl)-3-phenylpropanoic acid;
3-({4-[(4-{[(benzylamino)(imino)methyl]amino}benzoyl)
 amino]phenyl}sulfanyl)-3-phenylpropanoic acid;
3-{[2-({4-[(aminocarbonyl)amino]benzoyl}amino)phenyl]
 sulfanyl}-3-phenylpropanoic acid;
3-{[3-({4-[(aminocarbonyl)amino]benzoyl}amino)phenyl]
 sulfanyl}-3-phenylpropanoic acid;
3-{[4-({4-[(aminocarbonyl)amino]benzoyl}amino)phenyl]
 sulfanyl}-3-phenylpropanoic acid;
3-({2-[(4-{[(benzylamino)carbonyl]amino}benzoyl)amino]
 phenyl}sulfanyl)-3-phenylpropanoic acid;
3-({3-[(4-{[(benzylamino)carbonyl]amino}benzoyl)amino]
 phenyl}sulfanyl)-3-phenylpropanoic acid;
3-({4-[(4-{[(benzylamino)carbonyl]amino}benzoyl)amino]
 phenyl}sulfanyl)-3-phenylpropanoic acid;
3-[(2-{[4-(4,5-dihydro-1H-imidazol-2-ylamino)benzoyl]
 amino}phenyl)sulfanyl]-3-phenylpropanoic acid;
3-[(3-{[4-(4,5-dihydro-1H-imidazol-2-ylamino)benzoyl]
 amino}phenyl)sulfanyl]-3-phenylpropanoic acid;
3-[(4-{[4-(4,5-dihydro-1H-imidazol-2-ylamino)benzoyl]
 amino}phenyl)sulfanyl]-3-phenylpropanoic acid;
3-[(2-{[4-(1H-imidazol-2-ylamino)benzoyl]amino}phenyl)
 sulfanyl]-3-phenylpropanoic acid;
3-[(3-{[4-(1H-imidazol-2-ylamino)benzoyl]amino}phenyl)
 sulfanyl]-3-phenylpropanoic acid;
3-[(4-{[4-(1H-imidazol-2-ylamino)benzoyl]amino}phenyl)
 sulfanyl]-3-phenylpropanoic acid;
3-phenyl-3-[(2-{[4-(2-pyridinylamino)benzoyl]
 amino}phenyl)sulfanyl]-propanoic acid;
3-phenyl-3-[(3-{[4-(2-pyridinylamino)benzoyl]
 amino}phenyl)sulfanyl]-propanoic acid;
3-phenyl-3-[(4-{[4-(2-pyridinylamino)benzoyl]
 amino}phenyl)sulfanyl]-propanoic acid;
3-{2-[(4-{[amino(imino)methyl]amino}benzoyl)amino]
 phenoxy}-3-(3-pyridinyl)propanoic acid;
3-{3-[(4-{[amino(imino)methyl]amino}benzoyl)amino]
 phenoxy}-3-(3-pyridinyl)propanoic acid;
3-{4-[(4-{[amino(imino)methyl]amino}benzoyl)amino]
 phenoxy}-3-(3-pyridinyl)propanoic acid;
3-{2-[(4-{[(benzylamino)(imino)methyl]amino}benzoyl)
 amino]phenoxy}-3-(3-pyridinyl)propanoic acid;
3-{3-[(4-{[(benzylamino)(imino)methyl]amino}benzoyl)
 amino]phenoxy}-3-(3-pyridinyl)propanoic acid;
3-{4-[(4-{[(benzylamino)(imino)methyl]amino}benzoyl)
 amino]phenoxy}-3-(3-pyridinyl)propanoic acid;
3-[2-({4-[(aminocarbonyl)amino]benzoyl}amino)phe-
 noxy]-3-(3-pyridinyl)propanoic acid;
3-[3-({4-[(aminocarbonyl)amino]benzoyl}amino)phe-
 noxy]-3-(3-pyridinyl)propanoic acid;
3-[4-({4-[(aminocarbonyl)amino]benzoyl}amino)phe-
 noxy]-3-(3-pyridinyl)propanoic acid;
3-{2-[(4-{[(benzylamino)carbonyl]amino}benzoyl)amino]
 phenoxy}-3-(3-pyridinyl)propanoic acid;
3-{3-[(4-{[(benzylamino)carbonyl]amino}benzoyl)amino]
 phenoxy}-3-(3-pyridinyl)propanoic acid;
3-{4-[(4-{[(benzylamino)carbonyl]amino}benzoyl)amino]
 phenoxy}-3-(3-pyridinyl)propanoic acid;
3-(2-{[4-(4,5-dihydro-1H-imidazol-2-ylamino)benzoyl]
 amino}phenoxy)-3-(3-pyridinyl)propanoic acid;
3-(3-{[4-(4,5-dihydro-1H-imidazol-2-ylamino)benzoyl]
 amino}phenoxy)-3-(3-pyridinyl)propanoic acid;
3-(4-{[4-(4,5-dihydro-1H-imidazol-2-ylamino)benzoyl]
 amino}phenoxy)-3-(3-pyridinyl)propanoic acid;
3-(2-{[4-(1H-imidazol-2-ylamino)benzoyl]
 amino}phenoxy)-3-(3-pyridinyl)propanoic acid;
3-(3-{[4-(1H-imidazol-2-ylamino)benzoyl]
 amino}phenoxy)-3-(3-pyridinyl)propanoic acid;
3-(4-{[4-(1H-imidazol-2-ylamino)benzoyl]
 amino}phenoxy)-3-(3-pyridinyl)propanoic acid;
3-(3-pyridinyl)-3-(2-{[4-(2-pyridinylamino)benzoyl]
 amino}phenoxy)propanoic acid;
3-(3-pyridinyl)-3-(3-{[4-(2-pyridinylamino)benzoyl]
 amino}phenoxy)propanoic acid;
3-(3-pyridinyl)-3-(4-{[4-(2-pyridinylamino)benzoyl]
 amino}phenoxy)propanoic acid;
3-{2-[(3-{[amino(imino)methyl]amino}benzoyl)amino]
 phenoxy}-3-(3-pyridinyl)propanoic acid;
3-{3-[(3-{[amino(imino)methyl]amino}benzoyl)amino]
 phenoxy}-3-(3-pyridinyl)propanoic acid;
3-{4-[(3-{[amino(imino)methyl]amino}benzoyl)amino]
 phenoxy}-3-(3-pyridinyl)propanoic acid;
3-{2-[(3-{[(benzylamino)(imino)methyl]amino}benzoyl)
 amino]phenoxy}-3-(3-pyridinyl)propanoic acid;
3-{3-[(3-{[(benzylamino)(imino)methyl]amino}benzoyl)
 amino]phenoxy}-3-(3-pyridinyl)propanoic acid;
3-{4-[(3-{[(benzylamino)(imino)methyl]amino}benzoyl)
 amino]phenoxy}-3-(3-pyridinyl)propanoic acid;
3-[2-({3-[(aminocarbonyl)amino]benzoyl}amino)phe-
 noxy]-3-(3-pyridinyl)propanoic acid;
3-[3-({3-[(aminocarbonyl)amino]benzoyl}amino)phe-
 noxy]-3-(3-pyridinyl)propanoic acid;
3-[4-({3-[(aminocarbonyl)amino]benzoyl}amino)phe-
 noxy]-3-(3-pyridinyl)propanoic acid;
3-{2-[(3-{[(benzylamino)carbonyl]amino}benzoyl)amino]
 phenoxy}-3-(3-pyridinyl)propanoic acid;
3-{3-[(3-{[(benzylamino)carbonyl]amino}benzoyl)amino]
 phenoxy}-3-(3-pyridinyl)propanoic acid;
3-{4-[(3-{[(benzylamino)carbonyl]amino}benzoyl)amino]
 phenoxy}-3-(3-pyridinyl)propanoic acid;
3-(2-{[3-(4,5-dihydro-1H-imidazol-2-ylamino)benzoyl]
 amino}phenoxy)-3-(3-pyridinyl)propanoic acid;
3-(3-{[3-(4,5-dihydro-1H-imidazol-2-ylamino)benzoyl]
 amino}phenoxy)-3-(3-pyridinyl)propanoic acid;
3-(4-{[3-(4,5-dihydro-1H-imidazol-2-ylamino)benzoyl]
 amino}phenoxy)-3-(3-pyridinyl)propanoic acid;
3-(2-{[3-(1H-imidazol-2-ylamino)benzoyl]
 amino}phenoxy)-3-(3-pyridinyl)propanoic acid;
3-(3-{[3-(1H-imidazol-2-ylamino)benzoyl]
 amino}phenoxy)-3-(3-pyridinyl)propanoic acid;
3-(4-{[3-(1H-imidazol-2-ylamino)benzoyl]
 amino}phenoxy)-3-(3-pyridinyl)propanoic acid;

3-(3-pyridinyl)-3-(2-{[3-(2-pyridinylamino)benzoyl]
amino}phenoxy)propanoic acid;
3-(3-pyridinyl)-3-(3-{[3-(2-pyridinylamino)benzoyl]
amino}phenoxy)propanoic acid;
3-(3-pyridinyl)-3-(4-{[3-(2-pyridinylamino)benzoyl]
amino}phenoxy)propanoic acid;
3-{2-[(3-{[amino(imino)methyl]amino}benzoyl)amino]
phenoxy}-3-phenylpropanoic acid;
3-{3-[(3-{[amino(imino)methyl]amino}benzoyl)amino]
phenoxy}-3-phenylpropanoic acid;
3-{4-[(3-{[amino(imino)methyl]amino}benzoyl)amino]
phenoxy}-3-phenylpropanoic acid;
3-{2-[(3-{[(benzylamino)(imino)methyl]amino}benzoyl)
amino]phenoxy}-3-phenylpropanoic acid;
3-{3-[(3-{[(benzylamino)(imino)methyl]amino}benzoyl)
amino]phenoxy}-3-phenylpropanoic acid;
3-{4-[(3-{[(benzylamino)(imino)methyl]amino}benzoyl)
amino]phenoxy}-3-phenylpropanoic acid;
3-[2-({3-[(aminocarbonyl)amino]benzoyl}amino)phe-
noxy]-3-phenylpropanoic acid;
3-[3-({3-[(aminocarbonyl)amino]benzoyl}amino)phe-
noxy]-3-phenylpropanoic acid;
3-[4-({3-[(aminocarbonyl)amino]benzoyl}amino)phe-
noxy]-3-phenylpropanoic acid;
3-{2-[(3-{[(benzylamino)carbonyl]amino}benzoyl)amino]
phenoxy}-3-phenylpropanoic acid;
3-{3-[(3-{[(benzylamino)carbonyl]amino}benzoyl)amino]
phenoxy}-3-phenylpropanoic acid;
3-{4-[(3-{[(benzylamino)carbonyl]amino}benzoyl)amino]
phenoxy}-3-phenylpropanoic acid;
3-(2-{[3-(4,5-dihydro-1H-imidazol-2-ylamino)benzoyl]
amino}phenoxy)-3-phenylpropanoic acid;
3-(3-{[3-(4,5-dihydro-1H-imidazol-2-ylamino)benzoyl]
amino}phenoxy)-3-phenylpropanoic acid;
3-(4-{[3-(4,5-dihydro-1H-imidazol-2-ylamino)benzoyl]
amino}phenoxy)-3-phenylpropanoic acid;
3-(2-{[3-(1H-imidazol-2-ylamino)benzoyl]
amino}phenoxy)-3-phenylpropanoic acid;
3-(3-{[3-(1H-imidazol-2-ylamino)benzoyl]
amino}phenoxy)-3-phenylpropanoic acid;
3-(4-{[3-(1H-imidazol-2-ylamino)benzoyl]
amino}phenoxy)-3-phenylpropanoic acid;
3-phenyl-3-(2-{[3-(2-pyridinylamino)benzoyl]
amino}phenoxy)propanoic acid;
3-phenyl-3-(3-{[3-(2-pyridinylamino)benzoyl]
amino}phenoxy)propanoic acid;
3-phenyl-3-(4-{[3-(2-pyridinylamino)benzoyl]
amino}phenoxy)propanoic acid;
3-{2-[(4-{[amino(imino)methyl]amino}benzoyl)amino]
phenoxy}-3-phenylpropanoic acid;
3-{3-[(4-{[amino(imino)methyl]amino}benzoyl)amino]
phenoxy}-3-phenylpropanoic acid;
3-{4-[(4-{[amino(imino)methyl]amino}benzoyl)amino]
phenoxy}-3-phenylpropanoic acid;
3-{2-[(4-{[(benzylamino)(imino)methyl]amino}benzoyl)
amino]phenoxy}-3-phenylpropanoic acid;
3-{3-[(4-{[(benzylamino)(imino)methyl]amino}benzoyl)
amino]phenoxy}-3-phenylpropanoic acid;
3-{4-[(4-{[(benzylamino)(imino)methyl]amino}benzoyl)
amino]phenoxy}-3-phenylpropanoic acid;
3-[2-({4-[(aminocarbonyl)amino]benzoyl}amino)phe-
noxy]-3-phenylpropanoic acid;
3-[3-({4-[(aminocarbonyl)amino]benzoyl}amino)phe-
noxy]-3-phenylpropanoic acid;
3-[4-({4-[(aminocarbonyl)amino]benzoyl}amino)phe-
noxy]-3-phenylpropanoic acid;
3-{2-[(4-{[(benzylamino)carbonyl]amino}benzoyl)amino]
phenoxy}-3-phenylpropanoic acid;
3-{3-[(4-{[(benzylamino)carbonyl]amino}benzoyl)amino]
phenoxy}-3-phenylpropanoic acid;
3-{4-[(4-{[(benzylamino)carbonyl]amino}benzoyl)amino]
phenoxy}-3-phenylpropanoic acid;
3-(2-{[4-(4,5-dihydro-1H-imidazol-2-ylamino)benzoyl]
amino}phenoxy)-3-phenylpropanoic acid;
3-(3-{[4-(4,5-dihydro-1H-imidazol-2-ylamino)benzoyl]
amino}phenoxy)-3-phenylpropanoic acid;
3-(4-{[4-(4,5-dihydro-1H-imidazol-2-ylamino)benzoyl]
amino}phenoxy)-3-phenylpropanoic acid;
3-(2-{[4-(1H-imidazol-2-ylamino)benzoyl]
amino}phenoxy)-3-phenylpropanoic acid;
3-(3-{[4-(1H-imidazol-2-ylamino)benzoyl]
amino}phenoxy)-3-phenylpropanoic acid;
3-(4-{[4-(1H-imidazol-2-ylamino)benzoyl]
amino}phenoxy)-3-phenylpropanoic acid;
3-phenyl-3-(2-{[4-(2-pyridinylamino)benzoyl]
amino}phenoxy)propanoic acid;
3-phenyl-3-(3-{[4-(2-pyridinylamino)benzoyl]
amino}phenoxy)propanoic acid;
3-phenyl-3-(4-{[4-(2-pyridinylamino)benzoyl]
amino}phenoxy)propanoic acid;
3-({2-[(3-{[amino(imino)methyl]amino}benzoyl)amino]
phenyl}sulfinyl)-3-(3-pyridinyl)propanoic acid;
3-({3-[(3-{[amino(imino)methyl]amino}benzoyl)amino]
phenyl}sulfinyl)-3-(3-pyridinyl)propanoic acid;
3-({4-[(3-{[amino(imino)methyl]amino}benzoyl)amino]
phenyl}sulfinyl)-3-(3-pyridinyl)propanoic acid;
3-({2-[(3-{[(benzylamino)(imino)methyl]amino}benzoyl)
amino]phenyl}sulfinyl)-3-(3-pyridinyl)propanoic acid;
3-({3-[(3-{[(benzylamino)(imino)methyl]amino}benzoyl)
amino]phenyl}sulfinyl)-3-(3-pyridinyl)propanoic acid;
3-({4-{[(3-([benzylamino)(imino)methyl]amino}benzoyl)
amino]phenyl}sulfinyl)-3-(3-pyridinyl)propanoic acid;
3-{[2-({3-[(aminocarbonyl)amino]benzoyl}amino)phenyl]
sulfinyl}-3-(3-pyridinyl)propanoic acid;
3-{[3-({3-[(aminocarbonyl)amino]benzoyl}amino)phenyl]
sulfinyl}-3-(3-pyridinyl)propanoic acid;
3-({[4-({3-[(aminocarbonyl)amino]benzoyl}amino)phenyl]
sulfinyl}-3-(-3-pyridinyl)propanoic acid;
3-({2-[(3-{[(benzylamino)carbonyl]amino}benzoyl)amino]
phenyl}sulfinyl)-3-(3-pyridinyl)propanoic acid;
3-({3-[(3-{[(benzylamino)carbonyl]amino}benzoyl)amino]
phenyl}sulfinyl)-3-(3-pyridinyl)propanoic acid;
3-({4-[(3-{[(benzylamino)carbonyl]amino}benzoyl)amino]
phenyl}sulfinyl)-3-(3-pyridinyl)propanoic acid;
3-[(2-{[3-(4,5-dihydro-1H-imidazol-2-ylamino)benzoyl]
amino}phenyl)sulfinyl]-3-(3-pyridinyl)propanoic acid;
3-[(3-{[3-(4,5-dihydro-1H-imidazol-2-ylamino)benzoyl]
amino}phenyl)sulfinyl]-3-(3-pyridinyl)propanoic acid;
3-[(4-{[3-(4,5-dihydro-1H-imidazol-2-ylamino)benzoyl]
amino}phenyl)sulfinyl]-3-(3-pyridinyl)propanoic acid;
3-[(2-{[3-(1H-imidazol-2-ylamino)benzoyl]amino}phenyl)
sulfinyl]-3-(-3-pyridinyl)propanoic acid;
3-[(3-{[3-(1H-imidazol-2-ylamino)benzoyl]amino}phenyl)
sulfinyl]-3-(-3-pyridinyl)propanoic acid;
3-[(4-{[3-(1H-imidazol-2-ylamino)benzoyl]amino}phenyl)
sulfinyl]-3-(-3-pyridinyl)propanoic acid;
3-(3-pyridinyl)-3-[(2-{[3-(2-pyridinylamino)benzoyl]
amino}phenyl)sulfinyl]propanoic acid;
3-(3-pyridinyl)-3-[(3-{[3-(2-pyridinylamino)benzoyl]
amino}phenyl)sulfinyl]propanoic acid;
3-(3-pyridinyl)-3-[(4-{[3-(2-pyridinylamino)benzoyl]
amino}phenyl)sulfinyl]propanoic acid;

3-({2-[(4-{[amino(imino)methyl]amino}benzoyl)amino]
phenyl}sulfinyl)-3-(3-pyridinyl)propanoic acid;
3-({3-[(4-{[amino(imino)methyl]amino}benzoyl)amino]
phenyl}sulfinyl)-3-(3-pyridinyl)propanoic acid;
3-[({4-[(4-{[amino(imino)methyl]amino}benzoyl)amino]
phenyl}sulfinyl)-3-(3-pyridinyl)propanoic acid;
3-({2-[(4-{[(benzylamino)(imino)methyl]amino}benzoyl)
amino]phenyl}sulfinyl)-3-a(3-pyridinyl)propanoic acid;
3-({3-[(4-{[(benzylamino)(imino)methyl]amino}benzoyl)
amino]phenyl}sulfinyl)-3-(3-pyridinyl)propanoic acid;
3-[(4-[(4-{[(benzylamino)(imino)methyl]amino}benzoyl)
amino]phenyl}sulfinyl)-3-(3-pyridinyl)propanoic acid;
3-{[2-({4-[(aminocarbonyl)amino]benzoyl}amino)phenyl]
sulfinyl}-3-(3-pyridinyl)propanoic acid;
3-{[3-({4-[(aminocarbonyl)amino]benzoyl}amino)phenyl]
sulfinyl}-3-(3-pyridinyl)propanoic acid;
3-{[4-({4-[(aminocarbonyl)amino]benzoyl}amino)phenyl]
sulfinyl}-3-(3-pyridinyl)propanoic acid;
3-({2-[(4-{[(benzylamino)carbonyl]amino}benzoyl)amino]
phenyl}sulfinyl)-3-(3-pyridinyl)propanoic acid;
3-({3-[(4-{[(benzylamino)carbonyl]amino}benzoyl)amino]
phenyl}sulfinyl)-3-(3-pyridinyl)propanoic acid;
3-({4-[(4-{[(benzylamino)carbonyl]amino}benzoyl)amino]
phenyl}sulfinyl)-3-(3-pyridinyl)propanoic acid;
3-[(2-{[4-(4,5-dihydro-1H-imidazol-2-ylamino)benzoyl]
amino}phenyl)sulfinyl]-3-(3-pyridinyl)propanoic acid;
3-[(3-{[4-(4,5-dihydro-1H-imidazol-2-ylamino)benzoyl]
amino}phenyl)sulfinyl]-3-(pyridinyl)propanoic acid;
3-[(4-{[4-(4,5-dihydro-1H-imidazol-2-ylamino)benzoyl]
amino}phenyl)sulfinyl]-3-(3-pyridinyl)propanoic acid;
3-[(2-{[4-(1H-imidazol-2-ylamino)benzoyl]amino}phenyl)
sulfinyl]-3-(-3-pyridinyl)propanoic acid;
3-[(3-{[4-(1H-imidazol-2-ylamino)benzoyl]amino}phenyl)
sulfinyl]-3-(-3-pyridinyl)propanoic acid;
3-[(4-{[4-(1H-imidazol-2-ylamino)benzoyl]amino}phenyl)
sulfinyl]-3-(-3-pyridinyl)propanoic acid;
3-(3-pyridinyl)-3-[(2-{[4-(2-pyridinylamino)benzoyl]
amino}phenyl)sulfinyl]propanoic acid;
3-(3-pyridinyl)-3-[(3-{[4-(2-pyridinylamino)benzoyl]
amino}phenyl)sulfinyl]propanoic acid;
3-(3-pyridinyl)-3-[(4-{[4-(2-pyridinylamino)benzoyl]
amino}phenyl)sulfinyl]propanoic acid;
3-({2-[(3-{[amino(imino)methyl]amino}benzoyl)amino]
phenyl}sulfonyl)-3-(3-pyridinyl)propanoic acid;
3-({3-[(3-{[amino(imino)methyl]amino}benzoyl)amino]
phenyl}sulfonyl)-3-(3-pyridinyl)propanoic acid;
3-({4-[(3-{[amino(imino)methyl]amino}benzoyl)amino]
phenyl}sulfonyl)-3-(3-pyridinyl)propanoic acid;
3-({2-[(3-{[(benzylamino)(imino)methyl]amino}benzoyl)
amino]phenyl}sulfonyl)-3-(3-pyridinyl)propanoic acid;
3-({3-[(3-{[(benzylamino)(imino)methyl]amino}benzoyl)
amino]phenyl}sulfonyl)-3-(3-pyridinyl)propanoic acid;
3-({4-[(3-{[(benzylamino)(imino)methyl]amino}benzoyl)
amino]phenyl}sulfonyl)-3-(3-pyridinyl)propanoic acid;
3-{[2-({3-[(aminocarbonyl)amino]benzoyl}amino)phenyl]
sulfonyl}-3-(3-pyridinyl)propanoic acid;
3-{[3-({3-[(aminocarbonyl)amino]benzoyl}amino)phenyl]
sulfonyl}-3-(3-pyridinyl)propanoic acid;
3-{[4-({3-[(aminocarbonyl)amino]benzoyl}amino)phenyl]
sulfonyl}-3-(3-pyridinyl)propanoic acid;
3-({2-[(3-{[(benzylamino)carbonyl]amino}benzoyl)amino]
phenyl}sulfonyl)-3-(3-pyridinyl)propanoic acid;
3-({3-[(3-{[(benzylamino)carbonyl]amino}benzoyl)amino]
phenyl}sulfonyl)-3-(3-pyridinyl)propanoic acid;
3-({4-[(3-{[(benzylamino)carbonyl]amino}benzoyl)amino]
phenyl}sulfonyl)-3-(3-pyridinyl)propanoic acid;

3-[(2-{[3-(4,5-dihydro-1H-imidazol-2-ylamino)benzoyl]
amino}phenyl)sulfonyl]-3-(3-pyridinyl)propanoic acid;
3-[(3-{[3-(4,5-dihydro-1H-imidazol-2-ylamino)benzoyl]
amino}phenyl)sulfonyl]-3-(3-pyridinyl)propanoic acid;
3-[(4-{[3-(4,5-dihydro-1H-imidazol-2-ylamino)benzoyl]
amino}phenyl)sulfonyl]-3-(3-pyridinyl)propanoic acid;
3-(2-{[3-(1H-imidazol-2-ylamino)benzoyl]amino}phenyl)
sulfonyl]-3-(-3-pyridinyl)propanoic acid;
3-[(3-{[3-(1H-imidazol-2-ylamino)benzoyl]amino}phenyl)
sulfonyl]-3-(-3-pyridinyl)propanoic acid;
3-[(4-{[3-(1H-imidazol-2-ylamino)benzoyl]amino}phenyl)
sulfonyl]-3-(-3-pyridinyl)propanoic acid;
3-(3-pyridinyl)-3-[(2-{[3-(2-pyridinylamino)benzoyl]
amino}phenyl)sulfonyl]propanoic acid;
3-(3-pyridinyl)-3-[(3-{[3-(2-pyridinylamino)benzoyl]
amino}phenyl)sulfonyl]propanoic acid;
3-(3-pyridinyl)-3-[(4-{[3-(2-pyridinylamino)benzoyl]
amino}phenyl)sulfonyl]propanoic acid;
3-({2-[(4-{[amino(imino)methyl]amino}benzoyl)amino]
phenyl}sulfonyl)-3-(3-pyridinyl)propanoic acid;
3-({3-[(4-{[amino(imino)methyl]amino}benzoyl)amino]
phenyl}sulfonyl)-3-(3-pyridinyl)propanoic acid;
3-({4-[(4-{[amino(imino)methyl]amino}benzoyl)amino]
phenyl}sulfonyl)-3-(3-pyridinyl)propanoic acid;
3-({2-[(4-{[(benzylamino)(imino)methyl]amino}benzoyl)
amino]phenyl}sulfonyl)-3-(3-pyridinyl)propanoic acid;
3-({3-[(4-{[(benzylamino)(imino)methyl]amino}benzoyl)
amino]phenyl}sulfonyl)-3-(3-pyridinyl)propanoic acid;
3-({4-[(4-{[(benzylamino)(imino)methyl]amino}benzoyl)
amino]phenyl}sulfonyl)-3-(3-pyridinyl)propanoic acid;
3-{[2-({4-[(aminocarbonyl)amino]benzoyl}amino)phenyl]
sulfonyl)}-3-(3-pyridinyl)propanoic acid;
3-{[3-({4-[(aminocarbonyl)amino]benzoyl}amino)phenyl]
sulfonyl}-3-(3-pyridinyl)propanoic acid;
3-{[3-({4-[(aminocarbonyl)amino]benzoyl}amino)phenyl]
sulfonyl}-3-(3-pyridinyl)propanoic acid;
3-({2-[(4-{[(benzylamino)carbonyl]amino}benzoyl)amino]
phenyl}sulfonyl)-3-(3-pyridinyl)propanoic acid;
3-({3-[(4-{[(benzylamino)carbonyl]amino}benzoyl)amino]
phenyl}sulfonyl)-3-(3-pyridinyl)propanoic acid;
3-({4-[(4-{[(benzylamino)carbonyl]amino}benzoyl)amino]
phenyl}sulfonyl)-3-(3-pyridinyl)propanoic acid;
3-[(2-{[4-(4,5-dihydro-1H-imidazol-2-ylamino)benzoyl]
amino}phenyl)sulfonyl]-3-(3-pyridinyl)propanoic acid;
3-[(3-{[4-(4,5-dihydro-1H-imidazol-2-ylamino)benzoyl]
amino}phenyl)sulfonyl]-3-(3-pyridinyl)propanoic acid;
3-[(4-{[4-(4,5-dihydro-1H-imidazol-2-ylamino)benzoyl]
amino}phenyl)sulfonyl]-3-(3-pyridinyl)propanoic acid;
3-[(2-{[4-(1H-imidazol-2-ylamino)benzoyl]amino}phenyl)
sulfonyl]-3-(-3-pyridinyl)propanoic acid;
3-[(3-{[4-(1H-imidazol-2-ylamino)benzoyl]amino}phenyl)
sulfonyl]-3-(-3-pyridinyl)propanoic acid;
3-[(4-{[4-(1H-imidazol-2-ylamino)benzoyl]amino}phenyl)
sulfonyl]-3-(-3-pyridinyl)propanoic acid;
3-(3-pyridinyl)-3-[(2-{[4-(2-pyridinylamino)benzoyl]
amino}phenyl)sulfonyl]propanoic acid;
3-(3-pyridinyl)-3-[(3-{[4-(2-pyridinylamino)benzoyl]
amino}phenyl)sulfonyl]propanoic acid;
3-(3-pyridinyl)-3-[(4-{[4-(2-pyridinylamino)benzoyl]
amino}phenyl)sulfonyl]propanoic acid;
3-({3-[(3-{[amino(imino)methyl]amino}benzoyl)amino]
phenyl}sulfinyl)-3-phenylpropanoic acid;
3-({2-[(3-{[amino(imino)methyl]amino}benzoyl)amino]
phenyl}sulfinyl)-3-phenylpropanoic acid;
3-({4-[(3-{[amino(imino)methyl]amino}benzoyl)amino]
phenyl}sulfinyl)-1-3-phenylpropanoic acid;

3-({2-[(3-{[(benzylamino)(imino)methyl]amino}benzoyl)amino]phenyl}sulfinyl)-3-phenylpropanoic acid;
3-({3-[(3-{[(benzylamino)(imino)methyl]amino}benzoyl)amino]phenyl}sulfinyl)-3-phenylpropanoic acid;
3-[(4-{3-{[(benzylamino)(imino)methyl]amino}benzoyl)amino]phenyl}sulfinyl)-3-phenylpropanoic acid;
3-{[2-({3-[(aminocarbonyl)amino]benzoyl}amino)phenyl]sulfinyl}-3-phenylpropanoic acid;
3-{[3-({3-[(aminocarbonyl)amino]benzoyl}amino)phenyl]sulfinyl}-3-phenylpropanoic acid;
3-{[4-({3-[(aminocarbonyl)amino]benzoyl}amino)phenyl]sulfinyl}-3-phenylpropanoic acid;
3-({2-[(3-{[(benzylamino)carbonyl]amino}benzoyl)amino]phenyl}sulfinyl)-3-phenylpropanoic acid;
3-({3-[(3-{[(benzylamino)carbonyl]amino}benzoyl)amino]phenyl}sulfinyl)-3-phenylpropanoic acid;
3-({4-[(3-{[(benzylamino)carbonyl]amino}benzoyl)amino]phenyl}sulfinyl)-3-phenylpropanoic acid;
3-[(2-{[3-(4,5-dihydro-1H-imidazol-2-ylamino)benzoyl]amino}phenyl)sulfinyl]-3-phenylpropanoic acid;
3-[(3-{[3-(4,5-dihydro-1H-imidazol-2-ylamino)benzoyl]amino}phenyl)sulfinyl]-3-phenylpropanoic acid;
3-[(4-{[3-(4,5-dihydro-1H-imidazol-2-ylamino)benzoyl]amino}phenyl)sulfinyl]-3-phenylpropanoic acid;
3-[(2-{[3-(1H-imidazol-2-ylamino)benzoyl]amino}phenyl)sulfinyl]-3-phenylpropanoic acid;
3-[(3-{[3-(1H-imidazol-2-ylamino)benzoyl]amino}phenyl)sulfinyl]-3-phenylpropanoic acid;
3-[(4-{[3-(1H-imidazol-2-ylamino)benzoyl]amino}phenyl)sulfinyl]-3-phenylpropanoic acid;
3-phenyl-3-[(2-{[3-(2-pyridinylamino)benzoyl]amino}phenyl)sulfinyl]-propanoic acid;
3-phenyl-3-[(3-{[3-(2-pyridinylamino)benzoyl]amino}phenyl)sulfinyl]-propanoic acid;
3-phenyl-3-[(4-{[3-(2-pyridinylamino)benzoyl]amino}phenyl)sulfinyl]-propanoic acid;
3-({2-[(4-{[amino(imino)methyl]amino}benzoyl)amino]phenyl}sulfinyl)-3-phenylpropanoic acid;
3-({3-[(4-{[amino(imino)methyl]amino}benzoyl)amino]phenyl}sulfinyl)-3-phenylpropanoic acid;
3-({4-[(4-{[amino(imino)methyl]amino}benzoyl)amino]phenyl}sulfinyl)-3-phenylpropanoic acid;
3-({2-[(4-{[(benzylamino)(imino)methyl]amino}benzoyl)amino]phenyl}sulfinyl)-3-phenylpropanoic acid;
3-({3-[(4-{[(benzylamino)(imino)methyl]amino}benzoyl)amino]phenyl}sulfinyl)-3-phenylpropanoic acid;
3-({4-[(4-{[(benzylamino)(imino)methyl]amino}benzoyl)amino]phenyl}sulfinyl)-3-phenylpropanoic acid;
3-{[2-({4-[(aminocarbonyl)amino]benzoyl}amino)phenyl]sulfinyl}-3-phenylpropanoic acid;
3-{[3-({4-[(aminocarbonyl)amino]benzoyl}amino)phenyl]sulfinyl}-3-phenylpropanoic acid;
3-{[4-({4-[(aminocarbonyl)amino]benzoyl}amino)phenyl]sulfinyl}-3-phenylpropanoic acid;
3-({2-[(4-{[(benzylamino)carbonyl]amino}benzoyl)amino]phenyl}sulfinyl)-3-phenylpropanoic acid;
3-({3-[(4-{[(benzylamino)carbonyl]amino}benzoyl)amino]phenyl}sulfinyl)-3-phenylpropanoic acid;
3-({4-[(4-{[(benzylamino)carbonyl]amino}benzoyl)amino]phenyl}sulfinyl)-3-phenylpropanoic acid;
3-[(2-{[4-(4,5-dihydro-1H-imidazol-2-ylamino)benzoyl]amino}phenyl)sulfinyl]-3-phenylpropanoic acid;
3-[(3-{[4-(4,5-dihydro-1H-imidazol-2-ylamino)benzoyl]amino}phenyl)sulfinyl]-3-phenylpropanoic acid;
3-[(4-{[4-(4,5-dihydro-1H-imidazol-2-ylamino)benzoyl]amino}phenyl)sulfinyl]-3-phenylpropanoic acid;
3-[(2-{[4-(1H-imidazol-2-ylamino)benzoyl]amino}phenyl)sulfinyl]-3-phenylpropanoic acid;
3-[(3-{[4-(1H-imidazol-2-ylamino)benzoyl]amino}phenyl)sulfinyl]-3-phenylpropanoic acid;
3-[(4-{[4-(1H-imidazol-2-ylamino)benzoyl]amino}phenyl)sulfinyl]-3-phenylpropanoic acid;
3-phenyl-3-[(2-{[4-(2-pyridinylamino)benzoyl]amino}phenyl)sulfinyl]-propanoic acid;
3-phenyl-3-[(3-{[4-(2-pyridinylamino)benzoyl]amino}phenyl)sulfinyl]-propanoic acid;
3-phenyl-3-[(4-{[4-(2-pyridinylamino)benzoyl]amino}phenyl)sulfinyl]-propanoic acid;
3-({3-[(3-{[amino(imino)methyl]amino}benzoyl)amino]phenyl}sulfonyl)-3-phenylpropanoic acid;
3-({2-[(3-{[amino(imino)methyl]amino}benzoyl)amino]phenyl}sulfonyl)-3-phenylpropanoic acid;
3-({4-[(3-{[amino(imino)methyl]amino}benzoyl)amino]phenyl}sulfonyl)-3-phenylpropanoic acid;
3-({2-[(3-{[(benzylamino)(imino)methyl]amino}benzoyl)amino]phenyl}sulfonyl)-3-phenylpropanoic acid;
3-({3-[(3-{[(benzylamino)(imino)methyl]amino}benzoyl)amino]phenyl}sulfonyl)-3-phenylpropanoic acid;
3-({4-[(3-{[(benzylamino)(imino)methyl]amino}benzoyl)amino]phenyl}sulfonyl)-3-phenylpropanoic acid;
3-{[2-({3-[(aminocarbonyl)amino]benzoyl}amino)phenyl]sulfonyl}-3-phenylpropanoic acid;
3-{[3-({3-[(aminocarbonyl)amino]benzoyl}amino)phenyl]sulfonyl}-3-phenylpropanoic acid;
3-{[4-({3-[(aminocarbonyl)amino]benzoyl}amino)phenyl]sulfonyl}-3-phenylpropanoic acid;
3-({2-[(3-{[(benzylamino)carbonyl]amino}benzoyl)amino]phenyl}sulfonyl)-3-phenylpropanoic acid;
3-({3-[(3-{[(benzylamino)carbonyl]amino}benzoyl)amino]phenyl}sulfonyl)-3-phenylpropanoic acid;
3-({4-[(3-{[(benzylamino)carbonyl]amino}benzoyl)amino]phenyl}sulfonyl)-3-phenylpropanoic acid;
3-[(2-{[3-(4,5-dihydro-1H-imidazol-2-ylamino)benzoyl]amino}phenyl)sulfonyl]-3-phenylpropanoic acid;
3-[(3-{[3-(4,5-dihydro-1H-imidazol-2-ylamino)benzoyl]amino}phenyl)sulfonyl]-3-phenylpropanoic acid;
3-[(4-{[3-(4,5-dihydro-1H-imidazol-2-ylamino)benzoyl]amino}phenyl)sulfonyl]-3-phenylpropanoic acid;
3-[(2-{[3-(1H-imidazol-2-ylamino)benzoyl]amino}phenyl)sulfonyl]-3-phenylpropanoic acid;
3-[(3-{[3-(1H-imidazol-2-ylamino)benzoyl]amino}phenyl)sulfonyl]-3-phenylpropanoic acid;
3-[(4-{[3-(1H-imidazol-2-ylamino)benzoyl]amino}phenyl)sulfonyl]-3-phenylpropanoic acid;
3-phenyl-3-[(2-{[3-(2-pyridinylamino)benzoyl]amino}phenyl)sulfonyl]-propanoic acid;
3-phenyl-3-[(3-{[3-(2-pyridinylamino)benzoyl]amino}phenyl)sulfonyl]-propanoic acid;
3-phenyl-3-[(4-{[3-(2-pyridinylamino)benzoyl]amino}phenyl)sulfonyl]-propanoic acid;
3-({2-[(4-{[amino(imino)methyl]amino}benzoyl)amino]phenyl}sulfonyl)-3-phenylpropanoic acid;
3-({3-[(4-{[amino(imino)methyl]amino}benzoyl)amino]phenyl}sulfonyl)-3-phenylpropanoic acid;
3-({4-[(4-{[amino(imino)methyl]amino}benzoyl)amino]phenyl}sulfonyl)-3-phenylpropanoic acid;
3-({2-[(4-{[(benzylamino)(imino)methyl]amino}benzoyl)amino]phenyl}sulfonyl)-3-phenylpropanoic acid;
3-({3-[(4-{[(benzylamino)(imino)methyl]amino}benzoyl)amino]phenyl}sulfonyl)-3-phenylpropanoic acid;
3-({4-[(4-{[(benzylamino)(imino)methyl]amino}benzoyl)amino]phenyl}sulfonyl)-3-phenylpropanoic acid;

3-{[2-({4-[(aminocarbonyl)amino]benzoyl}amino)phenyl]sulfonyl}-3-phenylpropanoic acid;
3-{[3-({4-[(aminocarbonyl)amino]benzoyl}amino)phenyl]sulfonyl}-3-phenylpropanoic acid;
3-{[4-({4-[(aminocarbonyl)amino]benzoyl}amino)phenyl]sulfonyl}-3-phenylpropanoic acid;
3-({2-[(4-{[(benzylamino)carbonyl]amino}benzoyl)amino]phenyl}sulfonyl)-3-phenylpropanoic acid;
3-({3-[(4-{[(benzylamino)carbonyl]amino}benzoyl)amino]phenyl}sulfonyl)-3-phenylpropanoic acid;
3-({4-[(4-{[(benzylamino)carbonyl]amino}benzoyl)amino]phenyl}sulfonyl)-3-phenylpropanoic acid;
3-[(2-{[4-(4,5-dihydro-1H-imidazol-2-ylamino)benzoyl]amino}phenyl)sulfonyl]-3-phenylpropanoic acid;
3-[(3-{[4-(4,5-dihydro-1H-imidazol-2-ylamino)benzoyl]amino}phenyl)sulfonyl]-3-phenylpropanoic acid;
3-[(4-{[4-(4,5-dihydro-1H-imidazol-2-ylamino)benzoyl]amino}phenyl)sulfonyl]-3-phenylpropanoic acid;
3-[(2-{[4-(1H-imidazol-2-ylamino)benzoyl]amino}phenyl)sulfonyl]-3-phenylpropanoic acid;
3-[(3-{[4-(1H-imidazol-2-ylamino)benzoyl]amino}phenyl)sulfonyl]-3-phenylpropanoic acid;
3-[(4-{[4-(1H-imidazol-2-ylamino)benzoyl]amino}phenyl)sulfonyl]-3-phenylpropanoic acid;
3-phenyl-3-[(2-{[4-(2-pyridinylamino)benzoyl]amino}phenyl)sulfonyl]-propanoic acid;
3-phenyl-3-[(3-{[4-(2-pyridinylamino)benzoyl]amino}phenyl)sulfonyl]-propanoic acid;
3-phenyl-3-[(4-{[4-(2-pyridinylamino)benzoyl]amino}phenyl)sulfonyl]-propanoic acid;
3-phenyl-3-[(2-{[4-(2-pyridinylamino)benzoyl]amino}phenyl)sulfonyl]-propanoic acid;
3-phenyl-3-[(3-{[4-(2-pyridinylamino)benzoyl]amino}phenyl)sulfonyl]-propanoic acid;
3-phenyl-3-[(4-{[4-(2-pyridinylamino)benzoyl]amino}phenyl)sulfonyl]-propanoic acid;
3-(3-pyridinyl)-3-(2-f{[3-(1,4,5,6-tetrahydro-2-pyrimidinylamino)benzoyl]amino}phenoxy)propanoic acid;
3-(3-pyridinyl)-3-(3-{[3-(1,4,5,6-tetrahydro-2-pyrimidinylamino)benzoyl]amino}phenoxy)propanoic acid;
3-(3-pyridinyl)-3-(4-{[3-(1,4,5,6-tetrahydro-2-pyrimidinylamino)benzoyl]amino}phenoxy)propanoic acid;
3-(3-pyridinyl)-3-(2-{[4-(1,4,5,6-tetrahydro-2-pyrimidinylamino)benzoyl]amino}phenoxy)propanoic acid;
3-(3-pyridinyl)-3-(3-{[4-(1,4,5,6-tetrahydro-2-pyrimidinylamino)benzoyl]amino}phenoxy)propanoic acid;
3-(3-pyridinyl)-3-(4-{[4-(1,4,5,6-tetrahydro-2-pyrimidinylamino)benzoyl]amino}phenoxy)propanoic acid;
3-phenyl-3-(2-{[3-(1,4,5,6-tetrahydro-2-pyrimidinylamino)benzoyl]amino}phenoxy)propanoic acid;
3-phenyl-3-(3-{[3-(1,4,5,6-tetrahydro-2-pyrimidinylamino)benzoyl]amino}phenoxy)propanoic acid;
3-phenyl-3-(4-{[3-(1,4,5,6-tetrahydro-2-pyrimidinylamino)benzoyl]amino}phenoxy)propanoic acid;
3-phenyl-3-(2-{[4-(1,4,5,6-tetrahydro-2-pyrimidinylamino)benzoyl]amino}phenoxy)propanoic acid;
3-phenyl-3-(3-{[4-(1,4,5,6-tetrahydro-2-pyrimidinylamino)benzoyl]amino}phenoxy)propanoic acid;
3-phenyl-3-(4-{[4-(1,4,5,6-tetrahydro-2-pyrimidinylamino)benzoyl]amino}phenoxy)propanoic acid;
3-(3-pyridinyl)-3-[(2-{[3-(1,4,5,6-tetrahydro-2-pyrimidinylamino)benzoyl]amino}phenyl)sulfanyl]propanoic acid;
3-(3-pyridinyl)-3-[(3-{[3-(1,4,5,6-tetrahydro-2-pyrimidinylamino)benzoyl]amino}phenyl)sulfanyl]propanoic acid;
3-(3-pyridinyl)-3-[(4-{[3-(1,4,5,6-tetrahydro-2-pyrimidinylamino)benzoyl]amino}phenyl)sulfanyl]propanoic acid;
3-(3-pyridinyl)-3-[(2-{[4-(1,4,5,6-tetrahydro-2-pyrimidinylamino)benzoyl]amino}phenyl)sulfanyl]propanoic acid;
3-(3-pyridinyl)-3-[(3-{[4-(1,4,5,6-tetrahydro-2-pyrimidinylamino)benzoyl]amino}phenyl)sulfanyl]propanoic acid;
3-(3-pyridinyl)-3-[(4-{[4-(1,4,5,6-tetrahydro-2-pyrimidinylamino)benzoyl]amino}phenyl)sulfanyl]propanoic acid;
3-phenyl-3-[(2-{[3-(1,4,5,6-tetrahydro-2-pyrimidinylamino)benzoyl]amino}phenyl)sulfanyl]propanoic acid;
3-phenyl-3-[(3-{[3-(1,4,5,6-tetrahydro-2-pyrimidinylamino)benzoyl]amino}phenyl)sulfanyl]propanoic acid;
3-phenyl-3-[(4-{[3-(1,4,5,6-tetrahydro-2-pyrimidinylamino)benzoyl]amino}phenyl)sulfanyl]propanoic acid;
3-phenyl-3-[(2-{[4-(1,4,5,6-tetrahydro-2-pyrimidinylamino)benzoyl]amino}phenyl)sulfanyl]propanoic acid;
3-phenyl-3-[(3-{[4-(1,4,5,6-tetrahydro-2-pyrimidinylamino)benzoyl]amino}phenyl)sulfanyl]propanoic acid;
3-phenyl-3-[(4-{[4-(1,4,5,6-tetrahydro-2-pyrimidinylamino)benzoyl]amino}phenyl)sulfanyl]propanoic acid;
3-(3-pyridinyl)-3-[(2-{[3-(1,4,5,6-tetrahydro-2-pyrimidinylamino)benzoyl]amino}phenyl)sulfinyl]propanoic acid;
3-(3-pyridinyl)-3-[(3-{[3-(1,4,5,6-tetrahydro-2-pyrimidinylamino)benzoyl]amino)phenyl)sulfinyl]propanoic acid;
3-(3-pyridinyl)-3-[(4-([3-(1,4,5,6-tetrahydro-2-pyrimidinylamino)benzoyl]amino}phenyl)sulfinyl]propanoic acid;
3-(3-pyridinyl)-3-[(2-{[4-(1,4,5,6-tetrahydro-2-pyrimidinylamino)benzoyl]amino}phenyl)sulfinyl]propanoic acid;
3-(3-pyridinyl)-3-[(3-{[4-(1,4,5,6-tetrahydro-2-pyrimidinylamino)benzoyl]amino}phenyl)sulfinyl]propanoic acid;
3-(3-pyridinyl)-3-[(4-{[4-(1,4,5,6-tetrahydro-2-pyrimidinylamino)benzoyl]amino}phenyl)sulfinyl]propanoic acid;
3-phenyl-3-[(2-{[3-(1,4,5,6-tetrahydro-2-pyrimidinylamino)benzoyl]amino}phenyl)sulfinyl]propanoic acid;
3-phenyl-3-[(3-{[3-(1,4,5,6-tetrahydro-2-pyrimidinylamino)benzoyl]amino}phenyl)sulfinyl]propanoic acid;
3-phenyl-3-[(4-{[3-(1,4,5,6-tetrahydro-2-pyrimidinylamino)benzoyl]amino}phenyl)sulfinyl]propanoic acid;
3-phenyl-3-[(2-{[4-(1,4,5,6-tetrahydro-2-pyrimidinylamino)benzoyl]amino}phenyl)sulfinyl]propanoic acid;
3-phenyl-3-[(3-{[4-(1,4,5,6-tetrahydro-2-pyrimidinylamino)benzoyl]amino}phenyl)sulfinyl]propanoic acid;
3-phenyl-3-[(4-{[4-(1,4,5,6-tetrahydro-2-pyrimidinylamino)benzoyl]amino}phenyl)sulfinyl]propanoic acid;
3-(3-pyridinyl)-3-[(2-{[3-(1,4,5,6-tetrahydro-2-pyrimidinylamino)benzoyl]amino}phenyl)sulfonyl]propanoic acid;
3-(3-pyridinyl)-3-[(3-{[3-(1,4,5,6-tetrahydro-2-pyrimidinylamino)benzoyl]amino}phenyl)sulfonyl]propanoic acid;
3-(3-pyridinyl)-3-[(4-{[3-(1,4,5,6-tetrahydro-2-pyrimidinylamino)benzoyl]amino}phenyl)sulfonyl]propanoic acid;
3-(3-pyridinyl)-3-[(2-{[4-(1,4,5,6-tetrahydro-2-pyrimidinylamino)benzoyl]amino}phenyl)sulfonyl]propanoic acid;
3-(3-pyridinyl)-3-[(3-{[4-(1,4,5,6-tetrahydro-2-pyrimidinylamino)benzoyl]amino}phenyl)sulfonyl]propanoic acid;
3-(3-pyridinyl)-3-[(4-{[4-(1,4,5,6-tetrahydro-2-pyrimidinylamino)benzoyl]amino}phenyl)sulfonyl]propanoic acid;
3-phenyl-3-[(2-{[3-(1,4,5,6-tetrahydro-2-pyrimidinylamino)benzoyl]amino}phenyl)sulfonyl]propanoic acid;
3-phenyl-3-[(3-{[3-(1,4,5,6-tetrahydro-2-pyrimidinylamino)benzoyl]-amino}phenyl)sulfonyl]propanoic acid;
3-phenyl-3-[(4-{[3-(1,4,5,6-tetrahydro-2-pyrimidinylamino)benzoyl]amino}phenyl)sulfonyl]propanoic acid;
3-phenyl-3-[(2-{[4-(1,4,5,6-tetrahydro-2-pyrimidinylamino)benzoyl]amino}phenyl)sulfonyl]propanoic acid;
3-phenyl-3-[(3-{[4-(1,4,5,6-tetrahydro-2-pyrimidinylamino)benzoyl]amino}phenyl)sulfonyl]propanoic acid; and
3-phenyl-3-[(4-{[4-(1,4,5,6-tetrahydro-2-pyrimidinylamino)benzoyl]amino}phenyl)sulfonyl]propanoic acid;

either as a single isomer or as a mixture thereof, or a pharmaceutically acceptable salt thereof, in particular the hydrochloride or the trifluoroacetate.

A further object of the present invention is to provide a compound of formula (I)

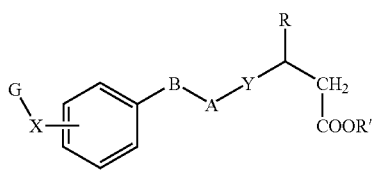

wherein:
G is a group selected among:

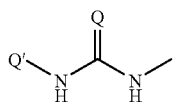

a)

wherein Q is NH or O and Q' is H, $C_1$-$C_6$ alkyl, phenyl, or phenyl-$C_1$-$C_4$-alkyl;

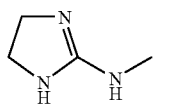

b)

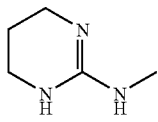

c)

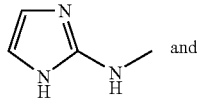

and d)

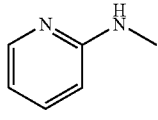

e)

X is a direct linkage, $CH_2$—CONH, —$(CH_2)_m$— or $(CH_2)_m$—X' wherein X' is O, S or NH and m is an integer of 1 to 4;

B is CONH, $CH_2$—CONH, a $C_2$-$C_4$ alkylene or $C_2$-$C_4$ alkenylene chain or —$(CH_2)_m$—X', wherein X' and m are as defined above;

A is a phenyl or pyridine ring, unsubstituted or optionally substituted by one to three substituents chosen independently from halogen, $CF_3$, $C_1$-$C_4$ alkyl, OH and $C_1$-$C_4$ alkoxy;

Y is selected from O or $S(O)_n$ wherein n is zero, 1 or 2;

R is $C_1$-$C_6$ alkyl or a phenyl or $C_5$-$C_7$ monocyclic heteroaryl ring containing one to three heteroatoms chosen from O, S, and N, unsubstituted or optionally substituted by one to three substituents chosen independently from halogen, $CF_3$, $C_1$-$C_4$ alkyl, hydroxy and $C_1$-$C_4$ alkoxy;

R' is hydrogen, $C_1$-$C_6$ alkyl, $C_2$-$C_4$ alkenyl, $C_2$-$C_4$ alkynyl, aryl or aryl-$C_1$-$C_4$ alkyl;

or a pharmaceutically acceptable salt thereof, for use in a method of treatment of the human or animal body by therapy, in particular for treating conditions mediated by the αvβ3 integrin.

Object of the present invention is also to provide a pharmaceutical composition comprising a pharmaceutically acceptable carrier and/or diluent and as an active principle, a compound of formula (I), as herein defined, or a pharmaceutically acceptable salt thereof.

The present invention also provides the use of a compound of formula (I), as defined above, in the preparation of a medicament having αvβ3 integrin inhibiting or antagonizing activity.

The present invention also provides a method for treating conditions mediated by the αvβ3 integrin in a mammal, including humans, in need of such treatment comprising administering to said mammal an effective αvβ3 inhibiting or antagonizing amount of a compound of formula (I)

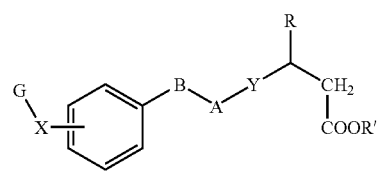

I wherein:
G is a group selected among:

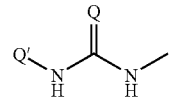

a)

wherein Q is NH or O and Q' is H, $C_1$-$C_6$ alkyl, phenyl, or phenyl-$C_1$-$C_4$-alkyl;

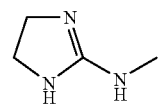

b)

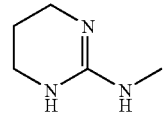

c)

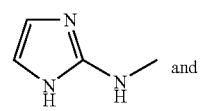

and d)

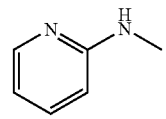

e)

X is a direct linkage, $CH_2$—CONH, —$(CH_2)_m$— or $(CH_2)_m$—X' wherein X' is O, S or NH and m is an integer of 1 to 4;

B is CONH, $CH_2$—CONH, a $C_2$-$C_4$ alkylene or $C_2$-$C_4$ alkenylene chain or —$(CH_2)_m$—X', wherein X' and m are as defined above;

A is a phenyl or pyridine ring, unsubstituted or optionally substituted by one to three substituents chosen independently from halogen, $CF_3$, $C_1$-$C_4$ alkyl, OH and $C_1$-$C_4$ alkoxy;

Y is selected from O or $S(O)_n$ wherein n is zero, 1 or 2;

R is $C_1$-$C_6$ alkyl or a phenyl or $C_5$-$C_7$ monocyclic heteroaryl ring containing one to three heteroatoms chosen from O, S, and N, unsubstituted or optionally substituted by one to three substituents chosen independently from halogen, $CF_3$, $C_1$-$C_4$ alkyl, hydroxy and $C_1$-$C_4$ alkoxy;

R' is hydrogen, $C_1$-$C_6$ alkyl, $C_2$-$C_4$ alkenyl, $C_2$-$C_4$ alkynyl, aryl or aryl-$C_1$-$C_4$ alkyl;

or a pharmaceutically acceptable salt thereof.

More specifically, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

The compounds of the invention and the salt thereof can be prepared by and analogy process. Accordingly, the compounds of formula I and the salts thereof, can be for instance obtained by a process which comprises:

a) reacting a compound of formula II

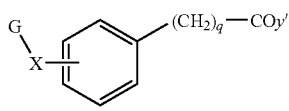

where q is zero or 1, y' is a reactive function, preferably halogen, and G and X are as defined above, with a compound of formula III

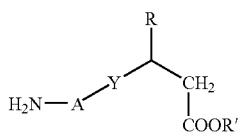

where A, Y, R, and R' are as defined above, thus obtaining a compound of formula I where B is CONH or $CH_2$—CONH; or b) reacting a compound of formula IV

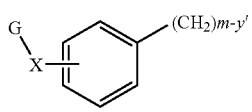

where y' is a reactive function, preferably halogen and G, X and m are as defined above, with a compound of formula V

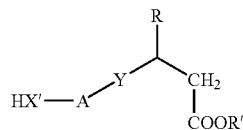

where X', A, Y, R, and R' are as defined above, thus obtaining a compound of formula I where B is —$(CH_2)_m$—X', wherein X' and m are as defined above; or c) reacting a compound of formula VI

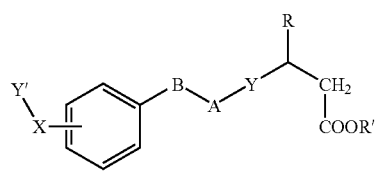

where X, B, A, Y, R, and R' are as defined above, and Y' is $NH_2$, with a suitable guanilating agent such as di-Boc-trifylguanidine, thus obtaining a compound of formula I where G is a guanidino group; or d) reacting a compound of formula VI where X, B, A, Y, R, R' and Y' are as defined above, with a benzyl cyanate or a cyanate salt, as e.g. a ammonium or sodium or potassium salt, thus obtaining a compound of formula I where G is an urea group; or e) reacting a compound of formula VI where X, B, A, Y, R, R' and Y' are as defined above, with an isocyanate of formula Q'NCO, where Q' is a group selected among C1-C6 alkyl, Phenyl, Phenyl-C1-C4-alkyl, thus obtaining a compound of formula I where G is a Q'NH(CO)NH— group, in which Q' is a group selected among C1-C6 alkyl, Phenyl, Phenyl-$C_1$-$C_4$-alkyl;

f) reacting a compound of formula VII

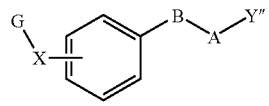

wherein G, X, B and A, are as defined above and Y" is a thiol group, with a compound of formula VIII,

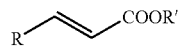

wherein R and R' are as defined above, thus obtaining a compound of formula (I) wherein Y is —S—; or g) reacting a compound of formula IX 1

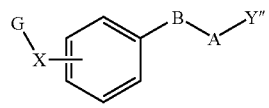

wherein G, X, B, A, are as defined above and Y" is a group Y—H with a compound of formula X,

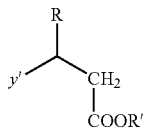

wherein R, R' and y' are as defined above, thus obtaining a compound of formula I;

h) hydrolyzing, preferably in acidic conditions, a carboxylic ester compound of formula I wherein G, X, B, A, Y, R are as defined above and R' is different from hydrogen, thus obtaining a compound of formula I wherein R' is hydrogen;

i) oxidizing with a suitable agent such as $NaIO_4$ or oxone or $H_2O_2$, a compound of formula I wherein G, X, B, A, R and R' are as defined above and Y is sulfur, thus obtaining a compound of formula I wherein G, X, B, A, R and R' are as defined above and Y is $S(O)_n$ wherein n is 1 or 2, i.e. Y is a sulfoxide or sulfone group;

l) cleaving a compound of formula I; wherein G, X, B, A, Y and R are as defined above and the group R' is represented by Wang (p-bezyloxybenzylalcohol) resin, with TFA in $CH_2Cl_2$, thus obtaining a compound of formula I wherein R' is hydrogen; and, if desired, salifying a compound of formula (I) and/or, if desired, converting a salt of a compound of formula (I) into a free compound and/or, if desired, separating a mixture of isomers of a compound of formula (I) into the single isomers.

Process-Variants a) to l), Respectively, Can for Instance be Carried out at Follows:

a) In a typical procedure the acid was added to a large excess of thionyl chloride (25 equivalents) kept under stirring at about 0.degree. C. under nitrogen atmosphere, the mixture heated at about 60.degree. C. for 1 hour, brought to mom temperature and thoroughly evaporated in vacuo. The acid chloride II was dissolved in DMF and added to a mixture of the intermediate required (III) (1 equivalent) and triethylamine (1 equivalent) in DMF or pyridine. The mixture was stirred at room temperature for 48-72 hours, the solvent removed, the residue taken with brine and extracted with dichloromethane. The compounds thus obtained were purified by silica gel flash chromatography eluting with $CH_2Cl_2$/MeOH 9:1.

b) In a typical procedure compounds of formula IV were added to a solution of V in solvents like DMF, acetone, in presence of a base (NaH, $K_2CO_3$, KHMSA) the temperature varying between room temperature and reflux, the time of reaction varying between 24-72 hours. The mixture filtered the solvent evaporated and the residue taken with brine and extracted with dichloromethane or ethyl acetate. The compounds were purified by silica gel flash chromatography eluting with $CH_2Cl_2$/MeOH 9:1 or Petroleum ether 40-60/Ethyl acetate 1:1.

c) In a typical procedure the amino derivatives of formula VI reacted with the guanilating agent, such as di-Boc-triflylguanidine, in dichloromethane in presence of stechiometric amounts of base such as triethylamine or diusopropylethylamine, the time of reaction varying between 24-72 hours. The compounds thus obtained did not request further purification. (FEICHTINGER, K.; ZAPF, C.; SINGS, H. L.; GOODMAN, M.; J Org 1998, 63 (12), 3804-3805). The protection groups were removed according to standard procedures, with TFA.

d) In a typical procedure the amino derivatives of formula VI reacted with a cyanate salt, as e.g. a ammonium or sodium or potassium salt, in solvent such as AcOH, $H_2O$ (Org. Synth. 1963, IV, 49) PNAS 1993, 90, 6909-6913) the temperature varying between 50-100.degree. C., the time of reaction varying e) In a typical procedure the amino derivatives of formula VI reacted with isocyanates in presence of triethylamine refuxing in solvents such as dichloromethane, acetonitrile, toluene or dioxane (JMC 1996, 39 (22) 4382-4395; Eur J Med Chem 1997, 32 (10), 795-804.) to give the substituted ureas, the temperature varying between room temperature and reflux, the time of reaction varying between 8-24 hours.

f) In a typical procedure to a stirred solution of the acids VIII (cinnamic or trans-3-(3-pyridyl)acrylic) as ethyl esters or polymer supported, in dichloromethane kept under vigorous stirring in nitrogen atmosphere, the amiothiophenols VII (2 eq) and DBU (0.1 equivalent) were added, the mixture was stirred at room temperature for about 24 hours, the solvent evaporated and the residue purified by silica gel flash chromatography eluting with petroleum ether 40-60/ethyl acetate 1:1, to give the intermediates required.

g) In a typical procedure compounds of formula X were added to a solution of IX in solvents like DMF, acetone, in presence of a base ($K_2CO_3$, NaH, KHMSA) the temperature varying between room temperature and reflux, time of reaction varying between 8-24 hours h) The ester compounds of formula I, were hydrolysed by treatment with a mixture of HCl 4N and ethanol overnight. Solvents were evaporated and the final compounds, obtained as hydrochlorides, purified by crystallisation with methanol and ether.

i) The sulfur functions of formula I were oxidised to solfones with 30% aq $H_2O_2$ (RAVIKUMAR, K. S.; BEGUE, J.-P.; BONNET-DELPON, D.; Tetrahedron Lett 1998, 39 (20), 3141-3144.) or with $NaIO_4$, in water and methanol, or acetone and water, according to a standard procedure (BEIER, C.; SCHAUMANN, E.; Synthesis 1997, (11), 1296-1300; LE MERRER, Y.; FUZIER, M.; DOSBAA, I.; FOGLIETTI, M.-J.; DEPEZAY, J.-C.; Tetrahedron 1997, 53 (49), 16731-16746.). The sulfur functions were oxidised to solfoxides according to a standard procedure by reacting with oxone in a mixture methanol/water as a solvent (HINTERBERGER, S.; HOFER, O.; GREGER, H.; Tetrahedron 1998, 54 (3), 487-496.)

l) Compounds of formula I linked to the Wang resin were cleaved as a final step with a mixture trifluoroacetic acid/dichloromethane, the time of reaction varying between 15-30 minutes.

Also the optional salification of a compound of formula (I) as well as the conversion of a salt into the free compound and the separation of a mixture of isomers into the single isomers may be carried our by conventional methods. For example, the separation of optical isomers may be carried out by salification with an optically active base or acid and by subsequent fractional crystallization of the diastereoisomeric salts, followed by recovering of the optically active isomeric-acids or, respectively, bases. When in the compound of formula (I), and in the intermediate products thereof, groups are present which need to be protected before submitting them to the here-above illustrated reactions, they may be protected before the reactions take place and then deprotected, according to well known methods in organic chemistry. The compounds of formulae (I) and the pharmaceutically acceptable salts thereof are herein defined as the "compounds of the present invention", the "compounds of the invention" and/or the "active principles of the pharmaceutical compositions of the invention".

For instance, according to process variant a) above, and according the indications herein provided, the compound 3-({4-[(3-{[amino(imino)methyl]amino}benzoyl)amino]-phenyl}sulfanyl)-3-(3-pyridinyl)propanoic acid (internal code PNU 277362F) can be provided. In particular compound PNU 277362F can be synthesized as bis-trifluoroacetate salt, as depicted in scheme 1, according to the procedures reported.

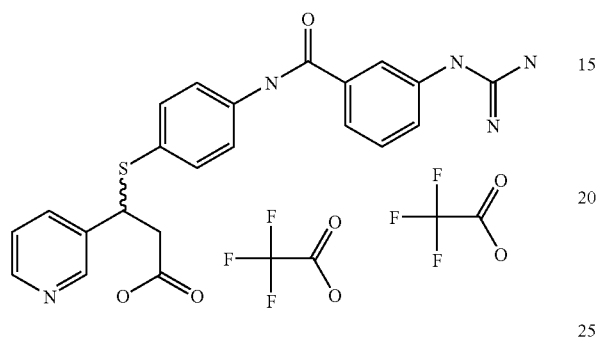

3-{4-[(3-{[amino(imino)methyl]amino}benzoyl)amino]phenyl}sulfanyl)}-3-(3-pyridinyl)propanoic acid bis-trifluoroacetate (PNU 277362F)

$^1$H-NMR (DMSO-$d_6$): 10.3 (s, 1H); 9.8 (s, 1H); 8.5 (m, 2H); 7.85 (m, 2H); 7.78 (m, 1H); 7.7 (d, 2H) 7.6-7.4 (m, 5H); 7.3 (d, 2H), 4.8 (t, 1H); 2.9 (m, 2H); Elemental analysis: Theoretic: C, 47.06%; H, 3.49%; F, 17.18%; N, 10.55%; S, 4.83%. Found: C, 44.32%; H, 3.49%; F, 16.70%; N, 9.95%; S, 4.44%.

Scheme 1

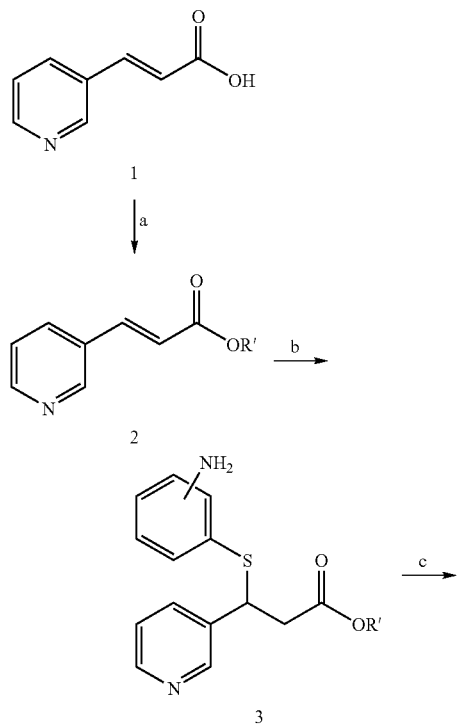

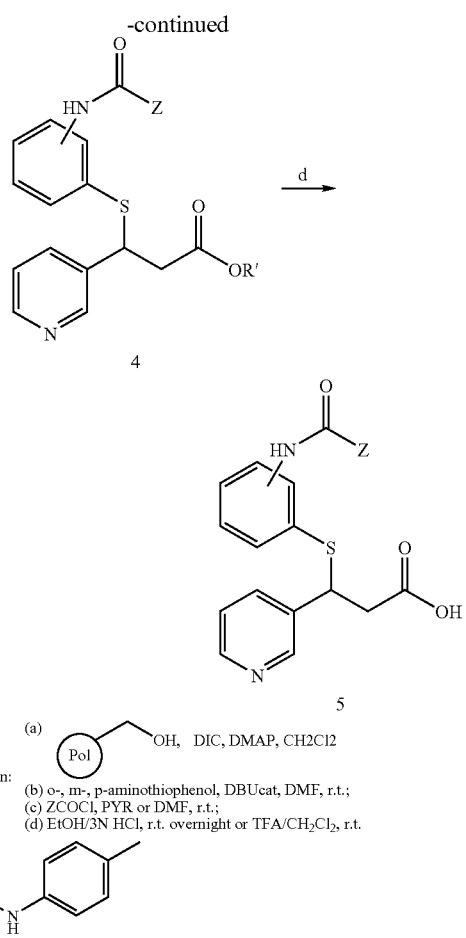

(a) <image src="Pol">OH, DIC, DMAP, CH2Cl2
if R' = Wang resin:
(b) o-, m-, p-aminothiophenol, DBUcat, DMF, r.t.;
(c) ZCOCl, PYR or DMF, r.t.;
(d) EtOH/3N HCl, r.t. overnight or TFA/CH$_2$Cl$_2$, r.t.

Z is

<image src="Z_structure" /> wherein
Pol=polymer of Wang resin; DIC=diisopropylcarbodiimide; DMAP=4-dimethylminopyridine; DBUcat=1,8-diazabicyclo[5,4,0]undec-7-ene in catalytic amount; DMF=dimethylformamide; TFA=trifluoro acetic acid.

Analogously, according to process variant d) above, the compound 3-{[4-({3-[(aminocarbonyl)amino]benzoyl}amino)phenyl]sulfanyl}-3-(3-pyridinyl) propanoic acid (internal code PNU 515440) is provided.

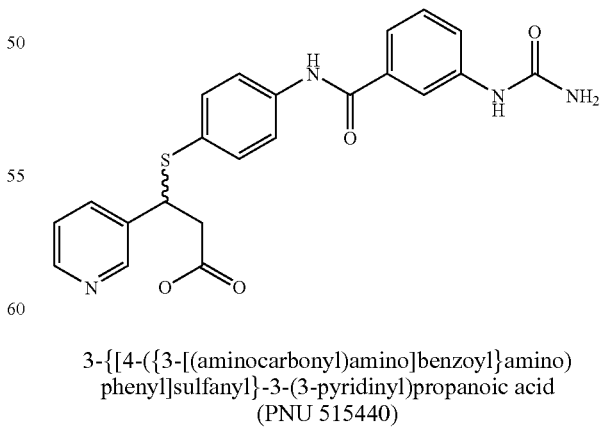

3-{[4-({3-[(aminocarbonyl)amino]benzoyl}amino)phenyl]sulfanyl}-3-(3-pyridinyl)propanoic acid (PNU 515440)

MS: m/z 437 (M+H$^+$). $^1$H-NMR (400 MHz), .delta. (DMSO-$d_6$): 2.82 (m, 211, CH$_2$), 4.65 (m, 111, CHS), 5.91 (s, 2H, CONH$_2$), 7.20-7.70 (m, 9H, ArH), 7.85 (m, 1H, ArH), 8.38 (m, 2H, pyridine hydrogens), 8.77 (s, 1H, NHCO), 10.24 (s, 1H, NHCO).

According to process variant e) above, the compound 3-{[4-({3-[(benzylamino)carbonyl])amino}benzoyl)amino]phenyl}sulfanyl)-3-(3-pyridinyl)propanoic acid (internal code PHA 515442E) is provided. The compound PNU 515442E can be synthesized as trifluoroacetate salts.

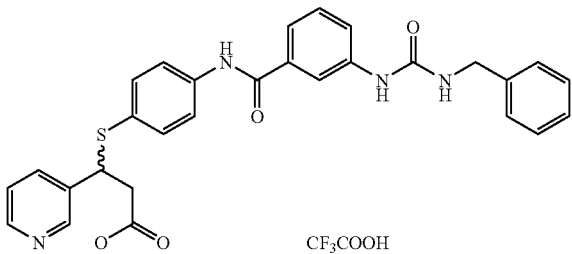 [SMILES: O=C(O)CC(Sc1ccc(NC(=O)c2cccc(NC(=O)NCc3ccccc3)c2)cc1)c1cccnc1 ; "CF3COOH"]

3-{[4-({3-[(benzylamino)carbonyl])amino}benzoyl)amino]phenyl}sulfanyl)-3-(3-pyridinyl)propanoic acid (PHA 515442E)

MS: m/z 527 (M+H$^+$). $^1$H-NMR (400 MHz), .delta. (DMSO-d$_6$): 2.97 (m, 2H, CH$_2$), 4.29 (d, 2H, J=5.7, CH$_2$NH), 4.71 (m, 1H, CHS), 7.20-7.70 (m, 14H, ArH), 7.88 (m, 1H, ArH), 8.53 (m, 2H, pyridine hydrogens), 8.77 (s, 1H, NHCO), 10.27 (s, 1H, NHCO).

In analogy to process variants a) to 1), the following compounds can be obtained:

3-({2-[(3-{[amino(imino)methyl]amino}benzoyl)amino]phenyl}sulfanyl)-3-(3-pyridinyl)propanoic acid;
3-({3-[(3-{[amino(imino)methyl]amino}benzoyl)amino]phenyl}sulfanyl)-3-(3-pyridinyl)propanoic acid;
3-({2-[(3-{[(benzylamino)(imino)methyl]amino}benzoyl)amino]phenyl}sulfanyl)-3-(3-pyridinyl)propanoic acid;
3-({3-[(3-{[(benzylamino)(imino)methyl]amino}benzoyl)amino]phenyl}sulfanyl)-3-(3-pyridinyl)propanoic acid;
3-{[2-({3-[(aminocarbonyl)amino]benzoyl}amino)phenyl]sulfanyl}-3-(3-pyridinyl)propanoic acid;
3-{[3-({3-[(aminocarbonyl)amino]benzoyl}amino)phenyl]sulfanyl}-3-(3-pyridinyl)propanoic acid;
3-({2-[(3-{[(benzylamino)carbonyl]amino}benzoyl)amino]phenyl}sulfanyl)-3-(3-pyridinyl)propanoic acid;
3-({3-[(3-{[(benzylamino)carbonyl]amino}benzoyl)amino]phenyl}sulfanyl)-3-(3-pyridinyl)propanoic acid;
3-({4-[(3-{[(benzylamino)carbonyl]amino}benzoyl)amino]phenyl}sulfanyl)-3-(3-pyridinyl)propanoic acid;
3-[(2-{[3-(4,5-dihydro-1H-imidazol-2-ylamino)benzoyl]amino}phenyl)sulfanyl]-3-(3-pyridinyl)propanoic acid;
3-[(3-{[3-(4,5-dihydro-1H-imidazol-2-ylamino)benzoyl]amino}phenyl)sulfanyl]-3-(3-pyridinyl)propanoic acid;
3-[(4-{[3-(4,5-dihydro-1H-imidazol-2-ylamino)benzoyl]amino}phenyl)sulfanyl]-3-(3-pyridinyl)propanoic acid;
3-[(2-{[3-(1H-imidazol-2-ylamino)benzoyl]amino}phenyl)sulfanyl]-3-(-3-pyridinyl)propanoic acid;
3-[(3-{[3-(1H-imidazol-2-ylamino)benzoyl]amino}phenyl)sulfanyl]-3-(-3-pyridinyl)propanoic acid;
3-[(4-{[3-(1H-imidazol-2-ylamino)benzoyl]amino}phenyl)sulfanyl]-3-(-3-pyridinyl)propanoic acid;
3-(3-pyridinyl)-3-[(2-{[3-(2-pyridinylamino)benzoyl]amino}phenyl)sulfanyl]propanoic acid;
3-(3-pyridinyl)-3-[(3-{[3-(2-pyridinylamino)benzoyl]amino}phenyl)sulfanyl]propanoic acid;
3-(3-pyridinyl)-3-[(4-{[3-(2-pyridinylamino)benzoyl]amino}phenyl)sulfanyl]propanoic acid;
3-({2-[(4-{[amino(imino)methyl]amino}benzoyl)amino]phenyl}sulfanyl)-3-(3-pyridinyl)propanoic acid;
3-({3-[(4-{[amino(imino)methyl]amino}benzoyl)amino]phenyl}sulfanyl)-3-(3-pyridinyl)propanoic acid;
3-({4-[(4-{[amino(imino)methyl]amino}benzoyl)amino]phenyl}sulfanyl)-3-(3-pyridinyl)propanoic acid;
3-({2-[(4-{[(benzylamino)(imino)methyl]amino}benzoyl)amino]phenyl}sulfanyl)-3-(3-pyridinyl)propanoic acid;
3-({3-[(4-{[(benzylamino)(imino)methyl]amino}benzoyl)amino]phenyl}sulfanyl)-3-(3-pyridinyl)propanoic acid;
3-({4-[(4-{[(benzylamino)(imino)methyl]amino}benzoyl)amino]phenyl}sulfanyl)-3-(3-pyridinyl)propanoic acid;
3-{[2-({4-[(aminocarbonyl)amino]benzoyl}amino)phenyl]sulfanyl}-3-(3-pyridinyl)propanoic acid;
3-{[3-({4-[(aminocarbonyl)amino]benzoyl}amino)phenyl]sulfanyl}-3-(3-pyridinyl)propanoic acid;
3-{[4-({4-[(aminocarbonyl)amino]benzoyl}amino)phenyl]sulfanyl}-3-(3-pyridinyl)propanoic acid;
3-({2-[(4-{[(benzylamino)carbonyl]amino}benzoyl)amino]phenyl}sulfanyl)-3-(3-pyridinyl)propanoic acid;
3-({3-[(4-{[(benzylamino)carbonyl]amino}benzoyl)amino]phenyl}sulfanyl)-3-(3-pyridinyl)propanoic acid;
3-({4-[(4-{[(benzylamino)carbonyl]amino}benzoyl)amino]phenyl}sulfanyl)-3-(3-pyridinyl)propanoic acid;
3-[(2-{[4-(4,5-dihydro-1H-imidazol-2-ylamino)benzoyl]amino}phenyl)sulfanyl]-3-(3-pyridinyl)propanoic acid;
3-[(3-{[4-(4,5-dihydro-1H-imidazol-2-ylamino)benzoyl]amino}phenyl)sulfanyl]-3-(3-pyridinyl)propanoic acid;
3-[(4-{[4-(4,5-dihydro-1H-imidazol-2-ylamino)benzoyl]amino}phenyl)sulfanyl]-3-(3-pyridinyl)propanoic acid;
3-[(2-{[4-(1H-imidazol-2-ylamino)benzoyl]amino}phenyl)sulfanyl]-3-(-3-pyridinyl)propanoic acid;
3-[(3-{[4-(1H-imidazol-2-ylamino)benzoyl]amino}phenyl)sulfanyl]-3-(-3-pyridinyl)propanoic acid;
3-[(4-{[4-(1H-imidazol-2-ylamino)benzoyl]amino}phenyl)sulfanyl]-3-(-3-pyridinyl)propanoic acid;
3-(3-pyridinyl)-3-[(2-{[4-(2-pyridinylamino)benzoyl]amino}phenyl)sulfanyl]propanoic acid;
3-(3-pyridinyl)-3-[(3-{[4-(2-pyridinylamino)benzoyl]amino}phenyl)sulfanyl]propanoic acid;
3-(3-pyridinyl)-3-[(4-{[4-(2-pyridinylamino)benzoyl]amino}phenyl)sulfanyl]propanoic acid;
3-({3-[(3-{[amino(imino)methyl]amino}benzoyl)amino]phenyl}sulfanyl)-3-phenylpropanoic acid;
3-({2-[(3-{[amino(imino)methyl]amino}benzoyl)amino]phenyl}sulfanyl)-3-phenylpropanoic acid;
3-({4-[(3-{[amino(imino)methyl]amino}benzoyl)amino]phenyl}sulfanyl)-3-phenylpropanoic acid;
3-({2-[(3-{[(benzylamino)(imino)methyl]amino}benzoyl)amino]phenyl}sulfanyl)-3-phenylpropanoic acid;
3-({3-[(3-{[(benzylamino)(imino)methyl]amino}benzoyl)amino]phenyl}sulfanyl)-3-phenylpropanoic acid;
3-({4-[(3-{[(benzylamino)(imino)methyl]amino}benzoyl)amino]phenyl}sulfanyl)-3-phenylpropanoic acid;
3-{[2-({3-[(aminocarbonyl)amino]benzoyl}amino)phenyl]sulfanyl}-3-phenylpropanoic acid;
3-{[3-({3-[(aminocarbonyl)amino]benzoyl}amino)phenyl]sulfanyl}-3-phenylpropanoic acid;
3-{[4-({3-[(aminocarbonyl)amino]benzoyl}amino)phenyl]sulfanyl}-3-phenylpropanoic acid;
3-({2-[(3-{[(benzylamino)carbonyl]amino}benzoyl)amino]phenyl}sulfanyl)-3-phenylpropanoic acid;
3-({3-[(3-{[(benzylamino)carbonyl]amino}benzoyl)amino]phenyl}sulfanyl)-3-phenylpropanoic acid;

3-({4-[(3-{[(benzylamino)carbonyl]amino}benzoyl)amino]phenyl}sulfanyl)-3-phenylpropanoic acid;
3-[(2-{[3-(4,5-dihydro-1H-imidazol-2-ylamino)benzoyl]amino}phenyl)sulfanyl]-3-phenylpropanoic acid;
3-[(3-{[3-(4,5-dihydro-1H-imidazol-2-ylamino)benzoyl]amino}phenyl)sulfanyl]-3-phenylpropanoic acid;
3-[(4-{[3-(4,5-dihydro-1H-imidazol-2-ylamino)benzoyl]amino}phenyl)sulfanyl]-3-phenylpropanoic acid;
3-[(2-{[3-(1H-imidazol-2-ylamino)benzoyl]amino}phenyl)sulfanyl]-3-phenylpropanoic acid;
3-[(3-{[3-(1H-imidazol-2-ylamino)benzoyl]amino}phenyl)sulfanyl]-3-phenylpropanoic acid;
3-[(4-{[3-(1H-imidazol-2-ylamino)benzoyl]amino}phenyl)sulfanyl]-3-phenylpropanoic acid;
3-phenyl-3-[(2-{[3-(2-pyridinylamino)benzoyl]amino}phenyl)sulfanyl]-propanoic acid;
3-phenyl-3-[(3-{[3-(2-pyridinylamino)benzoyl]amino}phenyl)sulfanyl]-propanoic acid;
3-phenyl-3-[(4-{[3-(2-pyridinylamino)benzoyl]amino}phenyl)sulfanyl]-propanoic acid;
3-({2-[(4-{[amino(imino)methyl]amino}benzoyl)amino]phenyl}sulfanyl)-3-phenylpropanoic acid;
3-({3-[(4-{[amino(imino)methyl]amino}benzoyl)amino]phenyl}sulfanyl)-3-phenylpropanoic acid;
3-({4-[(4-{[amino(imino)methyl]amino}benzoyl)amino]phenyl}sulfanyl)-3-phenylpropanoic acid;
3-({2-[(4-{[(benzylamino)(imino)methyl]amino}benzoyl)amino]phenyl}sulfanyl)-3-phenylpropanoic acid;
3-({3-[(4-{[(benzylamino)(imino)methyl]amino}benzoyl)amino]phenyl}sulfanyl)-3-phenylpropanoic acid;
3-({4-[(4-{[(benzylamino)(imino)methyl]amino}benzoyl)amino]phenyl}sulfanyl)-3-phenylpropanoic acid;
3-{[2-({4-[(aminocarbonyl)amino]benzoyl}amino)phenyl]sulfanyl}-3-phenylpropanoic acid;
3-{[3-({4-[(aminocarbonyl)amino]benzoyl}amino)phenyl]sulfanyl}-3-phenylpropanoic acid;
3-{[4-({4-[(aminocarbonyl)amino]benzoyl}amino)phenyl]sulfanyl}-3-phenylpropanoic acid;
3-({2-[(4-{[(benzylamino)carbonyl]amino}benzoyl)amino]phenyl}sulfanyl)-3-phenylpropanoic acid;
3-({3-[(4-{[(benzylamino)carbonyl]amino}benzoyl)amino]phenyl}sulfanyl)-3-phenylpropanoic acid;
3-({4-[(4-{[(benzylamino)carbonyl]amino}benzoyl)amino]phenyl}sulfanyl)-3-phenylpropanoic acid;
3-[(2-{[4-(4,5-dihydro-1H-imidazol-2-ylamino)benzoyl]amino}phenyl)sulfanyl]-3-phenylpropanoic acid;
3-[(3-{[4-(4,5-dihydro-1H-imidazol-2-ylamino)benzoyl]amino}phenyl)sulfanyl]-3-phenylpropanoic acid;
3-[(4-{[4-(4,5-dihydro-1H-imidazol-2-ylamino)benzoyl]amino}phenyl)sulfanyl]-3-phenylpropanoic acid;
3-[(2-{[4-(1H-imidazol-2-ylamino)benzoyl]amino}phenyl)sulfanyl]-3-phenylpropanoic acid;
3-[(3-{[4-(1H-imidazol-2-ylamino)benzoyl]amino}phenyl)sulfanyl]-3-phenylpropanoic acid;
3-[(4-{[4-(1H-imidazol-2-ylamino)benzoyl]amino}phenyl)sulfanyl]-3-phenylpropanoic acid;
3-phenyl-3-[(2-{[4-(2-pyridinylamino)benzoyl]amino}phenyl)sulfanyl]-propanoic acid;
3-phenyl-3-[(3-{[4-(2-pyridinylamino)benzoyl]amino}phenyl)sulfanyl]-propanoic acid;
3-phenyl-3-[(4-{[4-(2-pyridinylamino)benzoyl]amino}phenyl)sulfanyl]-propanoic acid;
3-{2-[(4-{[amino(imino)methyl]amino}benzoyl)amino]phenoxy}-3-(3-pyridinyl)propanoic acid;
3-{3-[(4-{[amino(imino)methyl]amino}benzoyl)amino]phenoxy}-3-(3-pyridinyl)propanoic acid;
3-{4-[(4-{[amino(imino)methyl]amino}benzoyl)amino]phenoxy}-3-(3-pyridinyl)propanoic acid;
3-{2-[(4-{[(benzylamino)(imino)methyl]amino}benzoyl)amino]phenoxy}-3-(3-pyridinyl)propanoic acid;
3-{3-[(4-{[(benzylamino)(imino)methyl]amino}benzoyl)amino]phenoxy}-3-(3-pyridinyl)propanoic acid;
3-{4-[(4-{[(benzylamino)(imino)methyl]amino}benzoyl)amino]phenoxy}-3-(3-pyridinyl)propanoic acid;
3-[2-({4-[(aminocarbonyl)amino]benzoyl}amino)phenoxy]-3-(3-pyridinyl)propanoic acid;
3-[3-({4-[(aminocarbonyl)amino]benzoyl}amino)phenoxy]-3-(3-pyridinyl)propanoic acid;
3-[4-({4-[(aminocarbonyl)amino]benzoyl}amino)phenoxy]-3-(3-pyridinyl)propanoic acid;
3-{2-[(4-{[(benzylamino)carbonyl]amino}benzoyl)amino]phenoxy}-3-(3-pyridinyl)propanoic acid;
3-{3-[(4-{[(benzylamino)carbonyl]amino}benzoyl)amino]phenoxy}-3-(3-pyridinyl)propanoic acid;
3-{4-[(4-{[(benzylamino)carbonyl]amino}benzoyl)amino]phenoxy}-3-(3-pyridinyl)propanoic acid;
3-(2-{[4-(4,5-dihydro-1H-imidazol-2-ylamino)benzoyl]amino}phenoxy)-3-(3-pyridinyl)propanoic acid;
3-(3-{[4-(4,5-dihydro-1H-imidazol-2-ylamino)benzoyl]amino}phenoxy)-3-(3-pyridinyl)propanoic acid;
3-(4-{[4-(4,5-dihydro-1H-imidazol-2-ylamino)benzoyl]amino}phenoxy)-3-(3-pyridinyl)propanoic acid;
3-(2-{[4-(1H-imidazol-2-ylamino)benzoyl]-amino}phenoxy)-3-(3-pyridinyl)propanoic acid;
3-(3-{[4-(1H-imidazol-2-ylamino)benzoyl]amino}phenoxy)-3-(3-pyridinyl)propanoic acid;
3-(4-{[4-(1H-imidazol-2-ylamino)benzoyl]amino}phenoxy)-3-(3-pyridinyl)propanoic acid;
3-(3-pyridinyl)-3-(2-{[4-(2-pyridinylamino)benzoyl]amino}phenoxy)propanoic acid;
3-(3-pyridinyl)-3-(3-{[4-(2-pyridinylamino)benzoyl]amino}phenoxy)propanoic acid;
3-(3-pyridinyl)-3-(4-{[4-(2-pyridinylamino)benzoyl]amino}phenoxy)propanoic acid;
3-{2-[(3-{[amino(imino)methyl]amino}benzoyl)amino]phenoxy}-3-(3-pyridinyl)propanoic acid;
3-{3-[(3-{[amino(imino)methyl]amino}benzoyl)amino]phenoxy}-3-(3-pyridinyl)propanoic acid;
3-{4-[(3-{[amino(imino)methyl]amino}benzoyl)amino]phenoxy}-3-(3-pyridinyl)propanoic acid;
3-{2-[(3-{[(benzylamino)(imino)methyl]amino}benzoyl)amino]phenoxy}-3-(3-pyridinyl)propanoic acid;
3-{3-[(3-{[(benzylamino)(imino)methyl]amino}benzoyl)amino]phenoxy}-3-(3-pyridinyl)propanoic acid;
3-{4-[(3-{[(benzylamino)(imino)methyl]amino}benzoyl)amino]phenoxy}-3-(3-pyridinyl)propanoic acid;
3-[2-({3-[(aminocarbonyl)amino]benzoyl}amino)phenoxy]-3-(3-pyridinyl)propanoic acid;
3-[3-({3-[(aminocarbonyl)amino]benzoyl}amino)phenoxy]-3-(3-pyridinyl)propanoic acid;
3-[4-({3-[(aminocarbonyl)amino]benzoyl}amino)phenoxy]-3-(3-pyridinyl)propanoic acid;
3-{2-[(3-{[(benzylamino)carbonyl]amino}benzoyl)amino]phenoxy}-3-(3-pyridinyl)propanoic acid;
3-{3-[(3-{[(benzylamino)carbonyl]amino}benzoyl)amino]phenoxy}-3-(3-pyridinyl)propanoic acid;
3-{4-[(3-{[(benzylamino)carbonyl]amino}benzoyl)amino]phenoxy}-3-(3-pyridinyl)propanoic acid;
3-(2-{[3-(4,5-dihydro-1H-imidazol-2-ylamino)benzoyl]amino}phenoxy)-3-(3-pyridinyl)propanoic acid;
3-(3-{[3-(4,5-dihydro-1H-imidazol-2-ylamino)benzoyl]amino}phenoxy)-3-(3-pyridinyl)propanoic acid;

3-(4-{[3-(4,5-dihydro-1H-imidazol-2-ylamino)benzoyl]amino}phenoxy)-3-(3-pyridinyl)propanoic acid;
3-(2-{[3-(1H-imidazol-2-ylamino)benzoyl]amino}phenoxy)-3-(3-pyridinyl)propanoic acid;
3-(3-{[3-(1H-imidazol-2-ylamino)benzoyl]amino}phenoxy)-3-(3-pyridinyl)propanoic acid;
3-(4-{[3-(1H-imidazol-2-ylamino)benzoyl]amino}phenoxy)-3-(3-pyridinyl)propanoic acid;
3-(3-pyridinyl)-3-(2-{[3-(2-pyridinylamino)benzoyl]amino}phenoxy)propanoic acid;
3-(3-pyridinyl)-3-(3-{[3-(2-pyridinylamino)benzoyl]amino}phenoxy)propanoic acid;
3-(3-pyridinyl)-3-(4-{[3-(2-pyridinylamino)benzoyl]amino}phenoxy)propanoic acid;
3-{2-[(3-{[amino(imino)methyl]amino}benzoyl)amino]phenoxy}-3-phenylpropanoic acid;
3-{3-[(3-{[amino(imino)methyl]amino}benzoyl)amino]phenoxy}-3-phenylpropanoic acid;
3-{4-[(3-{[amino(imino)methyl]amino}benzoyl)amino]phenoxy}-3-phenylpropanoic acid;
3-{2-[(3-{[(benzylamino)(imino)methyl]amino}benzoyl)amino]phenoxy}-3-phenylpropanoic acid;
3-{3-[(3-{[(benzylamino)(imino)methyl]amino}benzoyl)amino]phenoxy}-3-phenylpropanoic acid;
3-{4-[(3-{[(benzylamino)(imino)methyl]amino}benzoyl)amino]phenoxy}-3-phenylpropanoic acid;
3-[2-({3-[(aminocarbonyl)amino]benzoyl}amino)phenoxy]-3-phenylpropanoic acid;
3-[3-({3-[(aminocarbonyl)amino]benzoyl}amino)phenoxy]-3-phenylpropanoic acid;
3-[4-({3-[(aminocarbonyl)amino]benzoyl}amino)phenoxy]-3-phenylpropanoic acid;
3-{2-[(3-{[(benzylamino)carbonyl]amino}benzoyl)amino]phenoxy}-3-phenylpropanoic acid;
3-{3-[(3-{[(benzylamino)carbonyl]amino}benzoyl)amino]phenoxy}-3-phenylpropanoic acid;
3-{4-[(3-{[(benzylamino)carbonyl]amino}benzoyl)amino]phenoxy}-3-phenylpropanoic acid;
3-(2-{[3-(4,5-dihydro-1H-imidazol-2-ylamino)benzoyl]amino}phenoxy)-3-phenylpropanoic acid;
3-(3-{[3-(4,5-dihydro-1H-imidazol-2-ylamino)benzoyl]amino}phenoxy)-3-phenylpropanoic acid;
3-(4-{[3-(4,5-dihydro-1H-imidazol-2-ylamino)benzoyl]amino}phenoxy)-3-phenylpropanoic acid;
3-(2-{[3-(1H-imidazol-2-ylamino)benzoyl]amino}phenoxy)-3-phenylpropanoic acid;
3-(3-{[3-(1H-imidazol-2-ylamino)benzoyl]amino}phenoxy)-3-phenylpropanoic acid;
3-(4-{[3-(1H-imidazol-2-ylamino)benzoyl]amino}phenoxy)-3-phenylpropanoic acid;
3-phenyl-3-(2-{[3-(2-pyridinylamino)benzoyl]amino}phenoxy)propanoic acid;
3-phenyl-3-(3-{[3-(2-pyridinylamino)benzoyl]amino}phenoxy)propanoic acid;
3-phenyl-3-(4-{[3-(2-pyridinylamino)benzoyl]amino}phenoxy)propanoic acid;
3-{2-[(4-{[amino(imino)methyl]amino}benzoyl)amino]phenoxy}-3-phenylpropanoic acid;
3-{3-[(4-{[amino(imino)methyl]amino}benzoyl)amino]phenoxy}-3-phenylpropanoic acid;
3-{4-[(4-{[amino(imino)methyl]amino}benzoyl)amino]phenoxy}-3-phenylpropanoic acid;
3-{2-[(4-{[(benzylamino)(imino)methyl]amino}benzoyl)amino]phenoxy}-3-phenylpropanoic acid;
3-{3-[(4-{[(benzylamino)(imino)methyl]amino}benzoyl)amino]phenoxy}-3-phenylpropanoic acid;
3-{4-[(4-{[(benzylamino)(imino)methyl]amino}benzoyl)amino]phenoxy}-3-phenylpropanoic acid;
3-[2-({4-[(aminocarbonyl)amino]benzoyl}amino)phenoxy]-3-phenylpropanoic acid;
3-[3-({4-[(aminocarbonyl)amino]benzoyl}amino)phenoxy]-3-phenylpropanoic acid;
3-[4-({4-[(aminocarbonyl)amino]benzoyl}amino)phenoxy]-3-phenylpropanoic acid;
3-{2-[(4-{[(benzylamino)carbonyl]amino}benzoyl)amino]phenoxy}-3-phenylpropanoic acid;
3-{3-[(4-{[(benzylamino)carbonyl]amino}benzoyl)amino]phenoxy}-3-phenylpropanoic acid;
3-{4-[(4-{[(benzylamino)carbonyl]amino}benzoyl)amino]phenoxy}-3-phenylpropanoic acid;
3-(2-{[4-(4,5-dihydro-1H-imidazol-2-ylamino)benzoyl]amino}phenoxy)-3-phenylpropanoic acid;
3-(3-{[4-(4,5-dihydro-1H-imidazol-2-ylamino)benzoyl]amino}phenoxy)-3-phenylpropanoic acid;
3-(4-{[4-(4,5-dihydro-1H-imidazol-2-ylamino)benzoyl]amino}phenoxy)-3-phenylpropanoic acid;
3-(2-{[4-(1H-imidazol-2-ylamino)benzoyl]amino}phenoxy)-3-phenylpropanoic acid;
3-(3-{[4-(1H-imidazol-2-ylamino)benzoyl]amino}phenoxy)-3 phenylpropanoic acid;
3-(4-{[4-(1H-imidazol-2-ylamino)benzoyl]amino}phenoxy)-3-phenylpropanoic acid;
3-phenyl-3-(2-{[4-(2-pyridinylamino)benzoyl]amino}phenoxy)propanoic acid;
3-phenyl-3-(3-{[4-(2-pyridinylamino)benzoyl]amino}phenoxy)propanoic acid;
3-phenyl-3-(4-{[4-(2-pyridinylamino)benzoyl]amino}phenoxy)propanoic acid;
3-({2-[(3-{[amino(imino)methyl]amino}benzoyl)amino]phenyl}sulfinyl)-3-(3-pyridinyl)propanoic acid;
3-({3-[(3-{[amino(imino)methyl]amino}benzoyl)amino]phenyl}sulfinyl)-3-(3-pyridinyl)propanoic acid;
3-({4-[(3-{[amino(imino)methyl]amino}benzoyl)amino]phenyl}sulfinyl)-3-(3-pyridinyl)propanoic acid;
3-({2-[(3-{[(benzylamino)(imino)methyl]amino}benzoyl)amino]phenyl}sulfinyl)-3-(3-pyridinyl)propanoic acid;
3-({3-[(3-{[(benzylamino)(imino)methyl]amino}benzoyl)amino]phenyl}sulfinyl)-3-(3-pyridinyl)propanoic acid;
3-({4-[(3-{[(benzylamino)(imino)methyl]amino}benzoyl)amino]phenyl}sulfinyl)-3-(3-pyridinyl)propanoic acid;
3-{[2-({3-[(aminocarbonyl)amino]benzoyl}amino)phenyl]sulfinyl}-3-(3-pyridinyl)propanoic acid;
3-{[3-({3-[(aminocarbonyl)amino]benzoyl}amino)phenyl]sulfinyl}-3-(3-pyridinyl)propanoic acid;
3-{[4-({3-[(aminocarbonyl)amino]benzoyl}amino)phenyl]sulfinyl}-3-(3-pyridinyl)propanoic acid;
3-({2-[(3-{[(benzylamino)carbonyl]amino}benzoyl)amino]phenyl}sulfinyl)-3-(3-pyridinyl)propanoic acid;
3-({3-[(3-{[(benzylamino)carbonyl]amino}benzoyl)amino]phenyl}sulfinyl)-3-(3-pyridinyl)propanoic acid;
3-({4-[(3-{[(benzylamino)carbonyl]amino}benzoyl)amino]phenyl}sulfinyl)-3-(3-pyridinyl)propanoic acid;
3-[(2-{[3-(4,5-dihydro-1H-imidazol-2-ylamino)benzoyl]amino}phenyl)sulfinyl]-1-3-pyridinyl)propanoic acid;
3-[(3-{[3-(4,5-dihydro-1H-imidazol-2-ylamino)benzoyl]amino}phenyl)sulfinyl]-3-(3-pyridinyl)propanoic acid;
3-(4-{[3-(4,5-dihydro-1H-imidazol-2-ylamino)benzoyl]amino}phenyl)sulfinyl]-3-(3-pyridinyl)propanoic acid;
3-[(2-{[3-(1H-imidazol-2-ylamino)benzoyl]amino}phenyl)sulfinyl]-3-(-3-pyridinyl)propanoic acid;
3-[(3-{[3-(1H-imidazol-2-ylamino)benzoyl]amino}phenyl)sulfinyl]-3-(-3-pyridinyl)propanoic acid;

3-[(4-{[3-(1H-imidazol-2-ylamino)benzoyl]amino}phenyl)
sulfinyl]-3-(-3-pyridinyl)propanoic acid;
3-(3-pyridinyl)-3-[(2-{[3-(2-pyridinylamino)benzoyl]
amino}phenyl)sulfinyl]propanoic acid;
3-(3-pyridinyl)-3-[(3-{[3-(2-pyridinylamino)benzoyl]
amino}phenyl)sulfinyl]propanoic acid;
3-(3-pyridinyl)-3-[(4-{[3-(2-pyridinylamino)benzoyl]
amino}phenyl)sulfinyl]propanoic acid;
3-({2-[(4-{[amino(imino)methyl]amino}benzoyl)amino]
phenyl}sulfinyl)-3-(3-pyridinyl)propanoic acid;
3-({3-[(4-{[amino(imino)methyl]amino}benzoyl)amino]
phenyl}sulfinyl)-3-(3-pyridinyl)propanoic acid;
3-({4-[(4-{[amino(imino)methyl]amino}benzoyl)amino]
phenyl}sulfinyl)-3-(3-pyridinyl)propanoic acid;
3-({2-[(4-{[(benzylamino)(imino)methyl]amino}benzoyl)
amino]phenyl}sulfinyl)-3-(3-pyridinyl)propanoic acid;
3-({3-[(4-{[(benzylamino)(imino)methyl]amino}benzoyl)
amino]phenyl}sulfinyl)-3-(3-pyridinyl)propanoic acid;
3-({4-[(4-{[(benzylamino)(imino)methyl]amino}benzoyl)
amino]phenyl}sulfinyl)-3-(3-pyridinyl)propanoic acid;
3-{[2-({4-[(aminocarbonyl)amino]benzoyl}amino)phenyl]
sulfinyl}-3-(3-pyridinyl)propanoic acid;
3-{[3-({4-[(aminocarbonyl)amino]benzoyl}amino)phenyl]
sulfinyl}-3-(3-pyridinyl)propanoic acid;
3-{[4-({4-[(aminocarbonyl)amino]benzoyl}amino)phenyl]
sulfinyl}-3-(3-pyridinyl)propanoic acid;
3-({2-[(4-{[(benzylamino)carbonyl]amino}benzoyl)amino]
phenyl}sulfinyl)-3-(3-pyridinyl)propanoic acid;
3-({3-[(4-{[(benzylamino)carbonyl]amino}benzoyl)amino]
phenyl}sulfinyl)-3-(3-pyridinyl)propanoic acid;
3-({4-[(4-{[(benzylamino)carbonyl]amino}benzoyl)amino]
phenyl}sulfinyl)-3-(3-pyridinyl)propanoic acid:
3-[(2-{[4-(4,5-dihydro-1H-imidazol-2-ylamino)benzoyl]
amino}phenyl)sulfinyl]-3-(3-pyridinyl)propanoic acid;
3-[(3-{[4-(4,5-dihydro-1H-imidazol-2-ylamino)benzoyl]
amino}phenyl)sulfinyl]-3-(3-pyridinyl)propanoic acid;
3-[(4-{[4-(4,5-dihydro-1H-imidazol-2-ylamino)benzoyl]
amino}phenyl)sulfinyl]-3-(3-pyridinyl)propanoic acid;
3-[(2-{[4-(1H-imidazol-2-ylamino)benzoyl]amino}phenyl)
sulfinyl]-3-(-3-pyridinyl)propanoic acid;
3-[(3-{[4-(1H-imidazol-2-ylamino)benzoyl]amino}phenyl)
sulfinyl]-3-(-3-pyridinyl)propanoic acid;
3-[(4-{[4-(1H-imidazol-2-ylamino)benzoyl]amino)
phenyl}sulfinyl]-3-(-3-pyridinyl)propanoic acid;
3-(3-pyridinyl)-3-[(2-{[4-(2-pyridinylamino)benzoyl]
amino}phenyl)sulfinyl]propanoic acid;
3-(3-pyridinyl)-3-[(3-{[4-(2-pyridinylamino)benzoyl]
amino}phenyl)sulfinyl]propanoic acid;
3-(3-pyridinyl)-3-[(4-{[4-(2-pyridinylamino)benzoyl]
amino}phenyl)sulfinyl]propanoic acid;
3-({2-[(3-{[amino(imino)methyl]amino}benzoyl)amino]
phenyl}sulfonyl)-3-(3-pyridinyl)propanoic acid;
3-({3-[(3-{[amino(imino)methyl]amino}benzoyl)amino]
phenyl}sulfonyl)-3-(3-pyridinyl)propanoic acid;
3-({4-[(3-{[amino(imino)methyl]amino}benzoyl)amino]
phenyl}sulfonyl)-3-(3-pyridinyl)propanoic acid;
3-({2-[(3-{[(benzylamino)(imino)methyl]amino}benzoyl)
amino]phenyl}sulfonyl)-3-(3-pyridinyl)propanoic acid;
3-({3-[(3-{[(benzylamino)(imino)methyl]amino}benzoyl)
amino]phenyl}sulfonyl)-3-(3-pyridinyl)propanoic acid;
3-({4-[(3-{[(benzylamino)(imino)methyl]amino}benzoyl)
amino]phenyl}sulfonyl)-3-(3-pyridinyl)propanoic acid;
3-{[2-({3-[(aminocarbonyl)amino]benzoyl}amino)phenyl]
sulfonyl}-3-(3-pyridinyl)propanoic acid;
3-{[3-({3-[(aminocarbonyl)amino]benzoyl}amino)phenyl]
sulfonyl}-3-(3-pyridinyl)propanoic acid;
3-{[4-({3-[(aminocarbonyl)amino]benzoyl}amino)phenyl]
sulfonyl}-3-(3-pyridinyl)propanoic acid;
3-({2-[(3-{[(benzylamino)carbonyl]amino}benzoyl)amino]
phenyl}sulfonyl)-3-(3-pyridinyl)propanoic acid;
3-({3-[(3-{[(benzylamino)carbonyl]amino}benzoyl)amino]
phenyl}sulfonyl)-3-(3-pyridinyl)propanoic acid;
3-({4-[(3-{[(benzylamino)carbonyl]amino}benzoyl)amino]
phenyl}sulfonyl)-3-(3-pyridinyl)propanoic acid;
3-[(2-{[3-(4,5-dihydro-1H-imidazol-2-ylamino)benzoyl]
amino}phenyl)sulfonyl]-3-(3-pyridinyl)propanoic acid;
[{[3-(4,5-dihydro-1H-imidazol-2-ylamino)benzoyl]
amino}phenyl)sulfonyl]-3-(3-pyridinyl)propanoic acid;
3-[(4-{[3-(4,5-dihydro-1H-imidazol-2-ylamino)benzoyl]
amino}phenyl)sulfonyl]-3-(3-pyridinyl)propanoic acid;
3-[(2-{[3-(1H-imidazol-2-ylamino)benzoyl]amino}phenyl)
sulfonyl]-3-(-3-pyridinyl)propanoic acid;
3-[(3-{[3-(1H-imidazol-2-ylamino)benzoyl]amino}phenyl)
sulfonyl]-3-(-3-pyridinyl)propanoic acid;
3-[(4-{[3-(1H-imidazol-2-ylamino)benzoyl]amino}phenyl)
sulfonyl]-3-(-3-pyridinyl)propanoic acid;
3-(3-pyridinyl)-3-[(2-{[3-(2-pyridinylamino)benzoyl]
amino}phenyl)sulfonyl]propanoic acid;
3-(3-pyridinyl)-3-[(3-{[3-(2-pyridinylamino)benzoyl]
amino}phenyl)sulfonyl]propanoic acid;
3-(3-pyridinyl)-3-[(4-{[3-(2-pyridinylamino)benzoyl]
amino}phenyl)sulfonyl]propanoic acid;
3-({2-[(4-{[amino(imino)methyl]amino}benzoyl)amino]
phenyl}sulfonyl)-3-(3-pyridinyl)propanoic acid;
3-({3-[(4-{[amino(imino)methyl]amino}benzoyl)amino]
phenyl}sulfonyl)-3-(3-pyridinyl)propanoic acid;
3-({4-[(4-{[amino(imino)methyl]amino}benzoyl)amino]
phenyl}sulfonyl)-3-(3-pyridinyl)propanoic acid;
3-({2-[(4-{[(benzylamino)(imino)methyl]amino}benzoyl)
amino]phenyl}sulfonyl)-3-(3-pyridinyl)propanoic acid;
3-({3-[(4-{[(benzylamino)(imino)methyl]amino}benzoyl)
amino]phenyl}sulfonyl)-3-(3-pyridinyl)propanoic acid;
3-({4-[(4-{[(benzylamino)(imino)methyl]amino}benzoyl)
amino]phenyl}sulfonyl)-3-(3-pyridinyl)propanoic acid;
3-{[2-({4-[(aminocarbonyl)amino]benzoyl}amino)phenyl]
sulfonyl}-3-(3-pyridinyl)propanoic acid;
3-{[3-({4-[(aminocarbonyl)amino]benzoyl}amino)phenyl]
sulfonyl}-3-(3-pyridinyl)propanoic acid;
3-{[4-({4-[(aminocarbonyl)amino]benzoyl}amino)phenyl]
sulfonyl}-3-(3-pyridinyl)propanoic acid;
3-({2-[(4-{[(benzylamino)carbonyl]amino}benzoyl)amino]
phenyl}sulfonyl)-3-(3-pyridinyl)propanoic acid;
3-({3-[(4-{[(benzylamino)carbonyl]amino}benzoyl)amino]
phenyl}sulfonyl)-3-(3-pyridinyl)propanoic acid;
3-({4-[(4-{[(benzylamino)carbonyl]amino}benzoyl)amino]
phenyl}sulfonyl)-3-(3-pyridinyl)propanoic acid;
3-[(2-{[4-(4,5-dihydro-1H-imidazol-2-ylamino)benzoyl]
amino}phenyl)sulfonyl]-3-(3-pyridinyl)propanoic acid;
3-[(3-{[4-(4,5-dihydro-1H-imidazol-2-ylamino)benzoyl]
amino}phenyl)sulfonyl]-3-(3-pyridinyl)propanoic acid;
3-[(4-{[4-(4,5-dihydro-1H-imidazol-2-ylamino)benzoyl]
amino}phenyl)sulfonyl]-3-(3-pyridinyl)propanoic acid;
3-[(2-{[4-(1H-imidazol-2-ylamino)benzoyl]amino}phenyl)
sulfonyl]-3-(-3-pyridinyl)propanoic acid;
3-[(3-{[4-(1H-imidazol-2-ylamino)benzoyl]amino}phenyl)
sulfonyl]-3-(-3-pyridinyl)propanoic acid;
3-[(4-{[4-(1H-imidazol-2-ylamino)benzoyl]amino}phenyl)
sulfonyl]-3-(-3-pyridinyl)propanoic acid;
3-(3-pyridinyl)-3-[(2-{[4-(2-pyridinylamino)benzoyl]
amino}phenyl)sulfonyl]propanoic acid;
3-(3-pyridinyl)-3-[(3-{[4-(2-pyridinylamino)benzoyl]
amino}phenyl)sulfonyl]propanoic acid;

3-(3-pyridinyl)-3-[(4-{[4-(2-pyridinylamino)benzoyl] amino}phenyl)sulfonyl]propanoic acid;
3-({3-[(3-{[amino(imino)methyl]amino}benzoyl)amino] phenyl}sulfinyl)-3-phenylpropanoic acid;
3-({2-[(3-{[amino(imino)methyl]amino}benzoyl)amino] phenyl}sulfinyl)-3-phenylpropanoic acid;
3-({4-[(3-{[amino(imino)methyl]amino}benzoyl)amino] phenyl}sulfinyl)-1-3-phenylpropanoic acid;
3-({2-[(3-{[(benzylamino)(imino)methyl]amino}benzoyl) amino]phenyl}sulfinyl)-3-phenylpropanoic acid;
3-({3-[(3-{[(benzylamino)(imino)methyl]amino}benzoyl) amino]phenyl}sulfinyl)-3-phenylpropanoic acid;
3-({4-[(3-{[(benzylamino)(imino)methyl]amino}benzoyl) amino]phenyl}sulfinyl)-3-phenylpropanoic acid;
3-{[2-({3-[(aminocarbonyl)amino]benzoyl}amino)phenyl] sulfinyl}-3-phenylpropanoic acid;
3-{[3-({3-[(aminocarbonyl)amino]benzoyl}amino)phenyl] sulfinyl}-3-phenylpropanoic acid;
3-{[4-({3-[(aminocarbonyl)amino]benzoyl}amino)phenyl] sulfinyl}-3-phenylpropanoic acid;
3-({2-[(3-{[(benzylamino)carbonyl]amino}benzoyl)amino] phenyl}sulfinyl)-3-phenylpropanoic acid;
3-({3-[(3-{[(benzylamino)carbonyl]amino}benzoyl)amino] phenyl}sulfinyl)-3-phenylpropanoic acid;
3-({4-[(3-{[(benzylamino)carbonyl]amino}benzoyl)amino] phenyl}sulfinyl)-3-phenylpropanoic acid;
3-[(2-{[3-(4,5-dihydro-1H-imidazol-2-ylamino)benzoyl] amino}phenyl)sulfinyl]-3-phenylpropanoic acid;
3-[(3-{[3-(4,5-dihydro-1H-imidazol-2-ylamino)benzoyl] amino}phenyl)sulfinyl]-3-phenylpropanoic acid;
3-[(4-{[3-(4,5-dihydro-1H-imidazol-2-ylamino)benzoyl] amino}phenyl)sulfinyl]-3-phenylpropanoic acid;
3-[(2-{[3-(1H-imidazol-2-ylamino)benzoyl]amino}phenyl) sulfinyl]-3-phenylpropanoic acid;
3-[(3-{[3-(1H-imidazol-2-ylamino)benzoyl]amino}phenyl) sulfinyl]-3-phenylpropanoic acid;
3-[(4-{[3-(1H-imidazol-2-ylamino)benzoyl]amino}phenyl) sulfinyl]-3-phenylpropanoic acid;
3-phenyl-3-[(2-{[3-(2-pyridinylamino)benzoyl] amino}phenyl)sulfinyl]-propanoic acid;
3-phenyl-3-[(3-{[3-(2-pyridinylamino)benzoyl] amino}phenyl)sufinyl]-propanoic acid;
3-phenyl-3-[(4-{[3-(2-pyridinylamino)benzoyl] amino}phenyl)sulfinyl]-propanoic acid;
3-({2-[(4-{[amino(imino)methyl]amino}benzoyl)amino] phenyl}sulfinyl)-3-phenylpropanoic acid;
3-({3-[(4-{[amino(imino)methyl]amino}benzoyl)amino] phenyl}sulfinyl)-3-phenylpropanoic acid;
3-({4-[(4-{[amino(imino)methyl]amino}benzoyl)amino] phenyl}sulfinyl)-3-phenylpropanoic acid;
3-({2-[(4-{[(benzylamino)(imino)methyl]amino}benzoyl) amino]phenyl}sulfinyl)-3-phenylpropanoic acid;
3-({3-[(4-{[(benzylamino)(imino)methyl]amino}benzoyl) amino]phenyl}sulfinyl)-3-phenylpropanoic acid;
3-({4-[(4-{[(benzylamino)(imino)methyl]amino}benzoyl) amino]phenyl}sulfinyl)-3-phenylpropanoic acid;
3-{[2-({4-[(aminocarbonyl)amino]benzoyl}amino)phenyl] sulfinyl}-3-phenylpropanoic acid;
3-{[3-({4-[(aminocarbonyl)amino]benzoyl}amino)phenyl] sulfinyl}-3-phenylpropanoic acid;
3-{[4-({4-[(aminocarbonyl)amino]benzoyl}amino)phenyl] sulfinyl}-3-phenylpropanoic acid;
3-({2-[(4-{[(benzylamino)carbonyl]amino}benzoyl)amino] phenyl}sulfinyl)-3-phenylpropanoic acid;
3-({3-[(4-{[(benzylamino)carbonyl]amino}benzoyl)amino] phenyl}sulfinyl)-3-phenylpropanoic acid;
3-({4-[(4-{[(benzylamino)carbonyl]amino}benzoyl)amino] phenyl}sulfinyl)-3-phenylpropanoic acid;
3-[(2-{[4-(4,5-dihydro-1H-imidazol-2-ylamino)benzoyl] amino}phenyl)sulfinyl]-3-phenylpropanoic acid;
3-[(3-{[4-(4,5-dihydro-1H-imidazol-2-ylamino)benzoyl] amino}phenyl)sulfinyl]-3-phenylpropanoic acid;
3-(4-{[4-(4,5-dihydro-1H-imidazol-2-ylamino)benzoyl] amino}phenyl)sulfinyl]-3-phenylpropanoic acid;
3-[(2-{[4-(1H-imidazol-2-ylamino)benzoyl]amino}phenyl) sulfinyl]-3-phenylpropanoic acid;
3-(3-{[4-(1H-imidazol-2-ylamino)benzoyl]amino}phenyl) sufinyl]-3-phenylpropanoic acid;
3-(4-{[4-(1H-imidazol-2-ylamino)benzoyl]amino}phenyl) sulfinyl]-3-phenylpropanoic acid;
3-phenyl-3-[(2-{[4-(2-pyridinylamino)benzoyl] amino}phenyl)sulfinyl]-propanoic acid;
3-phenyl-3-[(3-{[4-(2-pyridinylamino)benzoyl] amino}phenyl)sulfinyl]-propanoic acid;
3-phenyl-3-[(4-{[4-(2-pyridinylamino)benzoyl] amino}phenyl)sulfinyl]-propanoic acid;
3-({3-[(3-{[amino(imino)methyl]amino}benzoyl)amino] phenyl}sulfonyl)-3-phenylpropanoic acid;
3-({2-[(3-{[amino(imino)methyl]amino}benzoyl)amino] phenyl}sulfonyl)-3-phenylpropanoic acid;
3-({4-[(3-{[amino(imino)methyl]amino}benzoyl)amino] phenyl}sulfonyl)-3-phenylpropanoic acid;
3-({2-[(3-{[(benzylamino)(imino)methyl]amino}benzoyl) amino]phenyl}sulfonyl)-3-phenylpropanoic acid;
3-({3-[(3-{[(benzylamino)(imino)methyl]amino}benzoyl) amino]phenyl}sulfonyl)-3-phenylpropanoic acid;
3-({4-[(3-{[(benzylamino)(imino)methyl]amino}benzoyl) amino]phenyl}sulfonyl)-3-phenylpropanoic acid;
3-{[2-({3-[(aminocarbonyl)amino]benzoyl}amino)phenyl] sulfonyl}-3-phenylpropanoic acid;
3-{[3-({3-[(aminocarbonyl)amino]benzoyl}amino)phenyl] sulfonyl}-3-phenylpropanoic acid;
3-{[4-({3-[(aminocarbonyl)amino]benzoyl}amino)phenyl] sulfonyl}-3-phenylpropanoic acid;
3-({2-[(3-{[(benzylamino)carbonyl]amino}benzoyl)amino] phenyl}sulfonyl)-3-phenylpropanoic acid;
3-({3-[(3-{[(benzylamino)carbonyl]amino}benzoyl)amino] phenyl}sulfonyl)-3-phenylpropanoic acid;
3-({4-[(3-{[(benzylamino)carbonyl]amino}benzoyl)amino] phenyl}sulfonyl)-3-phenylpropanoic acid;
3-[(2-{[3-(4,5-dihydro-1H-imidazol-2-ylamino)benzoyl] amino}phenyl)sulfonyl]-3-phenylpropanoic acid;
3-[(3-{[3-(4,5-dihydro-1H-imidazol-2-ylamino)benzoyl] amino}phenyl)sulfonyl]-3-phenylpropanoic acid;
3-[(4-{[3-(4,5-dihydro-1H-imidazol-2-ylamino)benzoyl] amino}phenyl)sulfonyl]-3-phenylpropanoic acid;
3-[(2-{[3-(1H-imidazol-2-ylamino)benzoyl]amino}phenyl) sulfonyl]-3-phenylpropanoic acid;
3-[(3-{[3-(1H-imidazol-2-ylamino)benzoyl]amino}phenyl) sulfonyl]-3-phenylpropanoic acid;
3-[(4-{[3-(1H-imidazol-2-ylamino)benzoyl]amino}phenyl) sulfonyl]-3-phenylpropanoic acid;
3-phenyl-3-[(2-{[3-(2-pyridinylamino)benzoyl] amino}phenyl)sulfonyl]-propanoic acid;
3-phenyl-3-[(3-{[3-(2-pyridinylamino)benzoyl] amino}phenyl)sulfonyl]-propanoic acid;
3-phenyl-3-[(4-{[3-(2-pyridinylamino)benzoyl] amino}phenyl)sulfonyl]-propanoic acid;
3-({2-[(4-{[amino(imino)methyl]amino}benzoyl)amino] phenyl}sulfonyl)-3-phenylpropanoic acid;
3-({3-[(4-{[amino(imino)methyl]amino}benzoyl)amino] phenyl}sulfonyl)-3-phenylpropanoic acid;

3-({4-[(4-{[amino(imino)methyl]amino}benzoyl)amino]phenyl}sulfonyl)-3-phenylpropanoic acid;
3-({2-[(4-{[(benzylamino)(imino)methyl]amino}benzoyl)amino]phenyl}sulfonyl)-3-phenylpropanoic acid;
3-({3-[(4-{[(benzylamino)(imino)methyl]amino}benzoyl)amino]phenyl}sulfonyl)-3-phenylpropanoic acid;
3-({4-[(4-{[(benzylamino)(imino)methyl]amino}benzoyl)amino]phenyl}sulfonyl)-3-phenylpropanoic acid;
3-{[2-({4-[(aminocarbonyl)amino]benzoyl}amino)phenyl]sulfonyl}-3-phenylpropanoic acid;
3-{[3-({4-[(aminocarbonyl)amino]benzoyl}amino)phenyl]sulfonyl}-3-phenylpropanoic acid;
3-{[4-({4-[(aminocarbonyl)amino]benzoyl}amino)phenyl]sulfonyl}-3-phenylpropanoic acid;
3-({2-[(4-{[(benzylamino)carbonyl]amino}benzoyl)amino]phenyl}sulfonyl)-3-phenylpropanoic acid;
3-({3-[(4-{[(benzylamino)carbonyl]amino}benzoyl)amino]phenyl}sulfonyl)-3-phenylpropanoic acid;
3-({4-[(4-{[(benzylamino)carbonyl]amino}benzoyl)amino]phenyl}sulfonyl)-3-phenylpropanoic acid;
3-[(2-{[4-(4,5-dihydro-1H-imidazol-2-ylamino)benzoyl]amino}phenyl)sulfonyl]-3-phenylpropanoic acid;
3-[(3-{[4-(4,5-dihydro-1H-imidazol-2-ylamino)benzoyl]amino}phenyl)sulfonyl]-3-phenylpropanoic acid;
3-[(4-{[4-(4,5-dihydro-1H-imidazol-2-ylamino)benzoyl]amino}phenyl)sulfonyl]-3-phenylpropanoic acid;
3-[(2-{[4-(1H-imidazol-2-ylamino)benzoyl]amino}phenyl)sulfonyl]-3-phenylpropanoic acid;
3-[(3-{[4-(1H-imidazol-2-ylamino)benzoyl]amino}phenyl)sulfonyl]-3-phenylpropanoic acid;
3-[(4-{[4-(1H-imidazol-2-ylamino)benzoyl]amino}phenyl)sulfonyl]-3-phenylpropanoic acid;
3-phenyl-3-[(2-{[4-(2-pyridinylamino)benzoyl]amino}phenyl)sulfonyl]-propanoic acid;
3-phenyl-3-[(3-{[4-(2-pyridinylamino)benzoyl]amino}phenyl)sulfonyl]-propanoic acid;
3-phenyl-3-[(4-{[4-(2-pyridinylamino)benzoyl]amino}phenyl)sulfonyl]-propanoic acid;
3-phenyl-3-[(2-{[4-(2-pyridinylamino)benzoyl]amino}phenyl)sulfonyl]-propanoic acid;
3-phenyl-3-[(3-{[4-(2-pyridinylamino)benzoyl]amino}phenyl)sulfonyl]-propanoic acid;
3-phenyl-3-[(4-{[4-(2-pyridinylamino)benzoyl]amino}phenyl)sulfonyl]-propanoic acid;
3-(3-pyridinyl)-3-(2-{[3-(1,4,5,6-tetrahydro-2-pyrimidinylamino)benzoyl]amino}phenoxy)propanoic acid;
3-(3-pyridinyl)-3-(3-{[3-(1,4,5,6-tetrahydro-2-pyrimidinylamino)benzoyl]amino}phenoxy)propanoic acid;
3-(3-pyridinyl)-3-(4-{[3-(1,4,5,6-tetrahydro-2-pyrimidinylamino)benzoyl]amino}phenoxy)propanoic acid;
3-(3-pyridinyl)-3-(2-{[4-(1,4,5,6-tetrahydro-2-pyrimidinylamino)benzoyl]amino}phenoxy)propanoic acid;
3-(3-pyridinyl)-3-(3-{[4-(1,4,5,6-tetrahydro-2-pyrimidinylamino)benzoyl]amino}phenoxy)propanoic acid;
3-(3-pyridinyl)-3-(4-{[4-(1,4,5,6-tetrahydro-2-pyrimidinylamino)benzoyl]amino}phenoxy)propanoic acid;
3-phenyl-3-(2-{[3-(1,4,5,6-tetrahydro-2-pyrimidinylamino)benzoyl]amino}phenoxy)propanoic acid;
3-phenyl-3-(3-{[3-(1,4,5,6-tetrahydro-2-pyrimidinylamino)benzoyl]amino}phenoxy)propanoic acid;
3-phenyl-3-(4-{[3-(1,4,5,6-tetrahydro-2-pyrimidinylamino)benzoyl]amino}phenoxy)propanoic acid;
3-phenyl-3-(2-{[4-(1,4,5,6-tetrahydro-2-pyrimidinylamino)benzoyl]amino}phenoxy)propanoic acid;
3-phenyl-3-(3-{[4-(1,4,5,6-tetrahydro-2-pyrimidinylamino)benzoyl]amino}phenoxy)propanoic acid;
3-phenyl-3-(4-{[4-(1,4,5,6-tetrahydro-2-pyrimidinylamino)benzoyl]amino}phenoxy)propanoic acid;
3-(3-pyridinyl)-3-[(2-{[3-(1,4,5,6-tetrahydro-2-pyrimidinylamino)benzoyl]amino}phenyl)sulfanyl]propanoic acid;
3-(3-pyridinyl)-3-[(3-{[3-(1,4,5,6-tetrahydro-2-pyrimidinylamino)benzoyl]amino}phenyl)sulfanyl]propanoic acid;
3-(3-pyridinyl)-3-[(4-{[3-(1,4,5,6-tetrahydro-2-pyrimidinylamino)benzoyl]amino}phenyl)sulfanyl]propanoic acid;
3-(3-pyridinyl)-3-[(2-{[4-(1,4,5,6-tetrahydro-2-pyrimidinylamino)benzoyl]amino}phenyl)sulfanyl]propanoic acid;
3-(3-pyridinyl)-3-[(3-{[4-(1,4,5,6-tetrahydro-2-pyrimidinylamino)benzoyl]amino}phenyl)sulfanyl]propanoic acid;
3-(3-pyridinyl)-3-[(4-{[4-(1,4,5,6-tetrahydro-2-pyrimidinylamino)benzoyl]amino}phenyl)sulfanyl]propanoic acid;
3-phenyl-3-[(2-{[3-(1,4,5,6-tetrahydro-2-pyrimidinylamino)benzoyl]amino}phenyl)sulfanyl]propanoic acid;
3-phenyl-3-[(3-{[3-(1,4,5,6-tetrahydro-2-pyrimidinylamino)benzoyl]amino}phenyl)sulfanyl]propanoic acid;
3-phenyl-3-[(4-{[3-(1,4,5,6-tetrahydro-2-pyrimidinylamino)benzoyl]amino}phenyl)sulfanyl]propanoic acid;
3-phenyl-3-[(2-{[4-(1,4,5,6-tetrahydro-2-pyrimidinylamino)benzoyl]amino}phenyl)sulfanyl]propanoic acid;
3-phenyl-3-[(3-{[4-(1,4,5,6-tetrahydro-2-pyrimidinylamino)benzoyl]amino}phenyl)sulfanyl]propanoic acid;
3-phenyl-3-[(4-{[4-(1,4,5,6-tetrahydro-2-pyrimidinylamino)benzoyl]amino}phenyl)sulfanyl]propanoic acid;
3-(3-pyridinyl)-3-[(2-{[3-(1,4,5,6-tetrahydro-2-pyrimidinylamino)benzoyl]amino}phenyl)sulfinyl]propanoic acid;
3-(3-pyridinyl)-3-[(3-{[3-(1,4,5,6-tetrahydro-2-pyrimidinylamino)benzoyl]amino}phenyl)sulfinyl]propanoic acid;
3-(3-pyridinyl)-3-[(4-{[3-(1,4,5,6-tetrahydro-2-pyrimidinylamino)benzoyl]amino}phenyl)sulfinyl]propanoic acid;
3-(3-pyridinyl)-3-[(2-{[4-(1,4,5,6-tetrahydro-2-pyrimidinylamino)benzoyl]amino}phenyl)sulfinyl]propanoic acid;
3-(3-pyridinyl)-3-[(3-{[4-(1,4,5,6-tetrahydro-2-pyrimidinylamino)benzoyl]amino}phenyl)sulfinyl]propanoic acid;
3-(3-pyridinyl)-3-[(4-{[4-(1,4,5,6-tetrahydro-2-pyrimidinylamino)benzoyl]amino}phenyl)sulfinyl]propanoic acid;
3-phenyl-3-[(2-{[3-(1,4,5,6-tetrahydro-2-pyrimidinylamino)benzoyl]amino}phenyl)sulfinyl]propanoic acid;
3-phenyl-3-[(3-{[3-(1,4,5,6-tetrahydro-2-pyrimidinylamino)benzoyl]amino}phenyl)sulfinyl]propanoic acid;
3-phenyl-3-[(4-{[3-(1,4,5,6-tetrahydro-2-pyrimidinylamino)benzoyl]amino}phenyl)sulfinyl]propanoic acid;
3-phenyl-3-[(2-{[4-(1,4,5,6-tetrahydro-2-pyrimidinylamino)benzoyl]amino}phenyl)sulfinyl]propanoic acid;
3-phenyl-3-[(3-{[4-(1,4,5,6-tetrahydro-2-pyrimidinylamino)benzoyl]amino}phenyl)sulfinyl]propanoic acid;
3-phenyl-3-[(4-{[4-(1,4,5,6-tetrahydro-2-pyrimidinylamino)benzoyl]amino}phenyl)sulfinyl]propanoic acid;
3-(3-pyridinyl)-3-[(2-{[3-(1,4,5,6-tetrahydro-2-pyrimidinylamino)benzoyl]amino}phenyl)sulfonyl]propanoic acid;
3-(3-pyridinyl)-3-[(3-{[3-(1,4,5,6-tetrahydro-2-pyrimidinylamino)benzoyl]amino}phenyl)sulfonyl]propanoic acid;
3-(3-pyridinyl)-3-[(4-{[3-(1,4,5,6-tetrahydro-2-pyrimidinylamino)benzoyl]amino}phenyl)sulfonyl]propanoic acid;
3-(3-pyridinyl)-3-[(2-{[4-(1,4,5,6-tetrahydro-2-pyrimidinylamino)benzoyl]amino}phenyl)sulfonyl]propanoic acid;
3-(3-pyridinyl)-3-[(3-{[4-(1,4,5,6-tetrahydro-2-pyrimidinylamino)benzoyl]amino}phenyl)sulfonyl]propanoic acid;
3-(3-pyridinyl)-3-[(4-{[4-(1,4,5,6-tetrahydro-2-pyrimidinylamino)benzoyl]amino}phenyl)sulfonyl]propanoic acid;
3-phenyl-3-[(2-{[3-(1,4,5,6-tetrahydro-2-pyrimidinylamino)benzoyl]amino}phenyl)sulfonyl]propanoic acid;
3-phenyl-3-[(3-{[3-(1,4,5,6-tetrahydro-2-pyrimidinylamino)benzoyl]amino}phenyl)sulfonyl]propanoic acid;

3-phenyl-3-[(4-{[3-(1,4,5,6-tetrahydro-2-pyrimidiny-lamino)benzoyl]amino}phenyl)sulfonyl]propanoic acid;
3-phenyl-3-[(2-{[4-(1,4,5,6-tetrahydro-2-pyrimidiny-lamino)benzoyl]amino}phenyl)sulfonyl]propanoic acid;
3-phenyl-3-[(3-{[4-(1,4,5,6-tetrahydro-2-pyrimidiny-lamino)benzoyl]amino}phenyl)sulfonyl]propanoic acid;
3-phenyl-3-[(4-{[4-(1,4,5,6-tetrahydro-2-pyrimidiny-lamino)benzoyl]amino}phenyl)sulfonyl]propanoic acid;

either as a free acid or a salt thereof, in particular the hydrochloride or the trifluoroacetate.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

All of the references cited herein, including published patents and patent applications are hereby incorporated in their entirety.

What is claimed is:

1. A method of reducing proteinuria in a subject having proteinuria associated with podocytes exhibiting increased uPAR-induced αvβ3 integrin activation, the method comprising:
   detecting, using an antibody-based assay, increased podocyte αvβ3 integrin activation in a subject having proteinuria, wherein the antibody based assay comprises contacting a kidney sample comprising podocytes from the subject having proteinuria with an antibody that binds to activated αvβ3 integrin;
   administering to the subject an antibody that specifically binds β3 integrin and inhibits the interaction of uPAR with αvβ3 integrin on the surface of podocytes in an amount effective to reduce the proteinuria; and
   measuring the subject's urinary protein prior to and after the administration of the antibody, wherein a reduction in the amount of urinary protein indicates that the proteinuria is reduced.

2. The method of claim 1, wherein the administered antibody is a monoclonal antibody that specifically binds β3 integrin.

3. The method of claim 1, wherein the antibody is administered to the subject intravenously.

4. A method of reducing proteinuria in a subject having proteinuria associated with podocytes exhibiting increased αvβ3 integrin activation, the method comprising:
   detecting, using an antibody-based assay, increased podocyte avβ3 integrin activation in a subject having proteinuria, wherein the antibody based assay comprises contacting a kidney sample comprising podocytes from the subject having proteinuria with an antibody that binds to activated αvβ3 integrin;
   administering to the subject an effective amount of an antibody that specifically binds αvβ3 integrin to reduce the proteinuria; and
   measuring the subject's urinary protein prior to and after the administration of the antibody, wherein a reduction in the amount of urinary protein indicates that the proteinuria is reduced.

5. The method of claim 4, wherein the administered antibody is a monoclonal antibody that specifically binds the β3 integrin of αvβ3 integrin.

6. The method of claim 4, wherein the antibody is administered to the subject intravenously.

7. The method according to claim 1, wherein measuring the subject's urinary protein prior to administration of the antibody comprises detecting 150 mg or more of protein in the urine of the subject.

8. The method according to claim 4, wherein measuring the subject's urinary protein prior to administration of the antibody comprises detecting 150 mg or more of protein in the urine of the subject.

9. The method of claim 1, wherein the administered antibody is an antibody fragment.

10. The method of claim 4, wherein the administered antibody is an antibody fragment.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cyclic peptide
<220> FEATURE:
<221> NAME/KEY: MOD_RES
<222> LOCATION: (4)..(4)
<223> OTHER INFORMATION: D-Phe

<400> SEQUENCE: 1

Arg Gly Asp Phe Val
1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtggagcaa caggaggaga                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caaggcaaag tgctcaaaca                                                     20

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term -H, acetyl or acyl
<220> FEATURE:
<221> NAME/KEY: MOD_RES
<222> LOCATION: (2)..(2)
<223> OTHER INFORMATION: Any amino acid
<220> FEATURE:
<223> OTHER INFORMATION: C-term -Oh, OR3 NH2, NHR3, N(R3)2
```

```
<400> SEQUENCE: 4

Arg Xaa Asp Leu Asp Ser Leu Arg
1               5

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cttcctgaag tgttgcaact a                                                  21

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(Psa)
<220> FEATURE:
<223> OTHER INFORMATION: C-term NH2

<400> SEQUENCE: 6

Arg Xaa Asp Leu Asp Ser Leu Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(F5-PSA)
<220> FEATURE:
<223> OTHER INFORMATION: C-term NH2

<400> SEQUENCE: 7

Arg Xaa Asp Leu Asp Ser Leu Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(2-NO2-PSA)
<220> FEATURE:
<223> OTHER INFORMATION: C-term NH2
```

```
<400> SEQUENCE: 8

Arg Xaa Asp Leu Asp Ser Leu Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(4-NO2-PSA)
<220> FEATURE:
<223> OTHER INFORMATION: C-term NH2

<400> SEQUENCE: 9

Arg Xaa Asp Leu Asp Ser Leu Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(2,4-NO2-PSA)
<220> FEATURE:
<223> OTHER INFORMATION: C-term NH2

<400> SEQUENCE: 10

Arg Xaa Asp Leu Asp Ser Leu Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(6-OMe-PSA)
<220> FEATURE:
<223> OTHER INFORMATION: C-term NH2

<400> SEQUENCE: 11

Arg Xaa Asp Leu Asp Ser Leu Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(2-CF3-PSA)
<220> FEATURE:
<223> OTHER INFORMATION: C-term NH2

<400> SEQUENCE: 12

Arg Xaa Asp Leu Asp Ser Leu Arg
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(3-CF3-PSA)
<220> FEATURE:
<223> OTHER INFORMATION: C-term NH2

<400> SEQUENCE: 13

Arg Xaa Asp Leu Asp Ser Leu Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(Me5-PSA)
<220> FEATURE:
<223> OTHER INFORMATION: C-term NH2

<400> SEQUENCE: 14

Arg Xaa Asp Leu Asp Ser Leu Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(4-tBu-PSA)
<220> FEATURE:
<223> OTHER INFORMATION: C-term NH2

<400> SEQUENCE: 15

Arg Xaa Asp Leu Asp Ser Leu Arg
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(BSA)
<220> FEATURE:
<223> OTHER INFORMATION: C-term NH2

<400> SEQUENCE: 16

Arg Xaa Asp Leu Asp Ser Leu Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(iPrs)
<220> FEATURE:
<223> OTHER INFORMATION: C-term NH2

<400> SEQUENCE: 17

Arg Xaa Asp Leu Asp Ser Leu Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(1-Nap)
<220> FEATURE:
<223> OTHER INFORMATION: C-term NH2

<400> SEQUENCE: 18

Arg Xaa Asp Leu Asp Ser Leu Arg
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
```

```
<222> LOCATION: (2)..(2)
<223> OTHER INFORMATION: Dap(2-Nap)
<220> FEATURE:
<223> OTHER INFORMATION: C-term NH2

<400> SEQUENCE: 19

Arg Xaa Asp Leu Asp Ser Leu Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Dap(4-Ph-Psa)
<220> FEATURE:
<223> OTHER INFORMATION: C-term NH2

<400> SEQUENCE: 20

Arg Xaa Asp Leu Asp Ser Leu Arg
1               5
```